US011535640B2

(12) United States Patent
Stoessel et al.

(10) Patent No.: US 11,535,640 B2
(45) Date of Patent: Dec. 27, 2022

(54) METAL COMPLEXES

(71) Applicant: Merck Patent GmbH, Darmstadt (DE)

(72) Inventors: Philipp Stoessel, Frankfurt am Main (DE); Armin Auch, Darmstadt (DE)

(73) Assignee: MERCK PATENT GMBH, Darmstadt (DE)

(*) Notice: Subject to any disclaimer, the term of this patent is extended or adjusted under 35 U.S.C. 154(b) by 352 days.

(21) Appl. No.: 16/634,012

(22) PCT Filed: Jul. 23, 2018

(86) PCT No.: PCT/EP2018/069854
§ 371 (c)(1),
(2) Date: Jan. 24, 2020

(87) PCT Pub. No.: WO2019/020538
PCT Pub. Date: Jan. 31, 2019

(65) Prior Publication Data
US 2020/0207794 A1 Jul. 2, 2020

(30) Foreign Application Priority Data

Jul. 25, 2017 (EP) .................................. 17182995

(51) Int. Cl.
H01L 51/00 (2006.01)
H01L 51/50 (2006.01)
C07F 15/00 (2006.01)

(52) U.S. Cl.
CPC ...... C07F 15/0033 (2013.01); H01L 51/0085 (2013.01); H01L 51/5016 (2013.01)

(58) Field of Classification Search
CPC ............. C07F 15/0033; H01L 51/0085; H01L 51/5016
See application file for complete search history.

(56) References Cited

U.S. PATENT DOCUMENTS

| 2006/0142604 | A1 | 6/2006 | Bach et al. | |
| 2018/0026209 | A1* | 1/2018 | Stoessel | H01L 51/0079 |
| | | | | 252/519.2 |
| 2018/0254416 | A1 | 9/2018 | Stoessel et al. | |
| 2020/0083463 | A1* | 3/2020 | Stoessel | C07F 15/0033 |
| 2021/0175441 | A1* | 6/2021 | Stoessel | C07F 15/0033 |

FOREIGN PATENT DOCUMENTS

| CN | 110959010 A | 4/2020 |
| EP | 3658564 B1 | 5/2021 |
| JP | 2011-530180 A | 12/2011 |
| JP | 2012-102024 A | 5/2012 |
| JP | 2013-243234 A | 12/2013 |
| JP | 2018-510903 A | 4/2018 |
| JP | 2018-531896 A | 11/2018 |
| JP | 2019-527684 A | 10/2019 |
| JP | 2019-529349 A | 10/2019 |
| JP | 2019-530681 A | 10/2019 |
| JP | 2019-533674 A | 11/2019 |
| JP | 2019-534244 A | 11/2019 |
| JP | 2019-535683 A | 12/2019 |
| JP | 2019-536752 A | 12/2019 |
| JP | 2019-537568 A | 12/2019 |
| JP | 2020-515602 A | 5/2020 |
| JP | 2020-515604 A | 5/2020 |
| JP | 2021-506759 A | 2/2021 |
| JP | 2021-513546 A | 5/2021 |
| JP | 2021-518404 A | 8/2021 |
| KR | 10-2020-0031148 A | 3/2020 |
| WO | 2004085449 A1 | 10/2004 |
| WO | 2016124304 A1 | 8/2016 |
| WO | 2017032439 A1 | 3/2017 |

OTHER PUBLICATIONS

Tamura Shinichiro, Molecular design, Applied physics, 69(12), 2000, pp. 1456-1461.

* cited by examiner

Primary Examiner — Igwe U Anya
(74) Attorney, Agent, or Firm — Faegre Drinker Biddle & Reath LLP

(57) ABSTRACT

The present invention relates to iridium complexes suitable for use in organic electroluminescent devices, especially as emitters.

17 Claims, No Drawings

METAL COMPLEXES

RELATED APPLICATIONS

This application is a national stage entry, filed pursuant to 35 U.S.C. § 371, of PCT/EP2018/069854, filed Jul. 23, 2018, which claims the benefit of European Patent Application No. 17182995.5, filed Jul. 25, 2017, which is incorporated herein by reference in its entirety.

The present invention relates to iridium complexes suitable for use in organic electroluminescent devices, especially as emitters.

According to the prior art, triplet emitters used in phosphorescent organic electroluminescent devices (OLEDs) are iridium complexes in particular, especially bis- and tris-ortho-metallated complexes having aromatic ligands, where the ligands bind to the metal via a negatively charged carbon atom and an uncharged nitrogen atom or via a negatively charged carbon atom and an uncharged carbene carbon atom. Examples of such complexes are tris(phenylpyridyl)iridium(III) and derivatives thereof, and a multitude of related complexes are known, for example with 1- or 3-phenylisoquinoline ligands, with 2-phenylquinoline ligands or with phenylcarbene ligands, where these complexes may also have acetylacetonate as auxiliary ligand. Complexes of this kind are also known with polypodal ligands, as described, for example, in WO 2016/124304. Even though these complexes having polypodal ligands show advantages over the complexes which otherwise have the same ligand structure except that the individual ligands therein do not have polypodal bridging, there is still a need for improvement. This lies especially in the efficiency of luminescence of the compounds, and in the sublimation temperature of the compounds. A lower sublimation temperature enables simpler purification of the complexes in the synthesis, and simplified processing when these are applied by vacuum vapour deposition in the OLED.

The problem addressed by the present invention is therefore that of providing novel and especially improved metal complexes suitable as emitters for use in OLEDs.

It has been found that, surprisingly, this problem is solved by metal complexes with a hexadentate tripodal ligand having the structure described below, which are of very good suitability for use in an organic electroluminescent device. The present invention therefore provides these metal complexes and organic electroluminescent devices comprising these complexes.

The invention thus provides a compound of the formula (1)

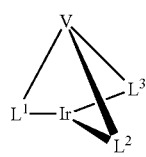

formula (1)

where the symbols used are as follows:

$L^1$ is a sub-ligand of the following formula (2) which coordinates to the iridium via the two Z groups and which is bonded to V via the dotted bond:

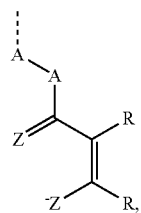

formula (2)

where:
A is the same or different at each instance and is $CR_2$, O, S or NR, where at least one A group is $CR_2$;
Z is the same or different at each instance and is O, S or NR;
$L^2$ is a bidentate, monoanionic sub-ligand which coordinates to the iridium via one carbon atom and one nitrogen atom or via two carbon atoms;
$L^3$ is a bidentate, monoanionic sub-ligand which coordinates to the iridium via one carbon atom and one nitrogen atom or via two carbon atoms, or is a sub-ligand of the above-detailed formula (2) which may be the same as or different from $L^1$;
V is a group of the formula (3), where the dotted bonds each represent the position of linkage of the sub-ligands $L^1$, $L^2$ and $L^3$,

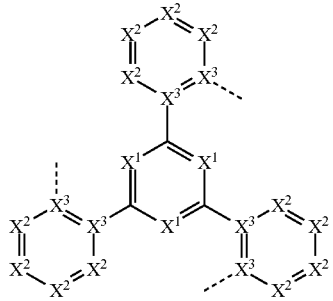

formula (3)

$X^1$ is the same or different at each instance and is CR or N;
$X^2$ is the same or different at each instance and is CR or N, or two adjacent $X^2$ groups together are NR, O or S, thus forming a five-membered ring; or two adjacent $X^2$ groups together are CR or N when one of the $X^3$ groups in the cycle is N, thus forming a five-membered ring; with the proviso that not more than two adjacent $X^2$ groups in each ring are N;
$X^3$ is C at each instance in one cycle or one $X^3$ group is N and the other $X^3$ group in the same cycle is C, where the $X^3$ groups in the three cycles may be selected independently, with the proviso that two adjacent $X^2$ groups together are CR or N when one of the $X^3$ groups in the cycle is N;
R is the same or different at each instance and is H, D, F, Cl, Br, I, $N(R^1)_2$, $OR^1$, $SR^1$, CN, $NO_2$, COOH, $C(=O)N(R^1)_2$, $Si(R^1)_3$, $B(OR^1)_2$, $C(=O)R^1$, $P(=O)(R^1)_2$, $S(=O)R^1$, $S(=O)_2R^1$, $OSO_2R^1$, a straight-chain alkyl group having 1 to 20 carbon atoms or an alkenyl or alkynyl group having 2 to 20 carbon atoms or a branched or cyclic alkyl group having 3 to 20 carbon atoms, where the alkyl, alkenyl or alkynyl group may in each case be substituted by one or more $R^1$ radicals and where one or more nonadjacent $CH_2$ groups may be replaced by Si(R$^1$)$_2$, C=O, NR$^1$, O, S or CONR$^1$, or an aromatic or heteroaromatic ring system which has 5 to 40 aromatic ring atoms and may be substituted in each case by one or more R$^1$ radicals; at the same time, two R radicals together may also form a ring system;

R$^1$ is the same or different at each instance and is H, D, F, Cl, Br, I, N(R$^2$)$_2$, OR$^2$, SR$^2$, CN, NO$_2$, Si(R$^2$)$_3$, B(OR$^2$)$_2$, C(=O)R$^2$, P(=O)(R$^2$)$_2$, S(=O)R$^2$, S(=O)$_2$R$^2$, OSO$_2$R$^2$, a straight-chain alkyl group having 1 to 20 carbon atoms or an alkenyl or alkynyl group having 2 to 20 carbon atoms or a branched or cyclic alkyl group having 3 to 20 carbon atoms, where the alkyl, alkenyl or alkynyl group may in each case be substituted by one or more R$^2$ radicals and where one or more nonadjacent CH$_2$ groups may be replaced by Si(R$^2$)$_2$, C=O, NR$^2$, O, S or CONR$^2$, or an aromatic or heteroaromatic ring system which has 5 to 40 aromatic ring atoms and may be substituted in each case by one or more R$^2$ radicals; at the same time, two or more R$^1$ radicals together may form a ring system;

R$^2$ is the same or different at each instance and is H, D, F or an aliphatic, aromatic and/or heteroaromatic organic radical, especially a hydrocarbyl radical, having 1 to 20 carbon atoms, in which one or more hydrogen atoms may also be replaced by F;

at the same time, the three bidentate ligands L$^1$, L$^2$ and L$^3$, apart from by the bridge V, may also be closed by a further bridge to form a cryptate.

According to the invention, the ligand is thus a hexadentate tripodal ligand having three bidentate sub-ligands L$^1$, L$^2$ and L$^3$. "Bidentate" means that the particular sub-ligand in the complex coordinates or binds to the iridium via two coordination sites. "Tripodal" means that the ligand has three sub-ligands bonded to the bridge V or the bridge of the formula (3). Since the ligand has three bidentate sub-ligands, the overall result is a hexadentate ligand, i.e. a ligand which coordinates or binds to the iridium via six coordination sites. The expression "bidentate sub-ligand" in the context of this application means that L$^1$, L$^2$ or L$^3$ would in each case be a bidentate ligand if the bridge V or the bridge of the formula (3) were not present. However, as a result of the formal abstraction of a hydrogen atom from this bidentate ligand and the attachment to the bridge of the formula (3), it is no longer a separate ligand but a portion of the hexadentate ligand which thus arises, and so the term "sub-ligand" is used therefor.

The ligand of the compound of the invention thus has the following structure (LIG):

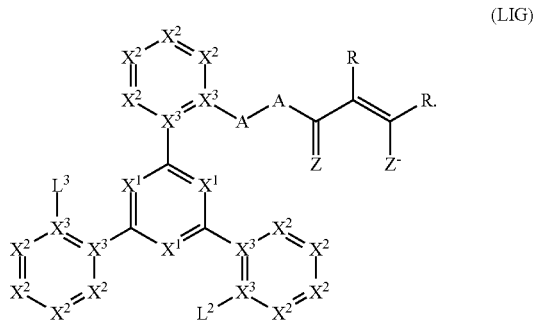

(LIG)

The bond of the ligand to the iridium may either be a coordinate bond or a covalent bond, or the covalent fraction of the bond may vary according to the ligand. When it is said in the present application that the ligand or the sub-ligand coordinates or binds to the iridium, this refers in the context of the present application to any kind of bond from the ligand or sub-ligand to the iridium, irrespective of the covalent component of the bond.

When two R or R$^1$ radicals together form a ring system, it may be mono- or polycyclic, and aliphatic, heteroaliphatic, aromatic or heteroaromatic. In this case, these radicals which together form a ring system may be adjacent, meaning that these radicals are bonded to the same carbon atom or to carbon atoms directly adjacent to one another, or they may be further removed from one another. For example, it is also possible for an R radical bonded to the X$^2$ group to form a ring with an R radical bonded to the X$^1$ group. When there is such ring formation between an R radical bonded to the X$^2$ group and an R radical bonded to the X$^1$ group, this ring is preferably formed by a group having three bridge atoms, preferably having three carbon atoms, and more preferably by a —(CR$_2$)$_3$— group.

The wording that two or more radicals together may form a ring, in the context of the present description, shall be understood to mean, inter alia, that the two radicals are joined to one another by a chemical bond with formal elimination of two hydrogen atoms. This is illustrated by the following scheme:

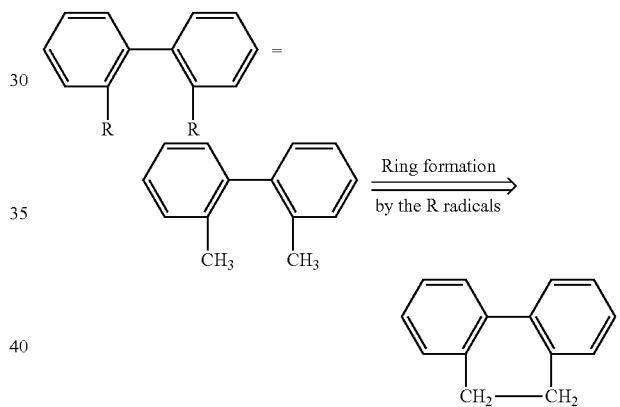

In addition, however, the abovementioned wording shall also be understood to mean that, if one of the two radicals is hydrogen, the second radical binds to the position to which the hydrogen atom was bonded, forming a ring. This shall be illustrated by the following scheme:

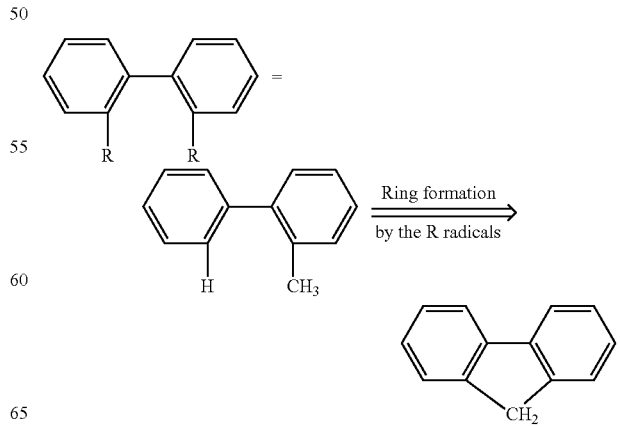

As described above, this kind of ring formation is possible in radicals bonded to carbon atoms directly adjacent to one another, or in radicals bonded to further-removed carbon atoms. Preference is given to this kind of ring formation in radicals bonded to carbon atoms directly bonded to one another.

An aryl group in the context of this invention contains 6 to 40 carbon atoms; a heteroaryl group in the context of this invention contains 2 to 40 carbon atoms and at least one heteroatom, with the proviso that the sum total of carbon atoms and heteroatoms is at least 5. The heteroatoms are preferably selected from N, O and/or S. The heteroaryl group in this case preferably contains not more than three heteroatoms. An aryl group or heteroaryl group is understood here to mean either a simple aromatic cycle, i.e. benzene, or a simple heteroaromatic cycle, for example pyridine, pyrimidine, thiophene, etc., or a fused aryl or heteroaryl group, for example naphthalene, anthracene, phenanthrene, quinoline, isoquinoline, etc.

An aromatic ring system in the context of this invention contains 6 to 40 carbon atoms in the ring system. A heteroaromatic ring system in the context of this invention contains 1 to 40 carbon atoms and at least one heteroatom in the ring system, with the proviso that the sum total of carbon atoms and heteroatoms is at least 5. The heteroatoms are preferably selected from N, O and/or S. An aromatic or heteroaromatic ring system in the context of this invention shall be understood to mean a system which does not necessarily contain only aryl or heteroaryl groups, but in which it is also possible for a plurality of aryl or heteroaryl groups to be interrupted by a nonaromatic unit (preferably less than 10% of the atoms other than H), for example a carbon, nitrogen or oxygen atom or a carbonyl group. For example, systems such as 9,9'-spirobifluorene, 9,9-diarylfluorene, triarylamine, diaryl ethers, stilbene, etc. shall thus also be regarded as aromatic ring systems in the context of this invention, and likewise systems in which two or more aryl groups are interrupted, for example, by a linear or cyclic alkyl group or by a silyl group. In addition, systems in which two or more aryl or heteroaryl groups are bonded directly to one another, for example biphenyl, terphenyl, quaterphenyl or bipyridine, shall likewise be regarded as an aromatic or heteroaromatic ring system.

A cyclic alkyl, alkoxy or thioalkoxy group in the context of this invention is understood to mean a monocyclic, bicyclic or polycyclic group.

In the context of the present invention, a $C_1$- to $C_{20}$-alkyl group in which individual hydrogen atoms or $CH_2$ groups may also be replaced by the abovementioned groups is understood to mean, for example, the methyl, ethyl, n-propyl, i-propyl, cyclopropyl, n-butyl, i-butyl, s-butyl, t-butyl, cyclobutyl, 2-methylbutyl, n-pentyl, s-pentyl, t-pentyl, 2-pentyl, neopentyl, cyclopentyl, n-hexyl, s-hexyl, t-hexyl, 2-hexyl, 3-hexyl, neohexyl, cyclohexyl, 1-methylcyclopentyl, 2-methylpentyl, n-heptyl, 2-heptyl, 3-heptyl, 4-heptyl, cycloheptyl, 1-methylcyclohexyl, n-octyl, 2-ethylhexyl, cyclooctyl, 1-bicyclo[2.2.2]octyl, 2-bicyclo[2.2.2]octyl, 2-(2,6-dimethyl)octyl, 3-(3,7-dimethyl)octyl, adamantyl, trifluoromethyl, pentafluoroethyl, 2,2,2-trifluoroethyl, 1,1-dimethyl-n-hex-1-yl, 1,1-dimethyl-n-hept-1-yl, 1,1-dimethyl-n-oct-1-yl, 1,1-dimethyl-n-dec-1-yl, 1,1-dimethyl-n-dodec-1-yl, 1,1-dimethyl-n-tetradec-1-yl, 1,1-dimethyl-n-hexadec-1-yl, 1,1-dimethyl-n-octadec-1-yl, 1,1-diethyl-n-hex-1-yl, 1,1-diethyl-n-hept-1-yl, 1,1-diethyl-n-oct-1-yl, 1,1-diethyl-n-dec-1-yl, 1,1-diethyl-n-dodec-1-yl, 1,1-diethyl-n-tetradec-1-yl, 1,1-diethyl-n-hexadec-1-yl, 1,1-diethyl-n-octadec-1-yl, 1-(n-propyl)cyclohex-1-yl, 1-(n-butyl) cyclohex-1-yl, 1-(n-hexyl)cyclohex-1-yl, 1-(n-octyl) cyclohex-1-yl and 1-(n-decyl)cyclohex-1-yl radicals. An alkenyl group is understood to mean, for example, ethenyl, propenyl, butenyl, pentenyl, cyclopentenyl, hexenyl, cyclohexenyl, heptenyl, cycloheptenyl, octenyl, cyclooctenyl or cyclooctadienyl. An alkynyl group is understood to mean, for example, ethynyl, propynyl, butynyl, pentynyl, hexynyl, heptynyl or octynyl. An $OR^1$ group is understood to mean, for example, methoxy, trifluoromethoxy, ethoxy, n-propoxy, i-propoxy, n-butoxy, i-butoxy, s-butoxy, t-butoxy or 2-methylbutoxy.

An aromatic or heteroaromatic ring system which has 5-40 aromatic ring atoms and may also be substituted in each case by the abovementioned radicals and which may be joined to the aromatic or heteroaromatic system via any desired positions is understood to mean, for example, groups derived from benzene, naphthalene, anthracene, benzanthracene, phenanthrene, benzophenanthrene, pyrene, chrysene, perylene, fluoranthene, benzofluoranthene, naphthacene, pentacene, benzopyrene, biphenyl, biphenylene, terphenyl, terphenylene, fluorene, spirobifluorene, dihydrophenanthrene, dihydropyrene, tetrahydropyrene, cis- or trans-indenofluorene, cis- or trans-monobenzoindenofluorene, cis- or trans-dibenzoindenofluorene, truxene, isotruxene, spirotruxene, spiroisotruxene, furan, benzofuran, isobenzofuran, dibenzofuran, thiophene, benzothiophene, isobenzothiophene, dibenzothiophene, pyrrole, indole, isoindole, carbazole, indolocarbazole, indenocarbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, benzopyridazine, pyrimidine, benzopyrimidine, quinoxaline, 1,5-diazaanthracene, 2,7-diazapyrene, 2,3-diazapyrene, 1,6-diazapyrene, 1,8-diazapyrene, 4,5-diazapyrene, 4,5,9,10-tetraazaperylene, pyrazine, phenazine, phenoxazine, phenothiazine, fluorubine, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole.

Stated hereinafter are preferred embodiments of the bridgehead V, i.e. the structure of the formula (3).

Suitable embodiments of the group of the formula (3) are the structures of the following formulae (4) to (7):

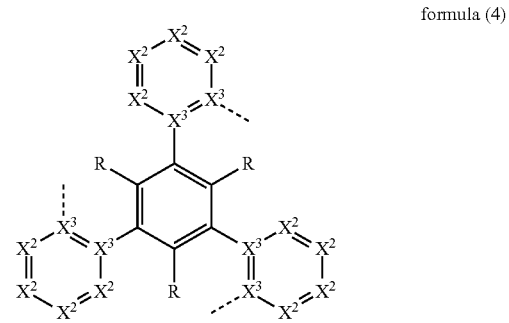

formula (4)

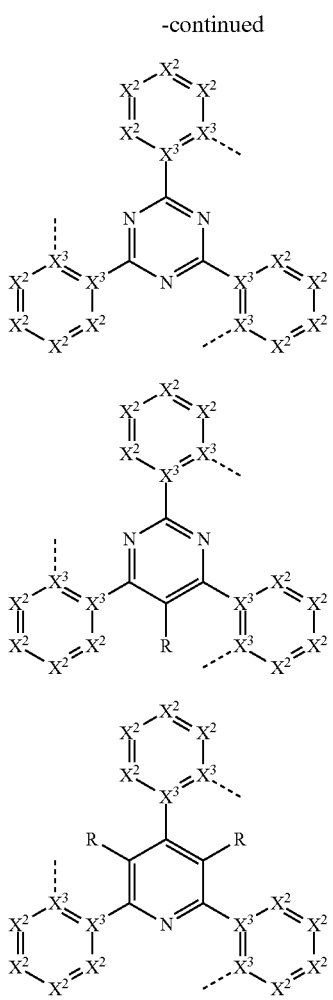

formula (5)

formula (6)

formula (7)

where the symbols used have the definitions given above.

In one preferred embodiment of the invention, all $X^1$ groups in the group of the formula (3) are CR, and so the central trivalent cycle of the formula (3) is a benzene. More preferably, all $X^1$ groups in the formulae (4), (6) and (7) are CH. In a further preferred embodiment of the invention, all $X^1$ groups are a nitrogen atom, and so the central trivalent cycle of the formula (3) is a triazine. Preferred embodiments of the formula (3) are thus the structures of the formulae (4) and (5).

The following is applicable in respect of preferred R radicals on the trivalent central benzene ring of the formula (4) or on the central pyrimidine ring of the formula (6) or on the central pyridine ring of the formula (7):

R is the same or different at each instance and is H, D, F, CN, $OR^1$, a straight-chain alkyl group having 1 to 10 carbon atoms or an alkenyl group having 2 to 10 carbon atoms or a branched or cyclic alkyl group having 3 to 10 carbon atoms, each of which may be substituted by one or more $R^1$ radicals but is preferably unsubstituted, or an aromatic or heteroaromatic ring system which has 5 to 24 aromatic ring atoms and may be substituted in each case by one or more $R^1$ radicals; at the same time, the R radical may also form a ring system with an R radical on $X^2$;

$R^1$ is the same or different at each instance and is H, D, F, CN, $OR^2$, a straight-chain alkyl group having 1 to 10 carbon atoms or an alkenyl group having 2 to 10 carbon atoms or a branched or cyclic alkyl group having 3 to 10 carbon atoms, each of which may be substituted by one or more $R^2$ radicals but is preferably unsubstituted, or an aromatic or heteroaromatic ring system which has 5 to 24 aromatic ring atoms and may be substituted in each case by one or more $R^2$ radicals; at the same time, two or more adjacent $R^1$ radicals together may form a ring system;

$R^2$ is the same or different at each instance and is H, D, F or an aliphatic, aromatic and/or heteroaromatic organic radical having 1 to 20 carbon atoms, in which one or more hydrogen atoms may also be replaced by F.

The following is applicable in respect of particularly preferred R radicals on the trivalent central benzene ring of the formula (4) or on the central pyrimidine ring of the formula (6) or on the central pyridine ring of the formula (7):

R is the same or different at each instance and is H, D, F, CN, a straight-chain alkyl group having 1 to 4 carbon atoms or a branched or cyclic alkyl group having 3 to 6 carbon atoms, each of which may be substituted by one or more $R^1$ radicals but is preferably unsubstituted, or an aromatic or heteroaromatic ring system which has 6 to 12 aromatic ring atoms and may be substituted in each case by one or more $R^1$ radicals; at the same time, the R radical may also form a ring system with an R radical on $X^2$;

$R^1$ is the same or different at each instance and is H, D, F, CN, a straight-chain alkyl group having 1 to 4 carbon atoms or a branched or cyclic alkyl group having 3 to 6 carbon atoms, each of which may be substituted by one or more $R^2$ radicals but is preferably unsubstituted, or an aromatic or heteroaromatic ring system which has 6 to 12 aromatic ring atoms and may be substituted in each case by one or more $R^2$ radicals; at the same time, two or more adjacent $R^1$ radicals together may form a ring system;

$R^2$ is the same or different at each instance and is H, D, F or an aliphatic or aromatic hydrocarbyl radical having 1 to 12 carbon atoms.

More preferably, the group of the formula (4) is a structure of the following formula (4'):

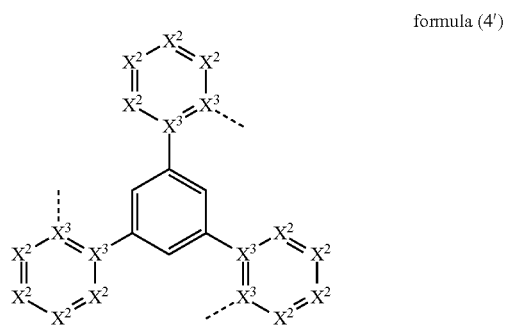

formula (4')

where the symbols used have the definitions given above.

There follows a description of preferred bivalent arylene or heteroarylene units as occur in the group of the formulae (3) to (7). As apparent from structures of the formulae (3) to (7), these structures contain three ortho-bonded bivalent arylene or heteroarylene units.

In a preferred embodiment of the invention, the symbol $X^3$ is C, and so the groups of the formulae (3) to (7) can be represented by the following formulae (3a) to (7a):

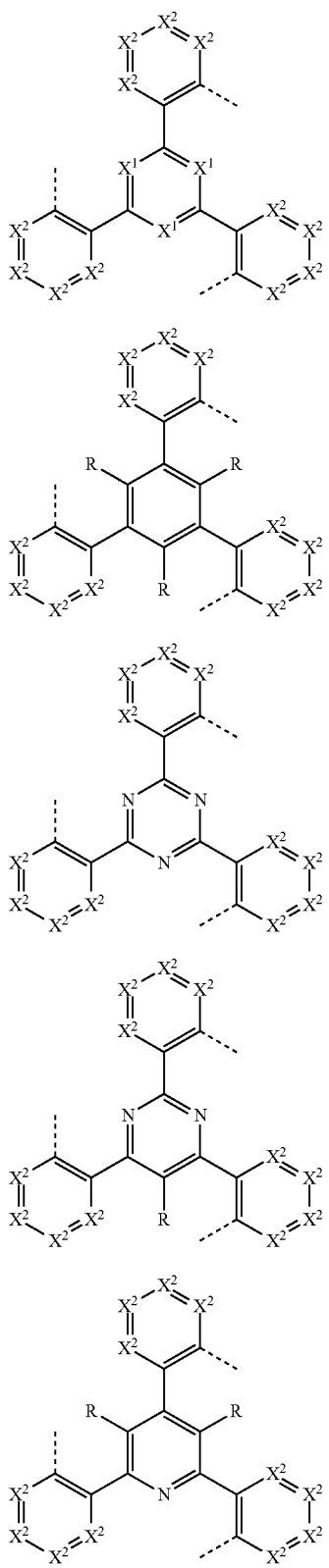

where the symbols have the definitions listed above.

The group of the formula (3) can be formally represented by the following formula (3'), where the formulae (3) and (3') encompass the same structures:

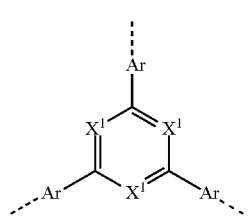

formula (3')

where Ar is the same or different in each case and is a group of the following formula (8):

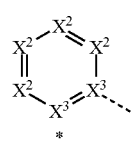

formula (8)

where the dotted bond in each case represents the position of the bond of the bidentate sub-ligands $L^1$, $L^2$ or $L^3$ to this structure, * represents the position of the linkage of the unit of the formula (8) to the central trivalent aryl or heteroaryl group and $X^2$ has the definitions given above. Preferred substituents in the group of the formula (8) are selected from the above-described substituents R.

The group of the formula (8) may represent a heteroaromatic five-membered ring or an aromatic or heteroaromatic six-membered ring. In a preferred embodiment of the invention, the group of the formula (8) contains not more than two heteroatoms in the aryl or heteroaryl group, more preferably not more than one heteroatom. This does not mean that any substituents bonded to this group cannot also contain heteroatoms. In addition, this definition does not mean that formation of rings by substituents cannot give rise to fused aromatic or heteroaromatic structures, for example naphthalene, benzimidazole, etc. The group of the formula (8) is preferably selected from benzene, pyridine, pyrimidine, pyrazine, pyridazine, pyrrole, furan, thiophene, pyrazole, imidazole, oxazole and thiazole.

When both $X^3$ groups in a cycle are carbon atoms, preferred embodiments of the group of the formula (8) are the structures of the following formulae (9) to (25):

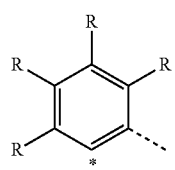

formula (9)

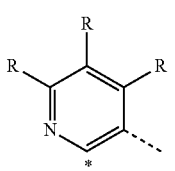

formula (10)

formula (11)
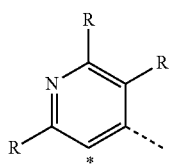

formula (12)
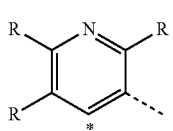

formula (13)
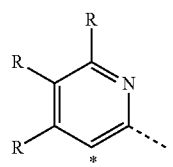

formula (14)
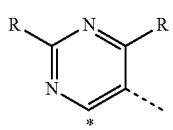

formula (15)
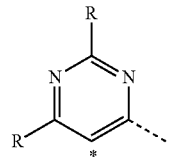

formula (16)
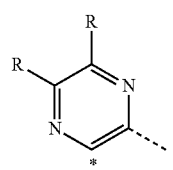

formula (17)
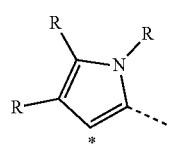

formula (18)
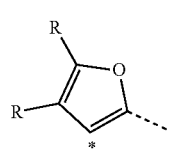

formula (19)
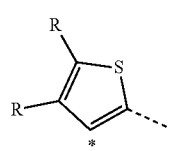

formula (20)
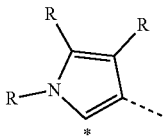

formula (21)
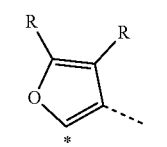

formula (22)
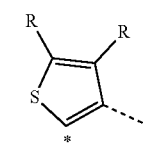

formula (23)
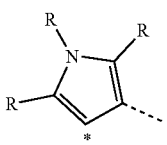

formula (24)
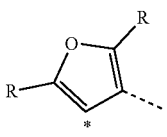

formula (25)
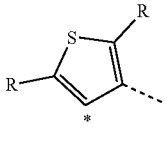

where the symbols used have the definitions given above.

When one $X^3$ group in a cycle is a carbon atom and the other $X^3$ group in the same cycle is a nitrogen atom, preferred embodiments of the group of the formula (8) are the structures of the following formulae (26) to (33):

formula (26)

formula (27)

formula (28)

formula (29)
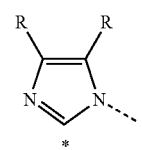

formula (30)
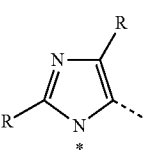

formula (31)

formula (32)
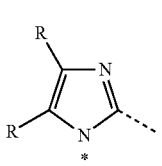

formula (33)
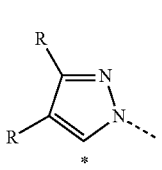

where the symbols used have the definitions given above.

Particular preference is given to the optionally substituted six-membered aromatic rings and six-membered heteroaromatic rings of the formulae (9) to (13) depicted above. Very particular preference is given to ortho-phenylene, i.e. a group of the abovementioned formula (9).

At the same time, as also described above in the description of the substituent, it is also possible for adjacent substituents together to form a ring system, such that fused structures, including fused aryl and heteroaryl groups, for example naphthalene, quinoline, benzimidazole, carbazole, dibenzofuran or dibenzothiophene, can form.

In this case, the three groups of the formula (8) present in the group of the formulae (3) to (7) or formula (3') may be the same or different. In a preferred embodiment of the invention, all three groups in the formula (8) are the same and also have the same substitution.

More preferably, the structures of the formula (4) to (7) are selected from the structures of the following formulae (4b) to (7b):

formula (4b)
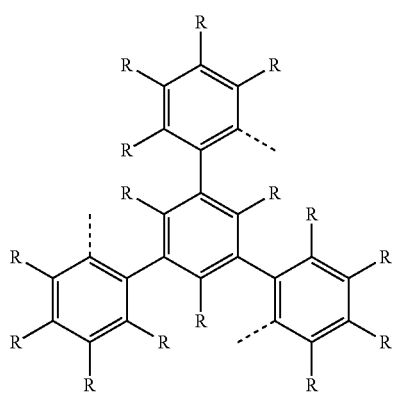

formula (5b)
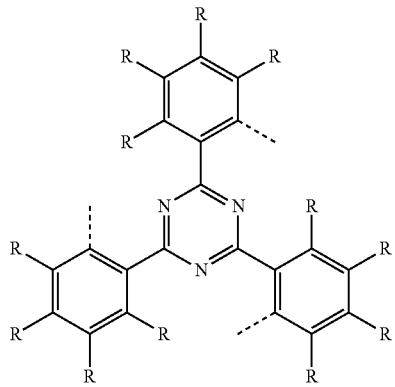

formula (6b)
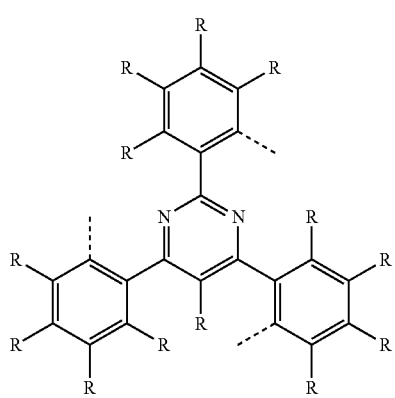

formula (7b)
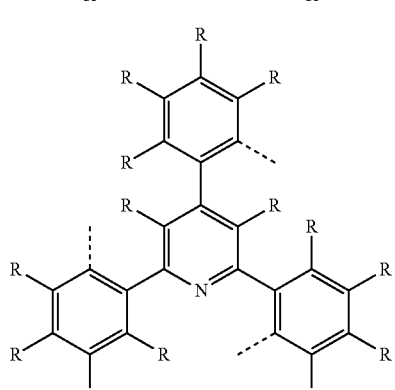

where the symbols used have the definitions given above.

A preferred embodiment of the formula (4b) is the structure of the following formula (4b'):

(formula (4b'))

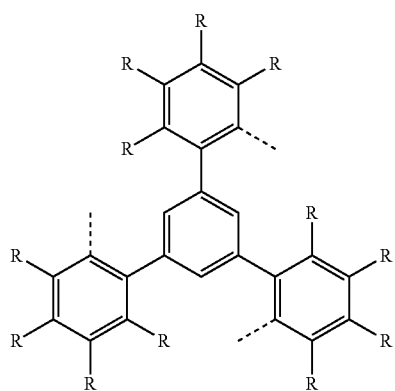

where the symbols used have the definitions given above.

More preferably, the R groups in the formulae (3) to (7) are the same or different at each instance and are H, D or an alkyl group having 1 to 4 carbon atoms. Most preferably, R=H. Very particular preference is thus given to the structures of the following formulae (4c) or (5c):

formula (4c)

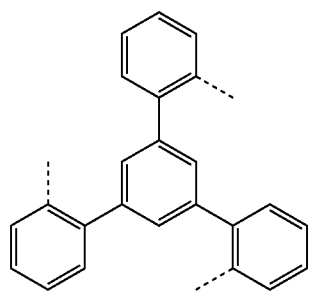

formula 5c)

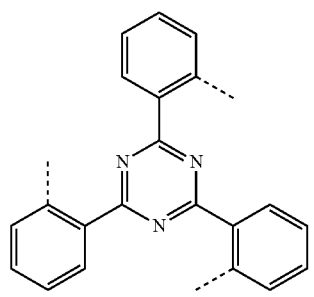

where the symbols used have the definitions given above.

There follows a description of the bidentate sub-ligands $L^1$. As described above, the sub-ligand $L^1$ has a structure of the formula (2).

In a preferred embodiment of the invention, both A groups are $CR_2$, more preferably $CH_2$.

In a further preferred embodiment of the invention, at least one Z group is O. More preferably, both Z groups are O.

$L^1$ is thus preferably a sub-ligand of the following formula (2a):

formula (2a)

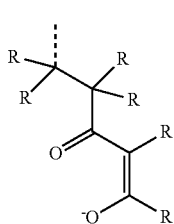

where the symbols used have the definitions given above.

It may also be preferred when two R radicals together form a ring. This is preferred especially when the two R radicals bind to the same carbon atom, i.e. in a $CR_2$ group, or between two R radicals that are directly adjacent within the acetylacetonate group. The ring is preferably an aliphatic cycle having 5 or 6 ring atoms or an aromatic cycle. Examples of suitable ring formation between the substituents are shown by the following structures ($L^1$-A) to ($L^1$-F):

formula ($L^1$-A)

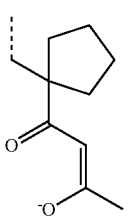

formula ($L^1$-B)

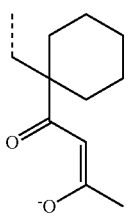

formula ($L^1$-C)

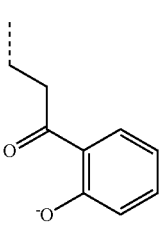

formula ($L^1$-D)

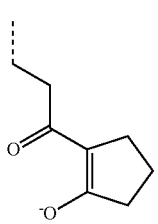

formula ($L^1$-E)

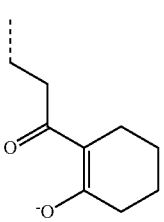

-continued

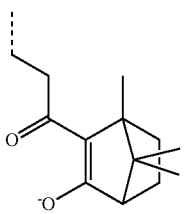

formula (L¹-F)

where these structures may also be substituted by one or more R¹ radicals, but are preferably unsubstituted.

L¹ is more preferably a sub-ligand of the following formula (2b):

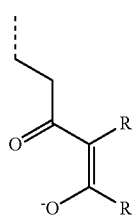

formula (2b)

where the symbols used have the definitions given above.

L¹ is most preferably a sub-ligand of the following formula (2c):

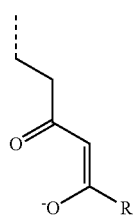

formula (2c)

where the symbols used have the definitions given above.

R in formula (2), (2a), (2b) and (2c) is the same or different at each instance and is selected from the group consisting of H, D, OR¹, a straight-chain alkyl group having 1 to 10 carbon atoms or a branched or cyclic alkyl group which has 3 to 10 carbon atoms and may be substituted in each case by one or more R¹ radicals, but is preferably unsubstituted, or an aromatic or heteroaromatic ring system which has 5 to 24 aromatic ring atoms and may be substituted in each case by one or more R¹ radicals; at the same time, it is also possible for two or more R radicals together to form a ring system. Particularly preferred R radicals are the same or different at each instance and are selected from the group consisting of H, D, a straight-chain alkyl group having 1 to 4 carbon atoms or a branched or cyclic alkyl group which has 3 to 6 carbon atoms and may be substituted in each case by one or more R¹ radicals, but is preferably unsubstituted, or an aromatic ring system which has 6 to 12 aromatic ring atoms and may be substituted in each case by one or more R¹ radicals; at the same time, it is also possible for two or more R radicals together to form a ring system. Particularly preferred alkyl groups are methyl, ethyl, isopropyl, isobutyl, tert-butyl and neopentyl, especially methyl.

In addition, R¹ is preferably selected from the group consisting of H, D, F, a straight-chain alkyl group having 1 to 10 carbon atoms or a branched or cyclic alkyl group which has 3 to 10 carbon atoms and may be substituted in each case by one or more R² radicals, but is preferably unsubstituted, or an aromatic or heteroaromatic ring system which has 5 to 24 aromatic ring atoms and may be substituted in each case by one or more R² radicals; at the same time, it is possible for two or more adjacent R¹ radicals together to form a ring system.

There follows a description of the bidentate sub-ligands L² and L³. As described above, L² coordinates to the iridium via one carbon atom and one nitrogen atom or via two carbon atoms. In addition, L³ is the same or different and is L¹ or L², i.e. is a sub-ligand of the formula (2) or is a sub-ligand that coordinates to the iridium via one carbon atom and one nitrogen atom or via two carbon atoms. In a preferred embodiment of the invention, L² and L³ are both sub-ligands, each of which coordinate to the iridium via one carbon atom and one nitrogen atom or via two carbon atoms. The two sub-ligands L² and L³ may be the same or different.

Preferably, at least one of the sub-ligands L² and L³ has one carbon atom and one nitrogen atom as coordinating atoms. Most preferably, both sub-ligands L² and L³ have one carbon atom and one nitrogen atom as coordinating atoms.

It is further preferable when the metallacycle which is formed from the iridium and the sub-ligand L² or L³ is a five-membered ring. This is shown schematically hereinafter:

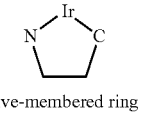

five-membered ring where N is a coordinating nitrogen atom and C is a coordinating carbon atom, and the carbon atoms shown are atoms of the sub-ligand L² or L³.

In a preferred embodiment of the invention, at least one of the sub-ligands L² and L³, more preferably both the sub-ligands L² and L³, are the same or different at each instance and are a structure of the following formulae (L-1) and (L-2):

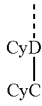

formula (L-1)

formula (L-2)

where the dotted bond represents the bond of the sub-ligand to the bridge of the formula (3) and the other symbols used are as follows:

CyC is the same or different at each instance and is a substituted or unsubstituted aryl or heteroaryl group which has 5 to 14 aromatic ring atoms and coordinates in each case to the metal via a carbon atom and which is bonded to CyD via a covalent bond;

CyD is the same or different at each instance and is a substituted or unsubstituted heteroaryl group which has 5 to 14 aromatic ring atoms and coordinates to the metal via a nitrogen atom or via a carbene carbon atom and which is bonded to CyC via a covalent bond;
at the same time, two or more of the optional substituents together may form a ring system; the optional radicals are preferably selected from the abovementioned R radicals.

CyD preferably coordinates via an uncharged nitrogen atom or via a carbene carbon atom. In addition, CyC coordinates via anionic carbon atoms.

When two or more of the substituents, especially two or more R radicals, together form a ring system, it is possible for a ring system to be formed from substituents bonded to directly adjacent carbon atoms. In addition, it is also possible that the substituents on CyC and CyD together form a ring, as a result of which CyC and CyD may also together form a single fused aryl or heteroaryl group as bidentate ligand.

It is possible here for the two sub-ligands $L^2$ and $L^3$ to have a structure of the formula (L-1), or for both sub-ligands $L^2$ and $L^3$ to have a structure of the formula (L-2), or for one of the sub-ligands $L^2$ and $L^3$ to have a structure of the formula (L-1) and the other of the sub-ligands to have a structure of the formula (L-2). In a preferred embodiment of the invention, one of the sub-ligands $L^2$ and $L^3$ has a structure of the formula (L-1), and the other of the sub-ligands $L^2$ and $L^3$ has a structure of the formula (L-2).

In a preferred embodiment of the present invention, CyC is an aryl or heteroaryl group having 6 to 13 aromatic ring atoms, more preferably having 6 to 10 aromatic ring atoms, most preferably having 6 aromatic ring atoms, which coordinates to the metal via a carbon atom, which may be substituted by one or more R radicals and which is bonded to CyD via a covalent bond.

Preferred embodiments of the CyC group are the structures of the following formulae (CyC-1) to (CyC-19) where the CyC group binds in each case at the position signified by # to CyD and at the position signified by * to the iridium,

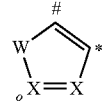
(CyC-1)

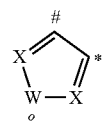
(CyC-2)

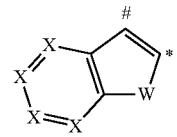
(CyC-3)

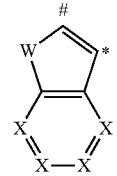
(CyC-4)

-continued

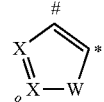
(CyC-5)

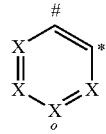
(CyC-6)

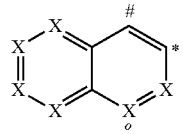
(CyC-7)

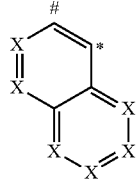
(CyC-8)

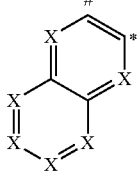
(CyC-9)

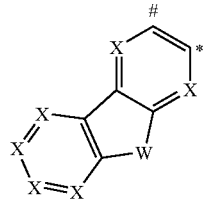
(CyC-10)

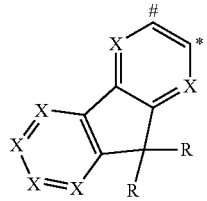
(CyC-11)

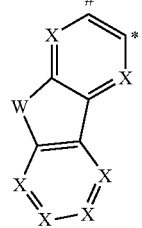
(CyC-12)

(CyC-13) 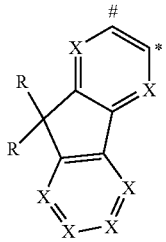

(CyC-14) 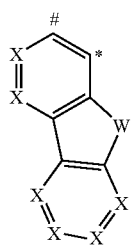

(CyC-15) 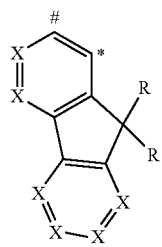

(CyC-16) 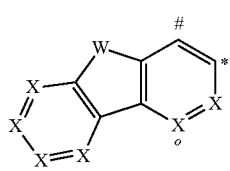

(CyC-17) 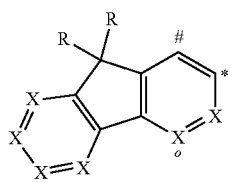

(CyC-18) 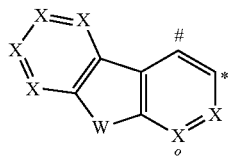

(CyC-19) 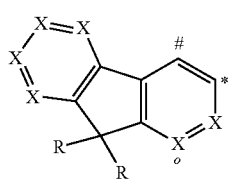

(CyC-20) 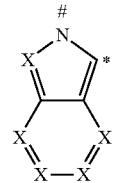

where R has the definitions given above and the other symbols used are as follows:

X is the same or different at each instance and is CR or N, with the proviso that not more than two symbols X per cycle are N;

W is the same or different at each instance and is NR, O or S;

with the proviso that, when the bridge of the formula (3) is bonded to CyC, one symbol X is C and the bridge of the formula (3) is bonded to this carbon atom. When the CyC group is bonded to the bridge of the formula (3), the bond is preferably via the position marked by "o" in the formulae depicted above, and so the symbol X marked by "o" in that case is preferably C. The above-depicted structures which do not contain any symbol X marked by "o" are preferably not bonded directly to the bridge of the formula (3), since such a bond to the bridge is not advantageous for steric reasons.

Preferably, a total of not more than two symbols X in CyC are N, more preferably not more than one symbol X in CyC is N, and most preferably all symbols X are CR, with the proviso that, when the bridge of the formula (3) is bonded to CyC, one symbol X is C and the bridge of the formula (3) is bonded to this carbon atom.

Particularly preferred CyC groups are the groups of the following formulae (CyC-1a) to (CyC-20a):

(CyC-1a) 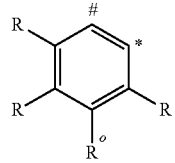

(CyC-1b) 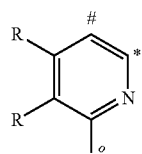

(CyC-1c) 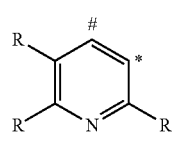

(CyC-1d) 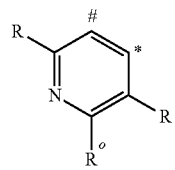

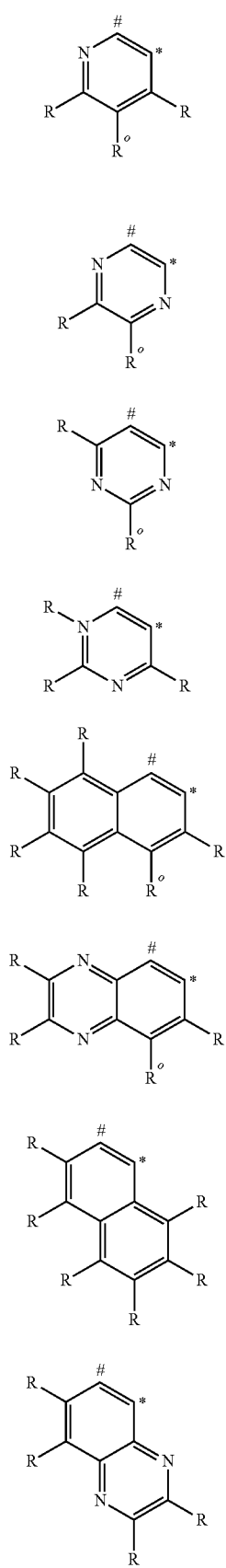
(CyC-1e)
(CyC-1f)
(CyC-1g)
(CyC-1h)
(CyC-2a)
(CyC-2b)
(CyC-3a)
(CyC-3b)
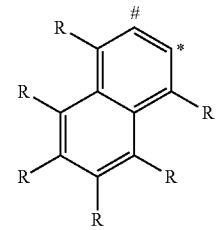
(CyC-4a)
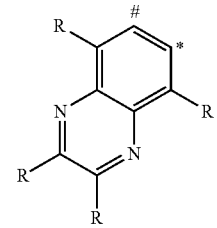
(CyC-4b)
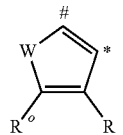
(CyC-5a)
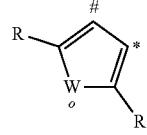
(CyC-6a)
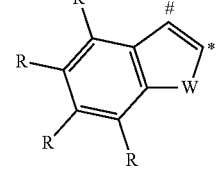
(CyC-7a)
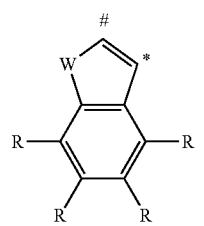
(CyC-8a)
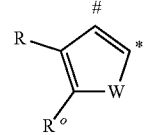
(CyC-9a)
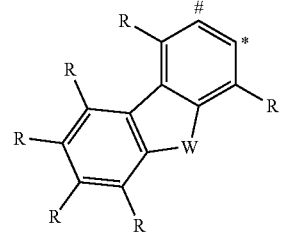
(CyC-10a)

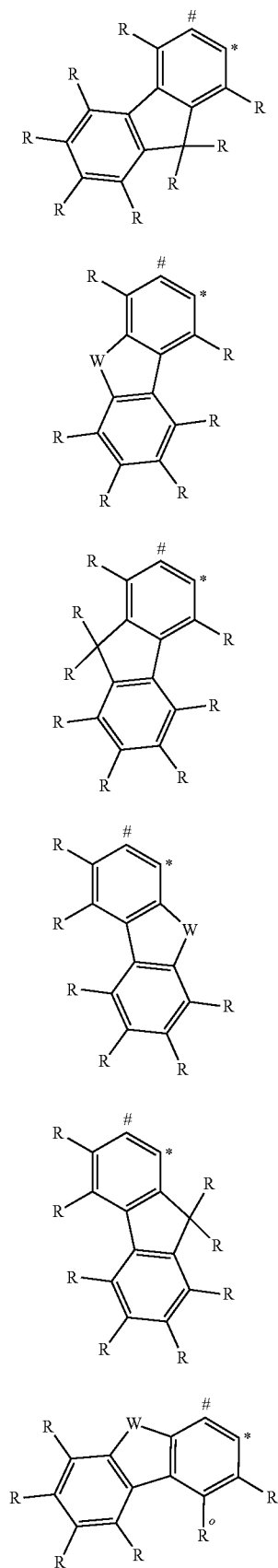

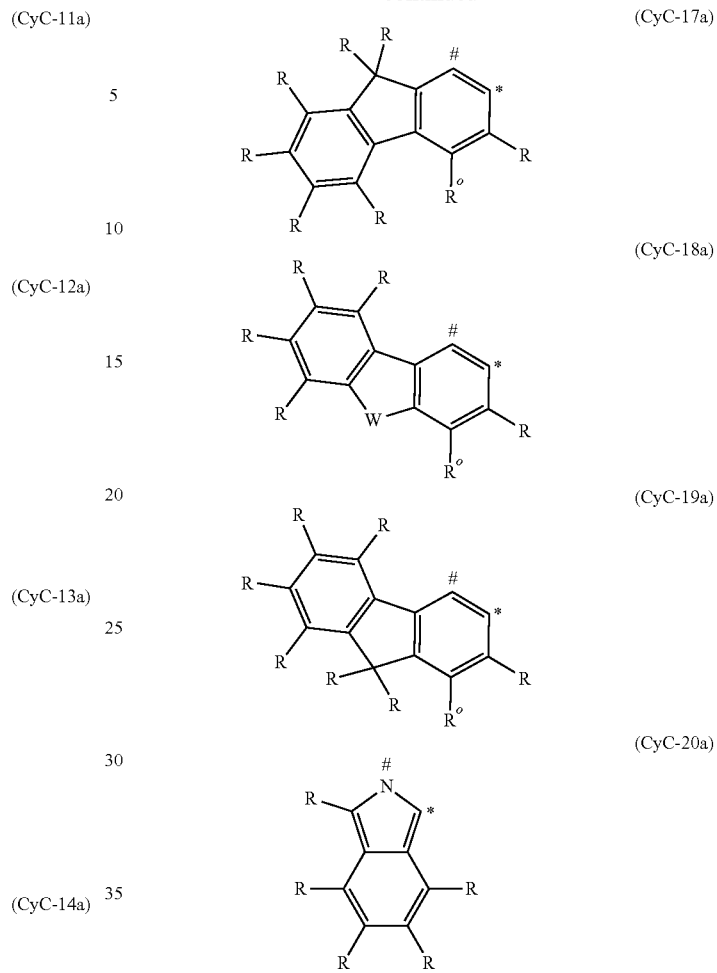

where the symbols used have the definitions given above and, when the bridge of the formula (3) is bonded to CyC, one R radical is not present and the bridge of the formula (3) is bonded to the corresponding carbon atom. When the CyC group is bonded to the bridge of the formula (3), the bond is preferably via the position marked by "o" in the formulae depicted above, and so the R radical in this position in that case is preferably absent. The above-depicted structures which do not contain any carbon atom marked by "o" are preferably not bonded directly to the bridge of the formula (3).

Preferred groups among the (CyC-1) to (CyC-19) groups are the (CyC-1), (CyC-3), (CyC-8), (CyC-10), (CyC-12), (CyC-13) and (CyC-16) groups, and particular preference is given to the (CyC-1a), (CyC-3a), (CyC-8a), (CyC-10a), (CyC-12a), (CyC-13a) and (CyC-16a) groups.

In a further preferred embodiment of the invention, CyD is a heteroaryl group having 5 to 13 aromatic ring atoms, more preferably having 6 to 10 aromatic ring atoms, which coordinates to the metal via an uncharged nitrogen atom or via a carbene carbon atom and which may be substituted by one or more R radicals and which is bonded via a covalent bond to $C_yC$.

Preferred embodiments of the CyD group are the structures of the following formulae (CyD-1) to (CyD-12) where the CyD group binds in each case at the position signified by # to CyC and coordinates at the position signified by * to the iridium,

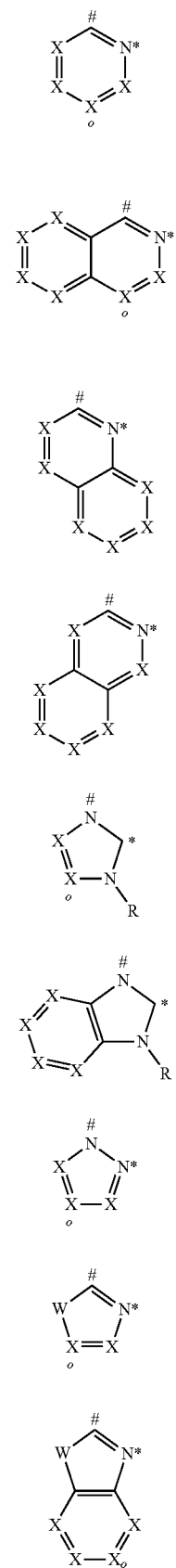

(CyD-1)
(CyD-2)
(CyD-3)
(CyD-4)
(CyD-5)
(CyD-6)
(CyD-7)
(CyD-8)
(CyD-9)
(CyD-10)
(CyD-11)
(CyD-12)

where X, W and R have the definitions given above, with the proviso that, when the bridge of the formula (3) is bonded to CyD, one symbol X is C and the bridge of the formula (3) is bonded to this carbon atom. When the CyD group is bonded to the bridge of the formula (3), the bond is preferably via the position marked by "o" in the formulae depicted above, and so the symbol X marked by "o" in that case is preferably C. The above-depicted structures which do not contain any symbol X marked by "o" are preferably not bonded directly to the bridge of the formula (3), since such a bond to the bridge is not advantageous for steric reasons.

In this case, the (CyD-1) to (CyD-4) and (CyD-7) to (CyD-12) groups coordinate to the metal via an uncharged nitrogen atom, and (CyD-5) and (CyD-6) groups via a carbene carbon atom.

Preferably, a total of not more than two symbols X in CyD are N, more preferably not more than one symbol X in CyD is N, and especially preferably all symbols X are CR, with the proviso that, when the bridge of the formula (3) is bonded to CyD, one symbol X is C and the bridge of the formula (3) is bonded to this carbon atom.

Particularly preferred CyD groups are the groups of the following formulae (CyD-1a) to (CyD-12b):

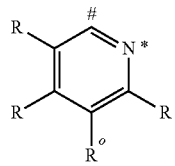

(CyD-1a)

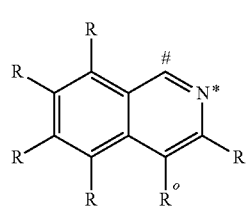

(CyD-2a)

(CyD-3a) 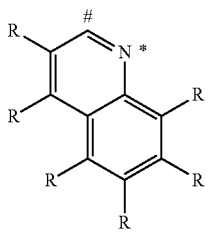

(CyD-3b) 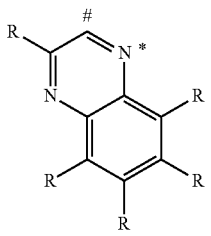

(CyD-4a) 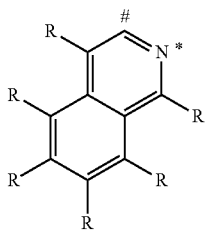

(CyD-5a) 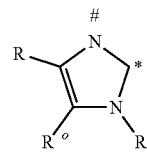

(CyD-6a) 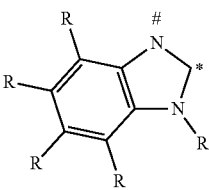

(CyD-7a) 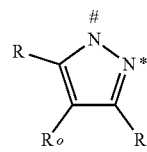

(CyD-8a) 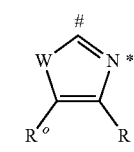

(CyD-9a) 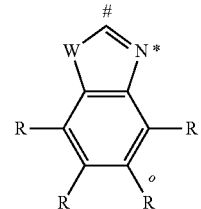

(CyD-10a) 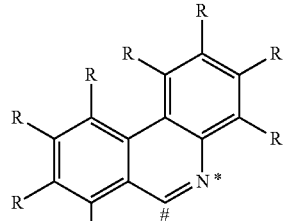

(CyD-11a) 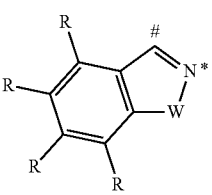

(CyD-12a) 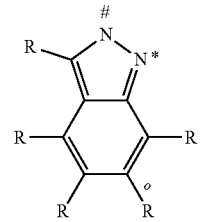

(CyD-12b) 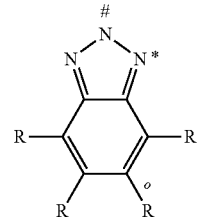

where the symbols used have the definitions given above and, when the bridge of the formula (3) is bonded to CyD, one R radical is not present and the bridge of the formula (3) is bonded to the corresponding carbon atom. When the CyD group is bonded to the bridge of the formula (3), the bond is preferably via the position marked by "o" in the formulae depicted above, and so the R radical in this position in that case is preferably absent. The above-depicted structures which do not contain any carbon atom marked by "o" are preferably not bonded directly to the bridge of the formula.

Preferred groups among the (CyD-1) to (CyD-12) groups are the (CyD-1), (CyD-2), (CyD-3), (CyD-4), (CyD-5) and (CyD-6) groups, especially (CyD-1), (CyD-2) and (CyD-3), and particular preference is given to the (CyD-1a), (CyD-2a), (CyD-3a), (CyD-4a), (CyD-5a) and (CyD-6a) groups, especially (CyD-1a), (CyD-2a) and (CyD-3a).

In a preferred embodiment of the present invention, CyC is an aryl or heteroaryl group having 6 to 13 aromatic ring atoms, and at the same time CyD is a heteroaryl group having 5 to 13 aromatic ring atoms. More preferably, CyC is an aryl or heteroaryl group having 6 to 10 aromatic ring atoms, and at the same time CyD is a heteroaryl group having 5 to 10 aromatic ring atoms. Most preferably, CyC is an aryl or heteroaryl group having 6 aromatic ring atoms, and CyD is a heteroaryl group having 6 to 10 aromatic ring atoms. At the same time, CyC and CyD may be substituted by one or more R radicals.

The abovementioned preferred (CyC-1) to (CyC-20) and (CyD-1) to (CyD-12) groups may be combined with one another as desired, provided that at least one of the CyC or CyD groups has a suitable attachment site to the bridge of the formula (3), suitable attachment sites being signified by "o" in the formulae given above.

It is especially preferable when the CyC and CyD groups specified above as particularly preferred, i.e. the groups of the formulae (CyC-1a) to (CyC-20a) and the groups of the formulae (CyD1-a) to (CyD-14b), are combined with one another, provided that at least one of the preferred CyC or CyD groups has a suitable attachment site to the bridge of the formula (3), suitable attachment sites being signified by "o" in the formulae given above. Combinations in which neither CyC nor CyD has such a suitable attachment site for the bridge of the formula (3) are therefore not preferred.

It is very particularly preferable when one of the (CyC-1), (CyC-3), (CyC-8), (CyC-10), (CyC-12), (CyC-13) and (CyC-16) groups and especially the (CyC-1a), (CyC-3a), (CyC-8a), (CyC-10a), (CyC-12a), (CyC-13a) and (CyC-16a) groups is combined with one of the (CyD-1), (CyD-2) and (CyD-3) groups and especially with one of the (CyD-1a), (CyD-2a) and (CyD-3a) groups.

Preferred sub-ligands (L-1) are the structures of the formulae (L-1-1) and (L-1-2), and preferred sub-ligands (L-2) are the structures of the formulae (L-2-1) to (L-2-4):

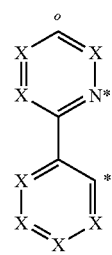
(L-1-1)

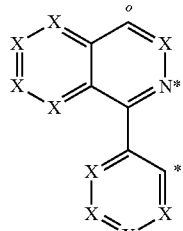
(L-1-2)

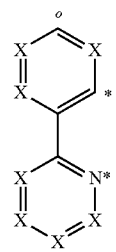
(L-2-1)

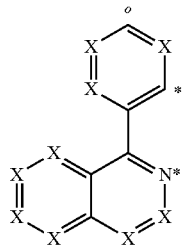
(L-2-2)

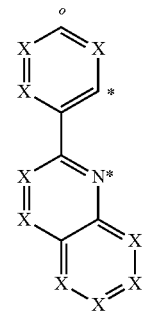
(L-2-3)

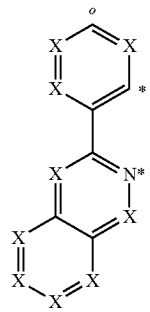
(L-2-4)

where the symbols used have the definitions given above and "o" represents the position of the bond to the bridge of the formula (3).

Particularly preferred sub-ligands (L-1) are the structures of the formulae (L-1-1a) and (L-1-2b), and particularly preferred sub-ligands (L-2) are the structures of the formulae (L-2-1a) to (L-2-4a)

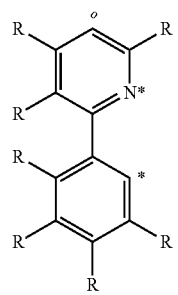
(L-1-1a)

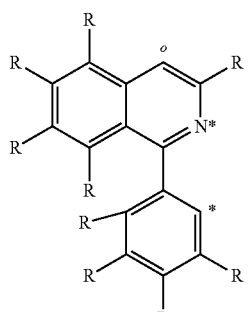
(L-1-2a)

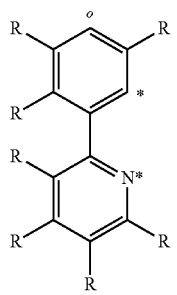
(L-2-1a)

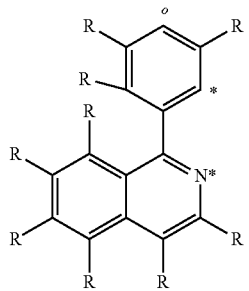
(L-2-2a)

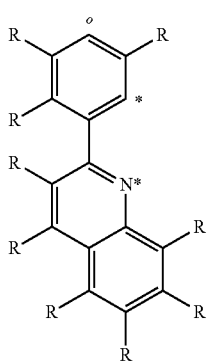
(L-2-3a)

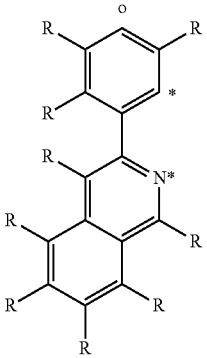
(L-2-4a)

where the symbols used have the definitions given above and "o" represents the position of the bond to the bridge of the formula (3).

When two R radicals of which one is bonded to CyC and the other to CyD together form an aromatic ring system, this can result in bridged sub-ligands and, for example, also in sub-ligands which overall constitute a single larger heteroaryl group, for example benzo[h]quinoline, etc. The ring between the substituents on CyC and CyD is preferably formed by a group of one of the following formulae (34) to (43):

formula (34)

formula (35)

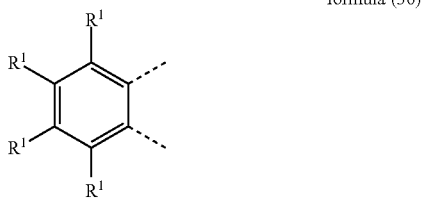
formula (36)

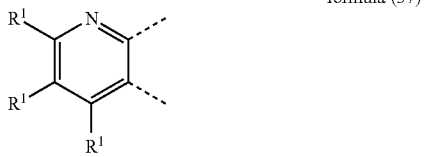
formula (37)

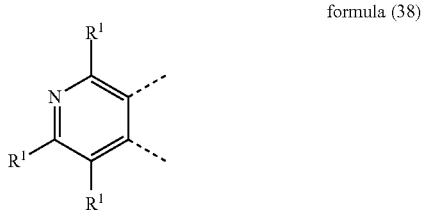
formula (38)

-continued formula (39)
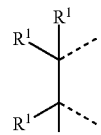

formula (40)
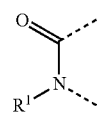

formula (41)
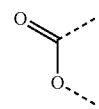

formula (42)

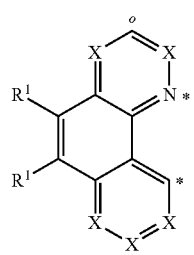  (this region described by the cropped images)

formula (43)

where R¹ has the definitions given above and the dotted bonds signify the bonds to CyC or CyD. At the same time, the unsymmetric groups among those mentioned above may be incorporated in each of the two possible options; for example, in the group of the formula (43), the oxygen atom may bind to the CyC group and the carbonyl group to the CyD group, or the oxygen atom may bind to the CyD group and the carbonyl group to the CyC group.

At the same time, the group of the formula (40) is preferred particularly when this results in ring formation to give a six-membered ring, as shown below, for example, by the formulae (L-21) and (L-22).

Preferred ligands which arise through ring formation between two R radicals in the different cycles are the structures of the formulae (L-3) to (L-30) shown below:

(L-3)
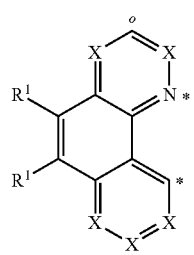

(L-4)
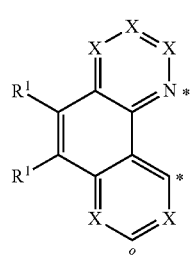

(L-5)
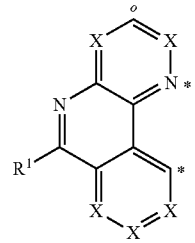

(L-6)
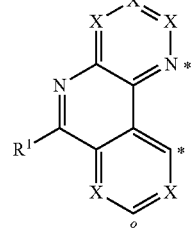

(L-7)
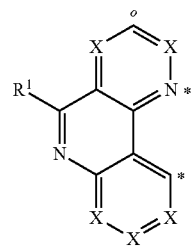

(L-8)
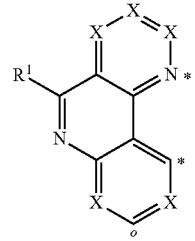

(L-9)
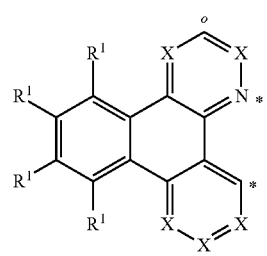

(L-10)
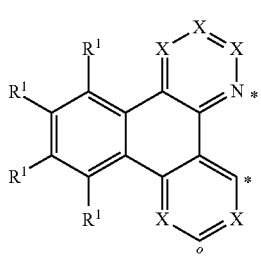

(L-11) 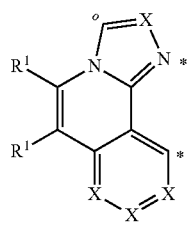
(L-12) 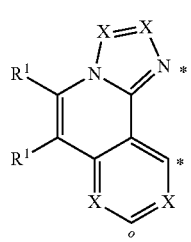
(L-13) 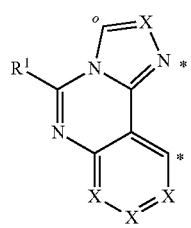
(L-14) 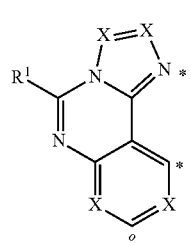
(L-15) 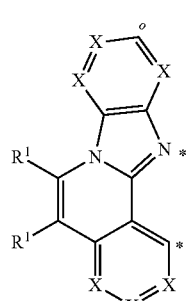
(L-16) 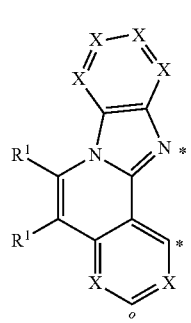
(L-17) 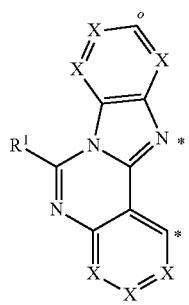
(L-18) 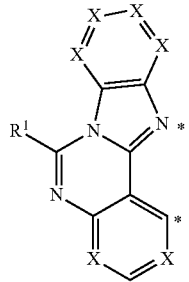
(L-19) 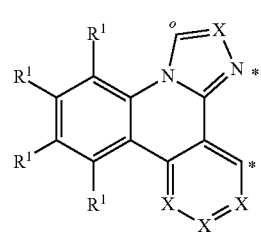
(L-20) 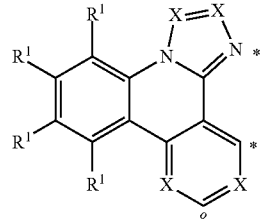
(L-21) 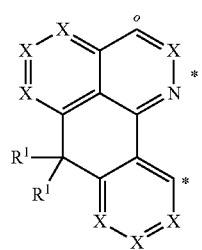
(L-22) 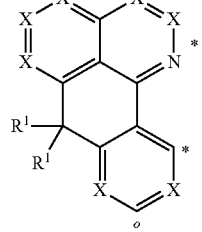

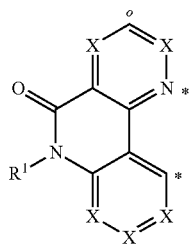 (L-23)

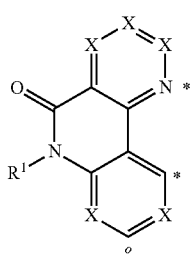 (L-24)

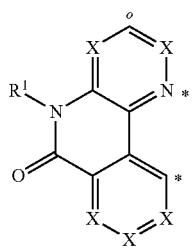 (L-25)

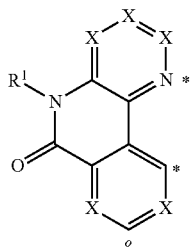 (L-26)

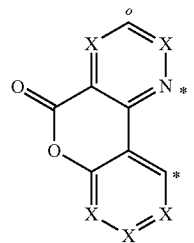 (L-27)

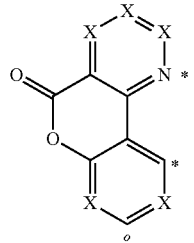 (L-28)

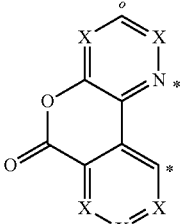 (L-29)

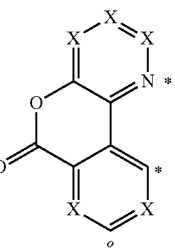 (L-30)

where the symbols used have the definitions given above and "o" indicates the position at which this sub-ligand is joined to the group of the formula (3).

In a preferred embodiment of the sub-ligands of the formulae (L-5) to (L-32), a total of one symbol X is N and the other symbols X are CR, or all symbols X are CR.

In a further embodiment of the invention, it is preferable if, in the groups (CyC-1) to (CyC-20) or (CyD-1) to (CyD-14) or in the sub-ligands (L-5) to (L-32), one of the atoms X is N when an R group bonded as a substituent adjacent to this nitrogen atom is not hydrogen or deuterium. This applies analogously to the preferred structures (CyC-1a) to (CyC-20a) or (CyD-1a) to (CyD-14b) in which a substituent bonded adjacent to a non-coordinating nitrogen atom is preferably an R group which is not hydrogen or deuterium.

In this case, this substituent R is preferably a group selected from $CF_3$, $OCF_3$, alkyl groups having 1 to 10 carbon atoms, especially branched or cyclic alkyl groups having 3 to 10 carbon atoms, $OR^1$ where $R^1$ is an alkyl group having 1 to 10 carbon atoms, especially a branched or cyclic alkyl group having 3 to 10 carbon atoms, a dialkylamino group having 2 to 10 carbon atoms, aromatic or heteroaromatic ring systems or aralkyl or heteroaralkyl groups. These groups are sterically demanding groups. Further preferably, this R radical may also form a cycle with an adjacent R radical.

A further suitable bidentate sub-ligand for metal complexes in which the metal is a transition metal is a sub-ligand of the following formula (L-31) or (L-32):

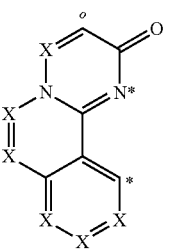 (L-31)

(L-32)

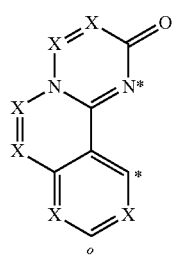

where R has the definitions given above, * represents the position of coordination to the metal, "o" represents the position of linkage of the sub-ligand to the group of the formula (3) and the other symbols used are as follows:

X is the same or different at each instance and is CR or N, with the proviso that not more than one X symbol per cycle is N.

When two R radicals bonded to adjacent carbon atoms in the sub-ligands (L-31) and (L-32) form an aromatic cycle with one another, this cycle together with the two adjacent carbon atoms is preferably a structure of the formula (44):

formula (44)

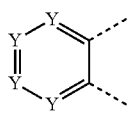

where the dotted bonds symbolize the linkage of this group within the sub-ligand and Y is the same or different at each instance and is $CR^1$ or N and preferably not more than one symbol Y is N.

In a preferred embodiment of the sub-ligand (L-31) or (L-32), not more than one group of the formula (44) is present. The sub-ligands are thus preferably sub-ligands of the following formulae (L-33) to (L-38):

(L-33)

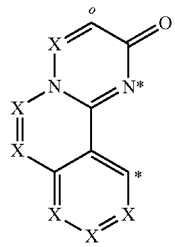

(L-34)

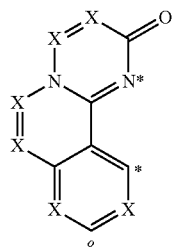

(L-35)

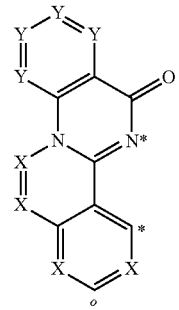

(L-36)

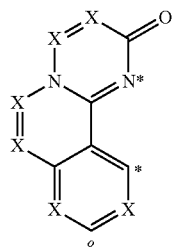

(L-37)

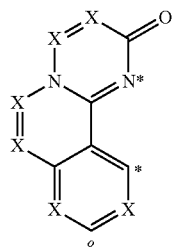

(L-38)

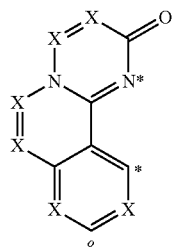

where X is the same or different at each instance and is CR or N, but the R radicals together do not form an aromatic or heteroaromatic ring system and the further symbols have the definitions given above.

In a preferred embodiment of the invention, in the sub-ligand of the formulae (L-31) to (L-38), a total of 0, 1 or 2 of the symbols X and, if present, Y are N. More preferably, a total of 0 or 1 of the symbols X and, if present, Y are N.

Preferred embodiments of the formulae (L-33) to (L-38) are the structures of the following formulae (L-33a) to (L-38f):

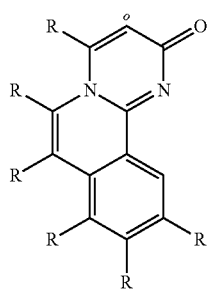
(L-33a)
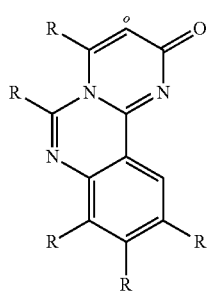
(L-33b)
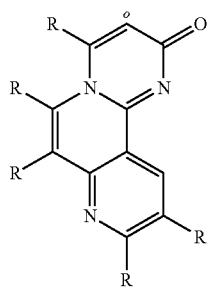
(L-33c)
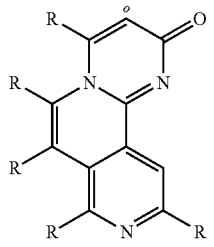
(L-33d)
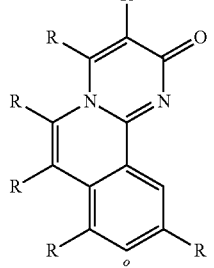
(L-34a)
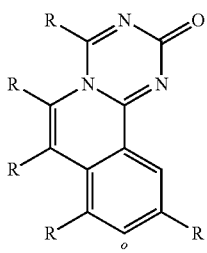
(L-34b)
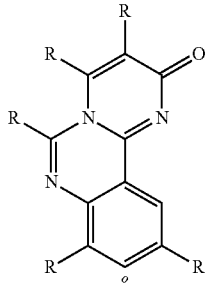
(L-34c)
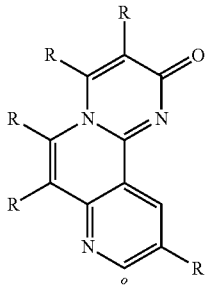
(L-34d)
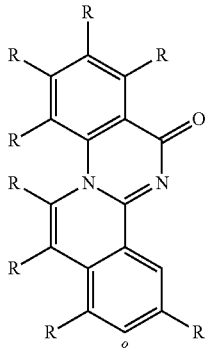
(L-35a)
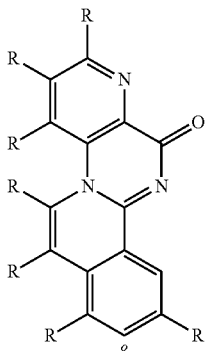
(L-35b)

-continued
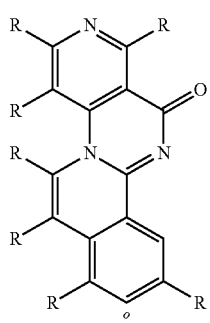
(L-35c)
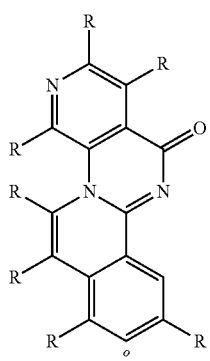
(L-35d)
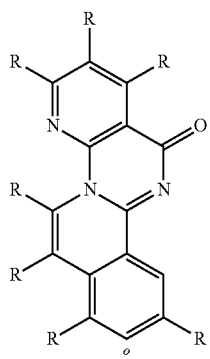
(L-35e)
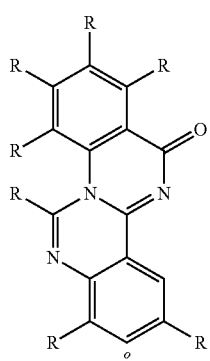
(L-35f)
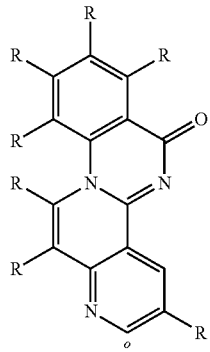
(L-35g)
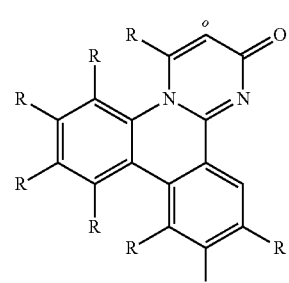
(L-36a)
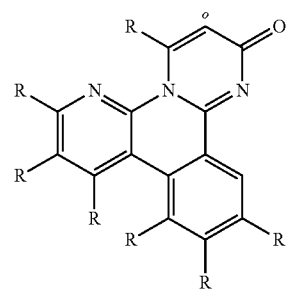
(L-36b)
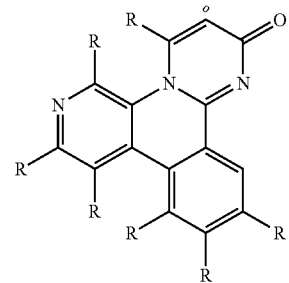
(L-36c)
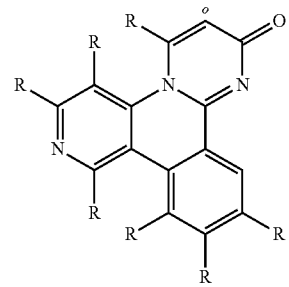
(L-36d)

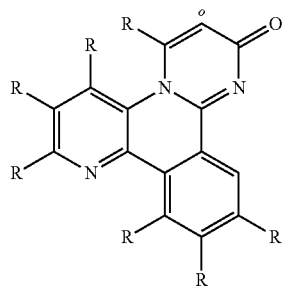
(L-37e)
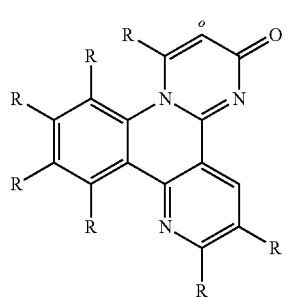
(L-37f)
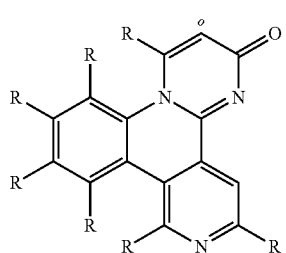
(L-36g)
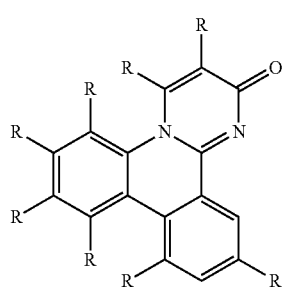
(L-37a)
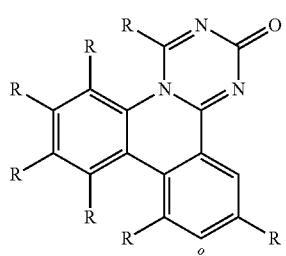
(L-37b)
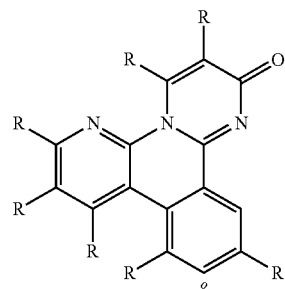
(L-37c)
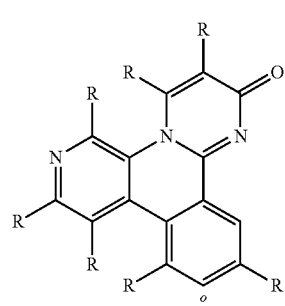
(L-37d)
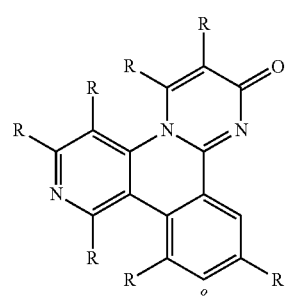
(L-37e)
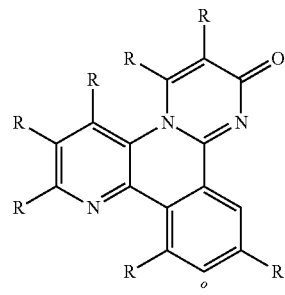
(L-37f)
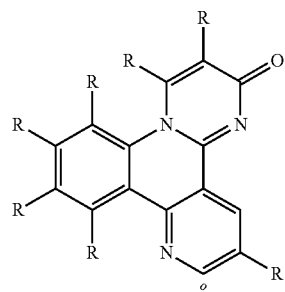
(L-37g)

(L-38a) 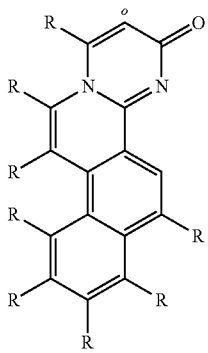

(L-38b) 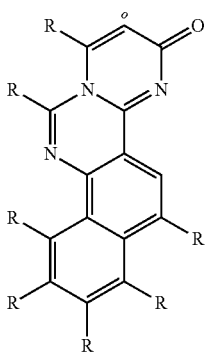

(L-38c) 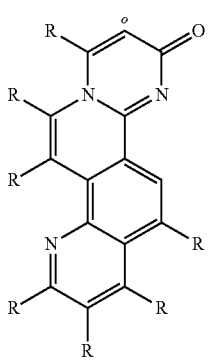

(L-38d) 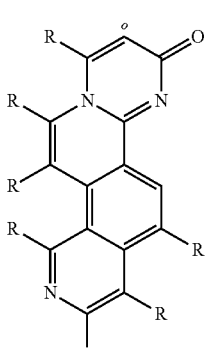

(L-38e) 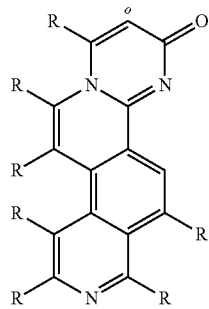

(L-38f) 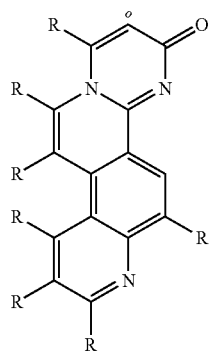

where the symbols used have the definitions given above and "o" indicates the position of the linkage to the group of the formula (3).

In a preferred embodiment of the invention, the X group in the ortho position to the coordination to the metal is CR. In this radical, R bonded in the ortho position to the coordination to the metal is preferably selected from the group consisting of H, D, F and methyl.

In a further embodiment of the invention, it is preferable, if one of the atoms X or, if present, Y is N, when a substituent bonded adjacent to this nitrogen atom is an R group which is not hydrogen or deuterium.

In this case, this substituent R is preferably a group selected from $CF_3$, $OCF_3$, alkyl groups having 1 to 10 carbon atoms, especially branched or cyclic alkyl groups having 3 to 10 carbon atoms, $OR^1$ where $R^1$ is an alkyl group having 1 to 10 carbon atoms, especially a branched or cyclic alkyl group having 3 to 10 carbon atoms, a dialkylamino group having 2 to 10 carbon atoms, aromatic or heteroaromatic ring systems or aralkyl or heteroaralkyl groups. These groups are sterically demanding groups. Further preferably, this R radical may also form a cycle with an adjacent R radical.

There follows a description of preferred substituents as may be present on the above-described sub-ligands $L^2$ and $L^3$, but also on the bivalent arylene or heteroarylene group in the structure of the formulae (3) to (7), i.e. in the structure of the formula (8).

In a preferred embodiment of the invention, the metal complex of the invention contains two R substituents or two $R^1$ substituents which are bonded to adjacent carbon atoms and together form an aliphatic ring according to one of the formulae described hereinafter. In this case, the two R substituents which form this aliphatic ring may be present on the bridge of the formula (3) and/or on one or more of the bidentate sub-ligands. The aliphatic ring which is formed by the ring formation by two R substituents together or by two $R^1$ substituents together is preferably described by one of the following formulae (45) to (51):

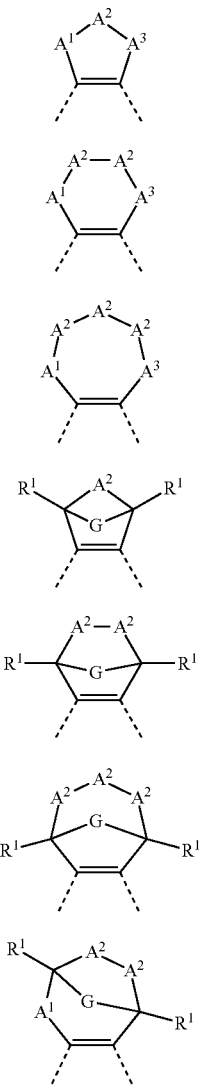

where $R^1$ and $R^2$ have the definitions given above, the dotted bonds signify the linkage of the two carbon atoms in the ligand and, in addition:
$A^1$, $A^3$ is the same or different at each instance and is $C(R^3)_2$, O, S, $NR^3$ or C(=O);
$A^2$ is $C(R^1)_2$, O, S, $NR^3$ or C(=O);
G is an alkylene group which has 1, 2 or 3 carbon atoms and may be substituted by one or more $R^2$ radicals, $-CR^2=CR^2-$ or an ortho-bonded arylene or heteroarylene group which has 5 to 14 aromatic ring atoms and may be substituted by one or more $R^2$ radicals;
$R^3$ is the same or different at each instance and is H, F, a straight-chain alkyl or alkoxy group having 1 to 10 carbon atoms, a branched or cyclic alkyl or alkoxy group having 3 to 10 carbon atoms, where the alkyl or alkoxy group may be substituted in each case by one or more $R^2$ radicals, where one or more nonadjacent $CH_2$ groups may be replaced by $R^2C=CR^2$, C≡C, $Si(R^2)_2$, C=O, $NR^2$, O, S or $CONR^2$, or an aromatic or heteroaromatic ring system which has 5 to 24 aromatic ring atoms and may be substituted in each case by one or more $R^2$ radicals, or an aryloxy or heteroaryloxy group which has 5 to 24 aromatic ring atoms and may be substituted by one or more $R^2$ radicals; at the same time, two $R^3$ radicals bonded to the same carbon atom together may form an aliphatic or aromatic ring system and thus form a spiro system; in addition, $R^3$ with an adjacent R or $R^1$ radical may form an aliphatic ring system;
with the proviso that no two heteroatoms in these groups are bonded directly to one another and no two C=O groups are bonded directly to one another.

In the above-depicted structures of the formulae (45) to (51) and the further embodiments of these structures specified as preferred, a double bond is depicted in a formal sense between the two carbon atoms. This is a simplification of the chemical structure when these two carbon atoms are incorporated into an aromatic or heteroaromatic system and hence the bond between these two carbon atoms is formally between the bonding level of a single bond and that of a double bond. The drawing of the formal double bond should thus not be interpreted so as to limit the structure; instead, it will be apparent to the person skilled in the art that this is an aromatic bond.

When adjacent radicals in the structures of the invention form an aliphatic ring system, it is preferable when the latter does not have any acidic benzylic protons. Benzylic protons are understood to mean protons which bind to a carbon atom bonded directly to the ligand. This can be achieved by virtue of the carbon atoms in the aliphatic ring system which bind directly to an aryl or heteroaryl group being fully substituted and not containing any bonded hydrogen atoms. Thus, the absence of acidic benzylic protons in the formulae (45) to (47) is achieved by virtue of $A^1$ and $A^3$, when they are $C(R^3)_2$, being defined such that $R^3$ is not hydrogen. This can additionally also be achieved by virtue of the carbon atoms in the aliphatic ring system which bind directly to an aryl or heteroaryl group being the bridgeheads in a bi- or polycyclic structure. The protons bonded to bridgehead carbon atoms, because of the spatial structure of the bi- or polycycle, are significantly less acidic than benzylic protons on carbon atoms which are not bonded within a bi- or polycyclic structure, and are regarded as non-acidic protons in the context of the present invention. Thus, the absence of acidic benzylic protons in formulae (48) to (51) is achieved by virtue of this being a bicyclic structure, as a result of which $R^1$, when it is H, is much less acidic than benzylic protons since the corresponding anion of the bicyclic structure is not mesomerically stabilized. Even when $R^1$ in formulae (48) to (51) is H, this is therefore a non-acidic proton in the context of the present application.

In a preferred embodiment of the invention, $R^3$ is not H.

In a preferred embodiment of the structure of the formulae (45) to (51), not more than one of the $A^1$, $A^2$ and $A^3$ groups is a heteroatom, especially O or $NR^3$, and the other groups are $C(R^3)_2$ or $C(R^1)_2$, or $A^1$ and $A^3$ are the same or different at each instance and are O or $NR^3$ and $A^2$ is $C(R^1)_2$. In a particularly preferred embodiment of the invention, $A^1$ and $A^3$ are the same or different at each instance and are $C(R^3)_2$, and $A^2$ is $C(R^1)_2$ and more preferably $C(R^3)_2$ or $CH_2$.

Preferred embodiments of the formula (45) are thus the structures of the formulae (45-A), (45-B), (45-C) and (45-D), and a particularly preferred embodiment of the formula (45-A) is the structures of the formulae (45-E) and (45-F):

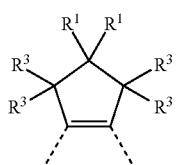

formula (45-A)

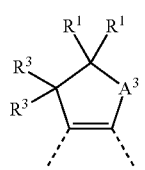

formula (45-B)

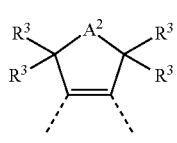

formula (45-C)

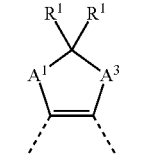

formula (45-D)

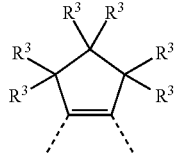

formula (45-E)

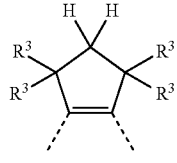

formula (45-F)

where $R^1$ and $R^3$ have the definitions given above and $A^1$, $A^2$ and $A^3$ are the same or different at each instance and are O or $NR^3$.

Preferred embodiments of the formula (46) are the structures of the following formulae (46-A) to (46-F):

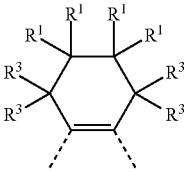

Formel (46-A)

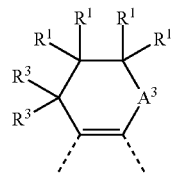

Formel (46-B)

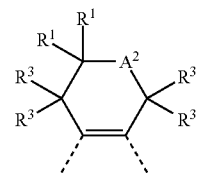

Formel (46-C)

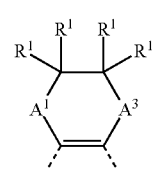

formula (46-D)

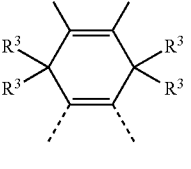

formula (46-E)

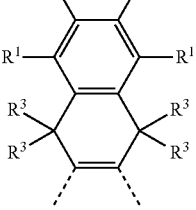

formula (46-F)

where $R^1$ and $R^3$ have the definitions given above and $A^1$, $A^2$ and $A^3$ are the same or different at each instance and are O or $NR^3$.

Preferred embodiments of the formula (47) are the structures of the following formulae (47-A) to (47-E):

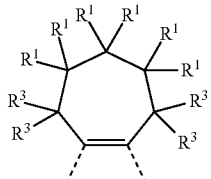

formula (47-A)

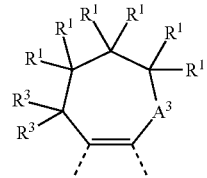

formula (47-B)

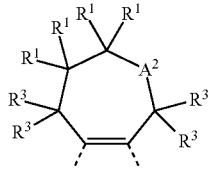

formula (47-C)

-continued

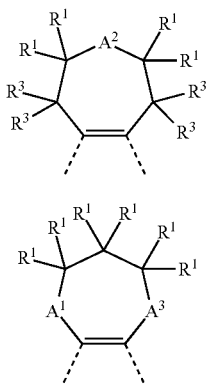

formula (47-D)

formula (47-E)

where $R^1$ and $R^3$ have the definitions given above and $A^1$, $A^2$ and $A^3$ are the same or different at each instance and are O or $NR^3$.

In a preferred embodiment of the structure of formula (48), the $R^1$ radicals bonded to the bridgehead are H, D, F or $CH_3$. Further preferably, $A^2$ is $C(R^1)_2$ or O, and more preferably $C(R^3)_2$. Preferred embodiments of the formula (48) are thus structures of the formulae (48-A) and (48-B), and a particularly preferred embodiment of the formula (48-A) is a structure of the formula (48-C):

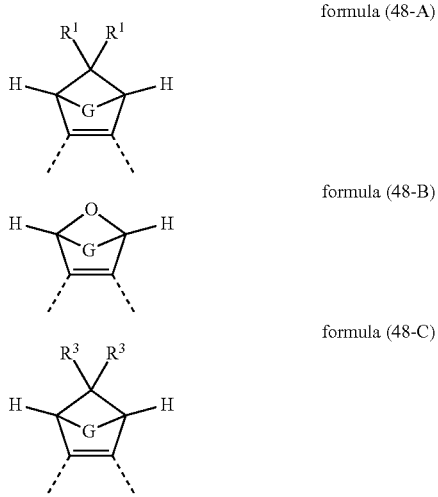

formula (48-A)

formula (48-B)

formula (48-C)

where the symbols used have the definitions given above.

In a preferred embodiment of the structure of formulae (49), (50) and (51), the $R^1$ radicals bonded to the bridgehead are H, D, F or $CH_3$. Further preferably, $A^2$ is $C(R^1)_2$. Preferred embodiments of the formulae (49), (50) and (51) are thus the structures of the formulae (49-A), (50-A) and (51-A):

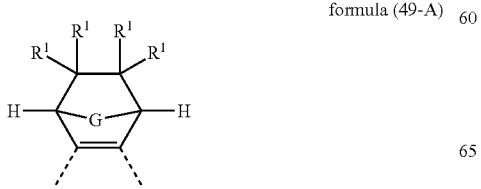

formula (49-A)

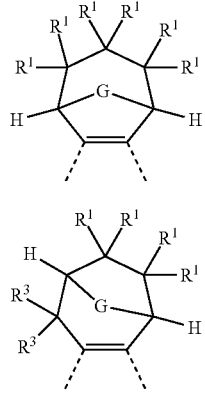

formula (50-A)

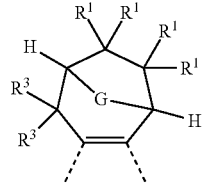

formula (51-A)

where the symbols used have the definitions given above.

Further preferably, the G group in the formulae (48), (48-A), (48-B), (48-C), (49), (49-A), (50), (50-A), (51) and (51-A) is a 1,2-ethylene group which may be substituted by one or more $R^2$ radicals, where $R^2$ is preferably the same or different at each instance and is H or an alkyl group having 1 to 4 carbon atoms, or an ortho-arylene group which has 6 to 10 carbon atoms and may be substituted by one or more $R^2$ radicals, but is preferably unsubstituted, especially an ortho-phenylene group which may be substituted by one or more $R^2$ radicals, but is preferably unsubstituted.

In a further preferred embodiment of the invention, $R^3$ in the groups of the formulae (45) to (51) and in the preferred embodiments is the same or different at each instance and is F, a straight-chain alkyl group having 1 to 10 carbon atoms or a branched or cyclic alkyl group having 3 to 20 carbon atoms, where one or more nonadjacent $CH_2$ groups in each case may be replaced by $R^2C=CR^2$ and one or more hydrogen atoms may be replaced by D or F, or an aromatic or heteroaromatic ring system which has 5 to 14 aromatic ring atoms and may be substituted in each case by one or more $R^2$ radicals; at the same time, two $R^3$ radicals bonded to the same carbon atom may together form an aliphatic or aromatic ring system and thus form a spiro system; in addition, $R^3$ may form an aliphatic ring system with an adjacent R or $R^1$ radical.

In a particularly preferred embodiment of the invention, $R^3$ in the groups of the formulae (45) to (51) and in the preferred embodiments is the same or different at each instance and is F, a straight-chain alkyl group having 1 to 3 carbon atoms, especially methyl, or an aromatic or heteroaromatic ring system which has 5 to 12 aromatic ring atoms and may be substituted in each case by one or more $R^2$ radicals, but is preferably unsubstituted; at the same time, two $R^3$ radicals bonded to the same carbon atom may together form an aliphatic or aromatic ring system and thus form a spiro system; in addition, $R^3$ may form an aliphatic ring system with an adjacent R or $R^1$ radical.

Examples of particularly suitable groups of the formula (45) are the structures listed below:

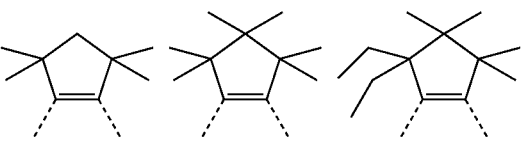

-continued
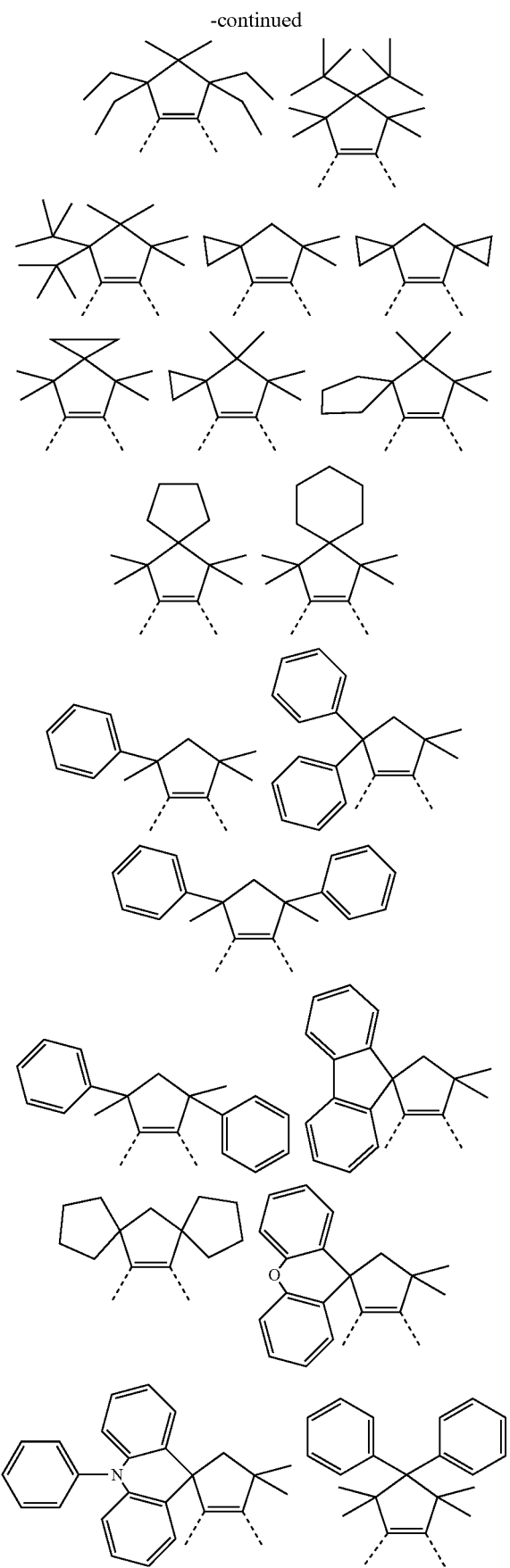
-continued
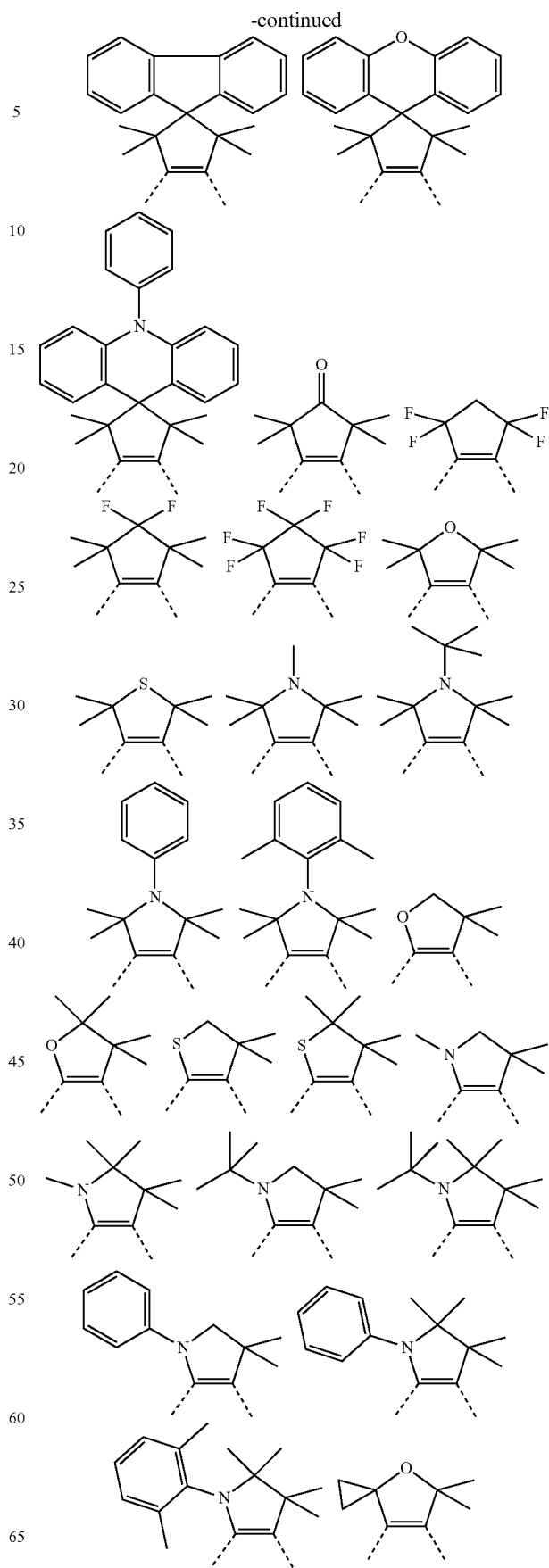

-continued
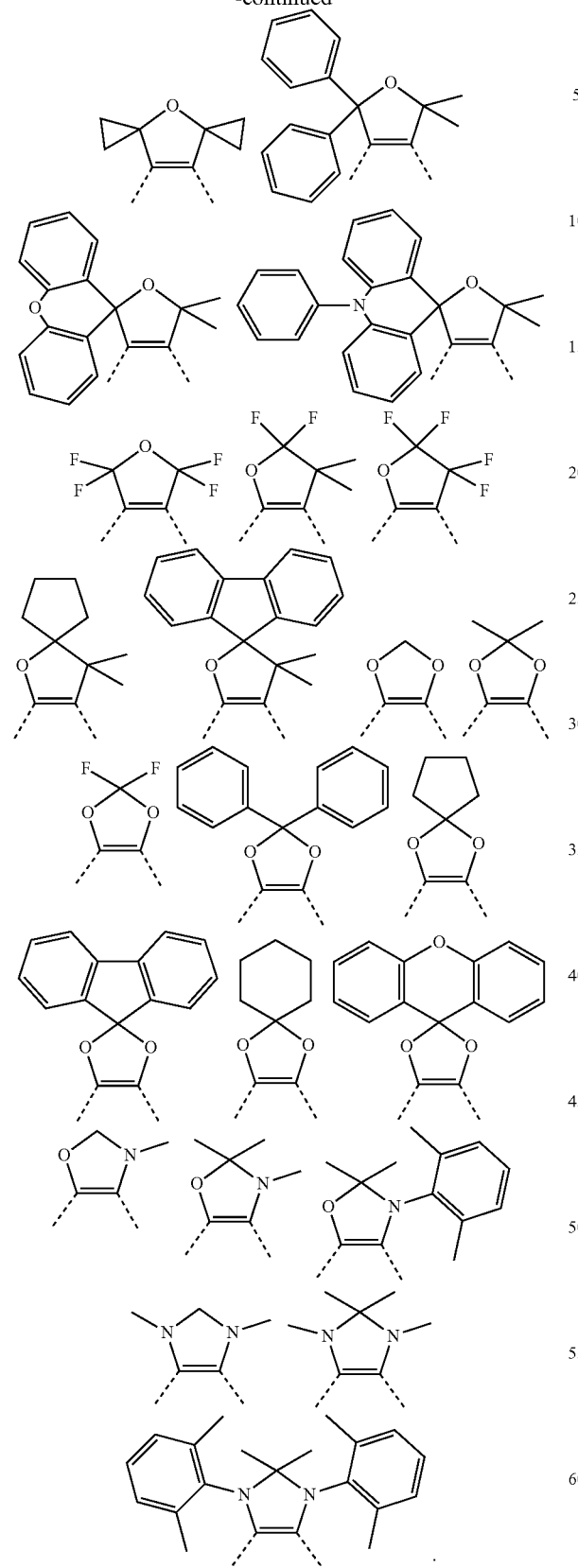
Examples of particularly suitable groups of the formula (46) are the structures listed below:
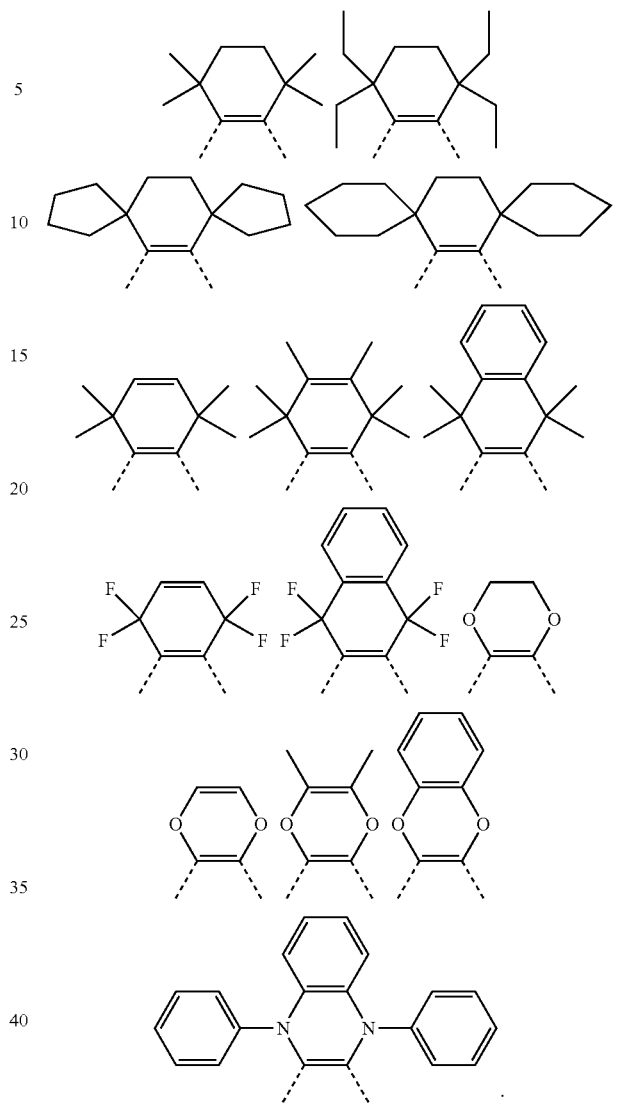
Examples of particularly suitable groups of the formulae (47), (49) and (50) are the structures listed below:
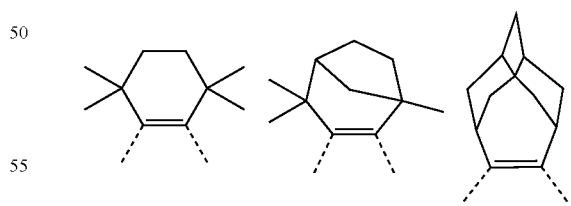
Examples of particularly suitable groups of the formula (48) are the structures listed below:
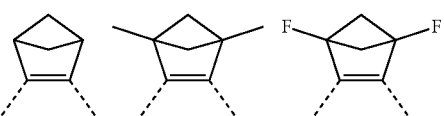

-continued

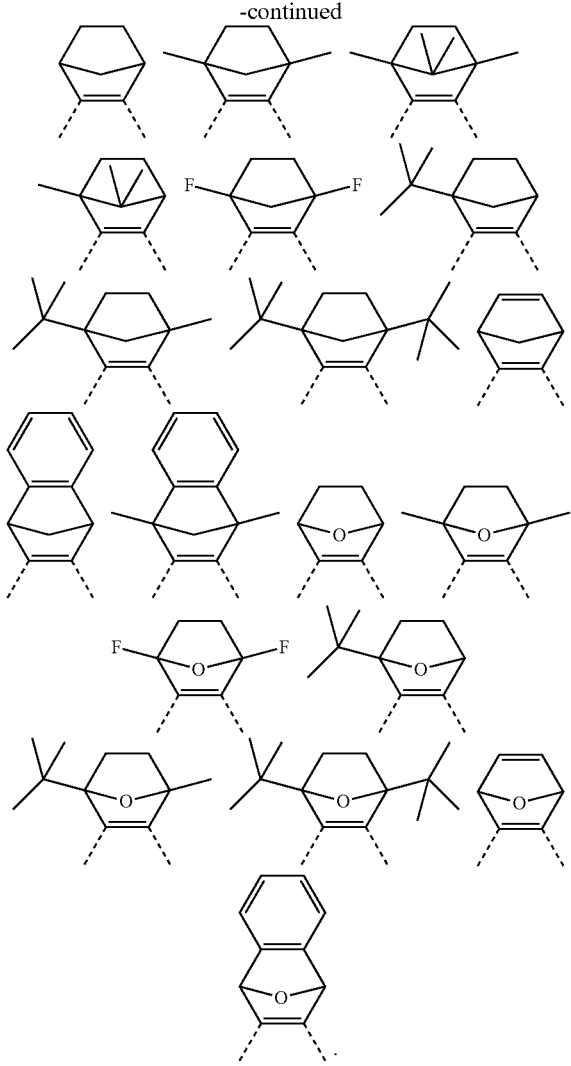

Examples of particularly suitable groups of the formula (49) are the structures listed below:

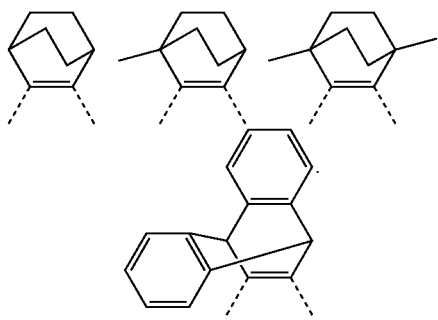

When R radicals are bonded within the bidentate subligands or within the bivalent arylene or heteroarylene groups of the formula (8) bonded within the formulae (3) to (7) or the preferred embodiments, these R radicals are the same or different at each instance and are preferably selected from the group consisting of H, D, F, Br, I, $N(R^1)_2$, CN, $Si(R^1)_3$, $B(OR^1)_2$, $C(=O)R^1$, a straight-chain alkyl group having 1 to 10 carbon atoms or an alkenyl group having 2 to 10 carbon atoms or a branched or cyclic alkyl group having 3 to 10 carbon atoms, where the alkyl or alkenyl group may be substituted in each case by one or more $R^1$ radicals, or an aromatic or heteroaromatic ring system which has 5 to 30 aromatic ring atoms and may be substituted in each case by one or more $R^1$ radicals; at the same time, two adjacent R radicals together or R together with $R^1$ may also form a mono- or polycyclic, aliphatic or aromatic ring system. More preferably, these R radicals are the same or different at each instance and are selected from the group consisting of H, D, F, $N(R^1)_2$, a straight-chain alkyl group having 1 to 6 carbon atoms or a branched or cyclic alkyl group having 3 to 10 carbon atoms, where one or more hydrogen atoms may be replaced by D or F, or an aromatic or heteroaromatic ring system which has 5 to 24 aromatic ring atoms and may be substituted in each case by one or more $R^1$ radicals; at the same time, two adjacent R radicals together or R together with $R^1$ may also form a mono- or polycyclic, aliphatic or aromatic ring system.

Preferred $R^1$ radicals bonded to R are the same or different at each instance and are H, D, F, $N(R^2)_2$, CN, a straight-chain alkyl group having 1 to 10 carbon atoms or an alkenyl group having 2 to 10 carbon atoms or a branched or cyclic alkyl group having 3 to 10 carbon atoms, where the alkyl group may be substituted in each case by one or more $R^2$ radicals, or an aromatic or heteroaromatic ring system which has 5 to 24 aromatic ring atoms and may be substituted in each case by one or more $R^2$ radicals; at the same time, two or more adjacent $R^1$ radicals together may form a mono- or polycyclic aliphatic ring system. Particularly preferred $R^1$ radicals bonded to R are the same or different at each instance and are H, F, CN, a straight-chain alkyl group having 1 to 5 carbon atoms or a branched or cyclic alkyl group having 3 to 5 carbon atoms, each of which may be substituted by one or more $R^2$ radicals, or an aromatic or heteroaromatic ring system which has 5 to 13 aromatic ring atoms and may be substituted in each case by one or more $R^2$ radicals; at the same time, two or more adjacent $R^1$ radicals together may form a mono- or polycyclic aliphatic ring system.

Preferred $R^2$ radicals are the same or different at each instance and are H, F or an aliphatic hydrocarbyl radical having 1 to 5 carbon atoms or an aromatic hydrocarbyl radical having 6 to 12 carbon atoms; at the same time, two or more $R^2$ substituents together may also form a mono- or polycyclic aliphatic ring system.

The abovementioned preferred embodiments can be combined with one another as desired. In a particularly preferred embodiment of the invention, the abovementioned preferred embodiments apply simultaneously.

Examples of suitable structures of the invention are the compounds depicted below.

1
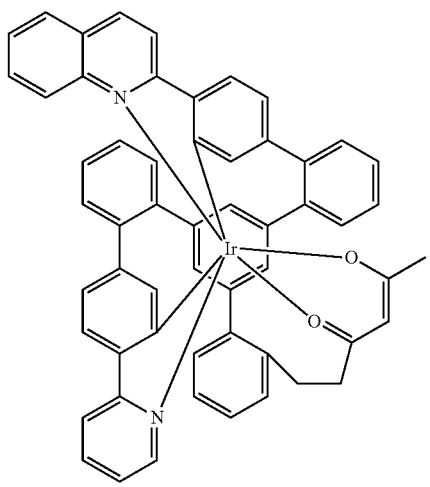
2
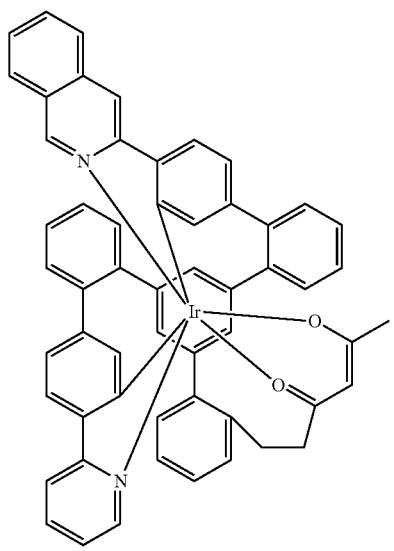
3
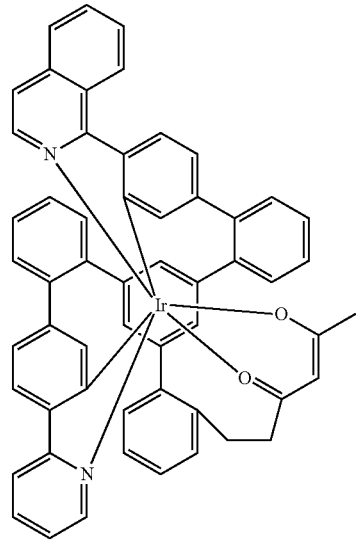
4
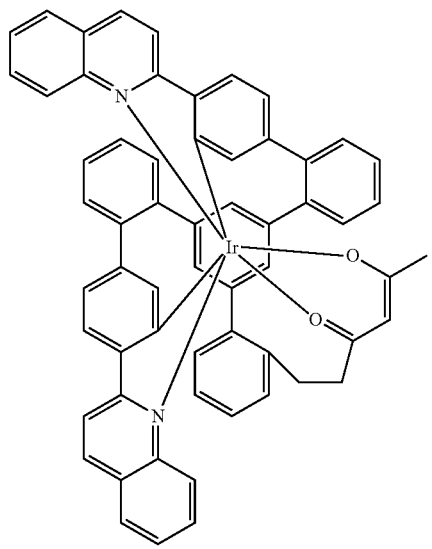
5
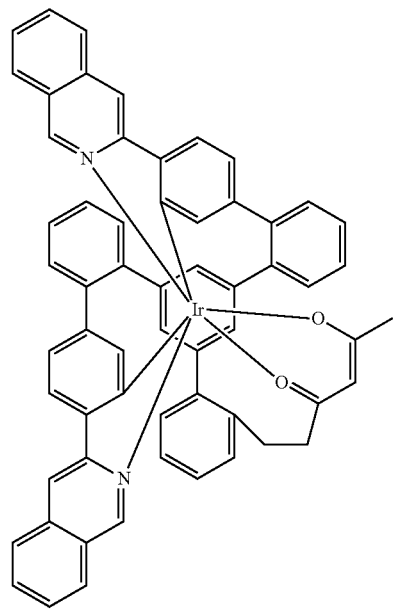

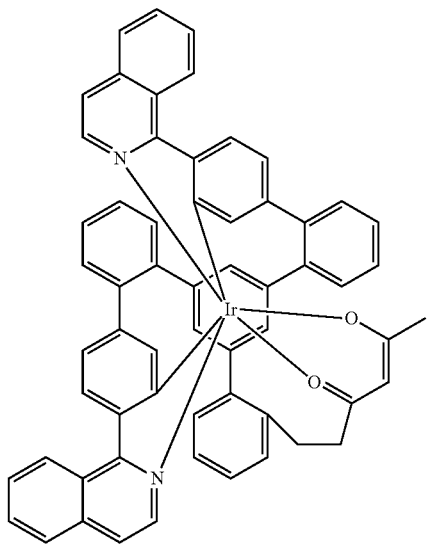
6
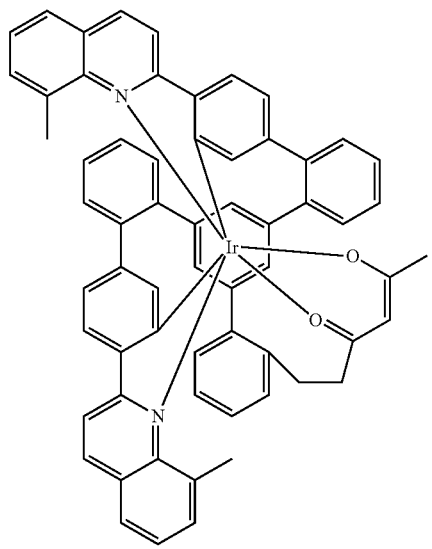
8
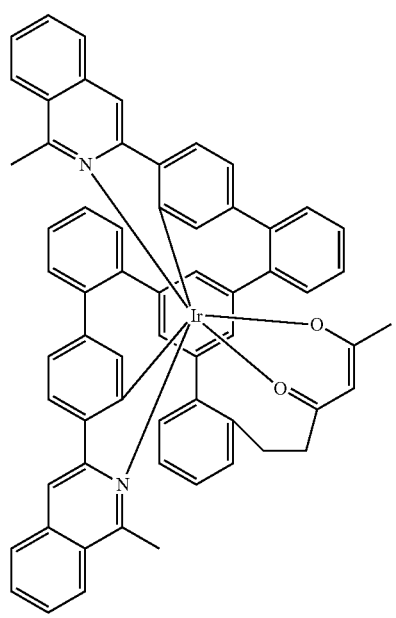
7
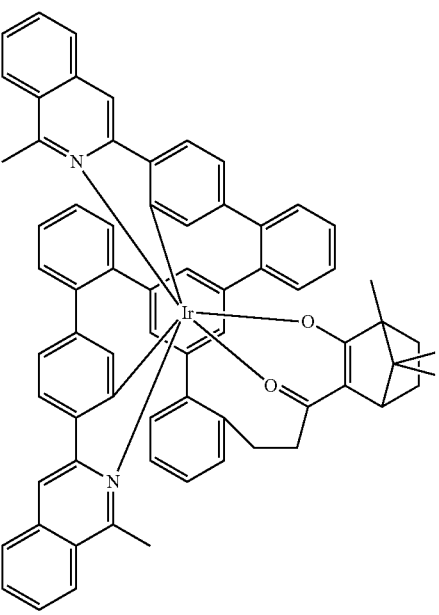
9
R

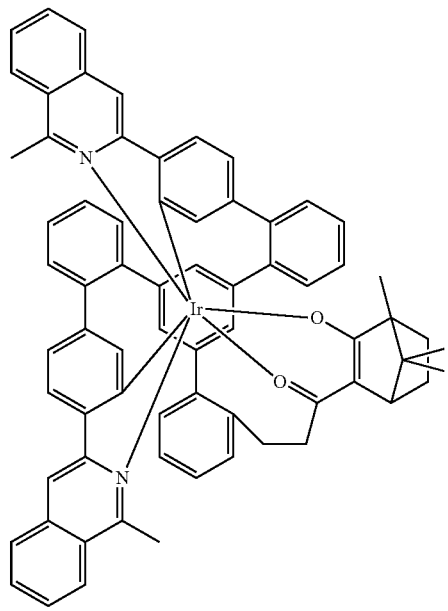
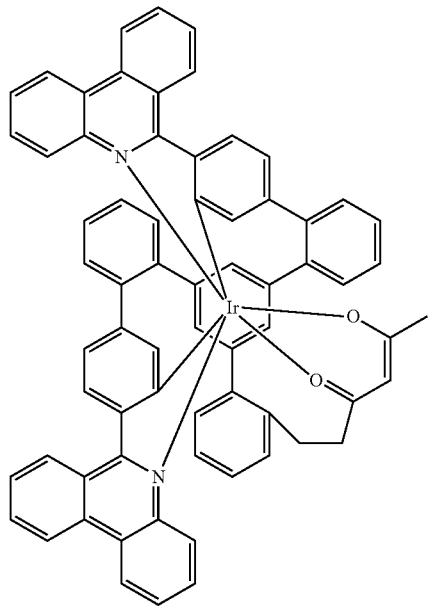
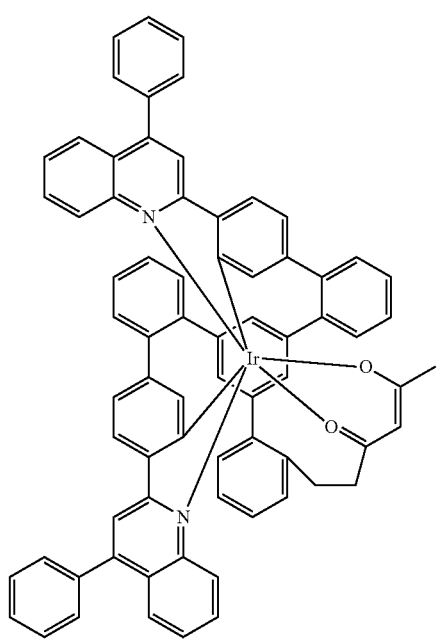
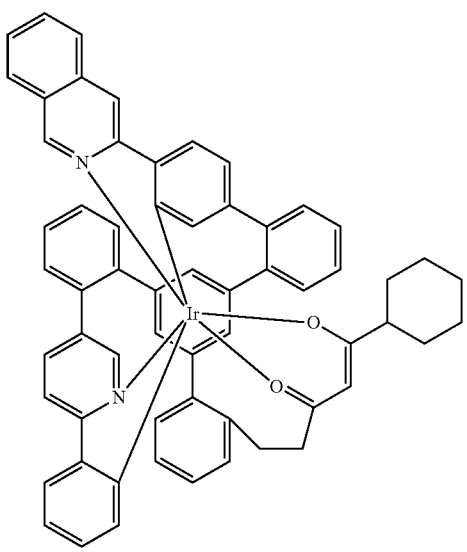

15
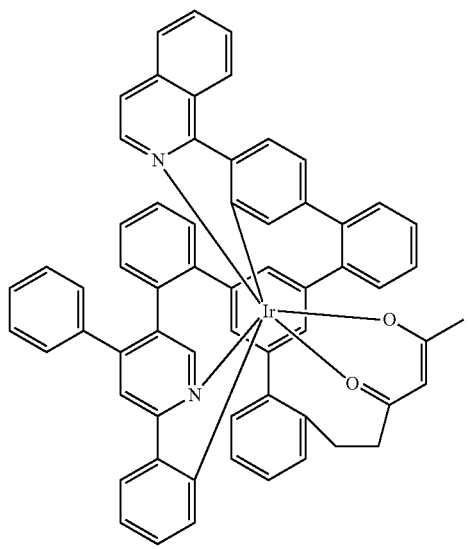
16
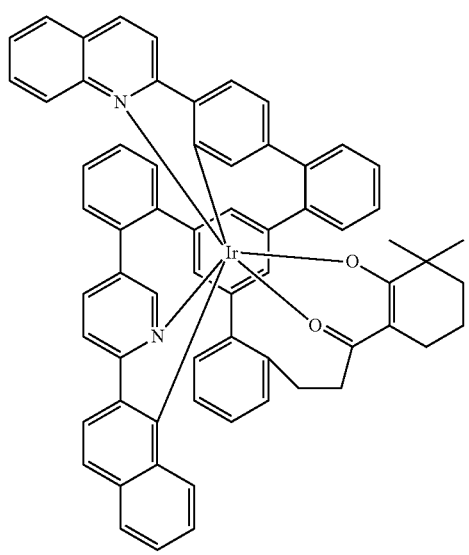
17
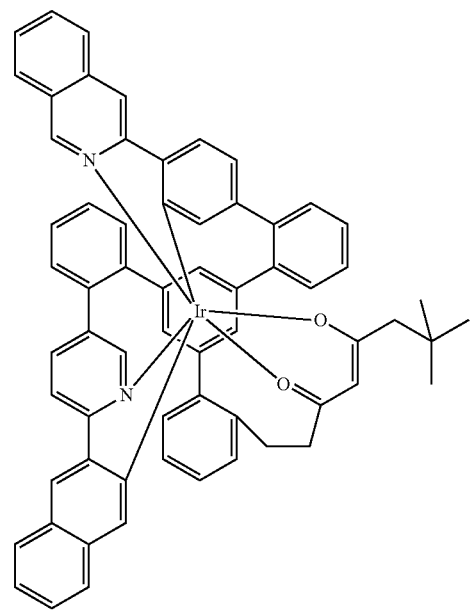
18
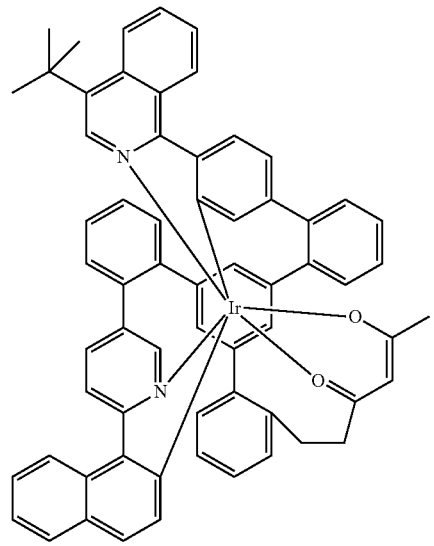

19
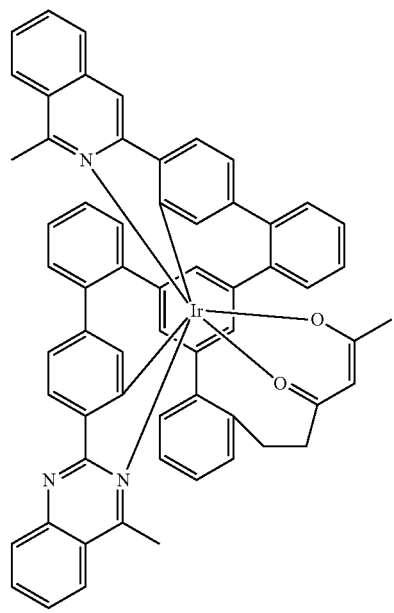
20
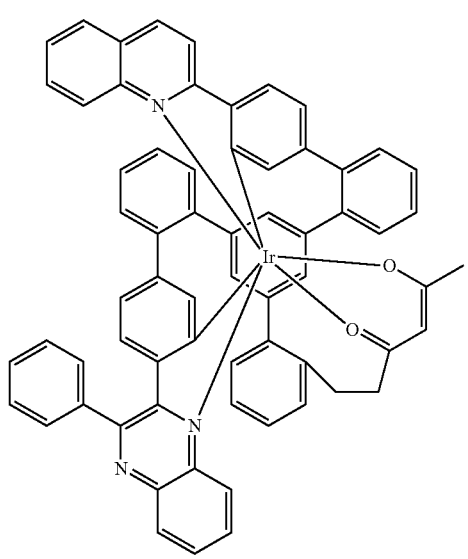
21
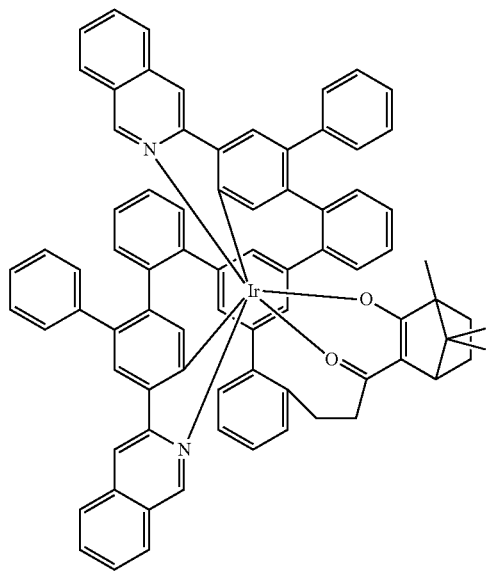
R
22
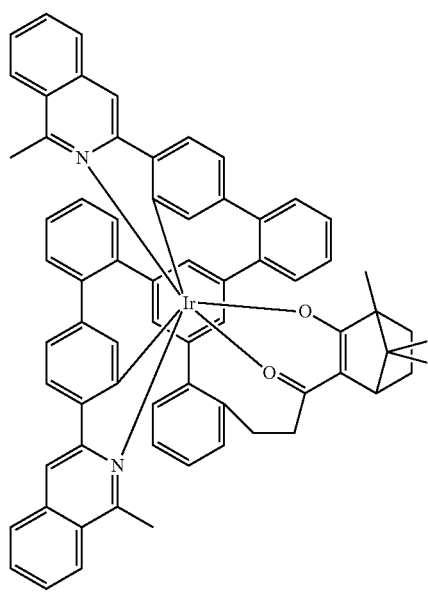
S

23
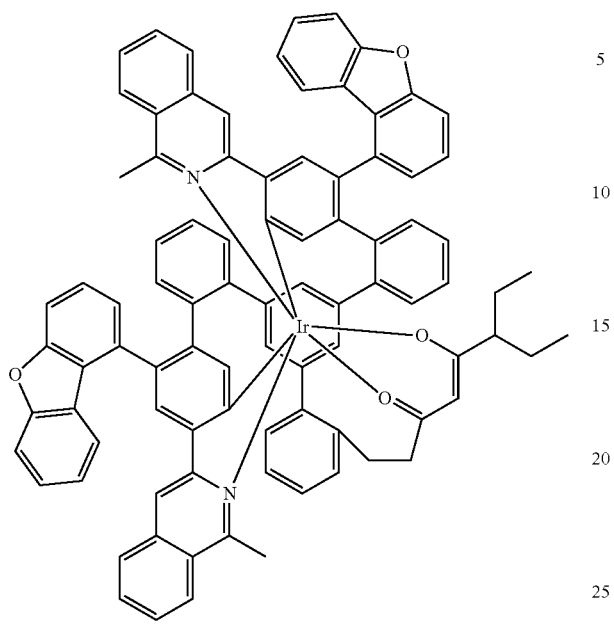
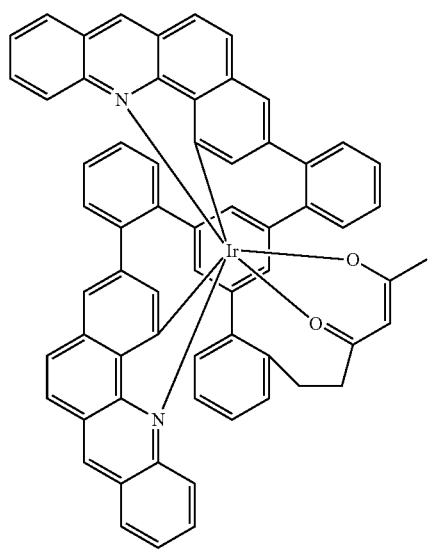
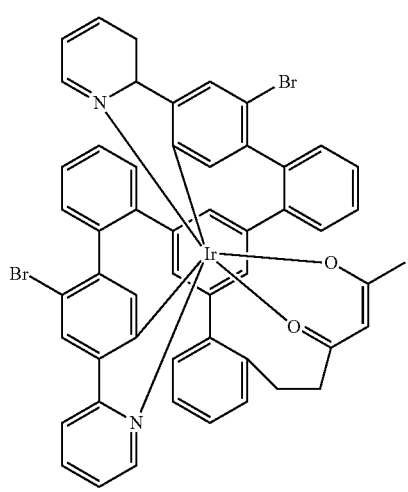
24
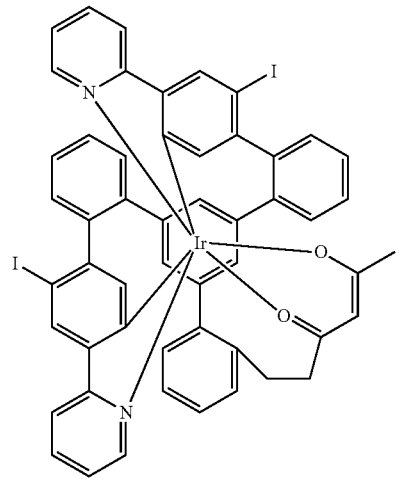
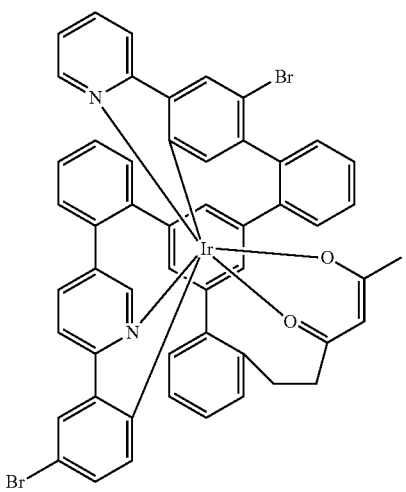
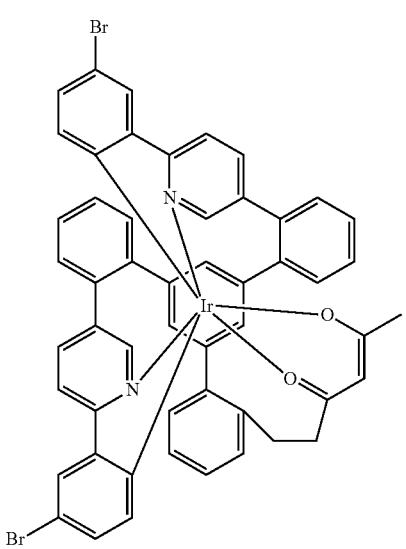

29
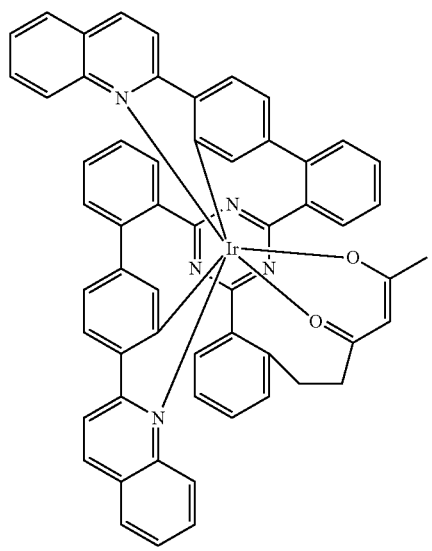
30
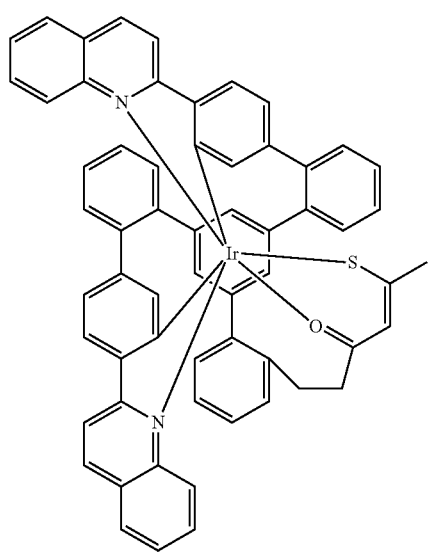
31
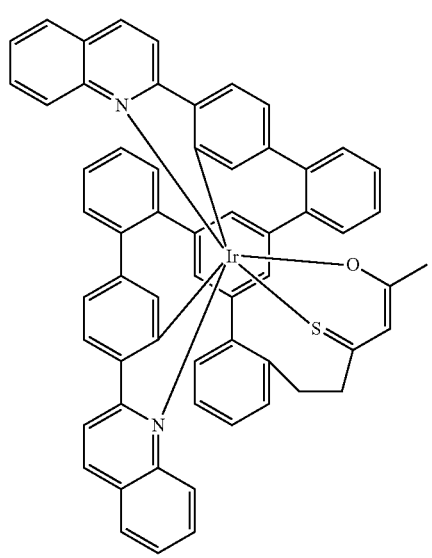
32
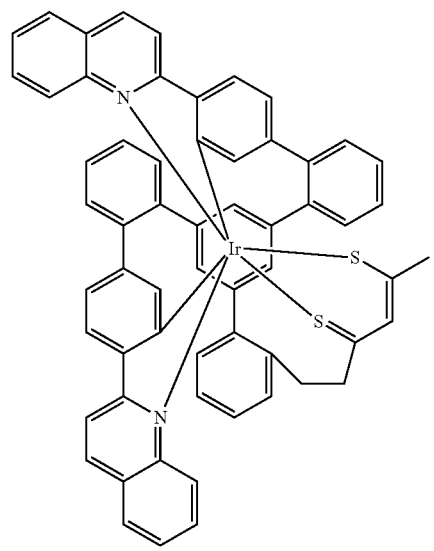
33
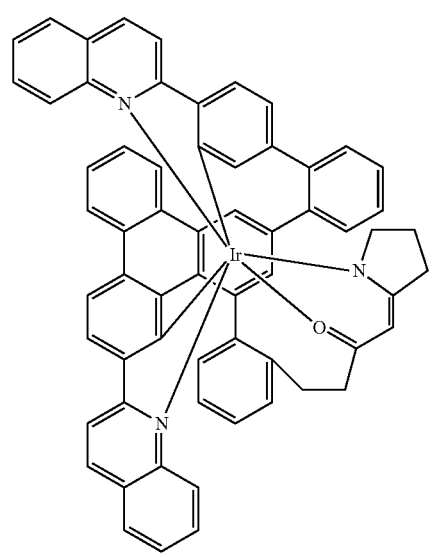
34
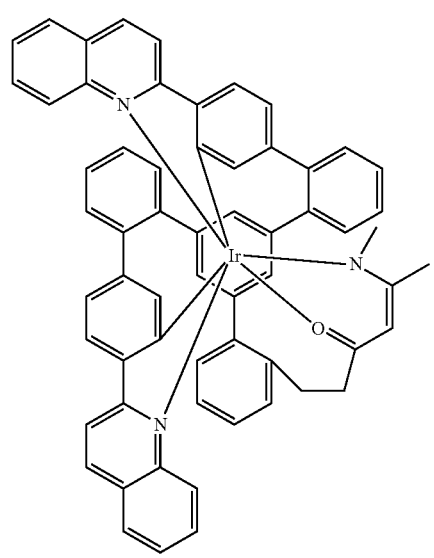

77
-continued
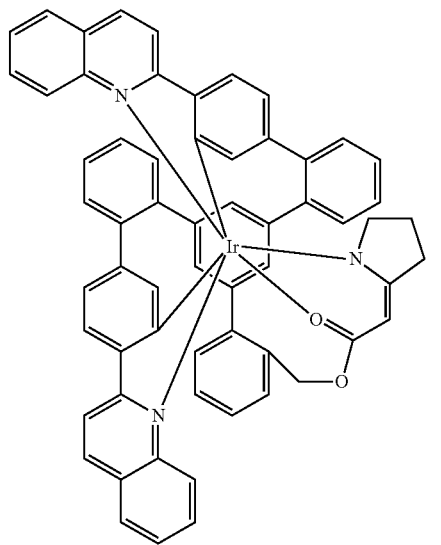
35
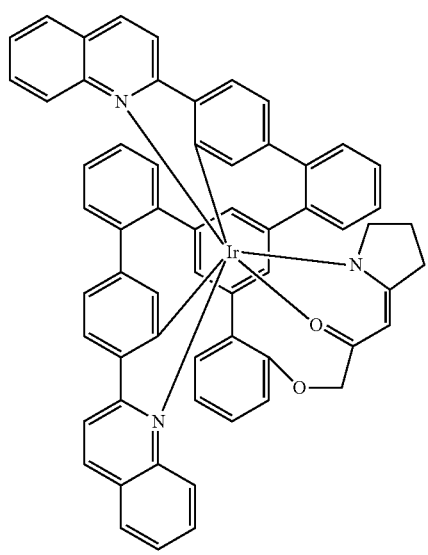
36
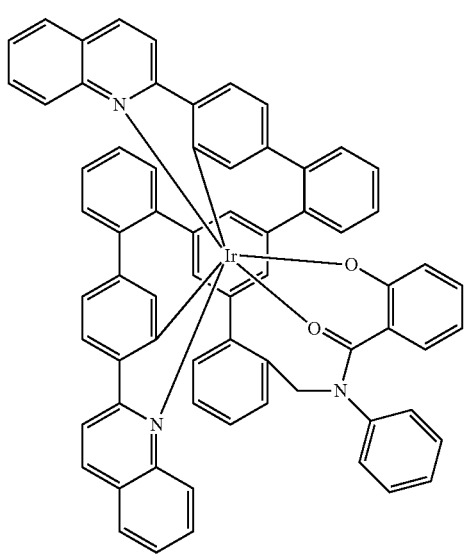
37
78
-continued
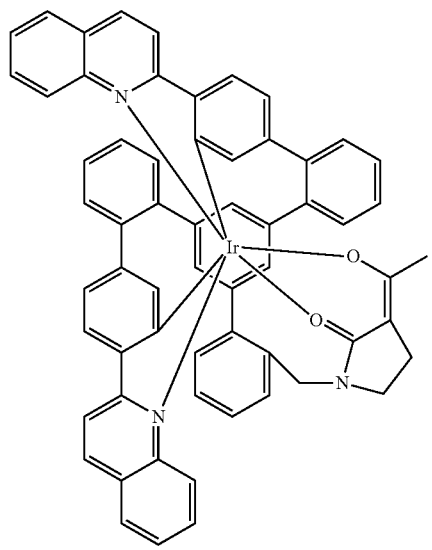
38
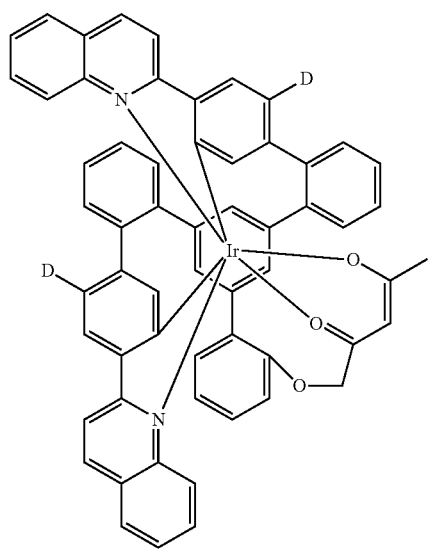
39
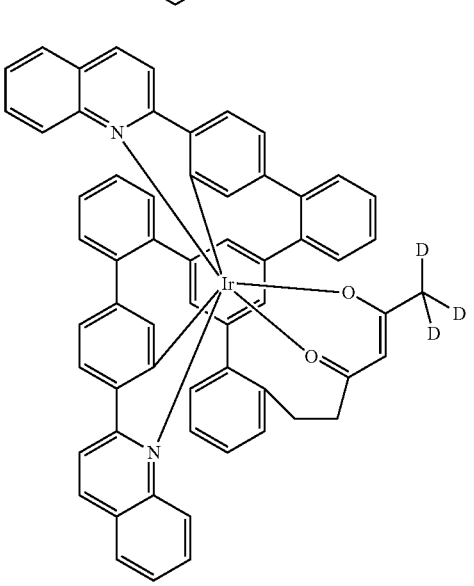
40

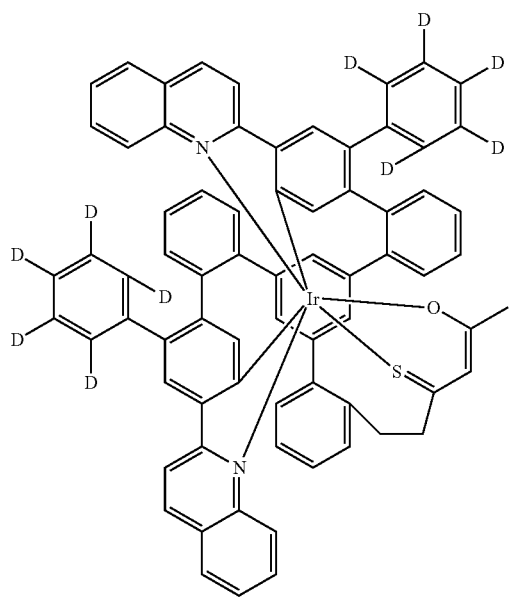
41
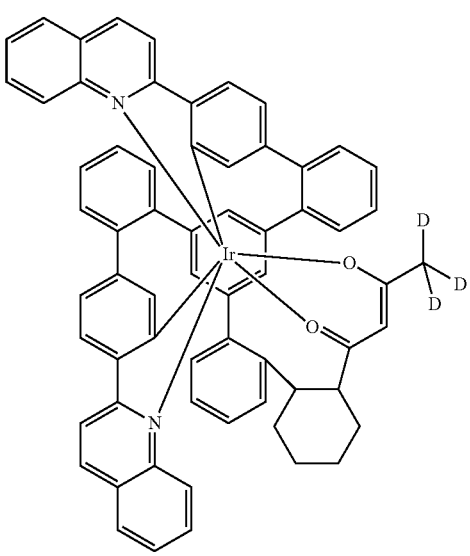
43
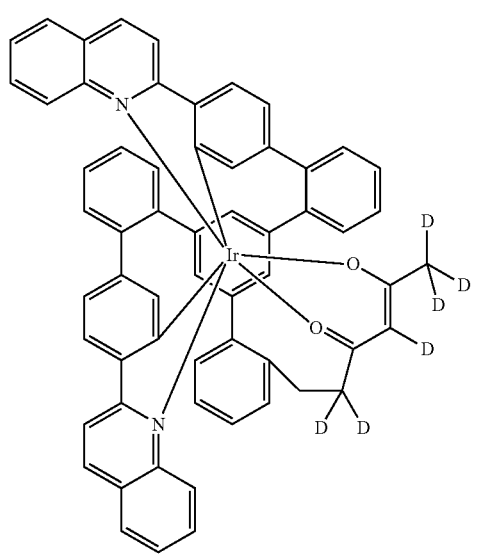
42
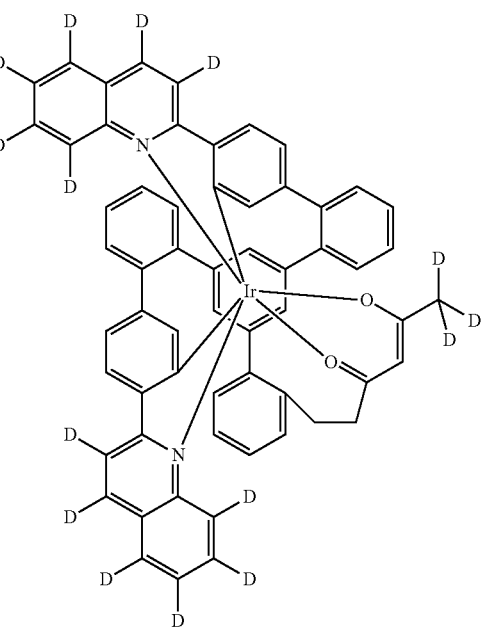
44

45
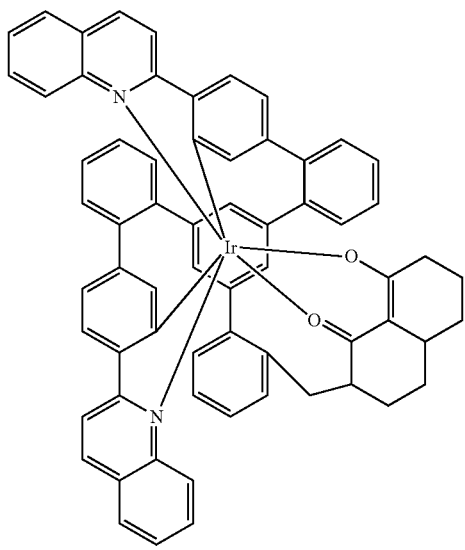
46
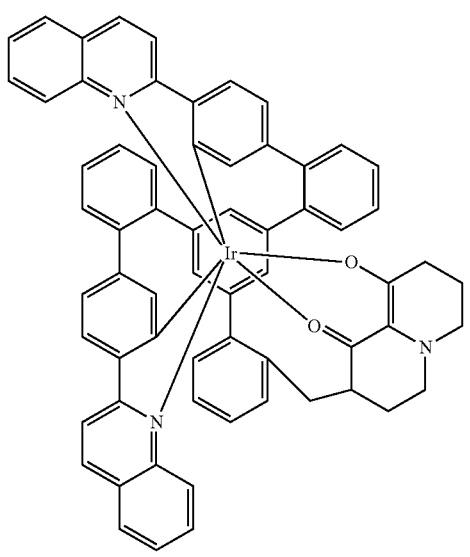
47
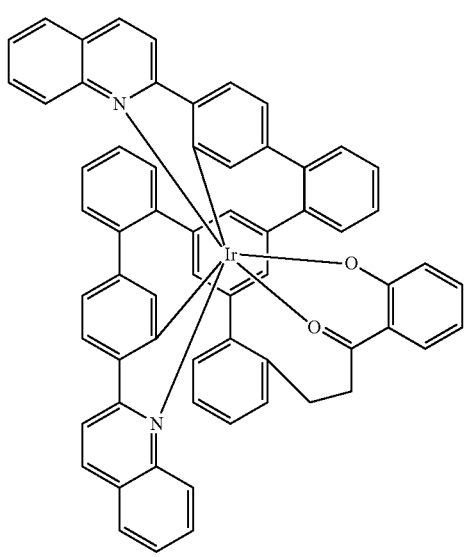
48
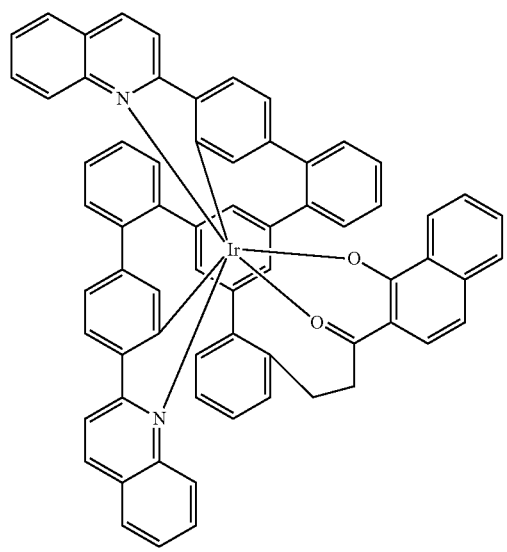
49
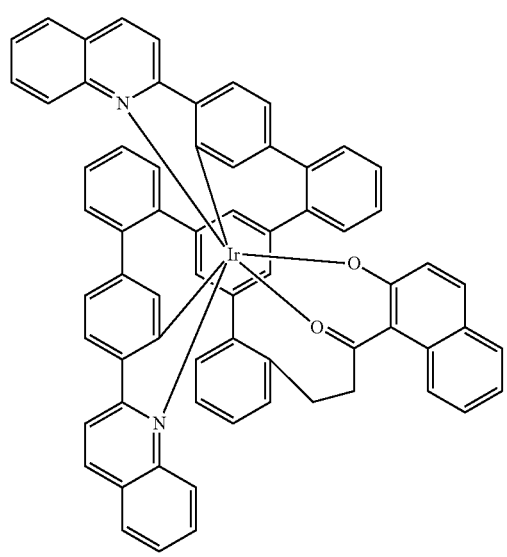
50
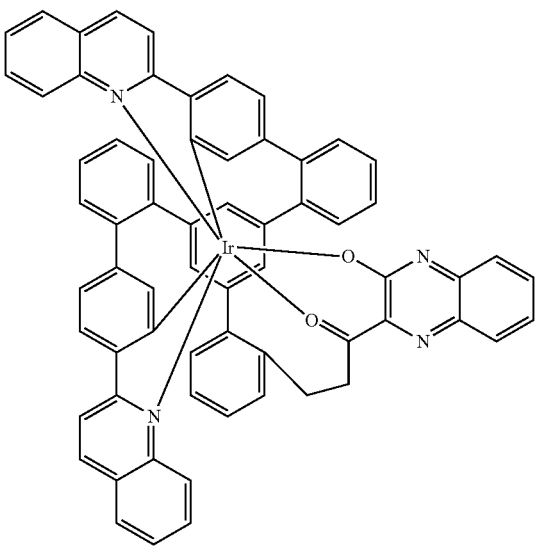

51
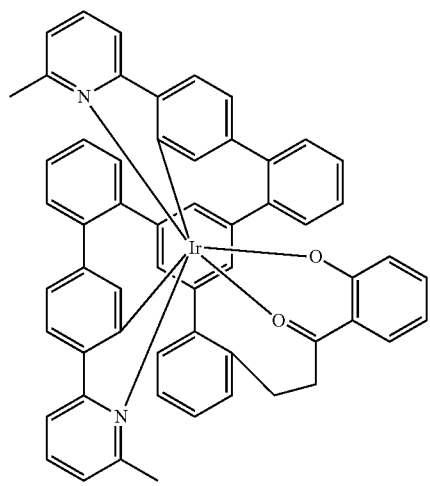
52
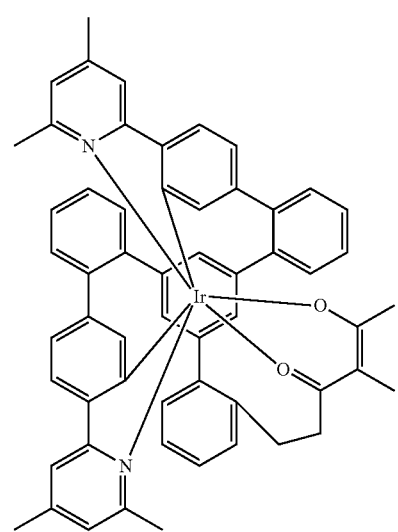
53
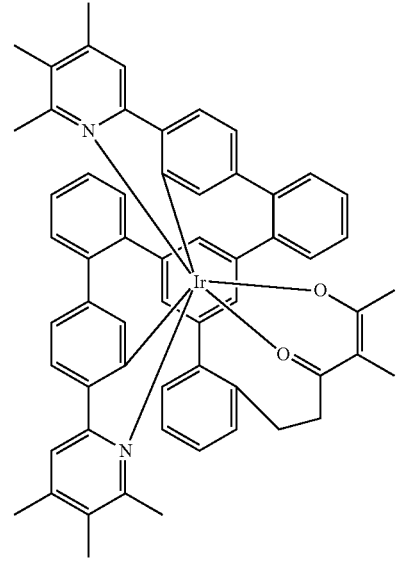
54
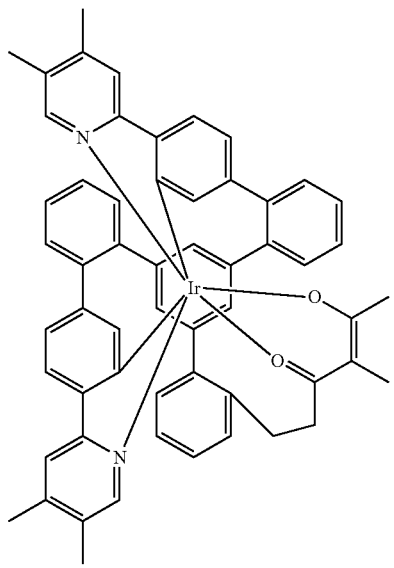
55
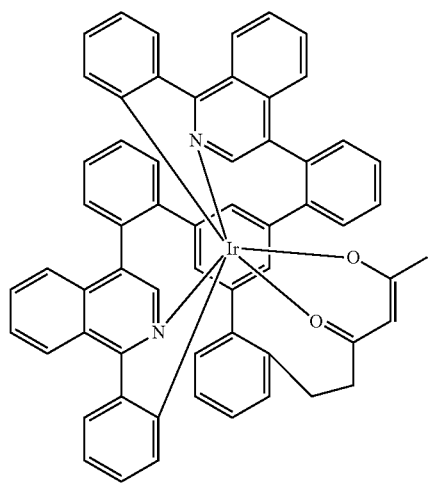
56
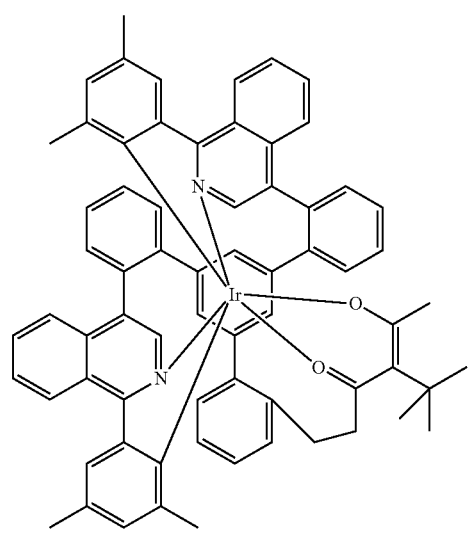

-continued
57
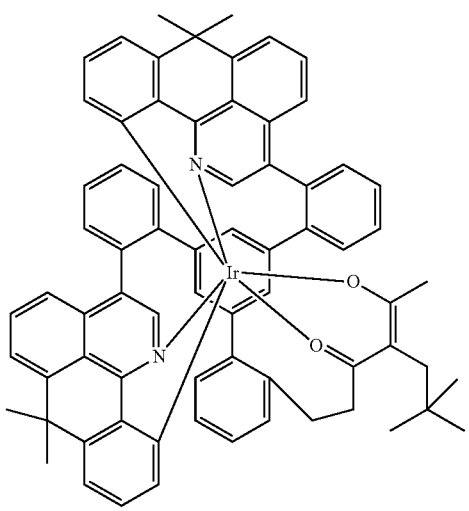
58
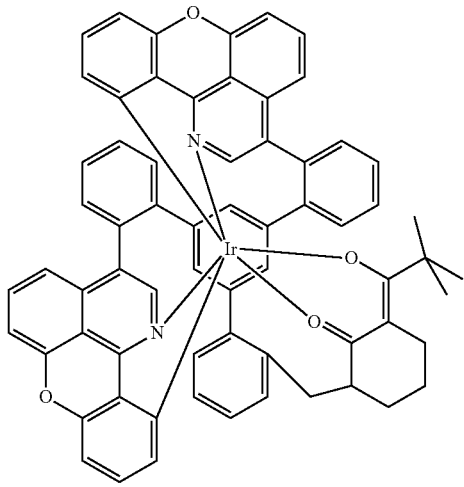
59
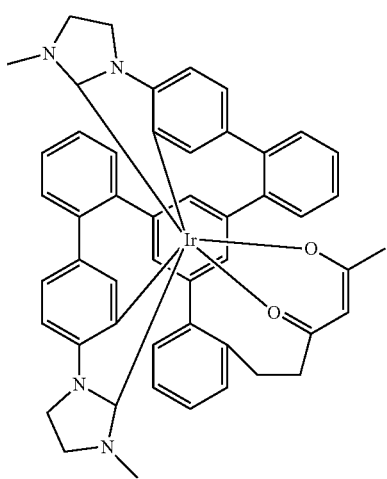
-continued
60
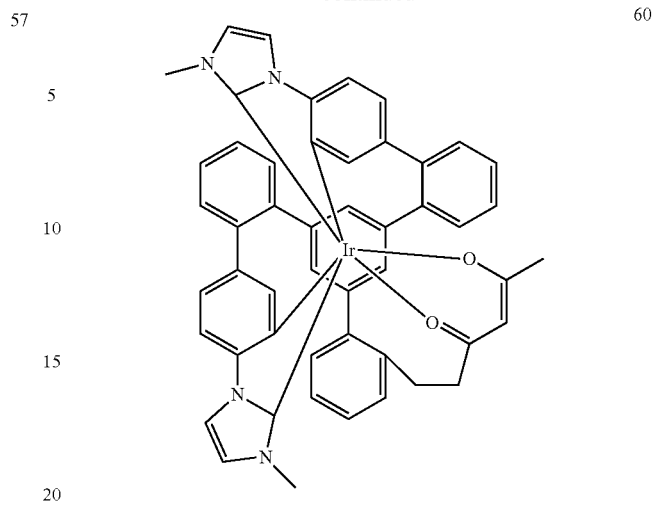
61
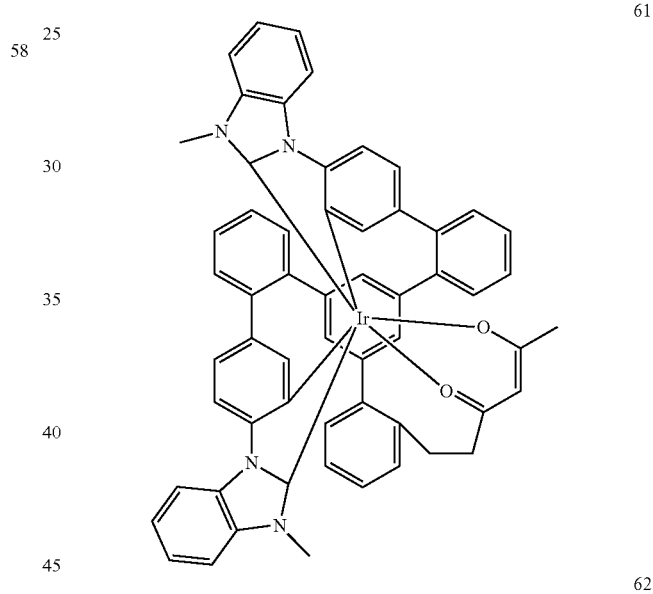
62
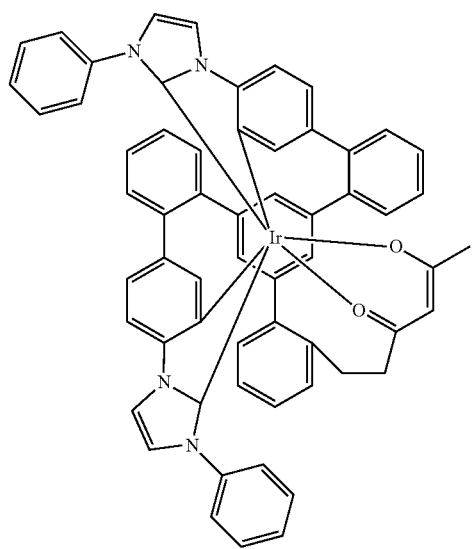

87
-continued
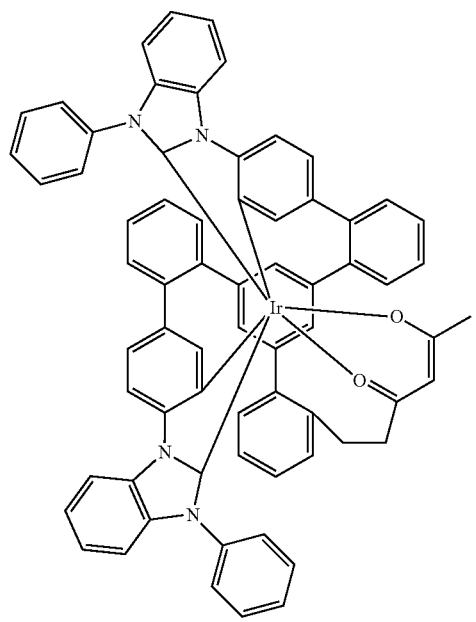
88
-continued
63
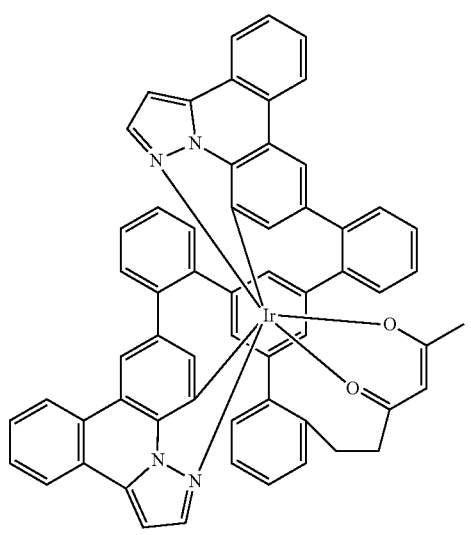
66
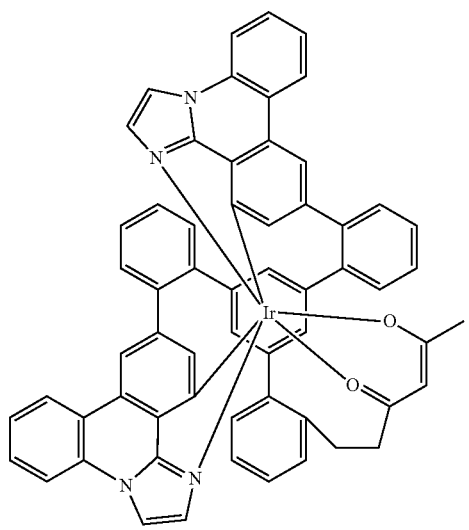
64
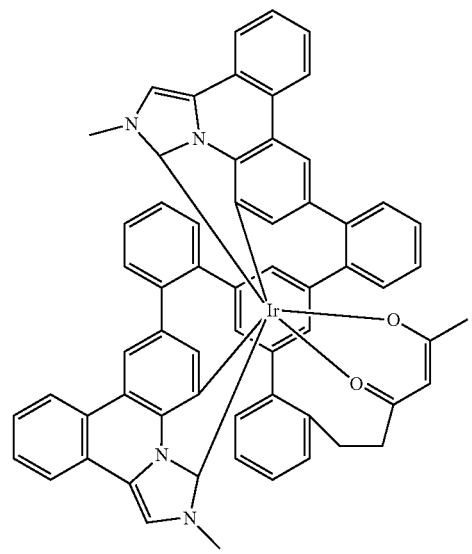
67
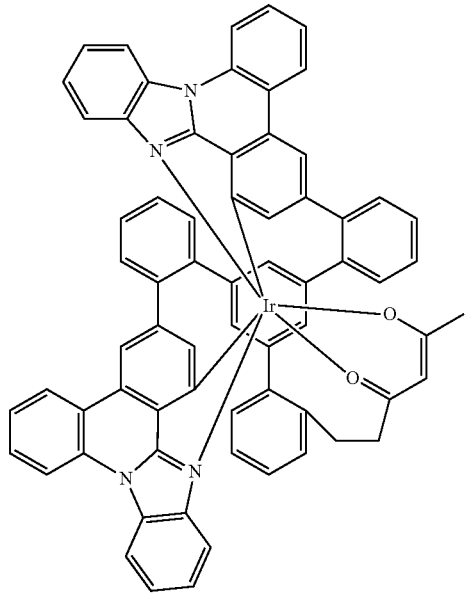

89
-continued
68
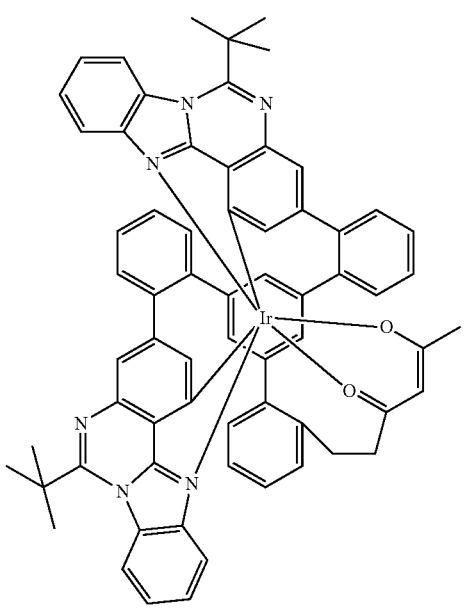
69
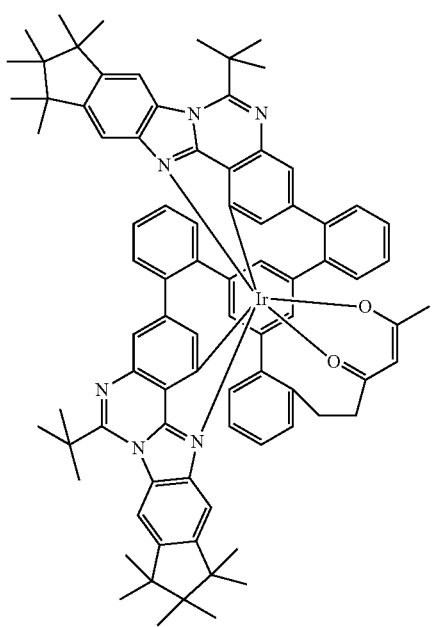
90
-continued
70
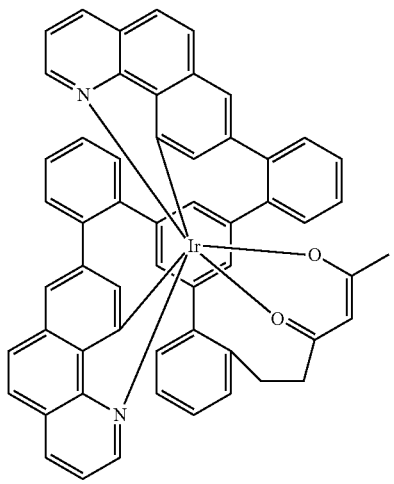
71
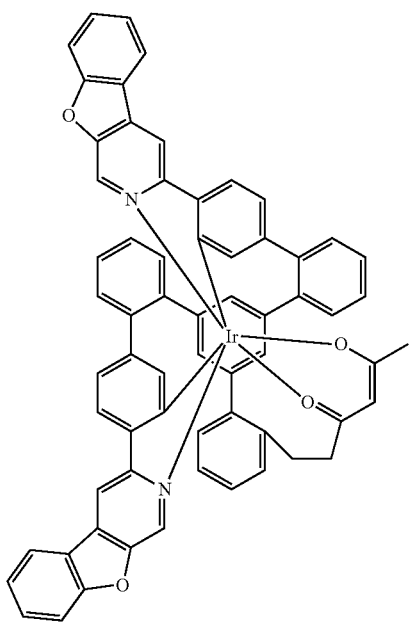
72

91 92
-continued -continued
73 75
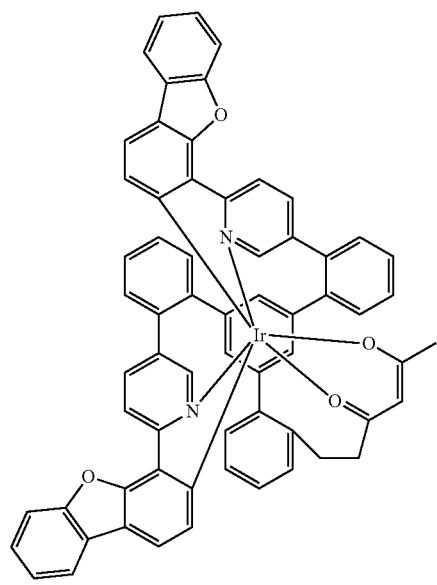
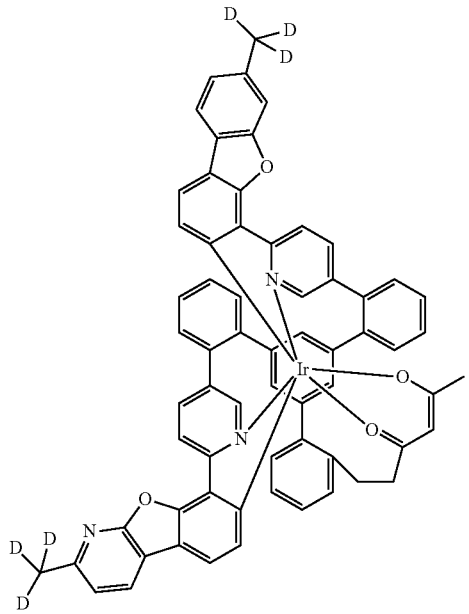
74 76
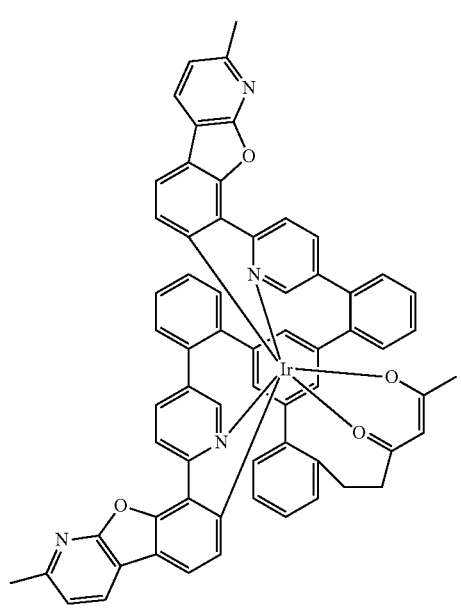
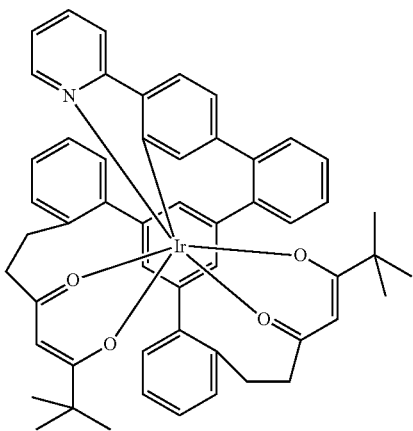
77

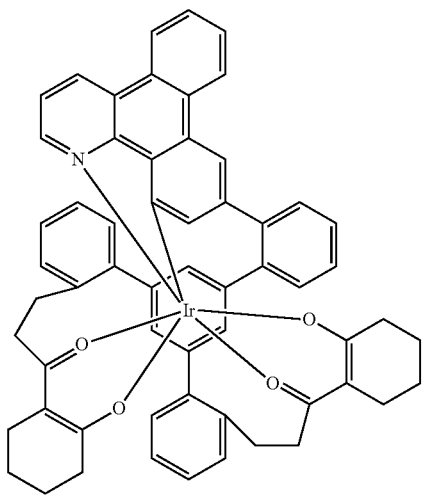

78

The iridium complexes of the invention are chiral structures. If the tripodal ligand of the complexes is additionally also chiral, the formation of diastereomers and multiple enantiomer pairs is possible. In that case, the complexes of the invention include both the mixtures of the different diastereomers or the corresponding racemates and the individual isolated diastereomers or enantiomers.

If $C_s$-symmetric ligands having two identical sub-ligands are used in the complexation reaction, what is typically obtained is a racemic mixture of the $C_1$-symmetric complexes, i.e. of the Δ and the Λ enantiomer. These may be separated by standard methods (chromatography on chiral materials/columns or optical resolution by crystallization). This is shown in the scheme which follows using the example of a $C_s$-symmetric ligand bearing two identical phenylpyridine sub-ligands and also applies analogously to all other $C_s$-symmetric ligands.

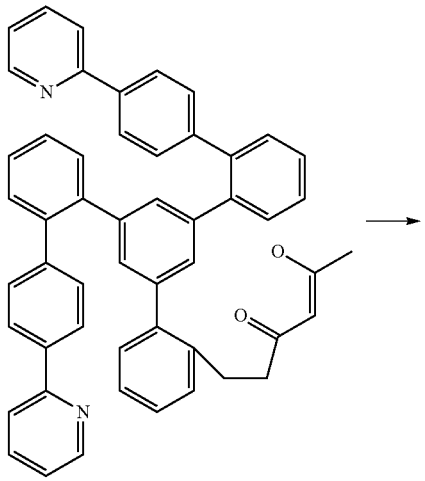

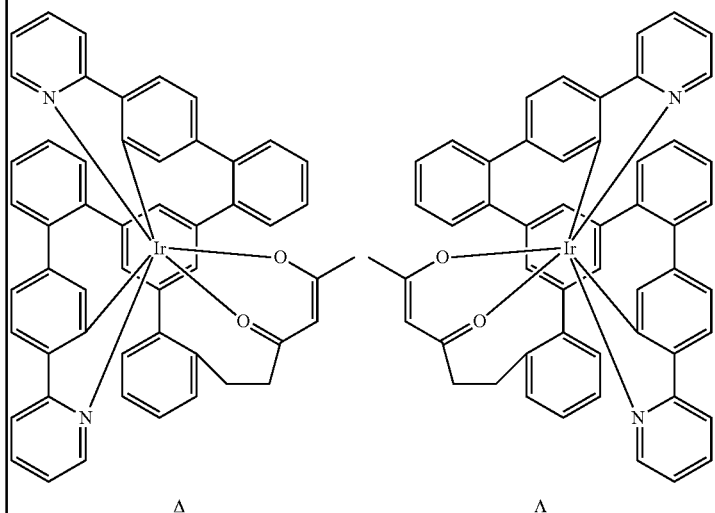

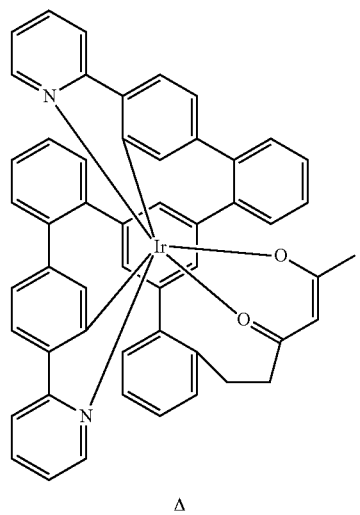

Δ

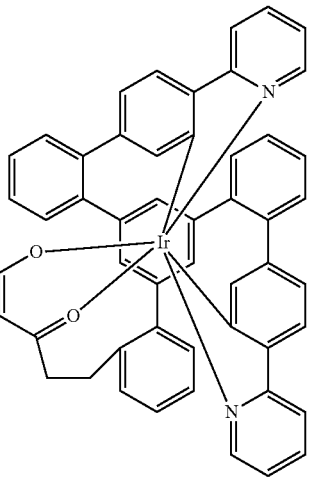

Λ

Separation via chromatography on chiral media or by fractional crystallization with chiral auxiliaries Optical resolution via fractional crystallization of diastereomeric salt pairs can be effected by customary methods. One option for this purpose is to oxidize the uncharged Ir(III) complexes (for example with peroxides or $H_2O_2$ or by electrochemical means), add the salt of an enantiomerically pure monoanionic base (chiral base) to the cationic Ir(IV) complexes thus produced, separate the diastereomeric salts thus produced by fractional crystallization, and then reduce them with the aid of a reducing agent (e.g. zinc, hydrazine hydrate, ascorbic acid, etc.) to give the enantiomerically pure uncharged complex, as shown schematically below:

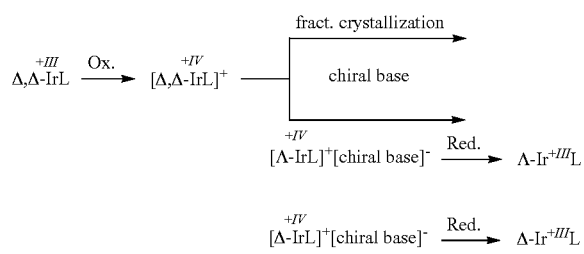

In addition, an enantiomerically pure or enantiomerically enriching synthesis is possible by complexation in a chiral medium (e.g. R- or S-1,1-binaphthol).

Analogous processes can also be conducted with complexes of $C_1$- or $C_s$-symmetric ligands.

If $C_1$-symmetric ligands are used in the complexation, what is typically obtained is a diastereomer mixture of the complexes which can be separated by standard methods (chromatography, crystallization).

The compounds of the invention are preparable in principle by various processes. In general, for this purpose, an iridium salt is reacted with the corresponding free ligand.

Therefore, the present invention further provides a process for preparing the compounds of the invention by reacting the appropriate free ligands with iridium alkoxides of the formula (52), with iridium ketoketonates of the formula (53), with iridium halides of the formula (54) or with iridium carboxylates of the formula (55)

$Ir(OR)_3$      formula (52)

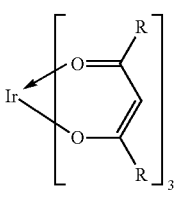      formula (53)

$IrHal_3$      formula (54)

$Ir(OOCR)_3$      formula (55)

where R has the definitions given above, Hal=F, Cl, Br or I and the iridium reactants may also take the form of the corresponding hydrates. R here is preferably an alkyl group having 1 to 4 carbon atoms.

It is likewise possible to use iridium compounds bearing both alkoxide and/or halide and/or hydroxyl and ketoketonate radicals. These compounds may also be charged. Corresponding iridium compounds of particular suitability as reactants are disclosed in WO 2004/085449. Particularly suitable are $[IrCl_2(acac)_2]^-$, for example $Na[IrCl_2(acac)_2]$, metal complexes with acetylacetonate derivatives as ligand, for example $Ir(acac)_3$ or tris(2,2,6,6-tetramethylheptane-3,5-dionato)iridium, and $IrCl_3 \cdot xH_2O$ where x is typically a number from 2 to 4.

The synthesis of the complexes is preferably conducted as described in WO 2002/060910 and in WO 2004/085449. In this case, the synthesis can, for example, also be activated by thermal or photochemical means and/or by microwave radiation. In addition, the synthesis can also be conducted in an autoclave at elevated pressure and/or elevated temperature.

The reactions can be conducted without addition of solvents or melting aids in a melt of the corresponding ligands to be o-metallated. It is optionally also possible to add solvents or melting aids. Suitable solvents are protic or aprotic solvents such as aliphatic and/or aromatic alcohols (methanol, ethanol, isopropanol, t-butanol, etc.), oligo- and polyalcohols (ethylene glycol, propane-1,2-diol, glycerol, etc.), alcohol ethers (ethoxyethanol, diethylene glycol, triethylene glycol, polyethylene glycol, etc.), ethers (di- and triethylene glycol dimethyl ether, diphenyl ether, etc.), aromatic, heteroaromatic and/or aliphatic hydrocarbons (toluene, xylene, mesitylene, chlorobenzene, pyridine, lutidine, quinoline, isoquinoline, tridecane, hexadecane, etc.), amides (DMF, DMAC, etc.), lactams (NMP), sulfoxides (DMSO) or sulfones (dimethyl sulfone, sulfolane, etc.). Suitable melting aids are compounds that are in solid form at room temperature but melt when the reaction mixture is heated and dissolve the reactants, so as to form a homogeneous melt. Particularly suitable are biphenyl, m-terphenyl, triphenyls, R- or S-binaphthol or else the corresponding racemate, 1,2-, 1,3- or 1,4-bisphenoxybenzene, triphenylphosphine oxide, 18-crown-6, phenol, 1-naphthol, hydroquinone, etc. Particular preference is given here to the use of hydroquinone.

It is possible by these processes, if necessary followed by purification, for example recrystallization or sublimation, to obtain the inventive compounds of formula (1) in high purity, preferably more than 99% (determined by means of $^1$H NMR and/or HPLC).

The compounds of the invention may also be rendered soluble by suitable substitution, for example by comparatively long alkyl groups (about 4 to 20 carbon atoms), especially branched alkyl groups, or optionally substituted aryl groups, for example xylyl, mesityl or branched terphenyl or quaterphenyl groups. Another particular method that leads to a distinct improvement in the solubility of the metal complexes is the use of fused-on aliphatic groups, as shown, for example, by the formulae (45) to (51) disclosed above. Such compounds are then soluble in sufficient concentration at room temperature in standard organic solvents, for example toluene or xylene, to be able to process the complexes from solution. These soluble compounds are of particularly good suitability for processing from solution, for example by printing methods.

For the processing of the iridium complexes of the invention from a liquid phase, for example by spin-coating or by printing methods, formulations of the iridium complexes of the invention are required. These formulations may, for example, be solutions, dispersions or emulsions. For this purpose, it may be preferable to use mixtures of two or more solvents. Suitable and preferred solvents are, for example, toluene, anisole, o-, m- or p-xylene, methyl benzoate, mesitylene, tetralin, veratrole, THF, methyl-THF, THP, chlorobenzene, dioxane, phenoxytoluene, especially 3-phenoxytoluene, (−)-fenchone, 1,2,3,5-tetramethylbenzene, 1,2,4,5-tetramethylbenzene, 1-methylnaphthalene, 2-methylbenzothiazole, 2-phenoxyethanol, 2-pyrrolidinone, 3-methylanisole, 4-methylanisole, 3,4-dimethylanisole, 3,5-dimethylanisole, acetophenone, α-terpineol, benzothiazole, butyl benzoate, cumene, cyclohexanol, cyclohexanone, cyclohexylbenzene, decalin, dodecylbenzene, ethyl benzoate, indane, NMP, p-cymene, phenetole, 1,4-diisopropylbenzene, dibenzyl ether, diethylene glycol butyl methyl ether, triethylene glycol butyl methyl ether, diethylene glycol dibutyl ether, triethylene glycol dimethyl ether, diethylene glycol monobutyl ether, tripropylene glycol dimethyl ether, tetraethylene glycol dimethyl ether, 2-isopropylnaphthalene, pentylbenzene, hexylbenzene, heptylbenzene, octylbenzene, 1,1-bis(3,4-dimethylphenyl)ethane, hexamethylindane, 2-methylbiphenyl, 3-methylbiphenyl, 1-methylnaphthalene, 1-ethylnaphthalene, ethyl octanoate, diethyl sebacate, octyl octanoate, heptylbenzene, menthyl isovalerate, cyclohexyl hexanoate or mixtures of these solvents.

The present invention therefore further provides a formulation comprising at least one compound of the invention and at least one further compound. The further compound may, for example, be a solvent, especially one of the abovementioned solvents or a mixture of these solvents. The further compound may alternatively be a further organic or inorganic compound which is likewise used in the electronic device, for example a matrix material. This further compound may also be polymeric.

The compound of the invention can be used in the electronic device as active component, preferably as emitter in the emissive layer or as hole or electron transport material in a hole- or electron-transporting layer, or as oxygen sensitizers or as photoinitiator or photocatalyst. The present invention thus further provides for the use of a compound of the invention in an electronic device or as oxygen sensitizer or as photoinitiator or photocatalyst. Enantiomerically pure iridium complexes of the invention are suitable as photocatalysts for chiral photoinduced syntheses.

The present invention still further provides an electronic device comprising at least one compound of the invention.

An electronic device is understood to mean any device comprising anode, cathode and at least one layer, said layer comprising at least one organic or organometallic compound. The electronic device of the invention thus comprises anode, cathode and at least one layer containing at least one iridium complex of the invention. Preferred electronic devices are selected from the group consisting of organic electroluminescent devices (OLEDs, PLEDs), organic integrated circuits (O-ICs), organic field-effect transistors (O-FETs), organic thin-film transistors (O-TFTs), organic light-emitting transistors (O-LETs), organic solar cells (O-SCs), the latter being understood to mean both purely organic solar cells and dye-sensitized solar cells, organic optical detectors, organic photoreceptors, organic field-quench devices (O-FQDs), light-emitting electrochemical cells (LECs), oxygen sensors and organic laser diodes (O-lasers), comprising at least one compound of the invention in at least one layer. Compounds that emit in the infrared are suitable for use in organic infrared electroluminescent devices and infrared sensors. Particular preference is given to organic electroluminescent devices. Active components are generally the organic or inorganic materials introduced between the anode and cathode, for example charge injection, charge transport or charge blocker materials, but especially emission materials and matrix materials. The compounds of the invention exhibit particularly good properties as emission material in organic electroluminescent devices. A preferred embodiment of the invention is therefore organic electroluminescent devices. In addition, the compounds of the invention can be used for production of singlet oxygen or in photocatalysis.

The organic electroluminescent device comprises cathode, anode and at least one emitting layer. Apart from these layers, it may comprise still further layers, for example in each case one or more hole injection layers, hole transport layers, hole blocker layers, electron transport layers, electron injection layers, exciton blocker layers, electron blocker layers, charge generation layers and/or organic or inorganic p/n junctions. In this case, it is possible that one or more hole transport layers are p-doped, for example with metal oxides such as $MoO_3$ or $WO_3$, or with (per)fluorinated electron-deficient aromatics or with electron-deficient cyano-substituted heteroaromatics (for example according to JP 4747558, JP 2006-135145, US 2006/0289882, WO 2012/095143), or with quinoid systems (for example according to EP1336208) or with Lewis acids, or with boranes (for example according to US 2003/0006411, WO 2002/051850, WO 2015/049030) or with carboxylates of the elements of main group 3, 4 or 5 (WO 2015/018539), and/or that one or more electron transport layers are n-doped.

It is likewise possible for interlayers to be introduced between two emitting layers, which have, for example, an exciton-blocking function and/or control charge balance in the electroluminescent device and/or generate charges (charge generation layer, for example in layer systems having two or more emitting layers, for example in white-emitting OLED components). However, it should be pointed out that not necessarily every one of these layers need be present.

In this case, it is possible for the organic electroluminescent device to contain an emitting layer, or for it to contain a plurality of emitting layers. If a plurality of emission layers are present, these preferably have several emission maxima between 380 nm and 750 nm overall, such that the overall result is white emission; in other words, various emitting compounds which may fluoresce or phosphoresce are used in the emitting layers. Especially preferred are three-layer systems where the three layers exhibit blue, green and orange or red emission (for the basic construction see, for example, WO 2005/011013), or systems having more than three emitting layers. The system may also be a hybrid system wherein one or more layers fluoresce and one or more other layers phosphoresce. A preferred embodiment is tandem OLEDs. White-emitting organic electroluminescent devices may be used for lighting applications or else with colour filters for full-colour displays.

In a preferred embodiment of the invention, the organic electroluminescent device comprises the iridium complex of the invention as emitting compound in one or more emitting layers.

When the iridium complex of the invention is used as emitting compound in an emitting layer, it is preferably used in combination with one or more matrix materials. The mixture of the iridium complex of the invention and the matrix material contains between 0.1% and 99% by volume, preferably between 1% and 90% by volume, more preferably between 3% and 40% by volume and especially between 5% and 15% by volume of the iridium complex of the invention, based on the overall mixture of emitter and matrix material. Correspondingly, the mixture contains between 99.9% and 1% by volume, preferably between 99% and 10% by volume, more preferably between 97% and 60% by volume and especially between 95% and 85% by volume of the matrix material, based on the overall mixture of emitter and matrix material.

The matrix material used may generally be any materials which are known for the purpose according to the prior art. The triplet level of the matrix material is preferably higher than the triplet level of the emitter.

Suitable matrix materials for the compounds of the invention are ketones, phosphine oxides, sulfoxides and sulfones, for example according to WO 2004/013080, WO 2004/093207, WO 2006/005627 or WO 2010/006680, triarylamines, carbazole derivatives, e.g. CBP (N,N-biscarbazolylbiphenyl), m-CBP or the carbazole derivatives disclosed in WO 2005/039246, US 2005/0069729, JP 2004/288381, EP 1205527, WO 2008/086851 or US 2009/0134784, biscarbazole derivatives, indolocarbazole derivatives, for example according to WO 2007/063754 or WO 2008/056746, indenocarbazole derivatives, for example according to WO 2010/136109 or WO 2011/000455, azacarbazoles, for example according to EP 1617710, EP 1617711, EP 1731584, JP 2005/347160, bipolar matrix materials, for example according to WO 2007/137725, silanes, for example according to WO 2005/111172, azaboroles or boronic esters, for example according to WO 2006/117052, diazasilole derivatives, for example according to WO 2010/054729, diazaphosphole derivatives, for example according to WO 2010/054730, triazine derivatives, for example according to WO 2010/015306, WO 2007/063754 or WO 2008/056746, zinc complexes, for example according to EP 652273 or WO 2009/062578, dibenzofuran derivatives, for example according to WO 2009/148015 or WO 2015/169412, or bridged carbazole derivatives, for example according to US 2009/0136779, WO 2010/050778, WO 2011/042107 or WO 2011/088877. Suitable matrix materials for solution-processed OLEDs are also polymers, for example according to WO 2012/008550 or WO 2012/048778, oligomers or dendrimers, for example according to Journal of Luminescence 183 (2017), 150-158.

It may also be preferable to use a plurality of different matrix materials as a mixture, especially at least one electron-conducting matrix material and at least one hole-conducting matrix material. A preferred combination is, for example, the use of an aromatic ketone, a triazine derivative or a phosphine oxide derivative with a triarylamine derivative or a carbazole derivative as mixed matrix for the metal complex of the invention.

Preference is likewise given to the use of a mixture of a charge-transporting matrix material and an electrically inert matrix material (called a "wide bandgap host") having no significant involvement, if any, in the charge transport, as described, for example, in WO 2010/108579 or WO 2016/184540. Preference is likewise given to the use of two electron-transporting matrix materials, for example triazine derivatives and lactam derivatives, as described, for example, in WO 2014/094964.

Depicted below are examples of compounds that are suitable as matrix materials for the compounds of the invention.

Examples of triazines and pyrimidines which can be used as electron-transporting matrix materials are the following structures:

101
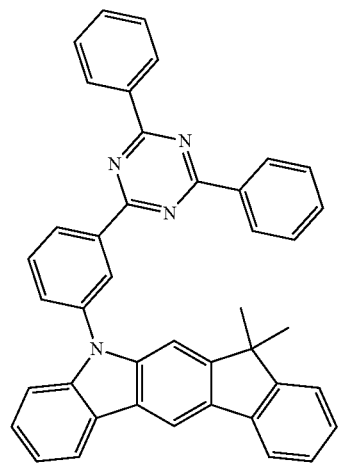
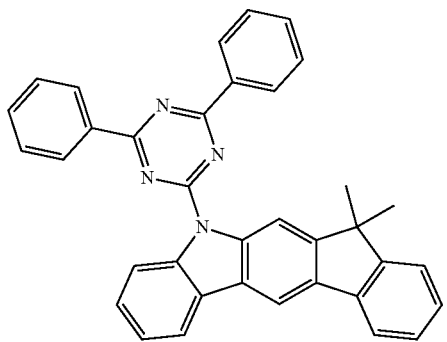
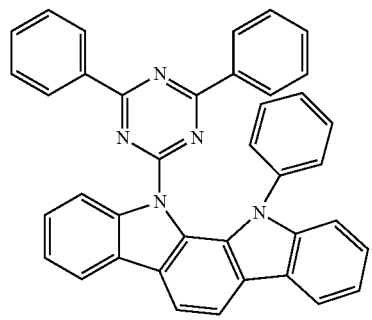
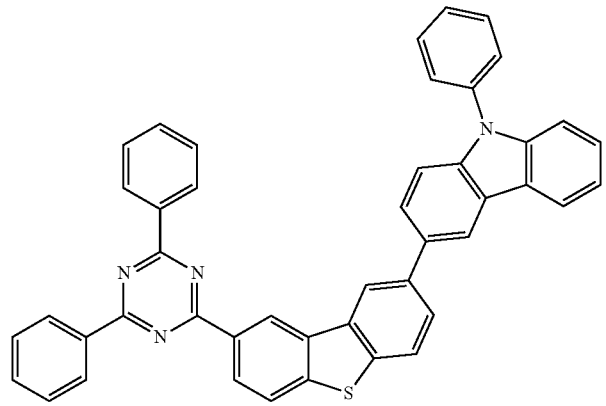
102
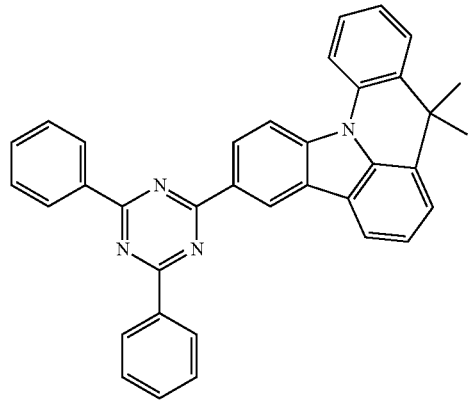
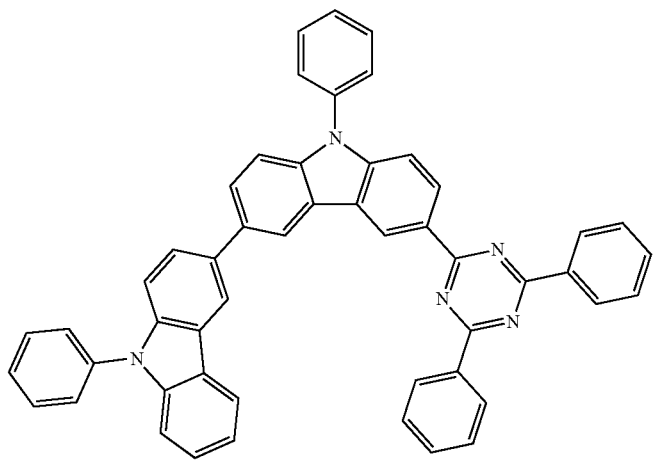

103
104
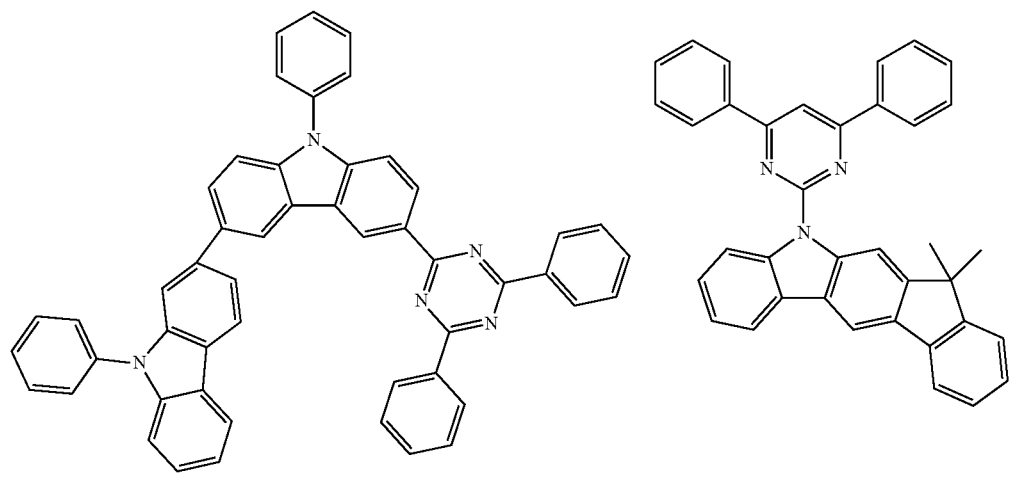
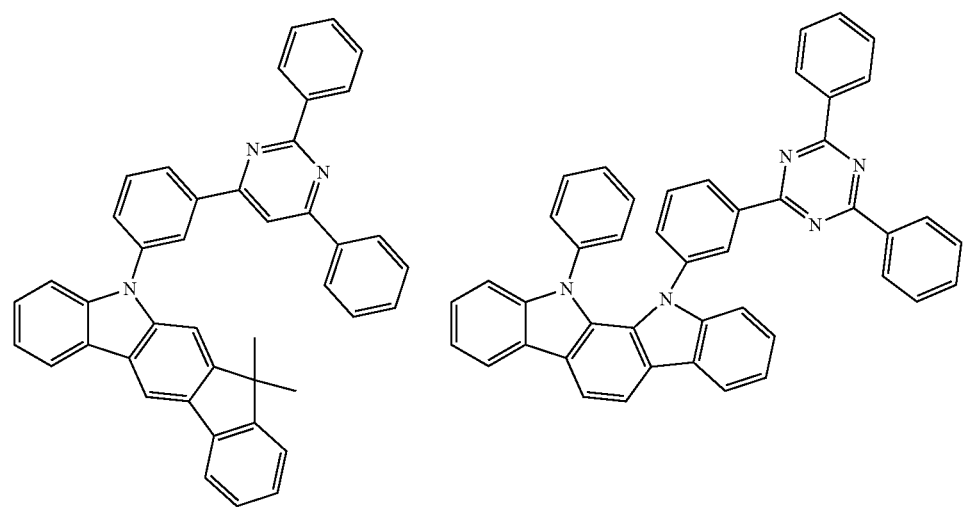
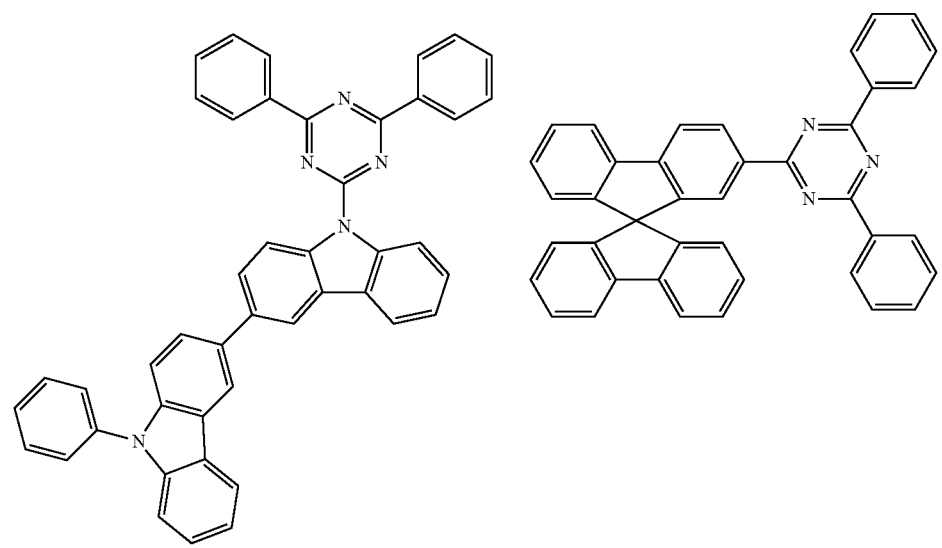

-continued
105
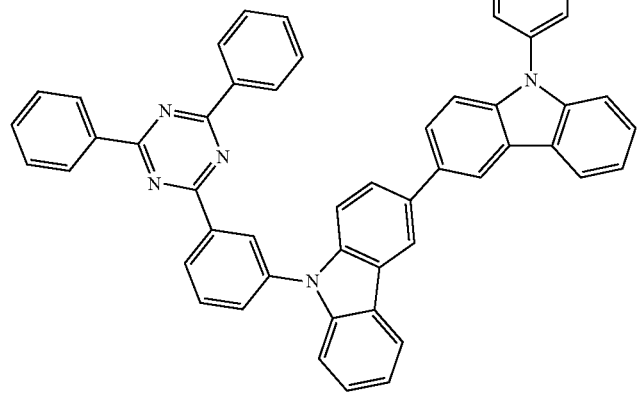
106
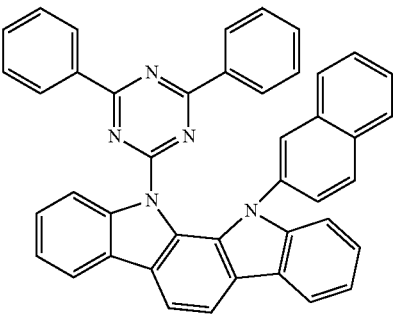
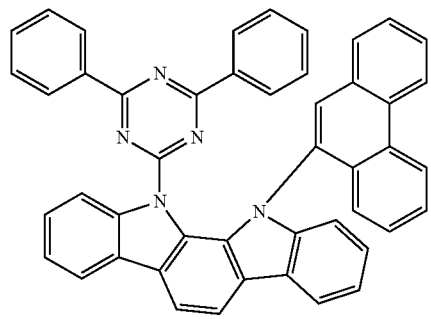
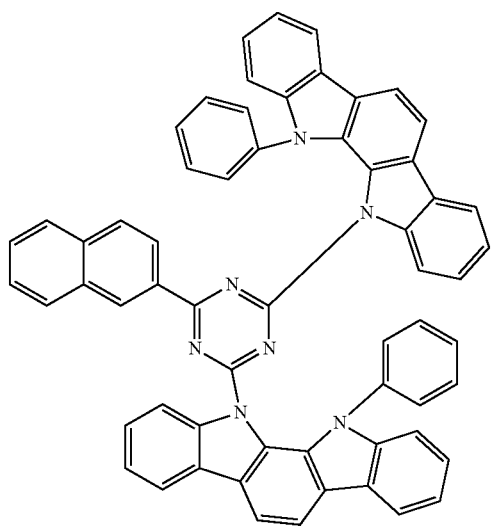
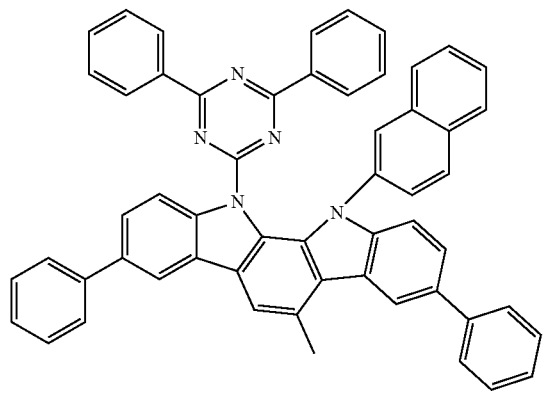
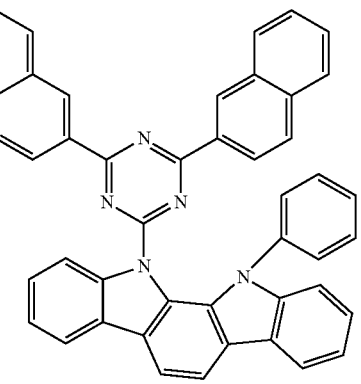

-continued
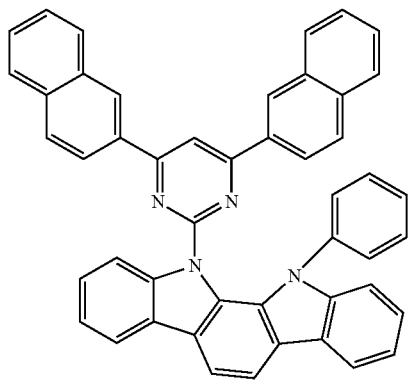
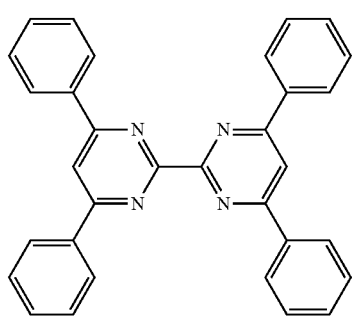
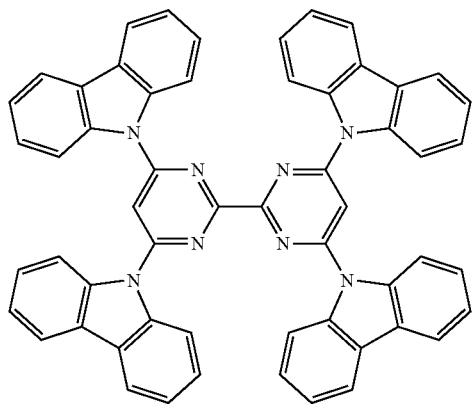
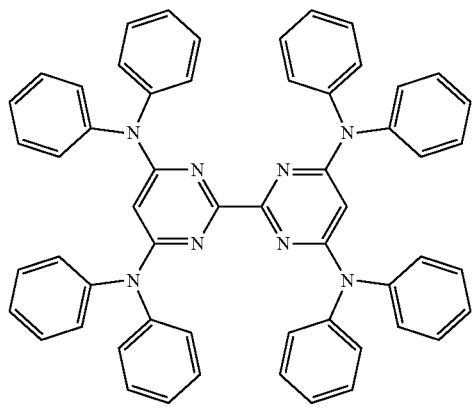
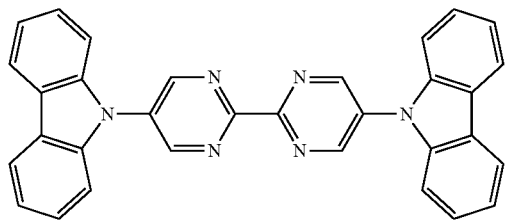
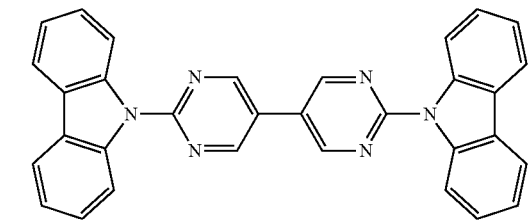
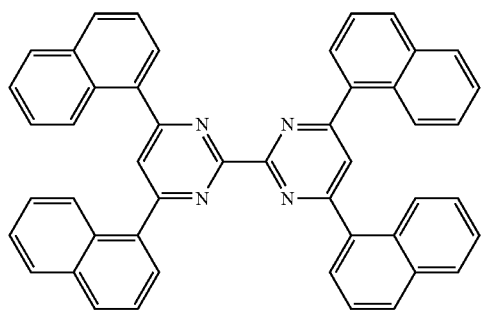
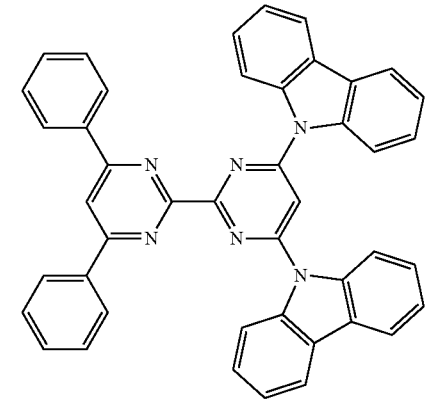

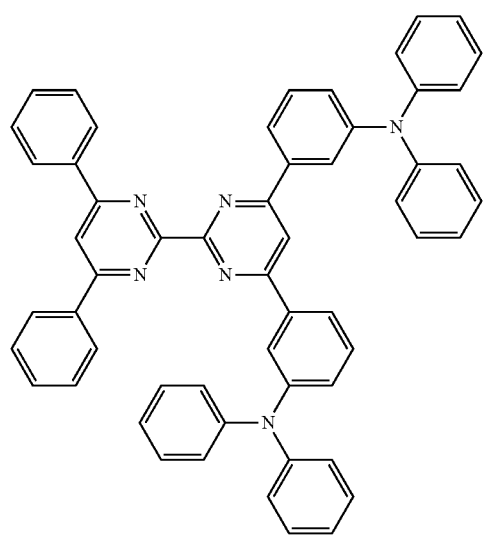
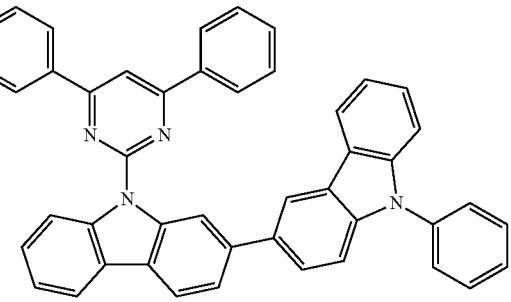
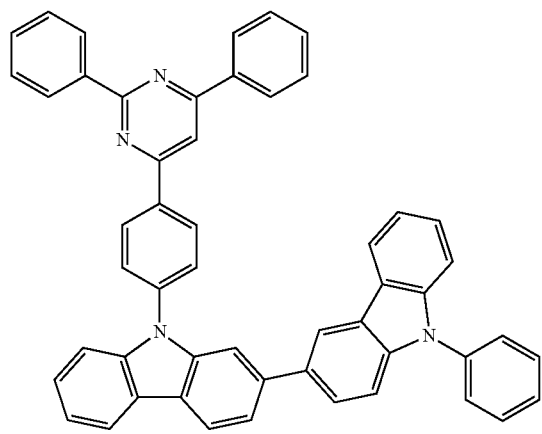
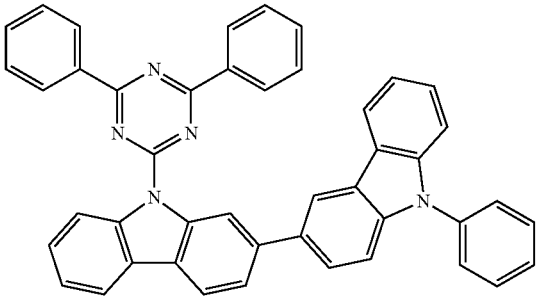
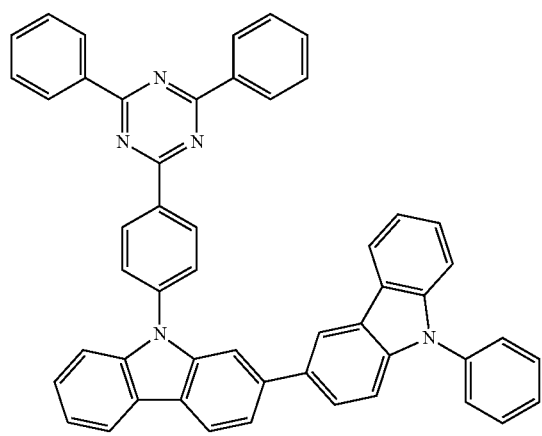

111
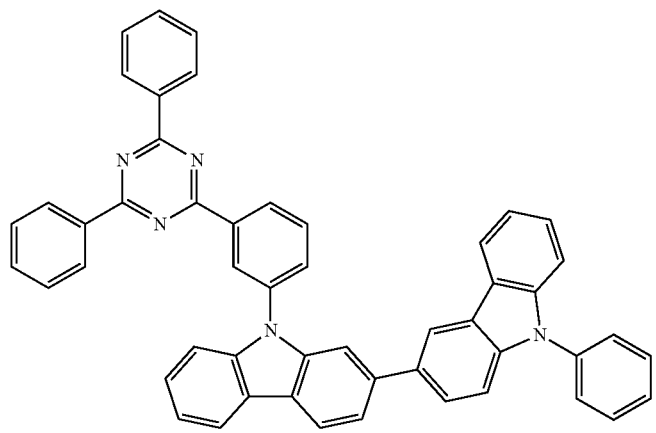
112
-continued
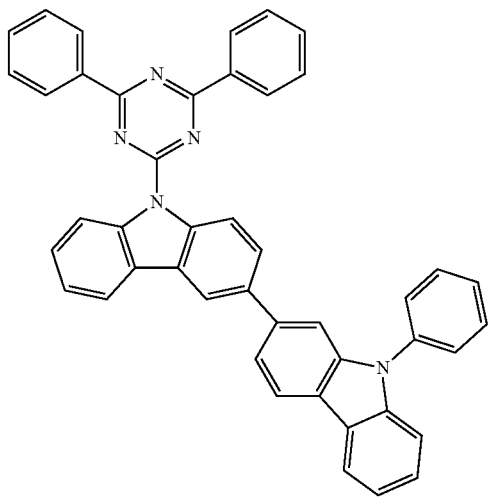
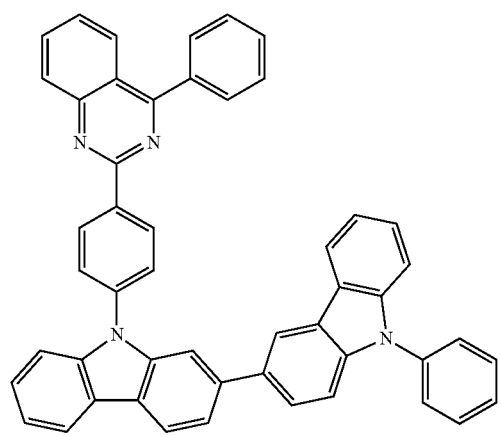
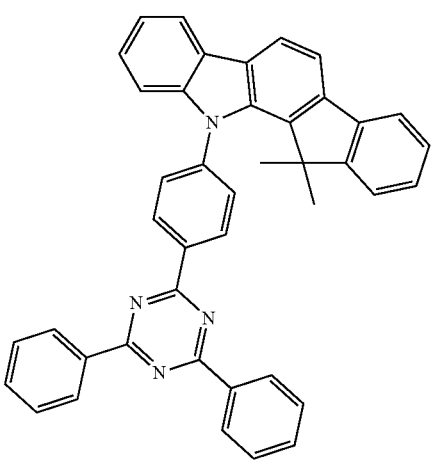
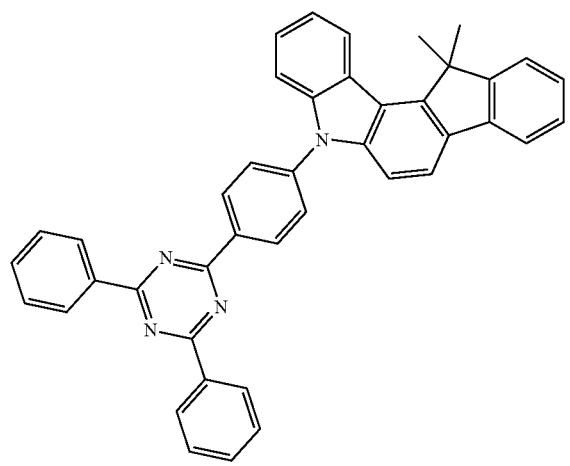
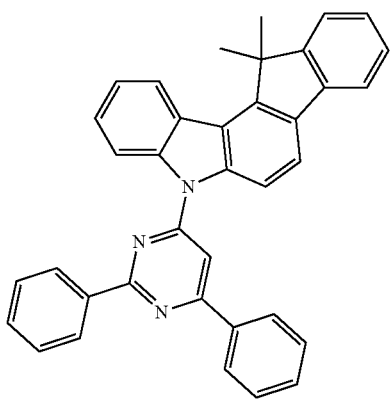

-continued
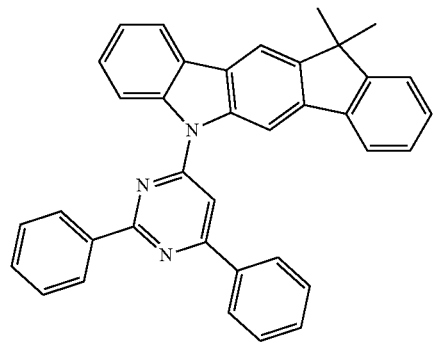
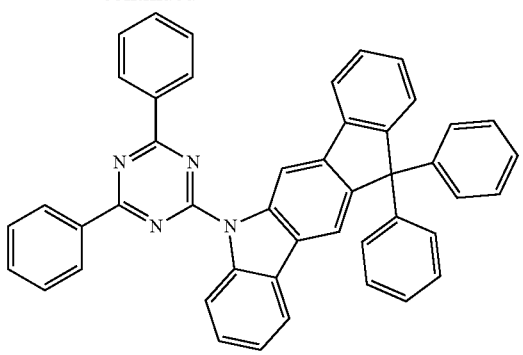
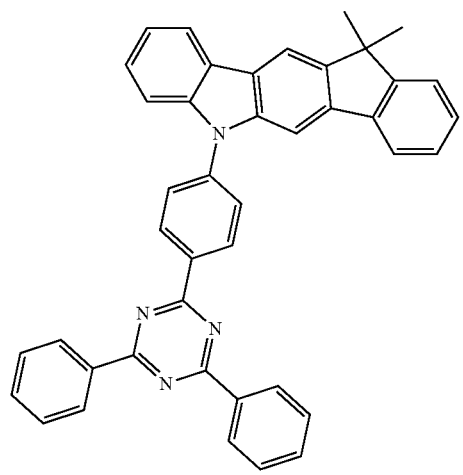
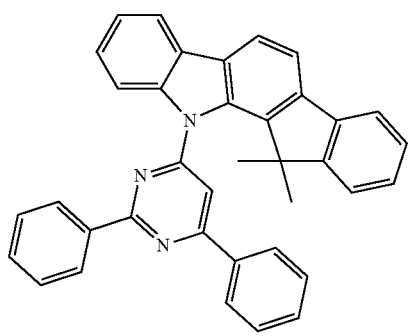
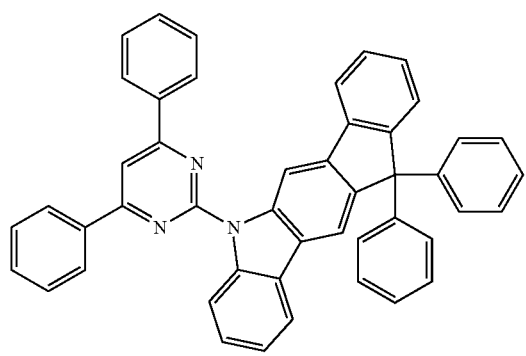
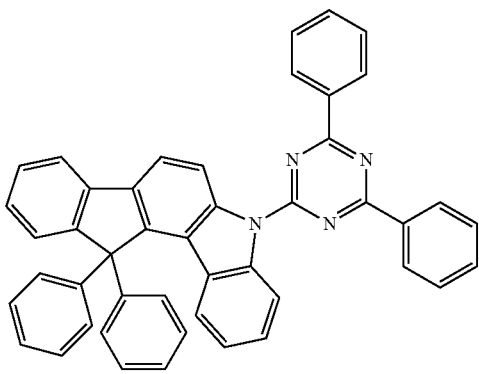
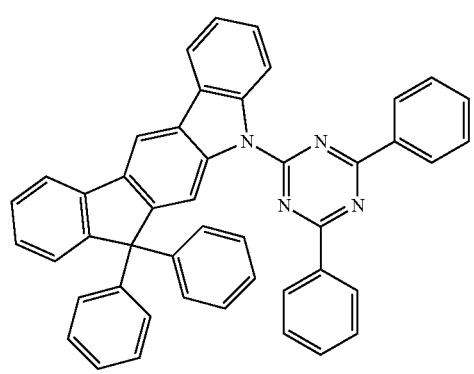
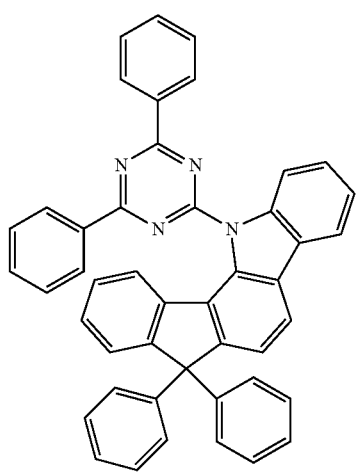

115
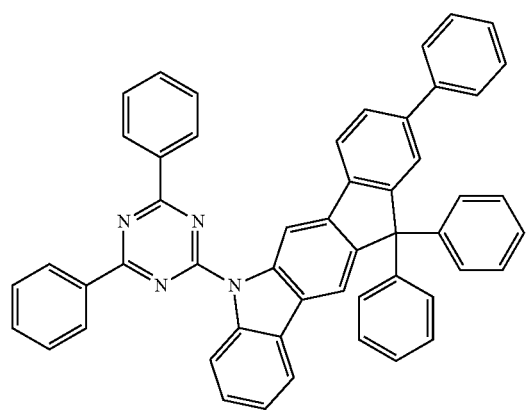
116
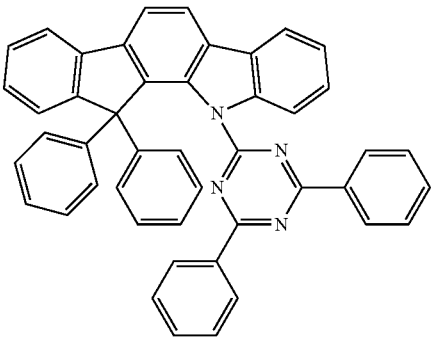
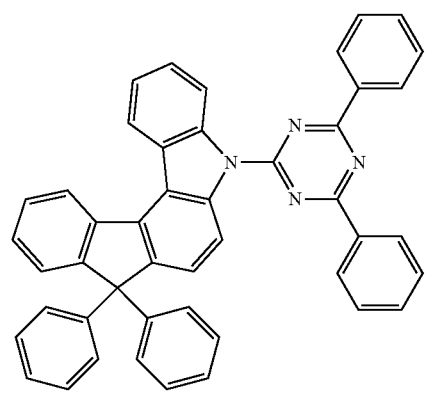
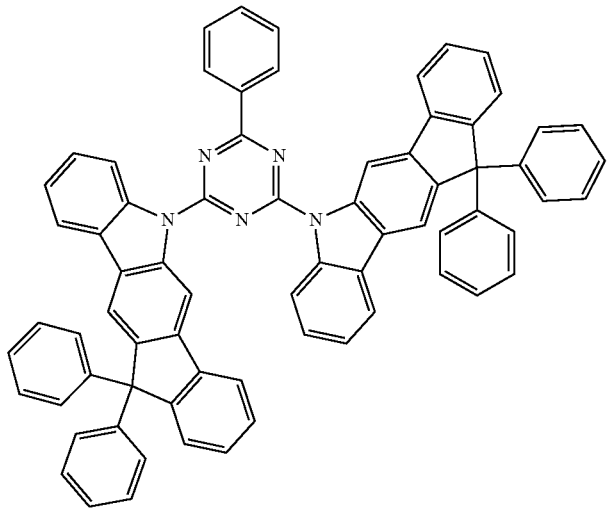
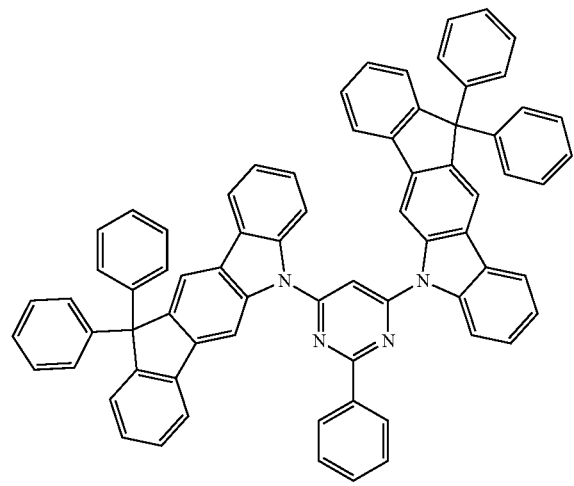
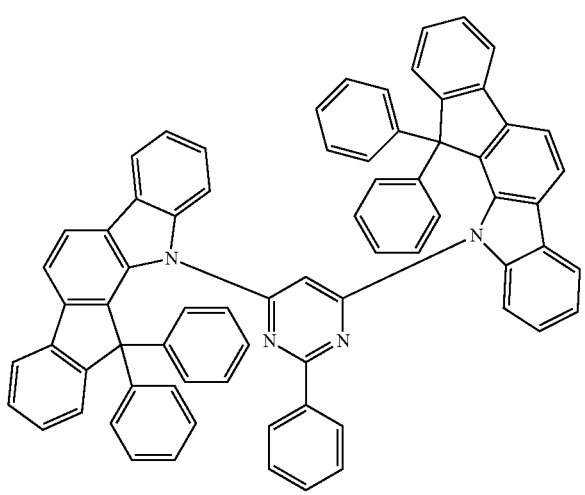

-continued
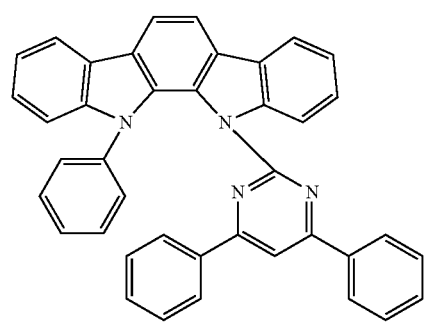
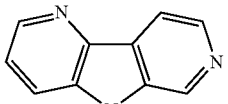
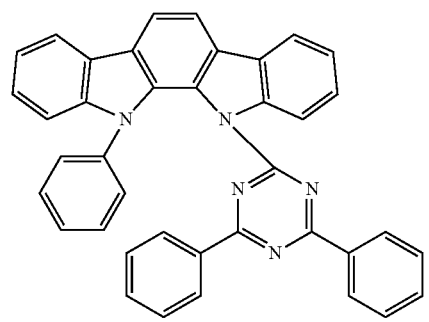
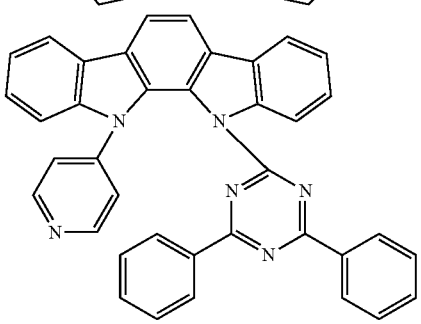
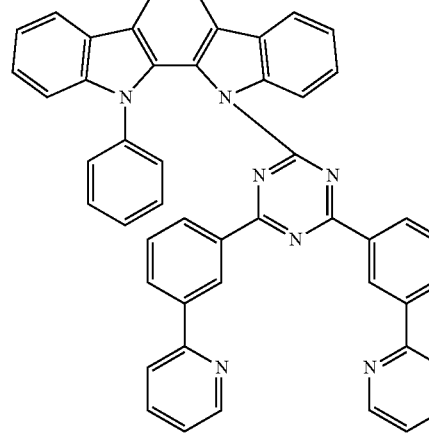
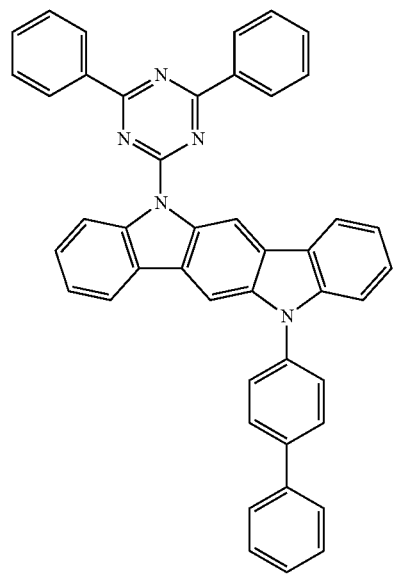
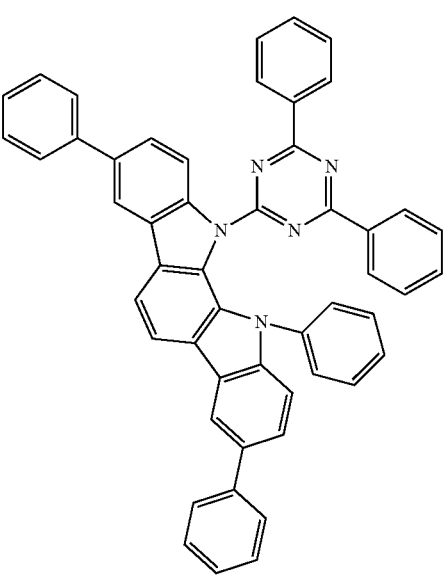

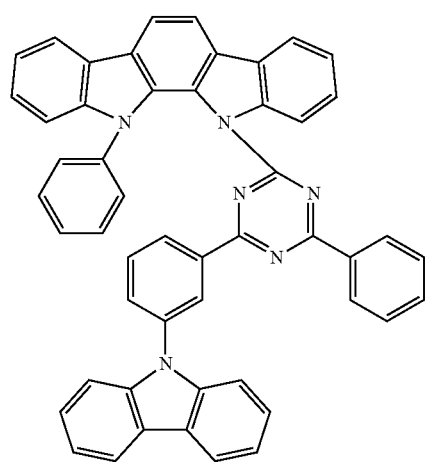
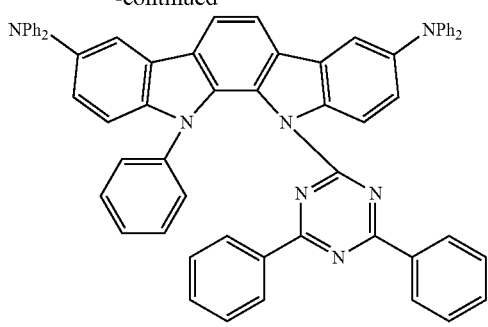
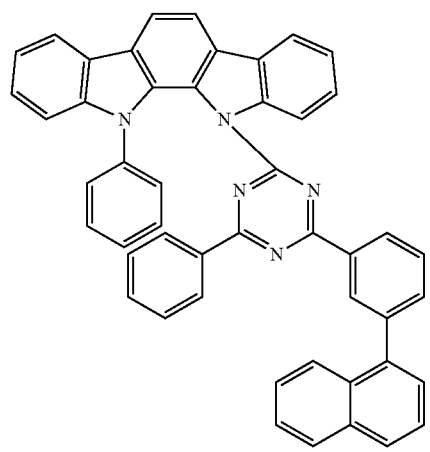
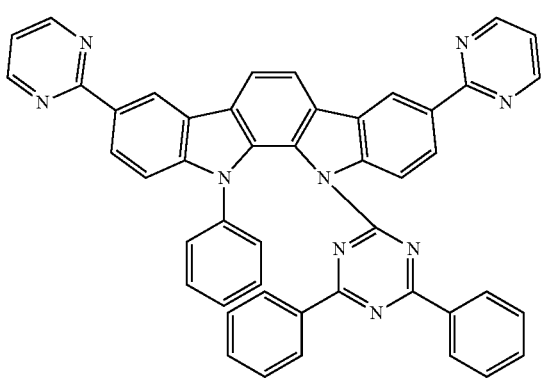
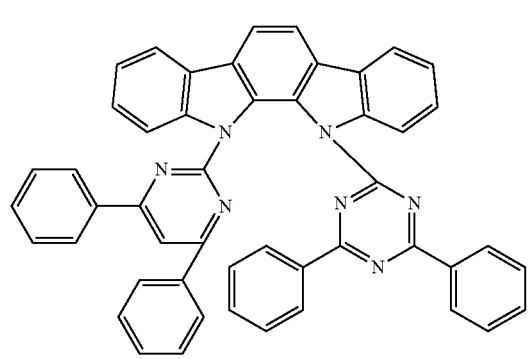
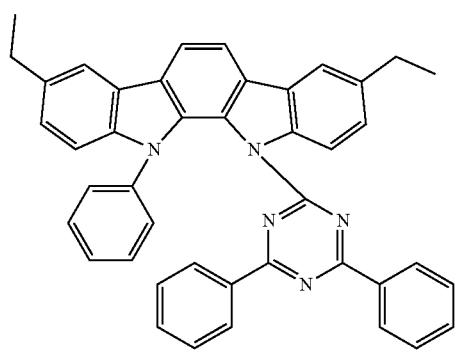
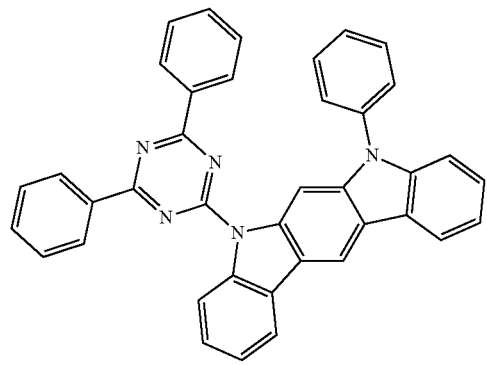
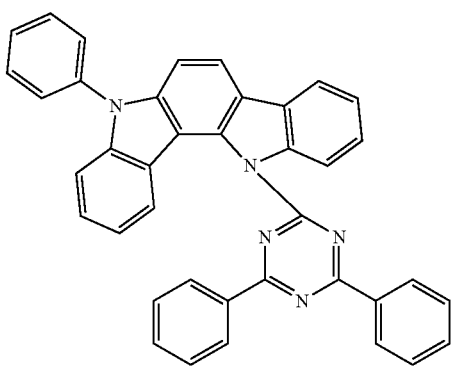

-continued
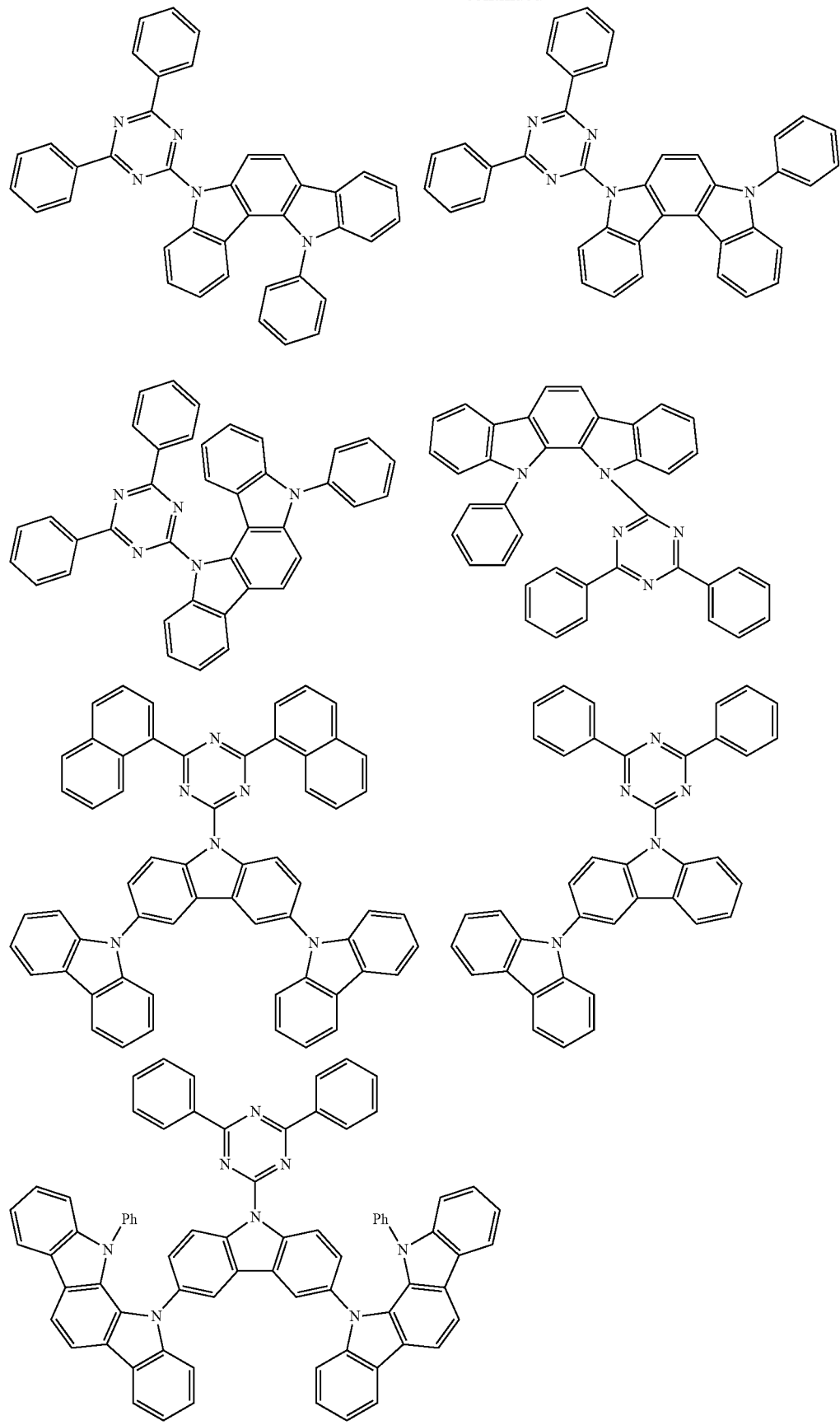

-continued
123
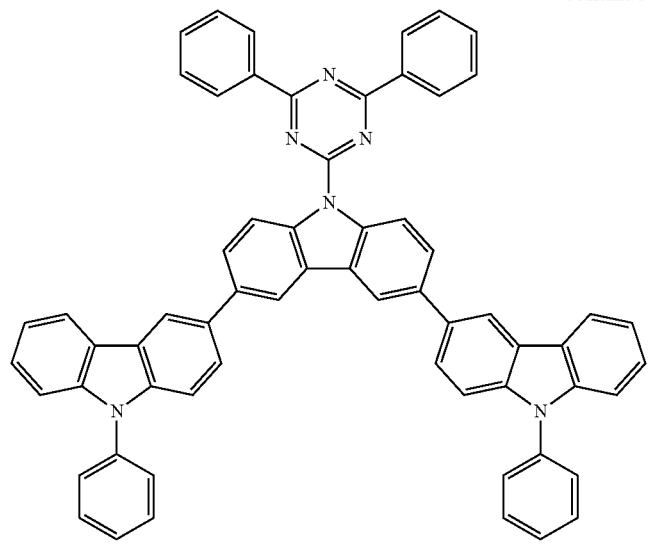
124
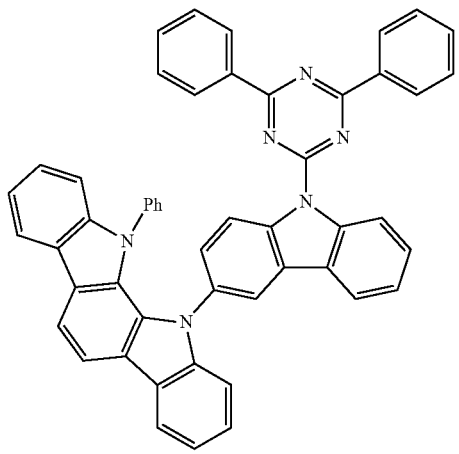
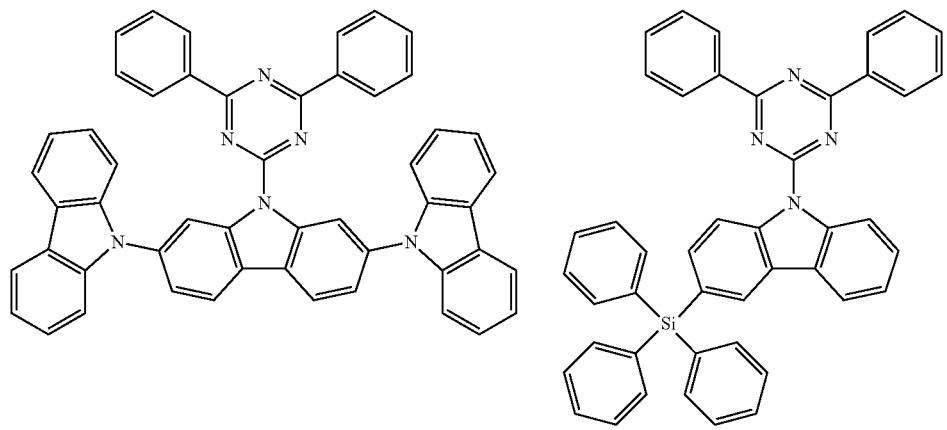
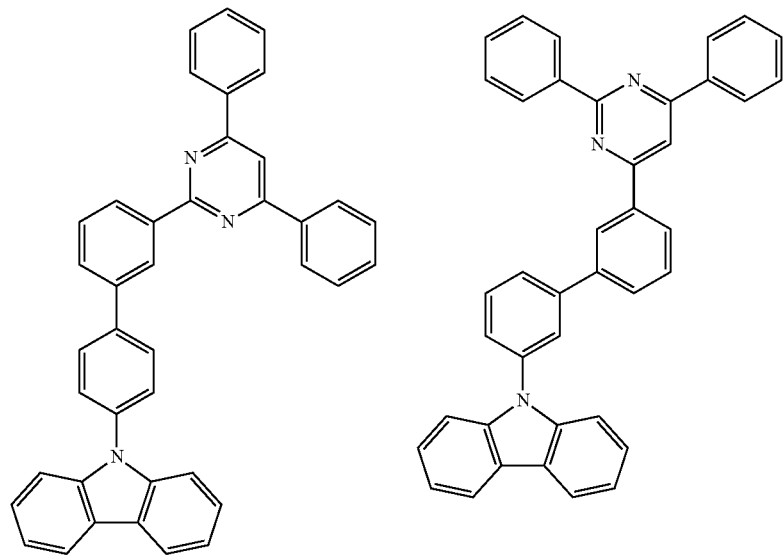

125
126
-continued
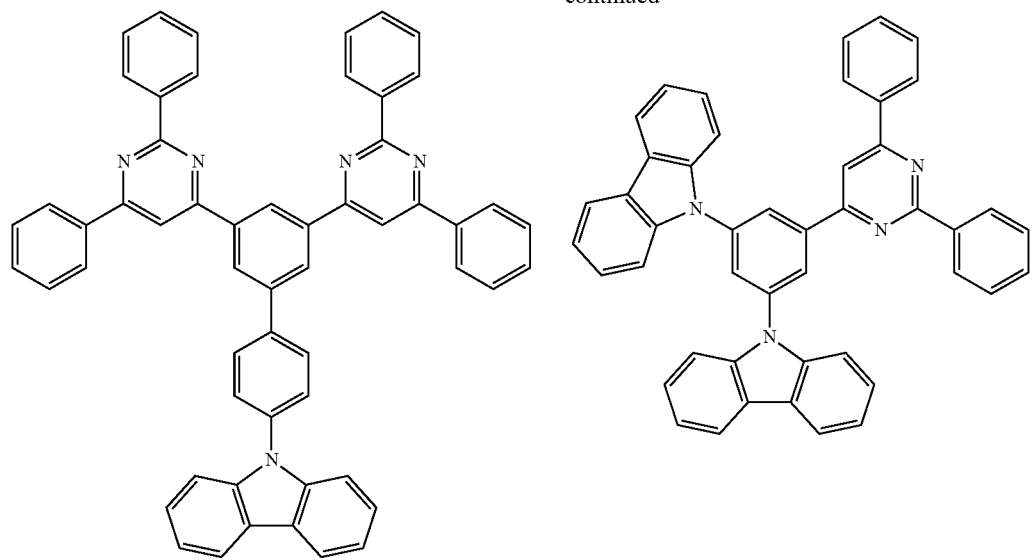
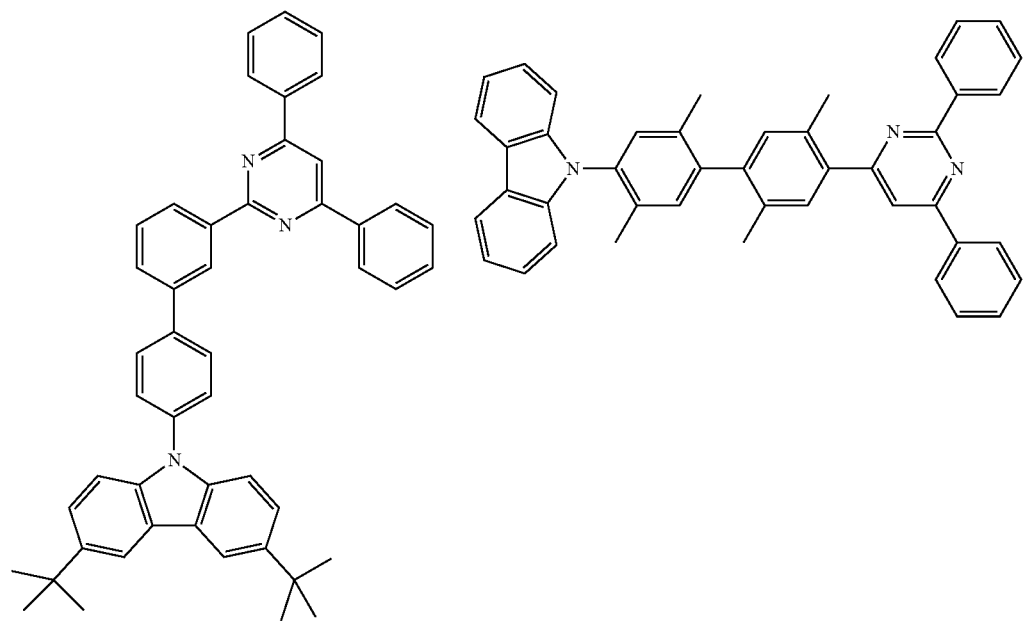
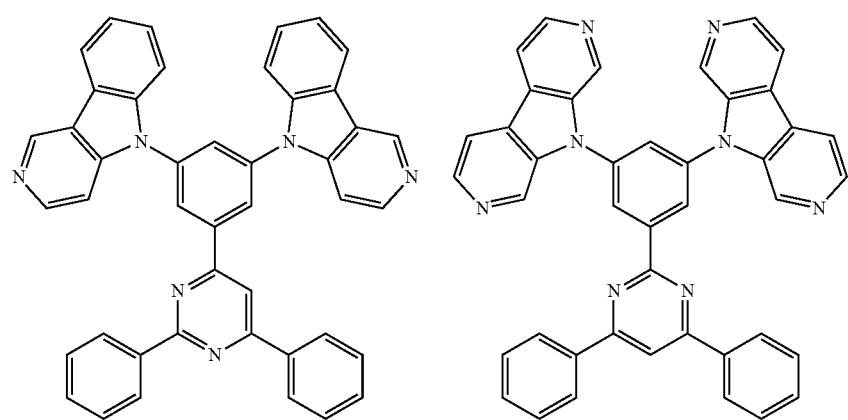

-continued
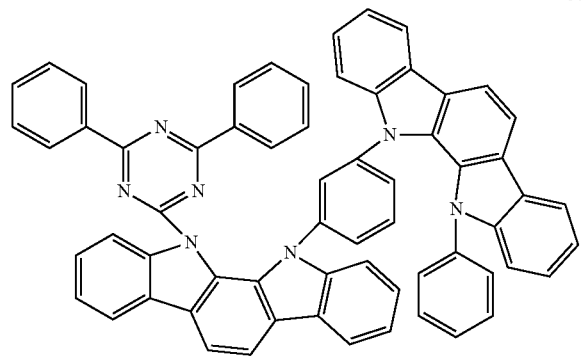
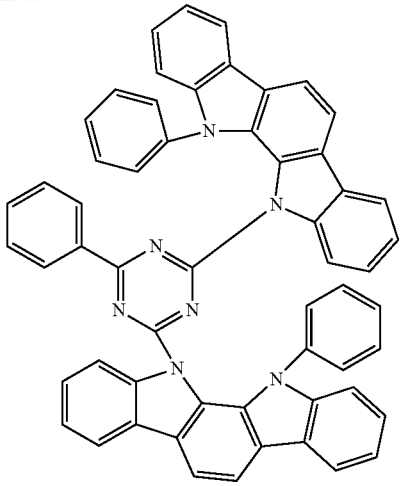
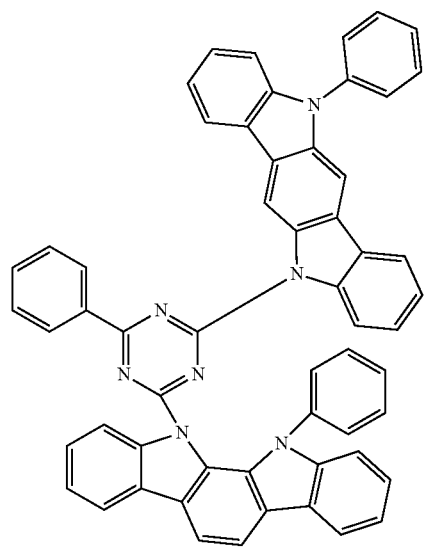
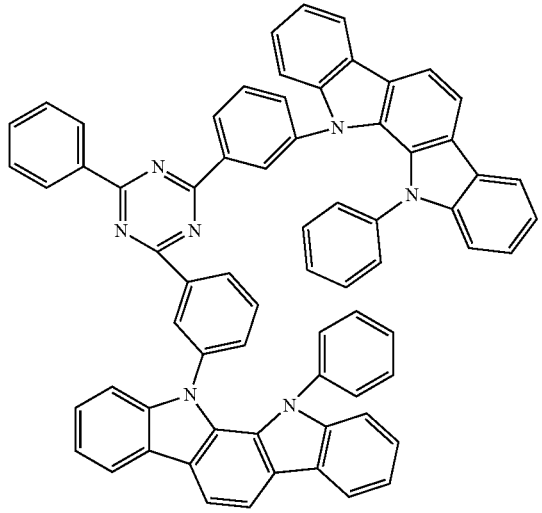
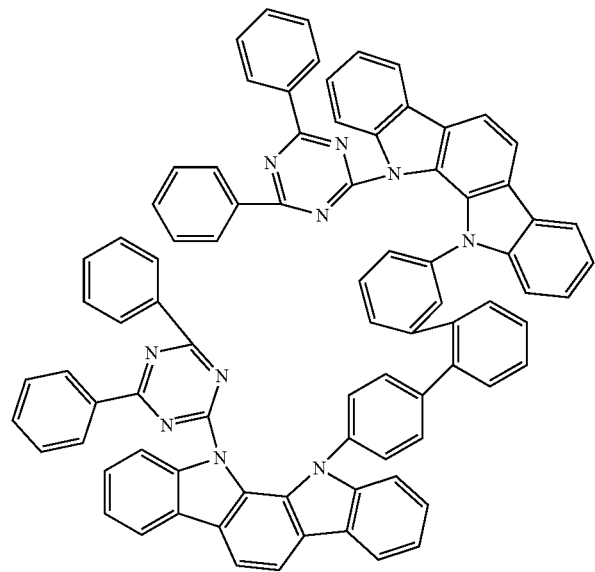
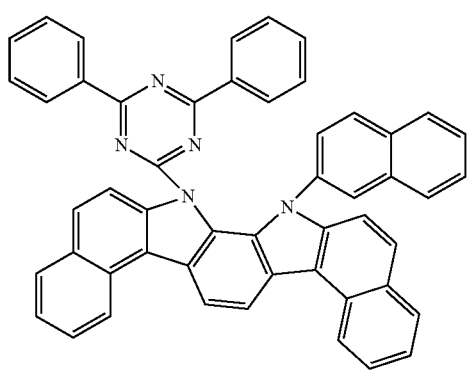

-continued
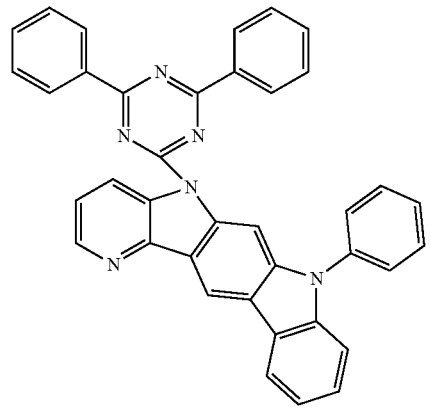
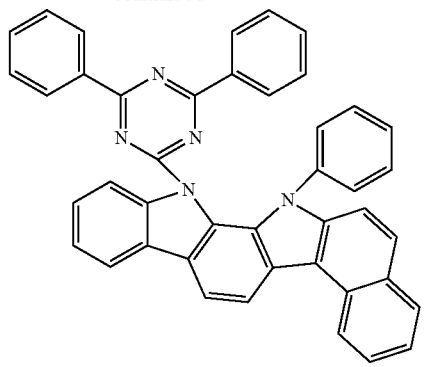
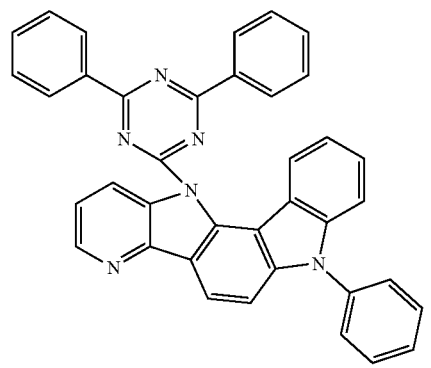
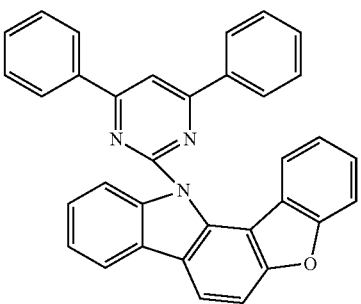
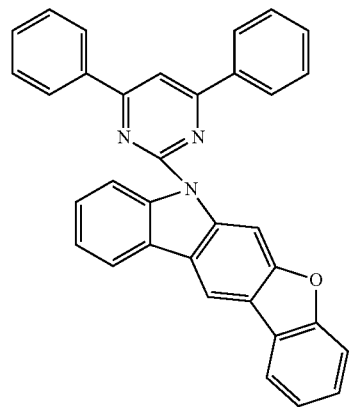
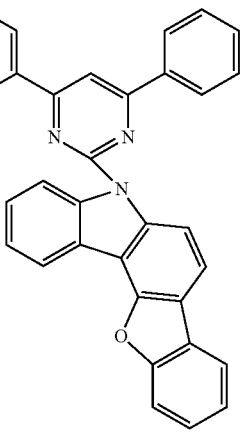
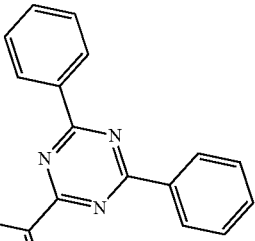
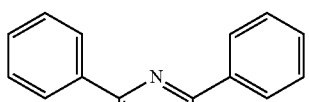
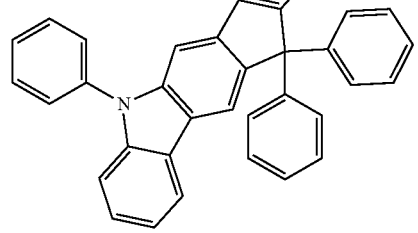
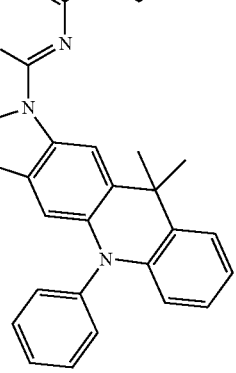

-continued
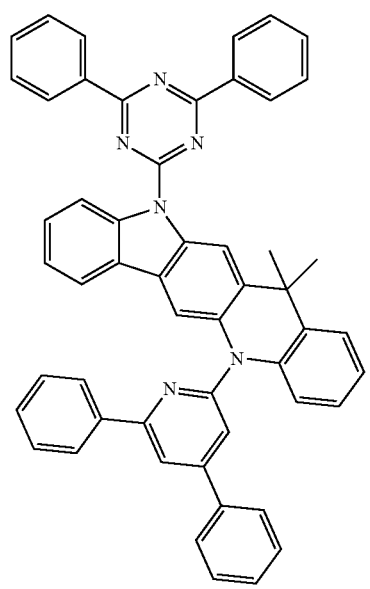
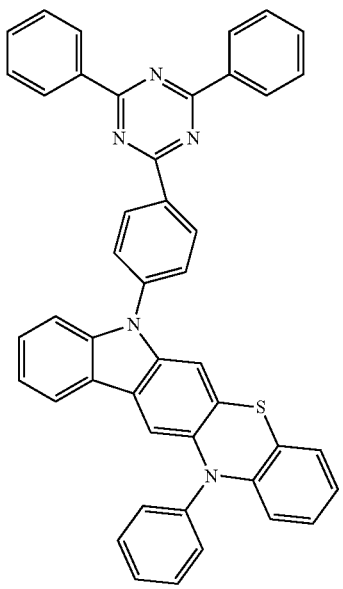
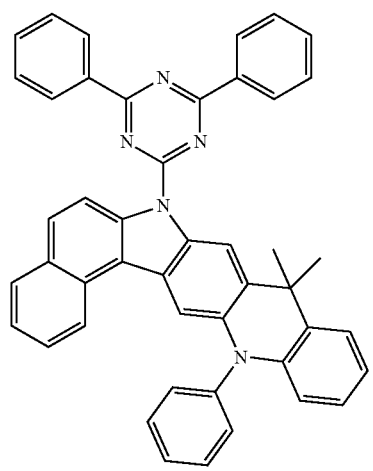
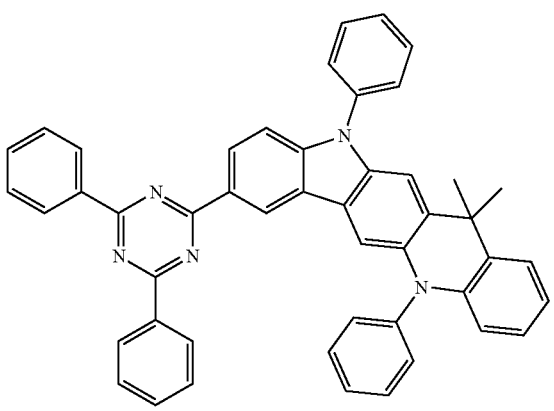
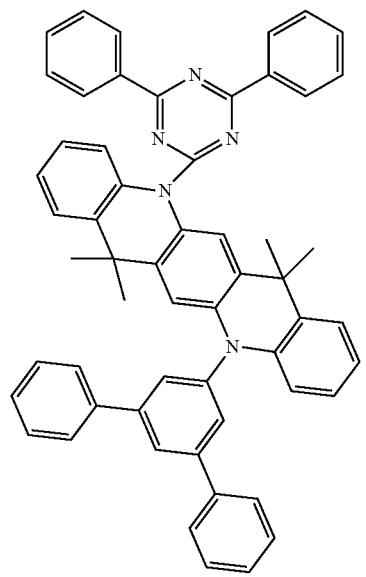
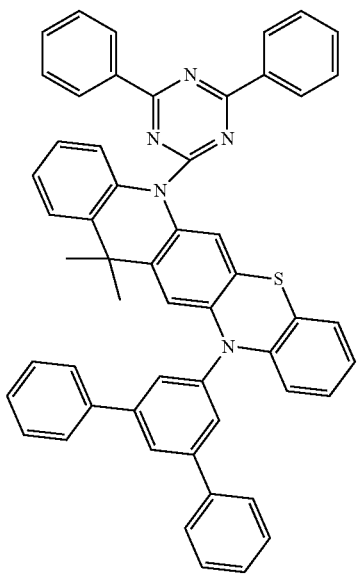

133
134
-continued
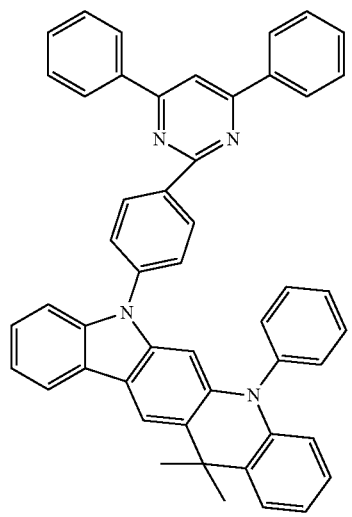
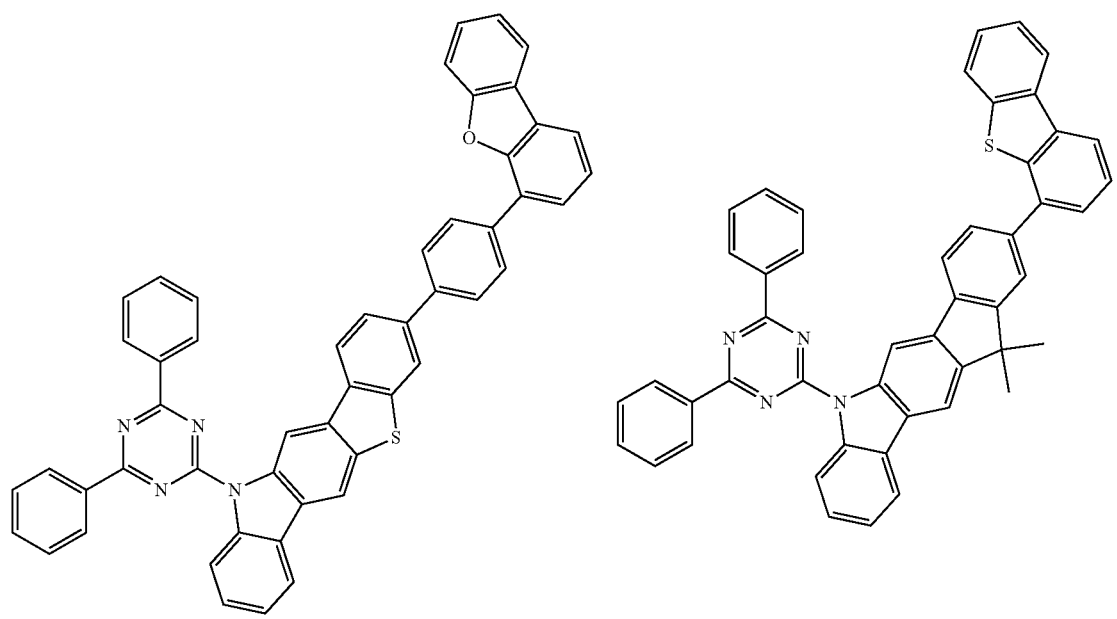
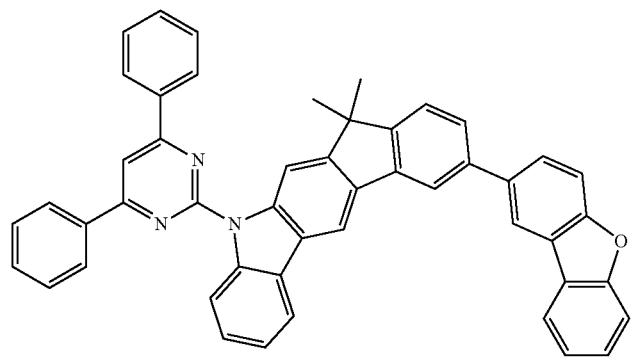

-continued
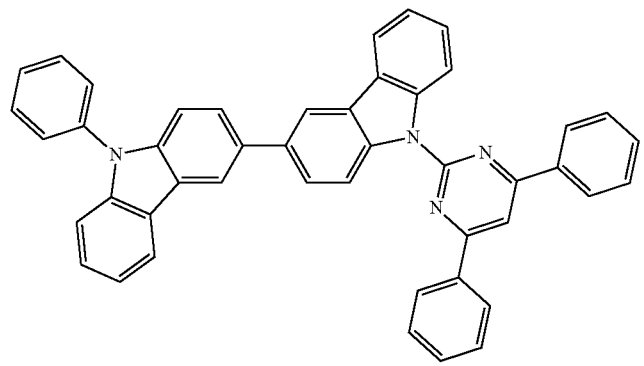
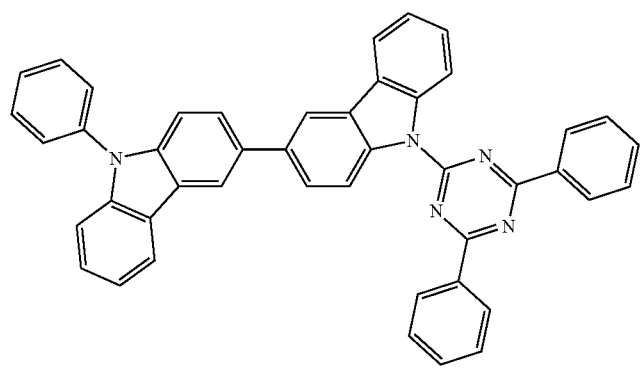
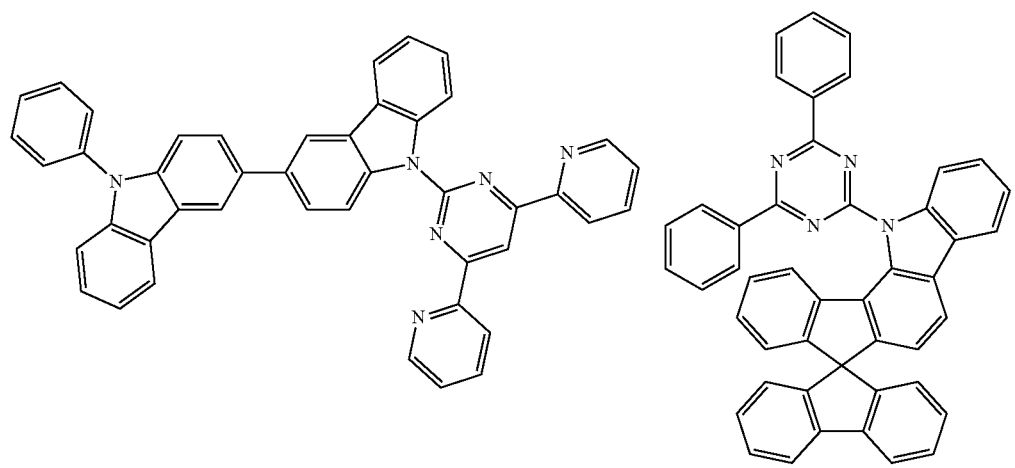
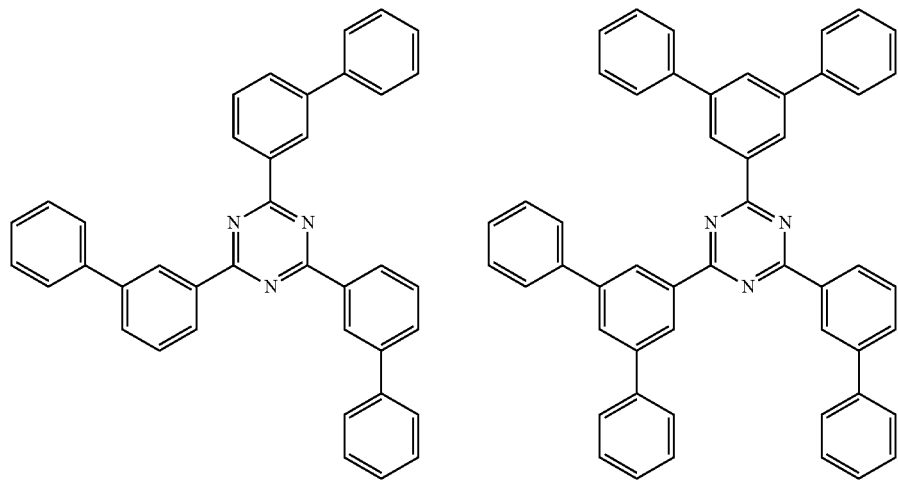

137 138
-continued
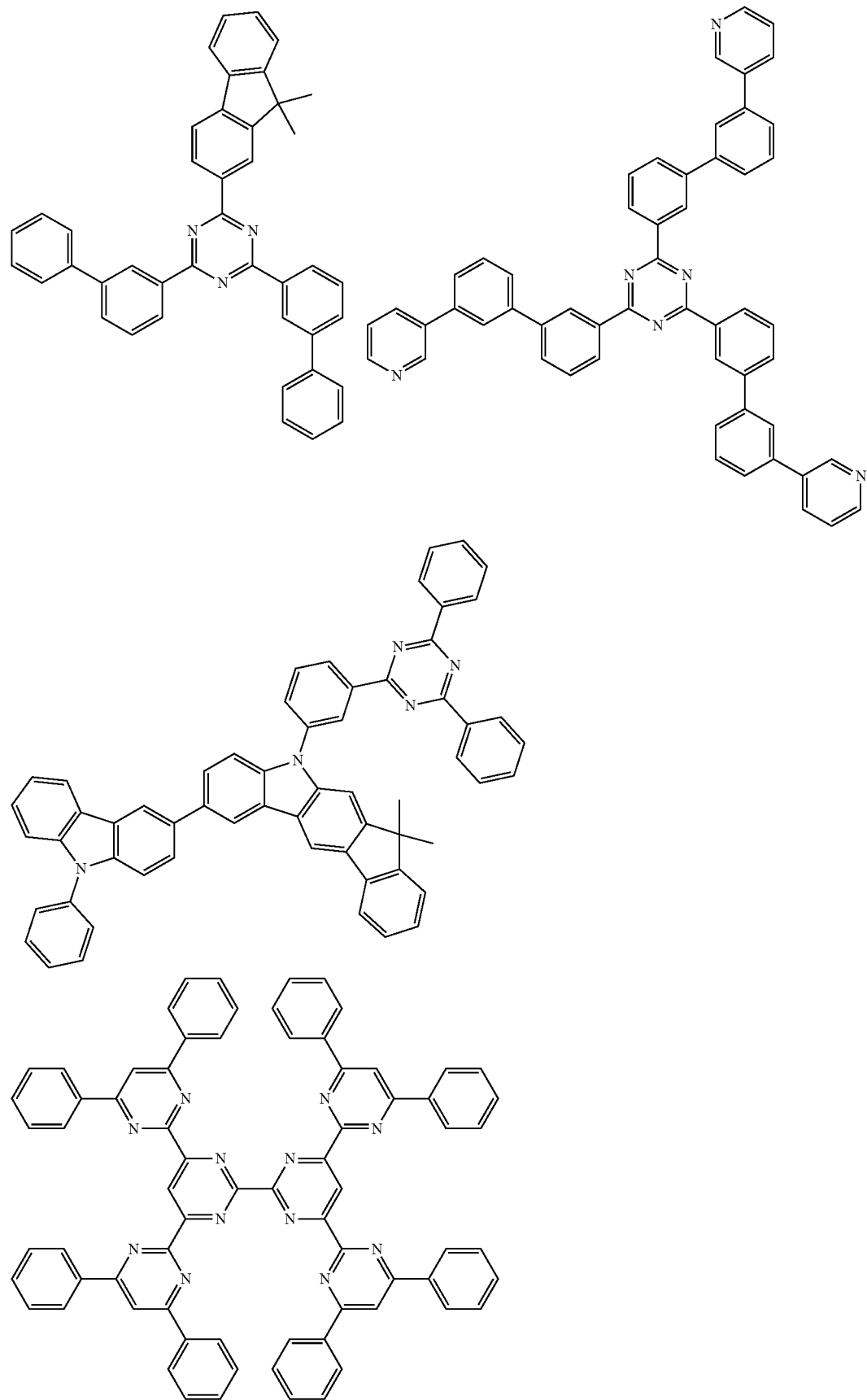

-continued
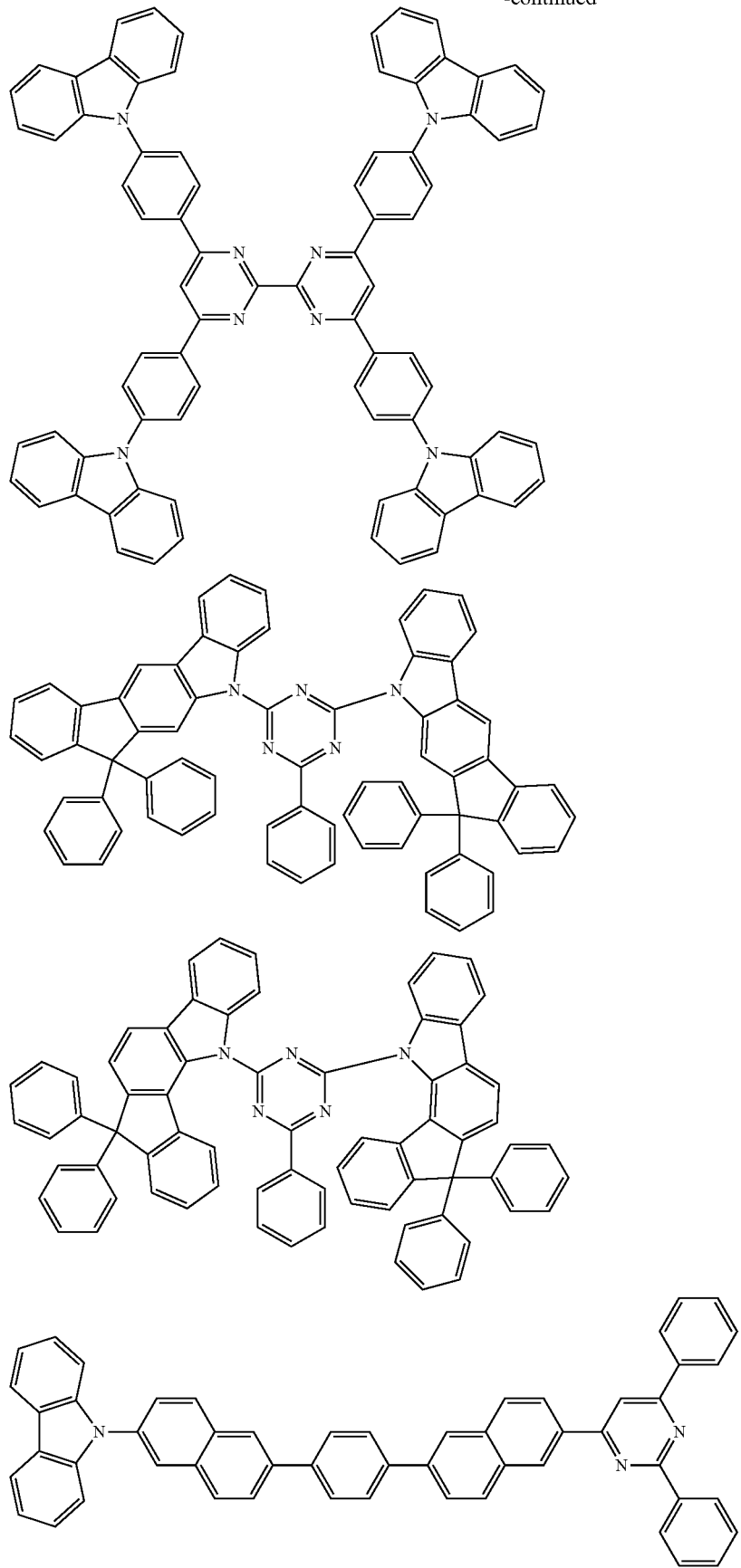

-continued
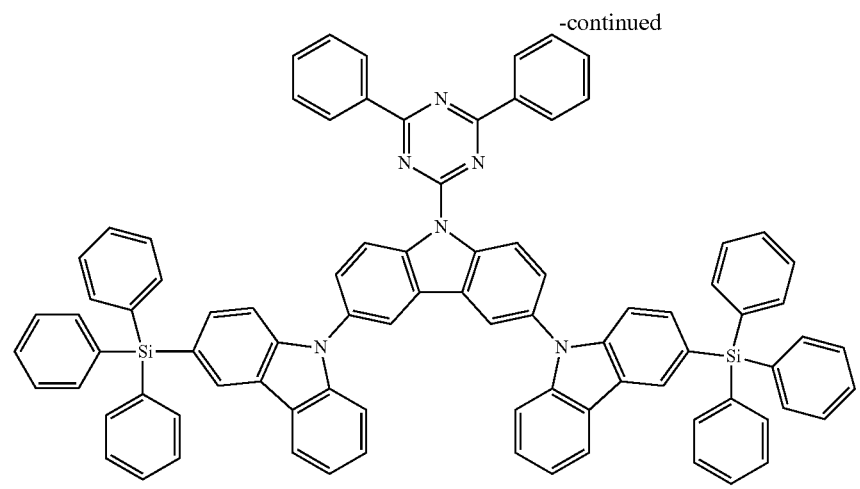
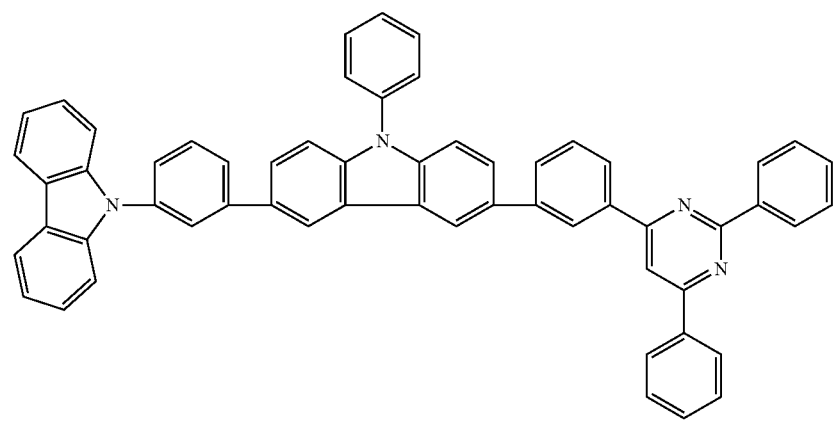
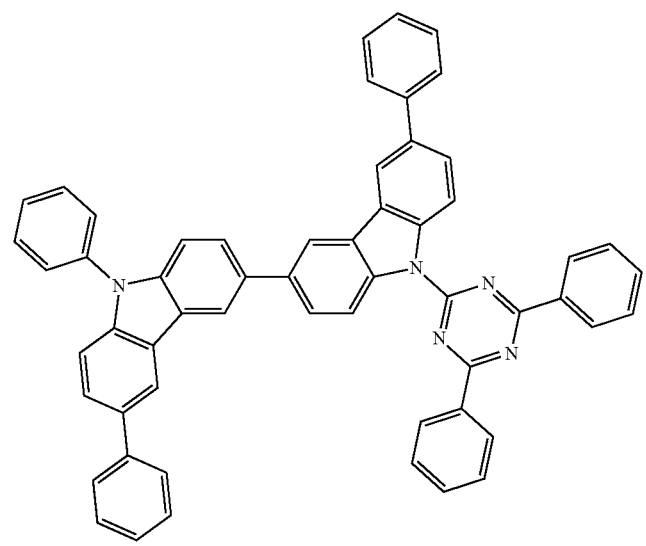

-continued
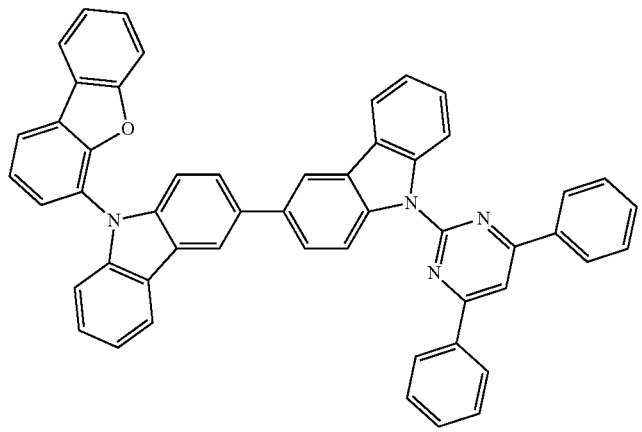
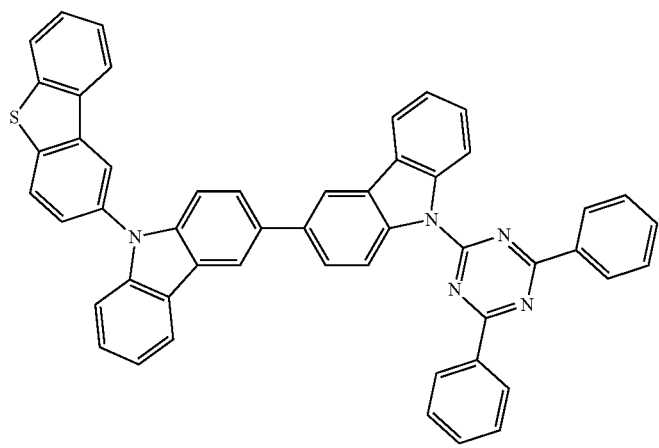
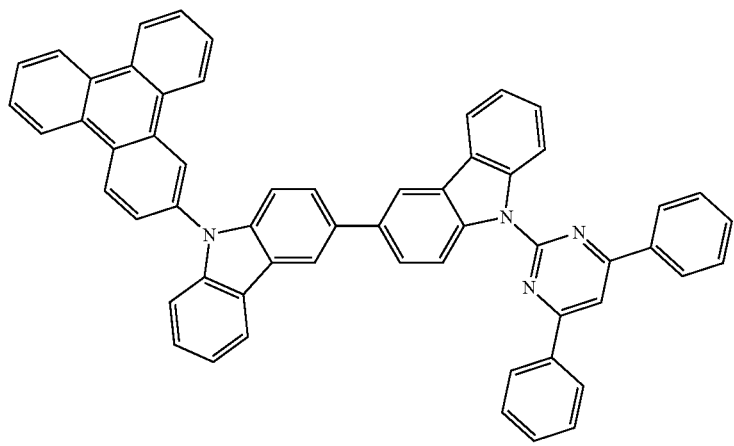
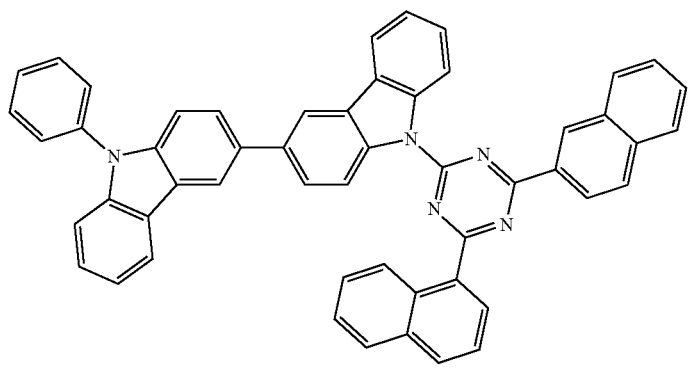

-continued
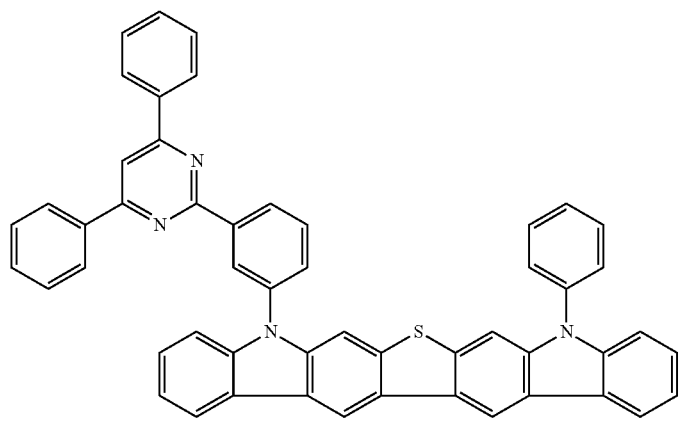
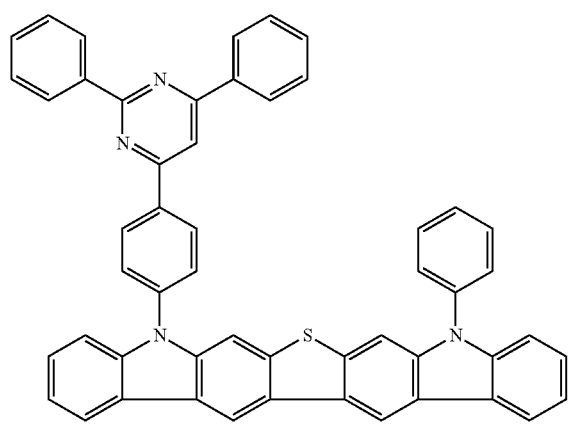
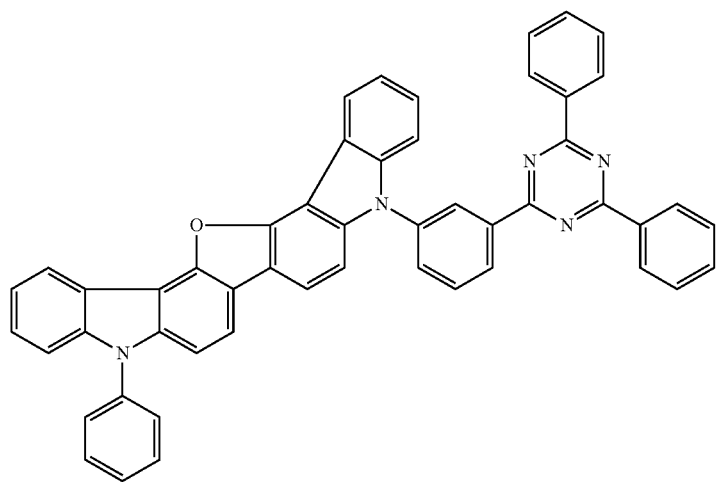

-continued
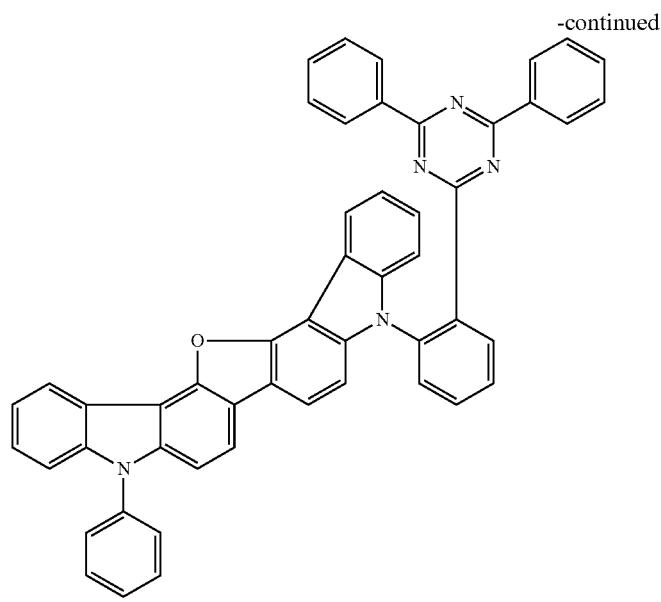
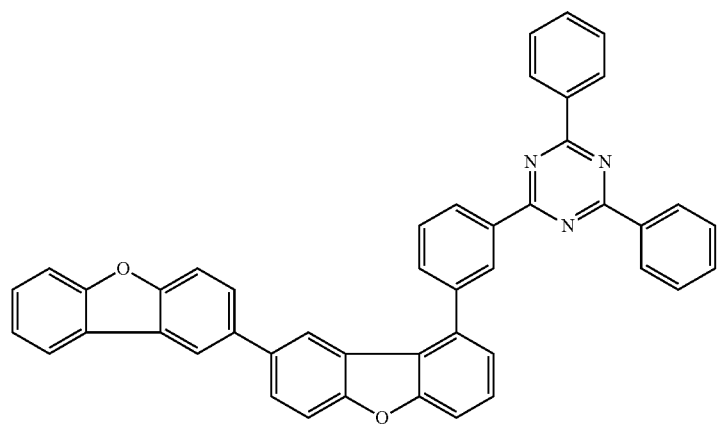
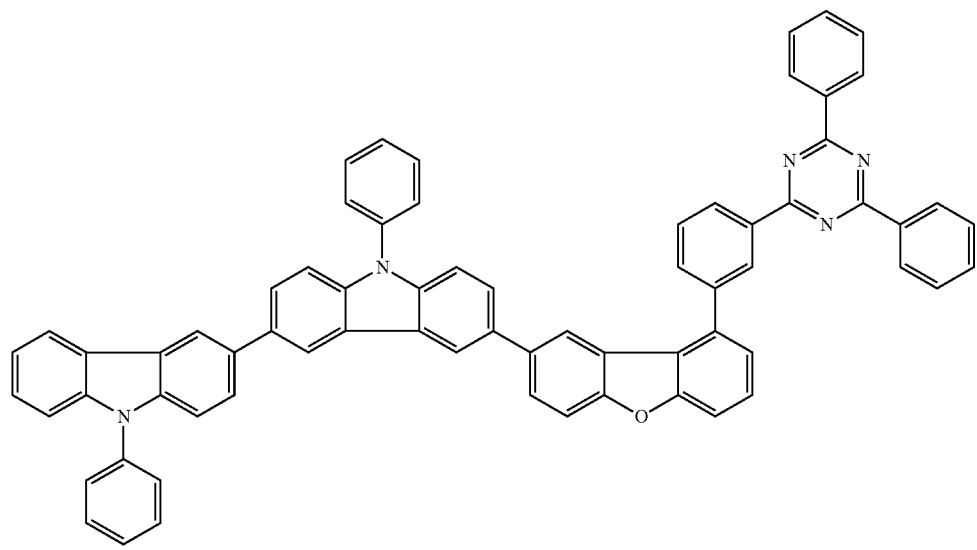

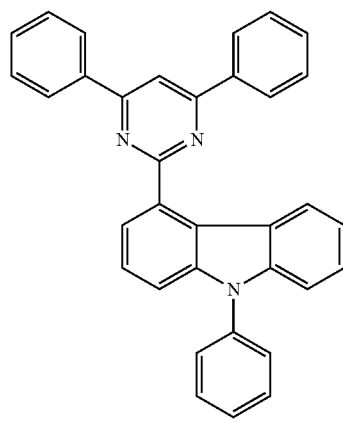
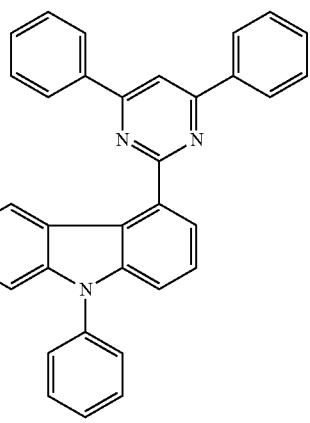
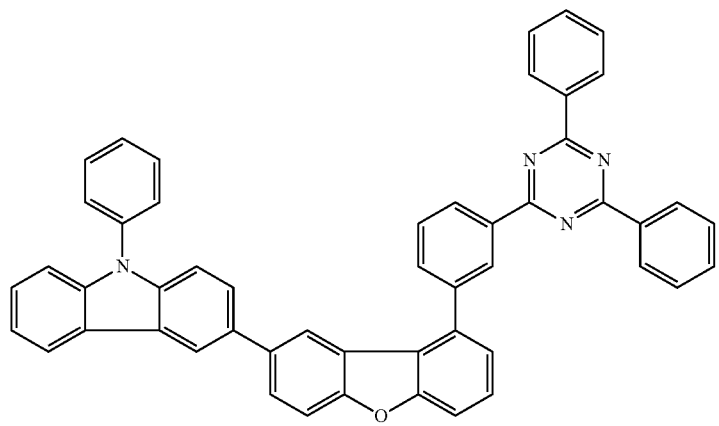
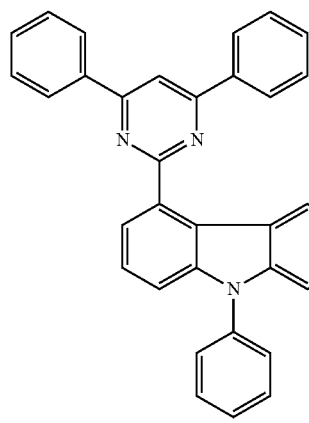
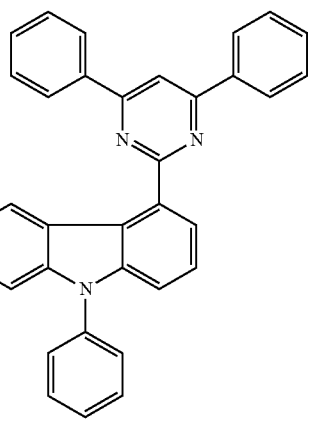
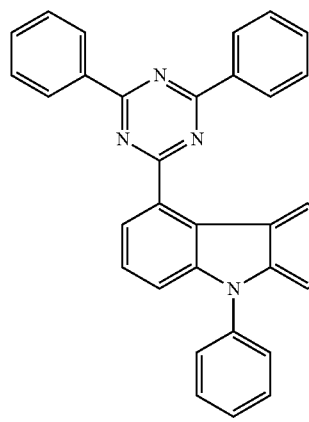
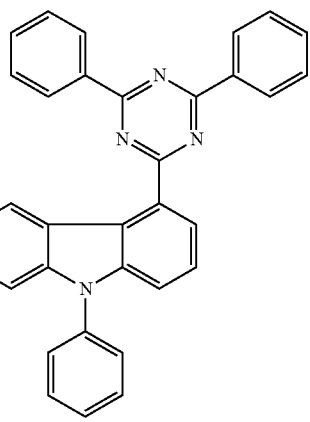

151
-continued
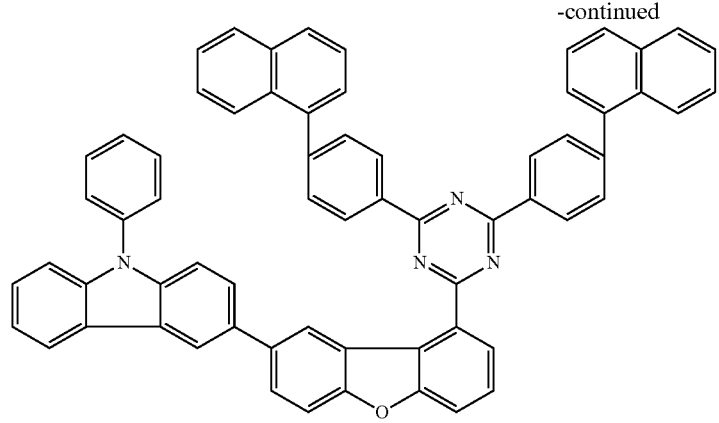
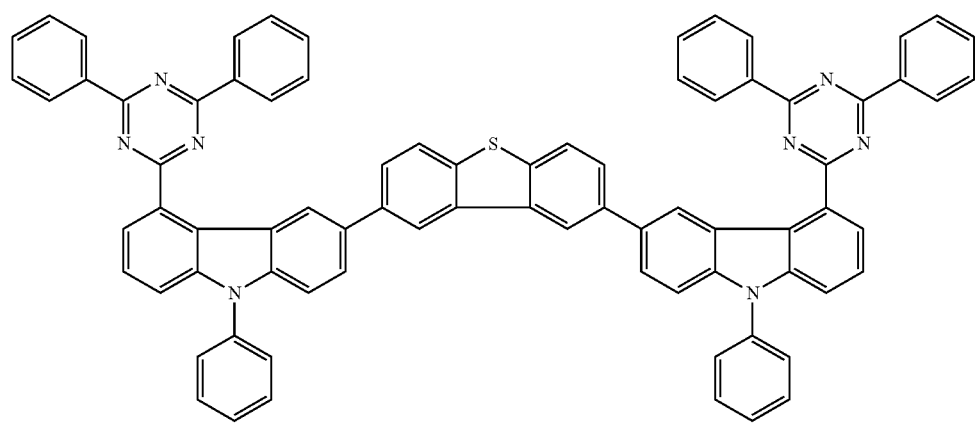
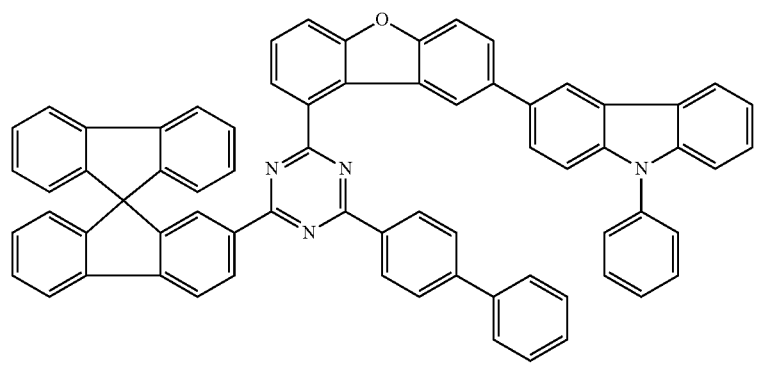
152
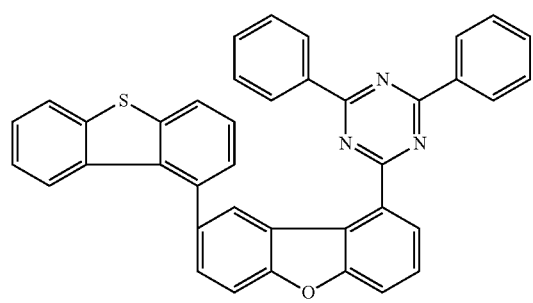

-continued
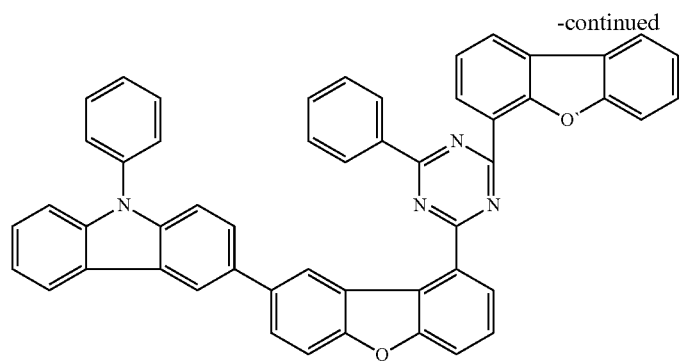
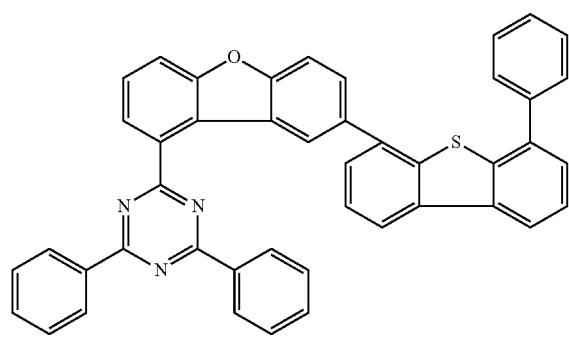
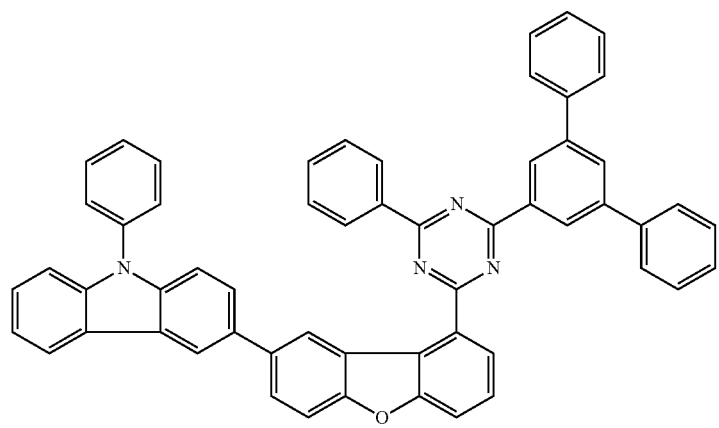
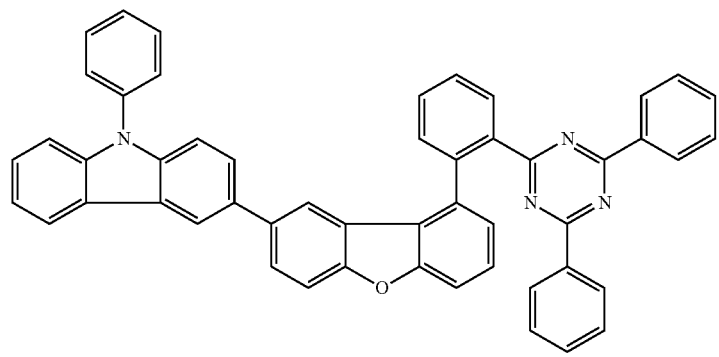

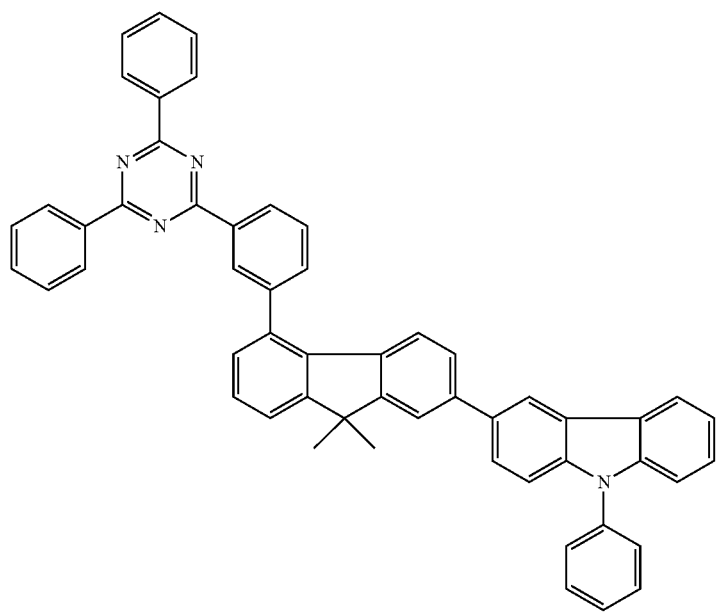
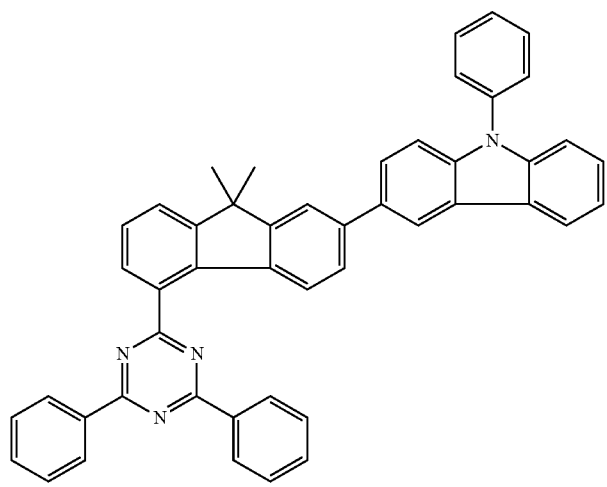
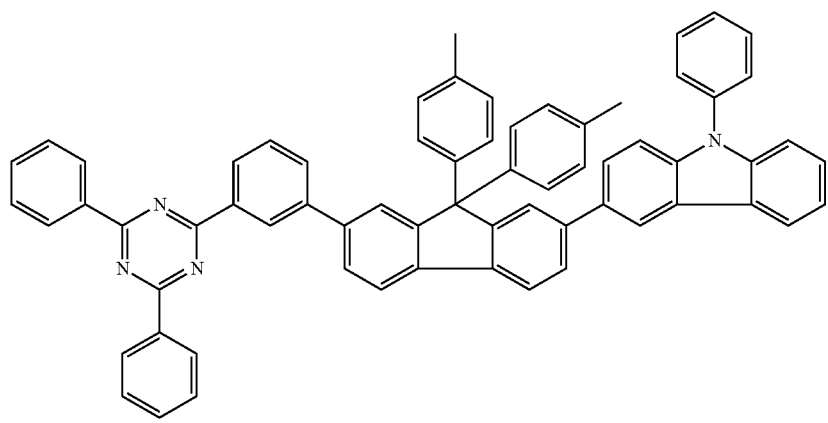

157
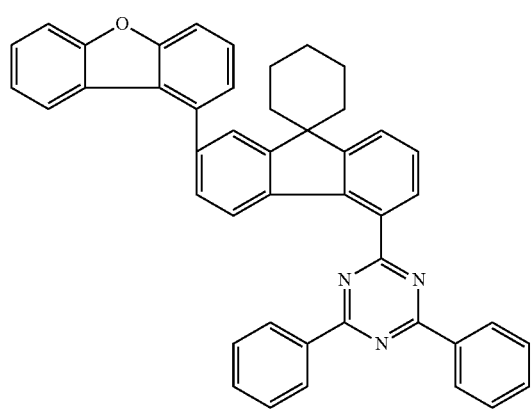
158
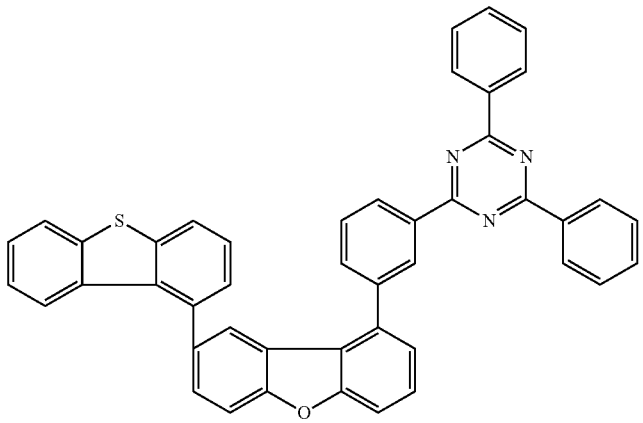
-continued
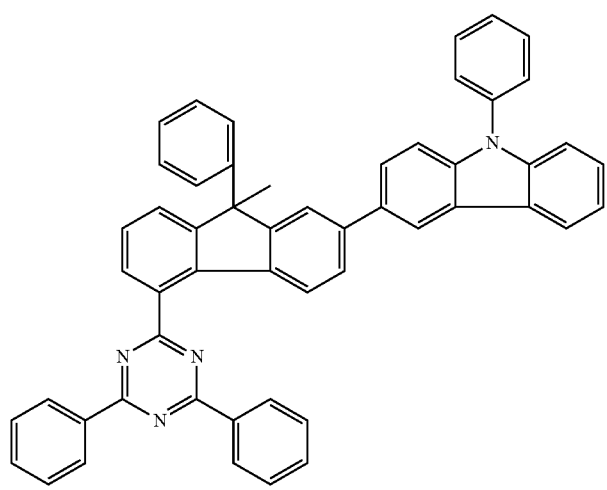
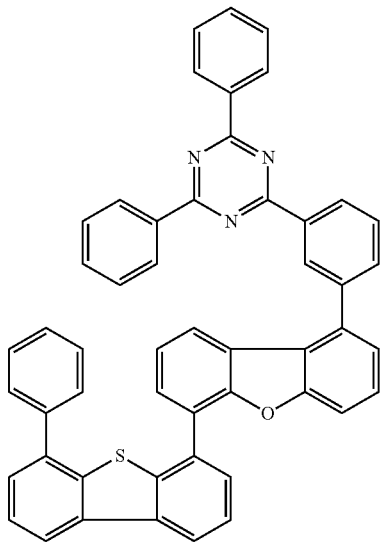
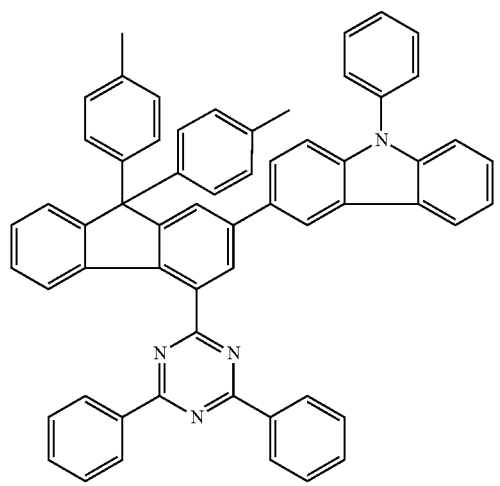

-continued
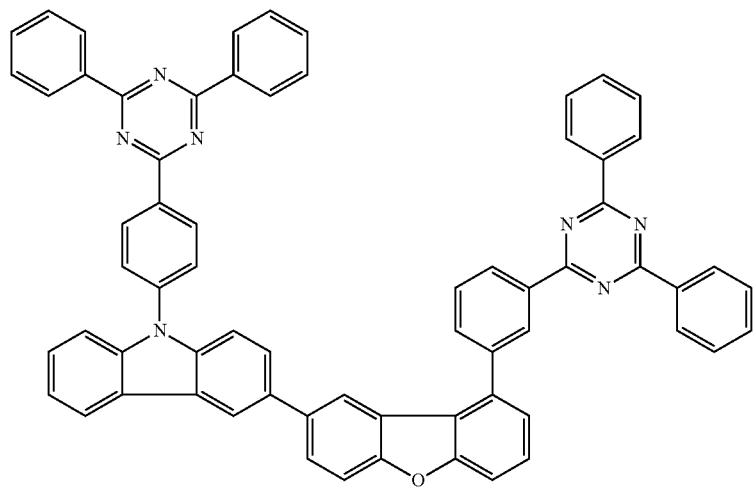
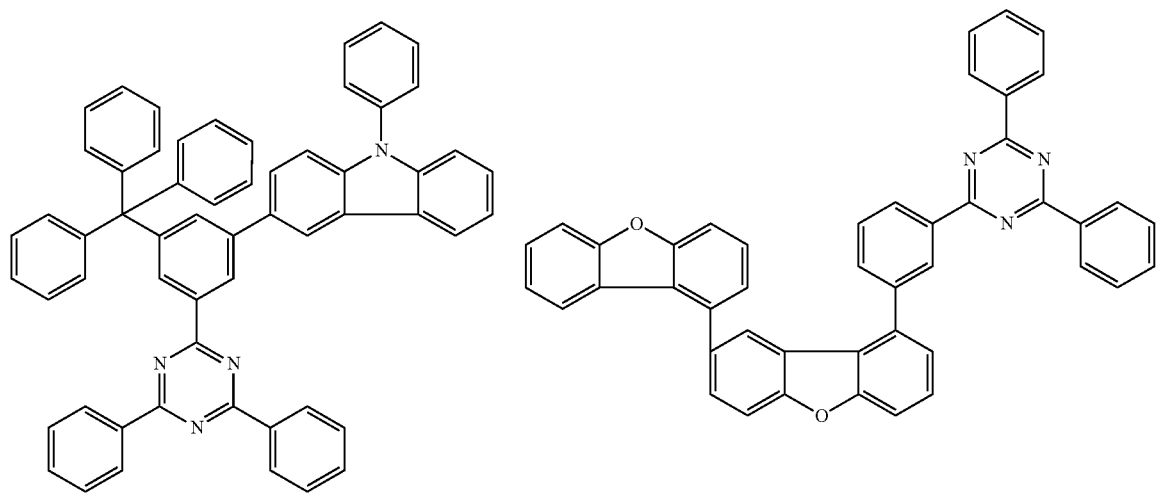
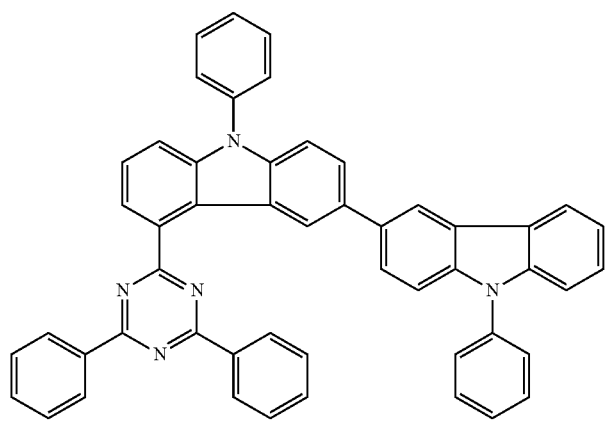

-continued
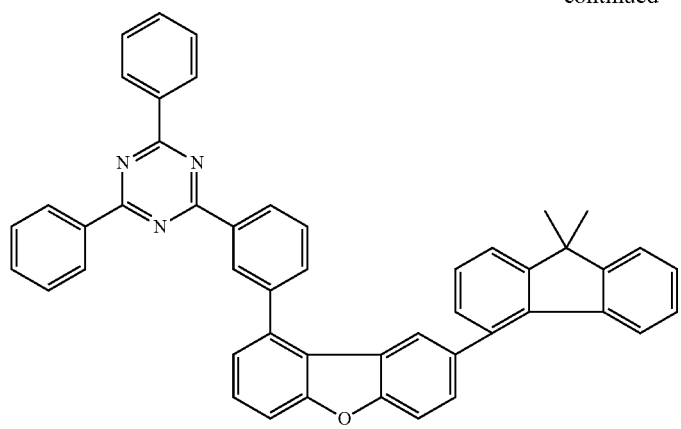
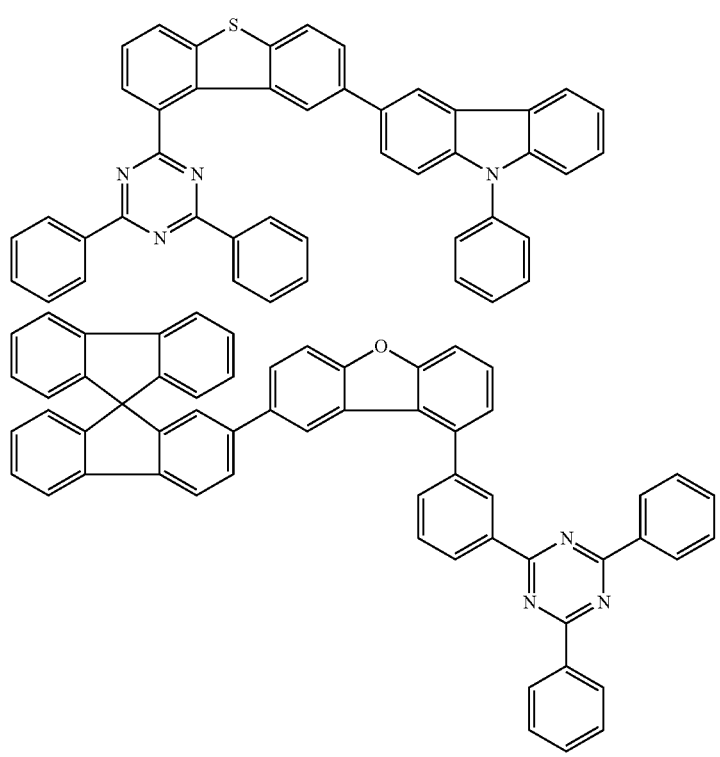
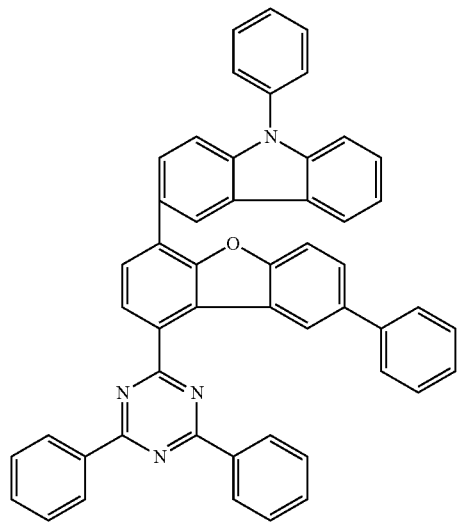

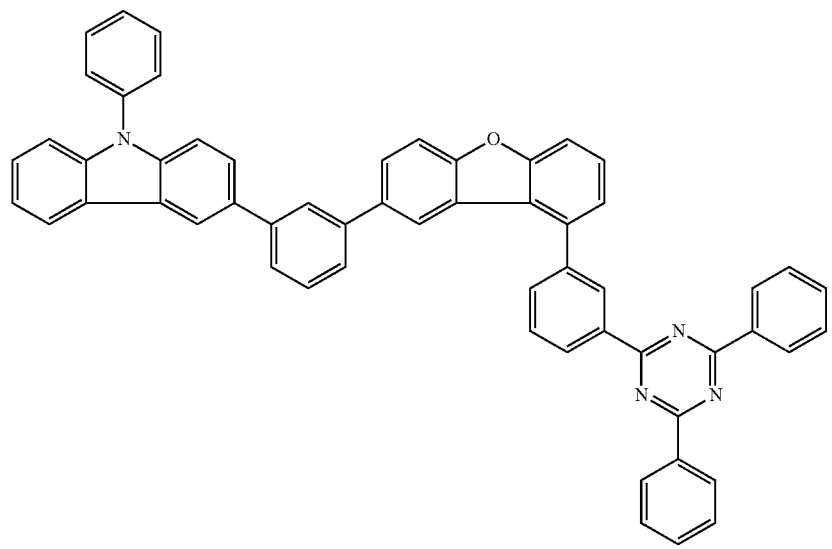

-continued
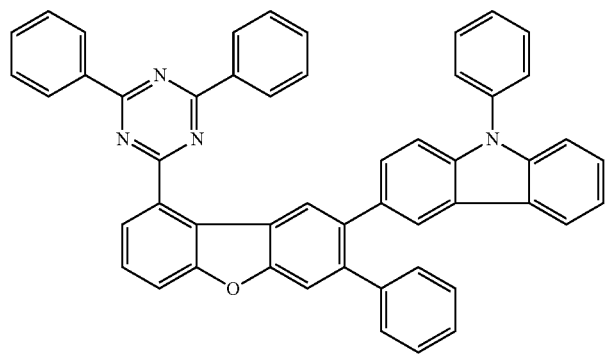
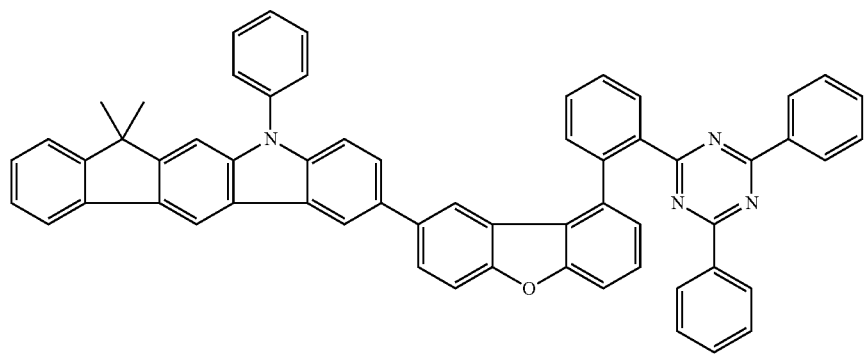
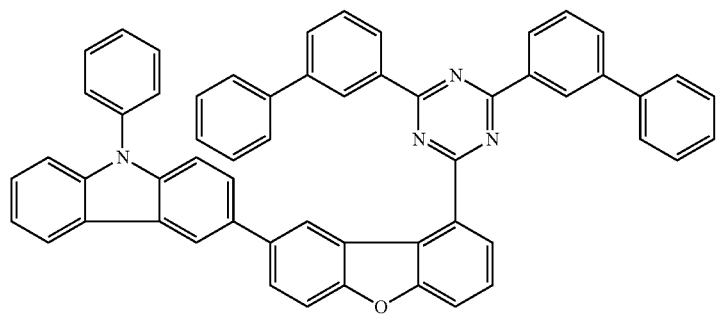
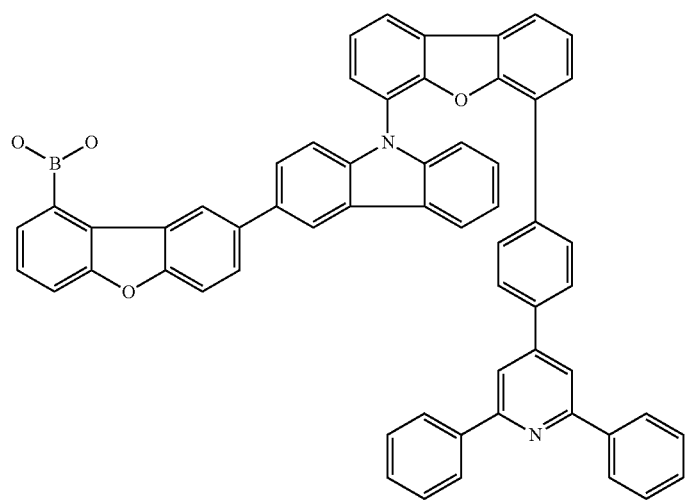

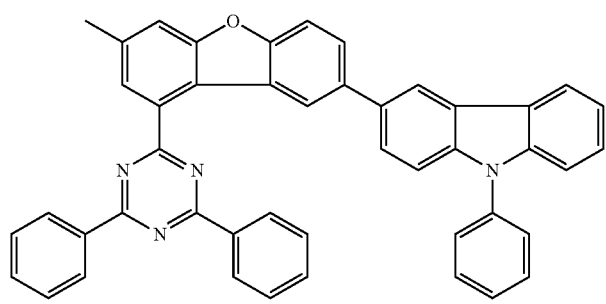
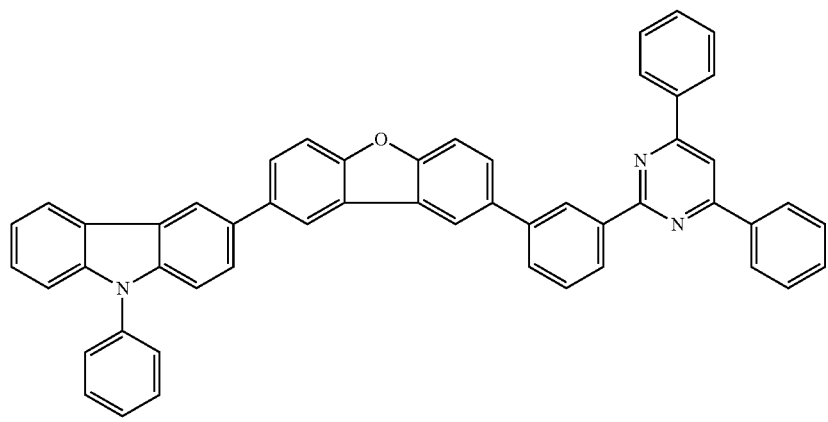
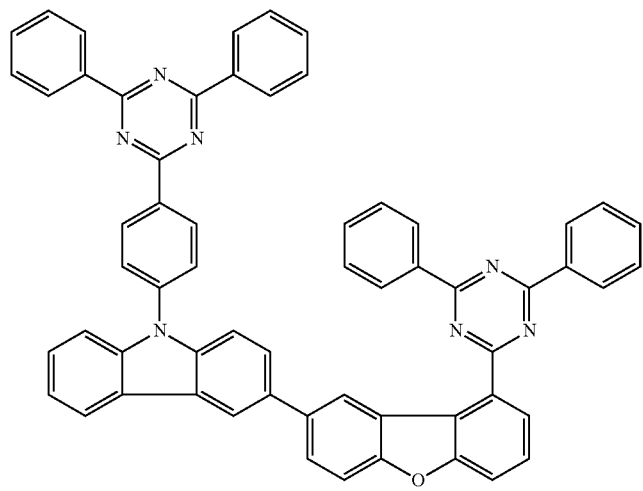
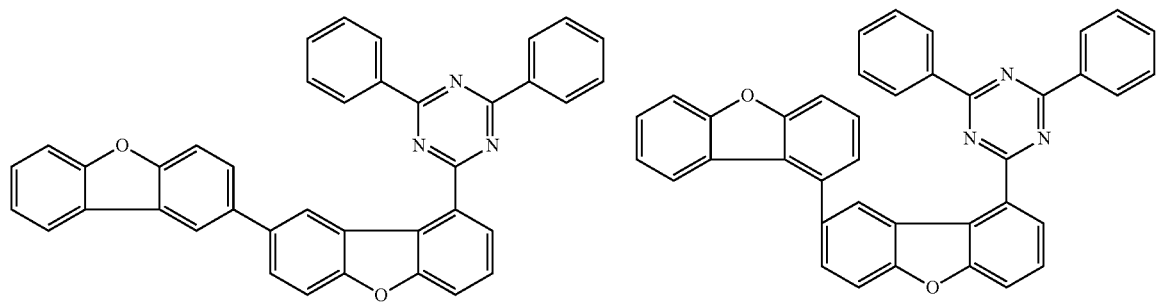

-continued
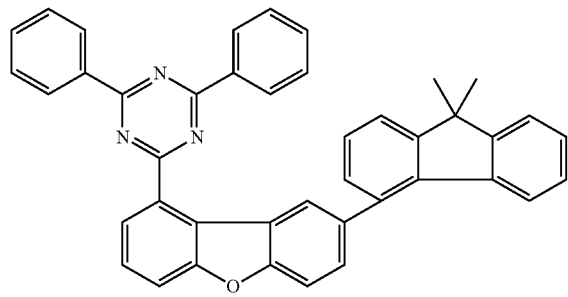
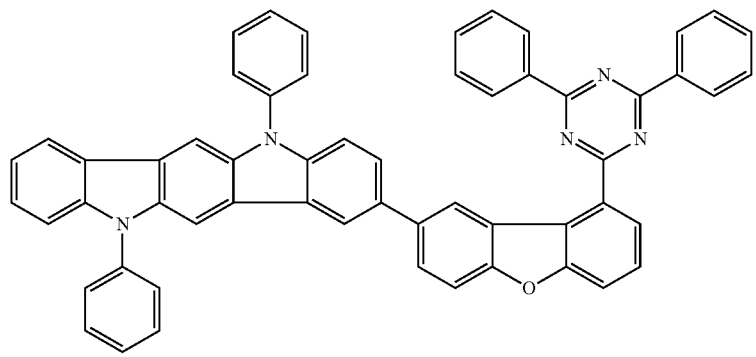
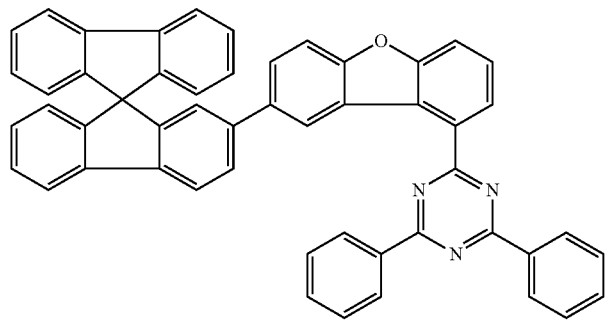
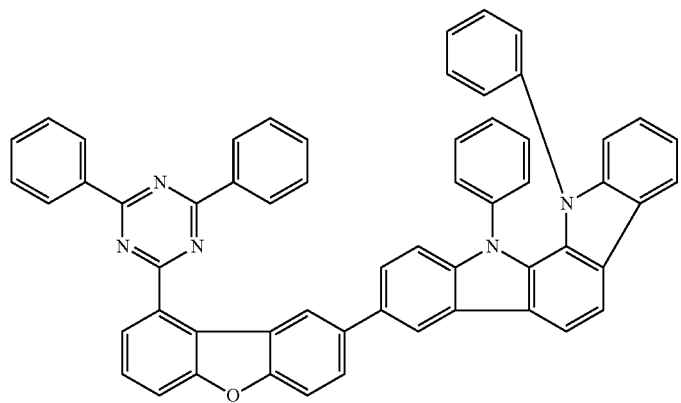

-continued
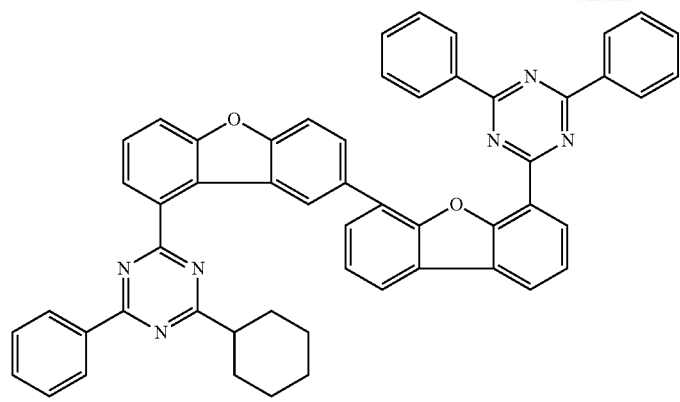
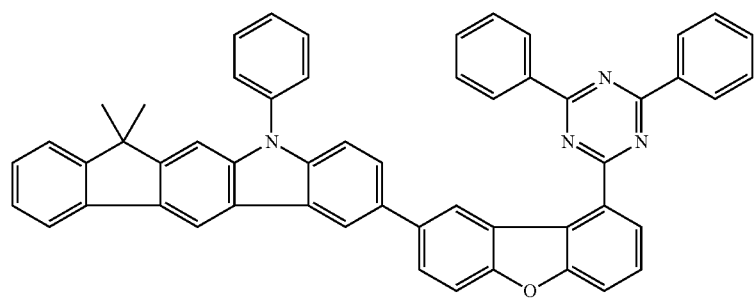
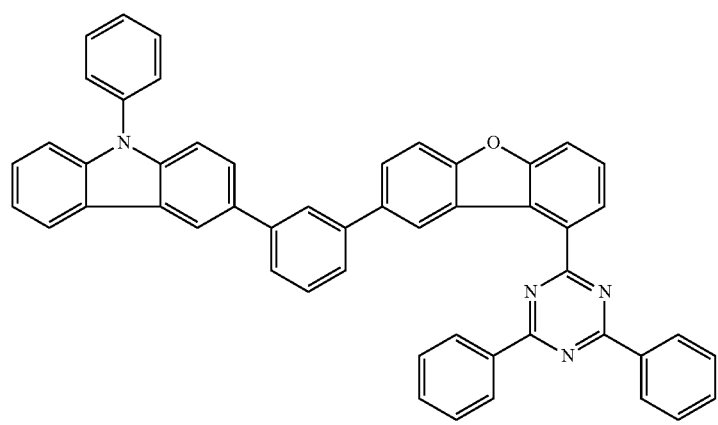
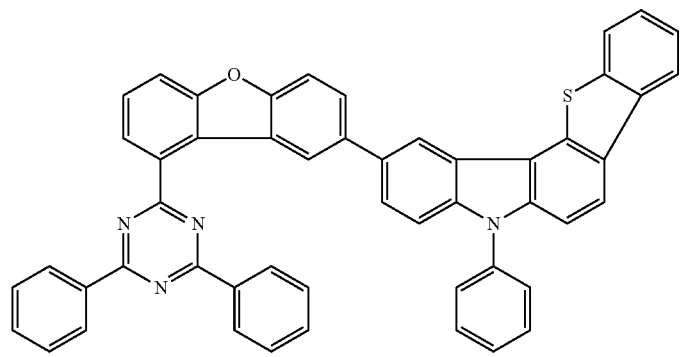

-continued
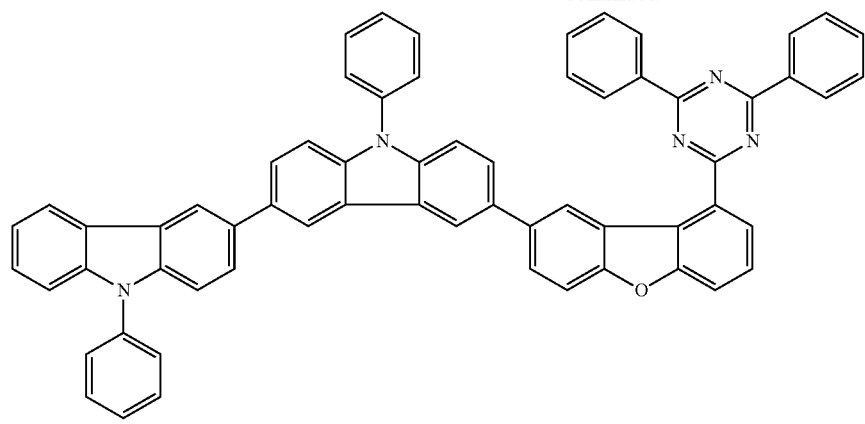
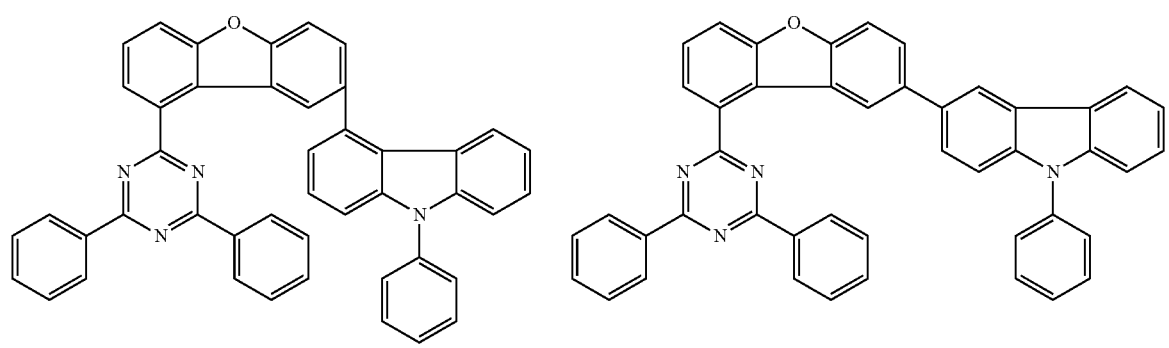
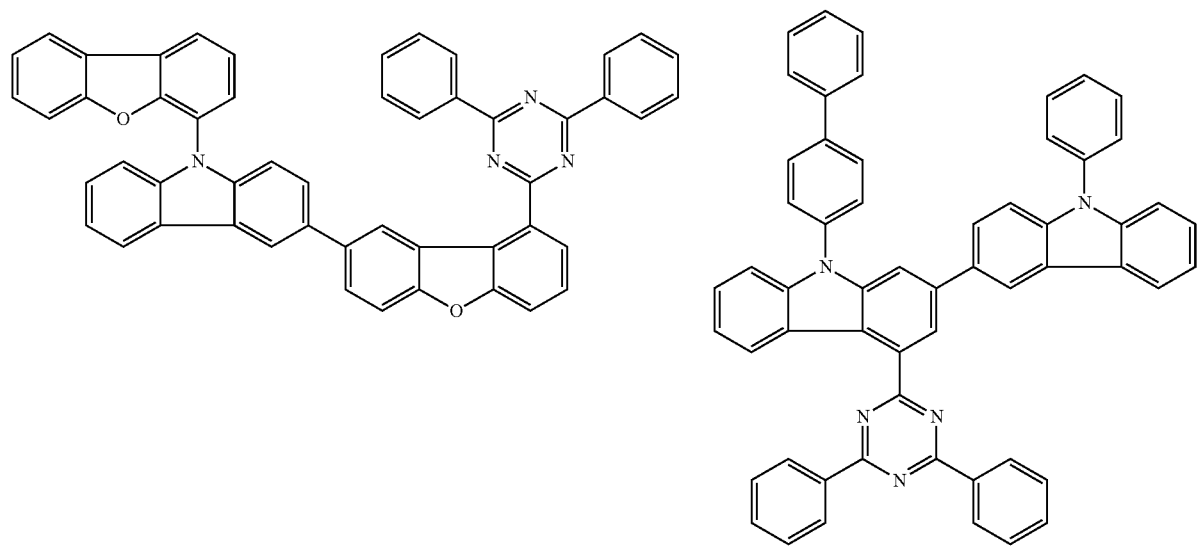

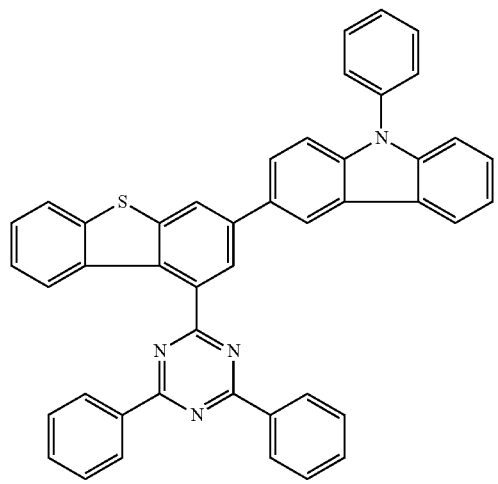
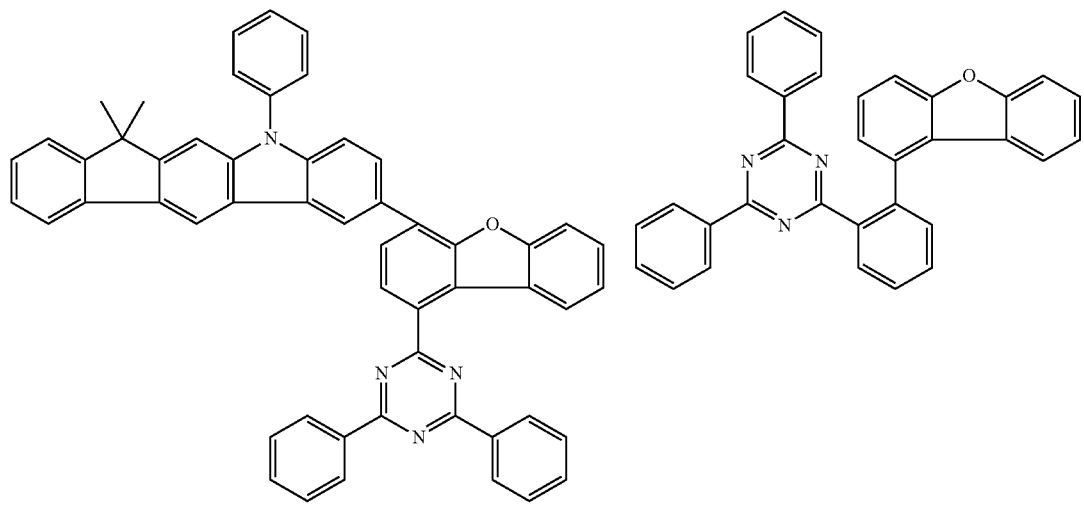
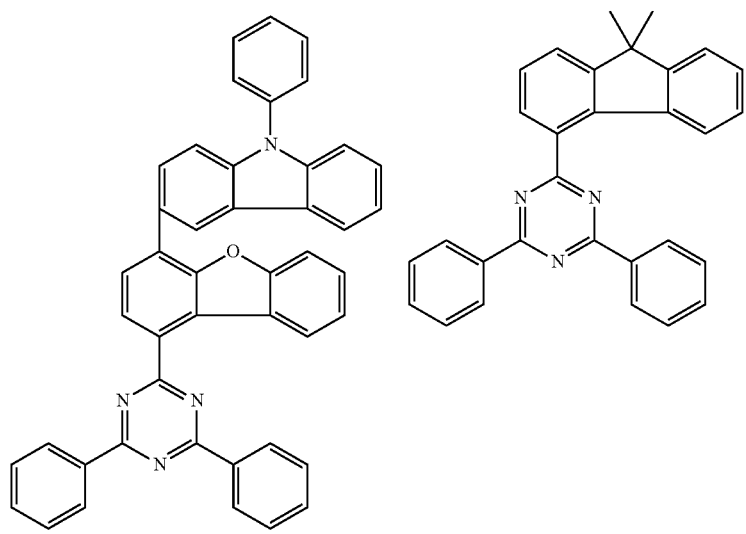

177
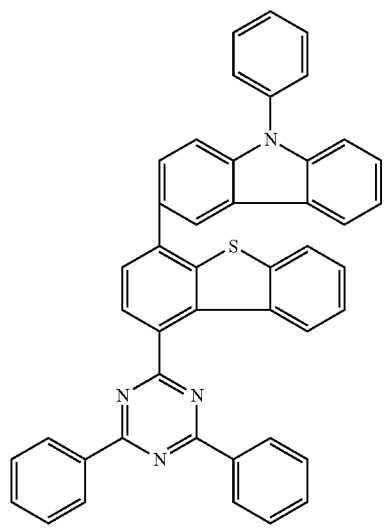
-continued
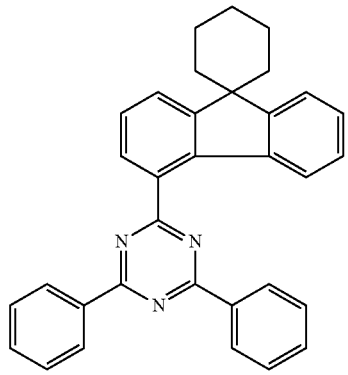
178
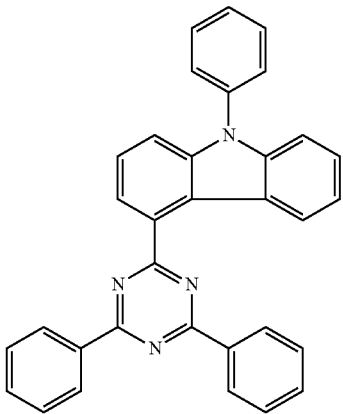
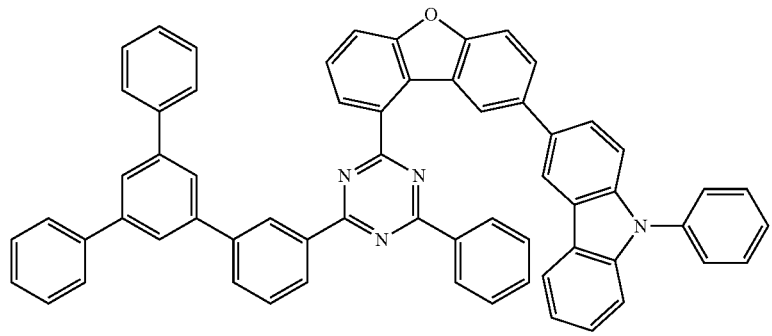
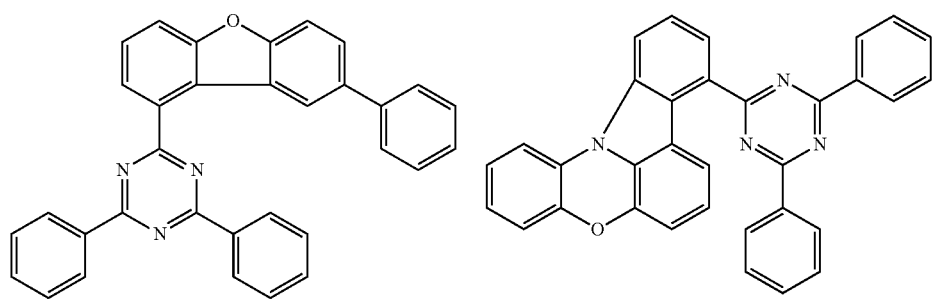
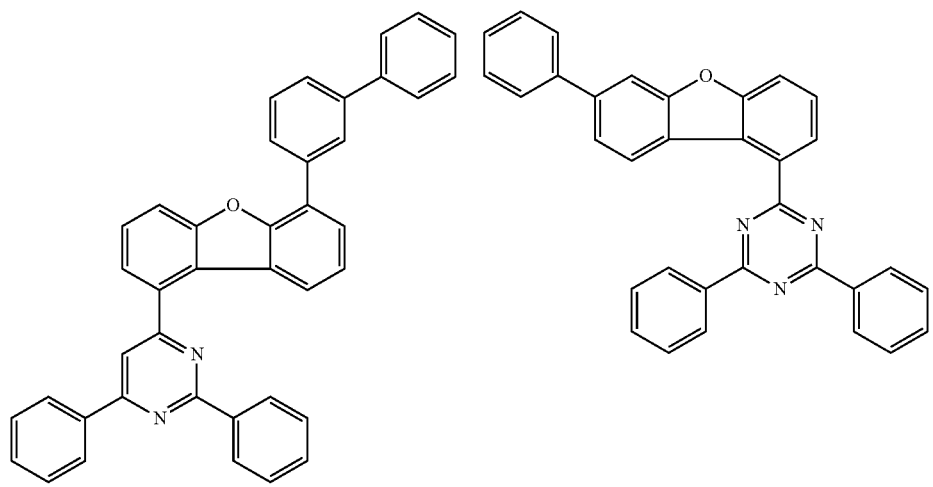

-continued
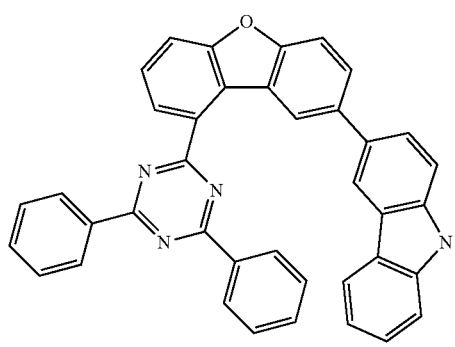 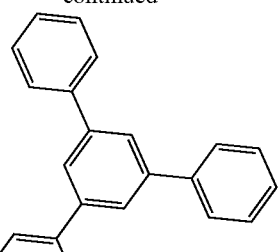 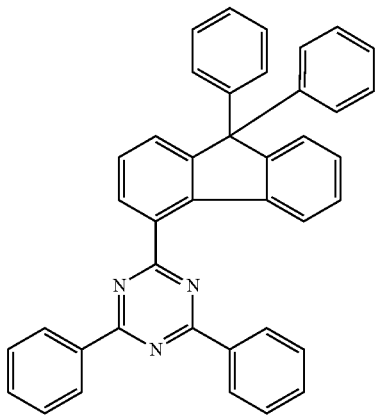
Examples of lactams which can be used as electron-transporting matrix materials are the following structures:
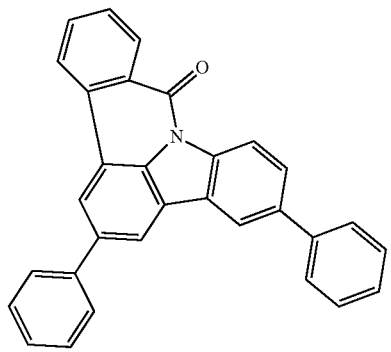
-continued
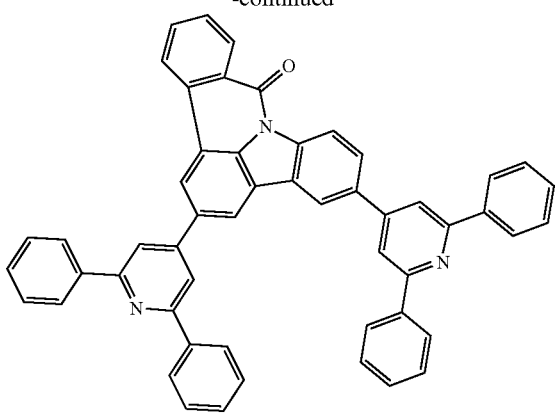
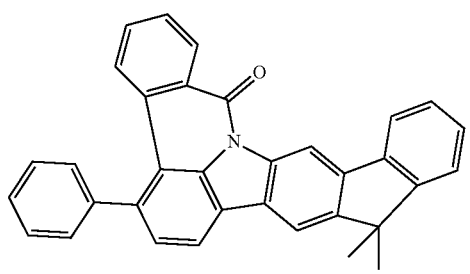
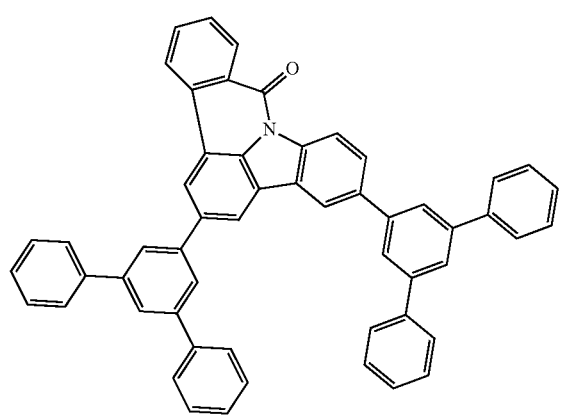
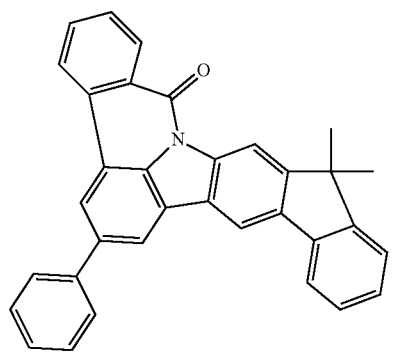

181
-continued
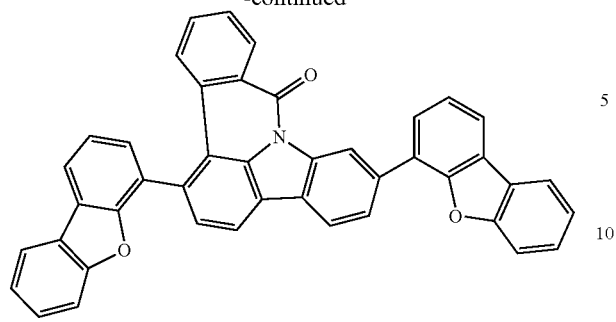
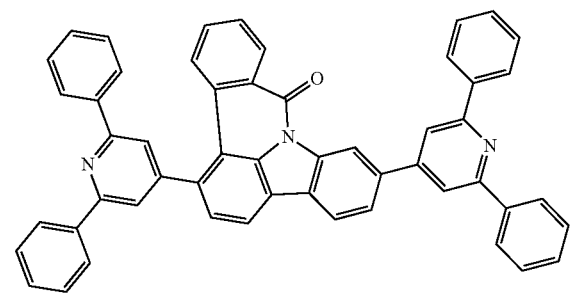
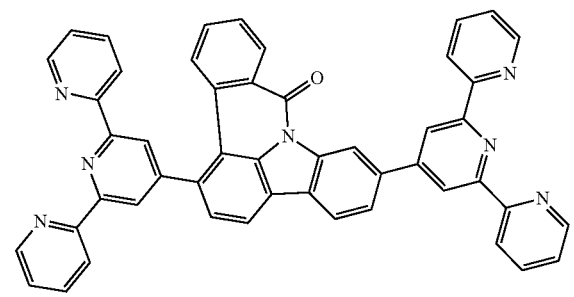
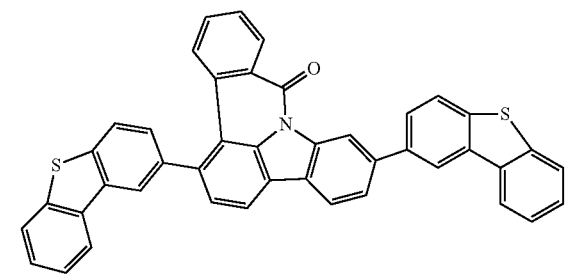
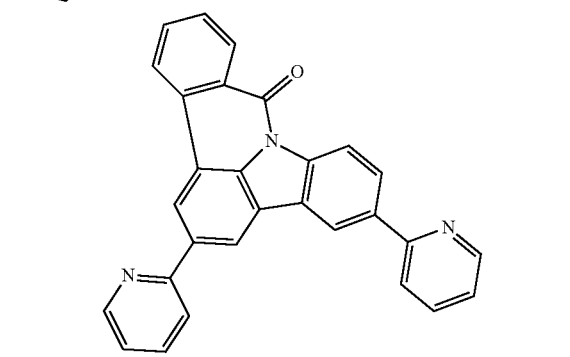
182
-continued
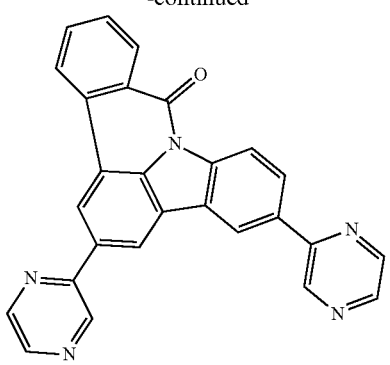
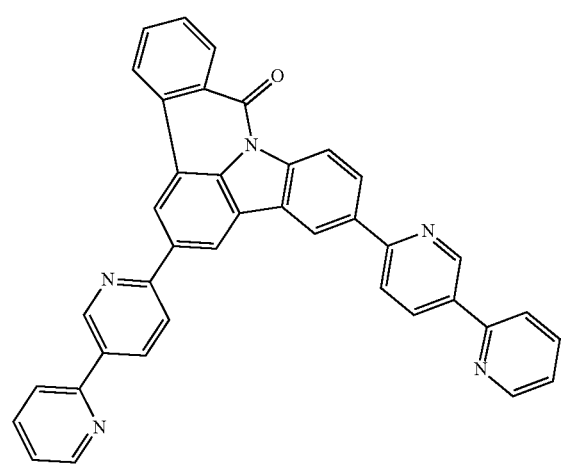
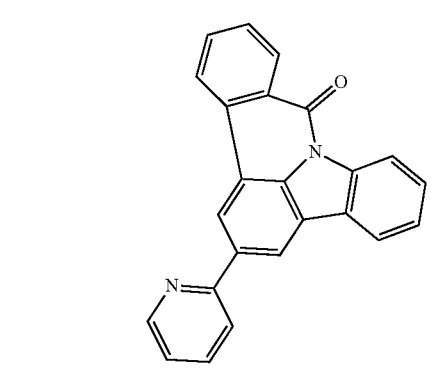
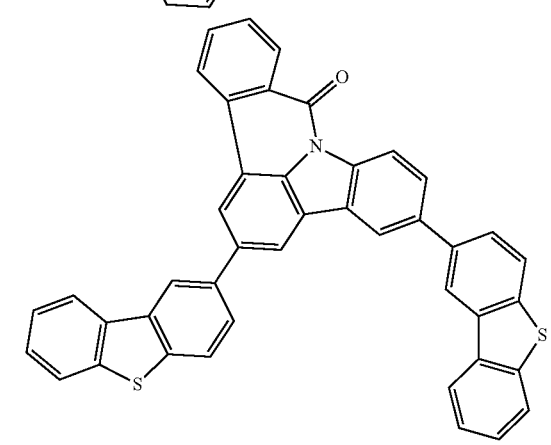

183
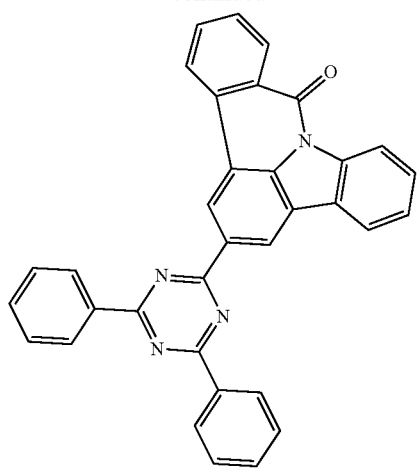
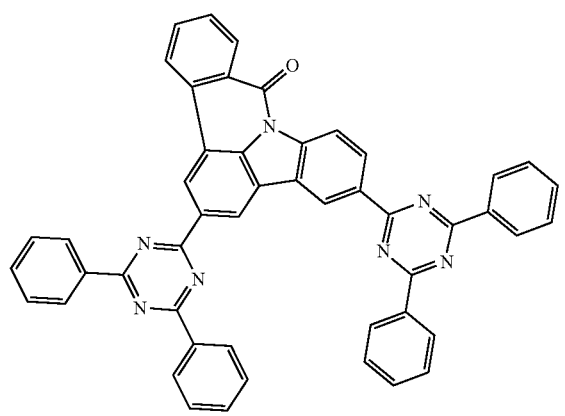
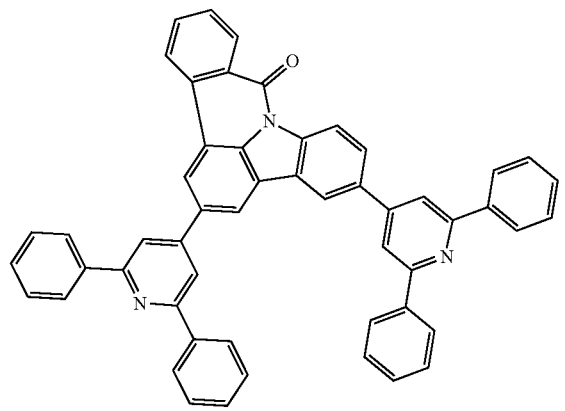
184
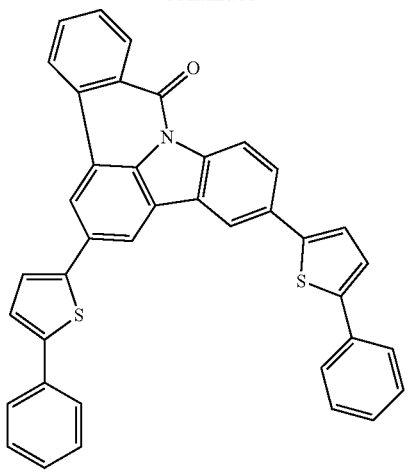
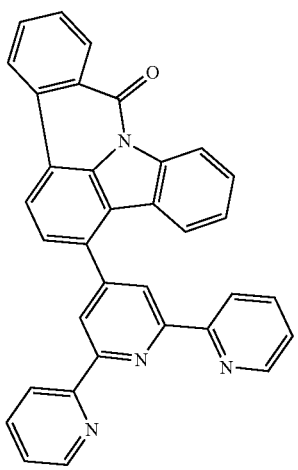
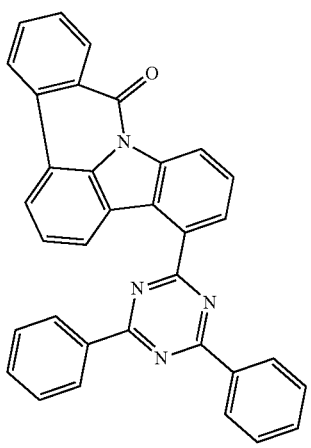

-continued
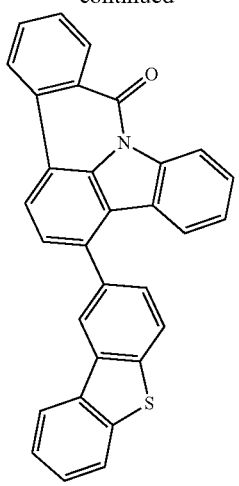
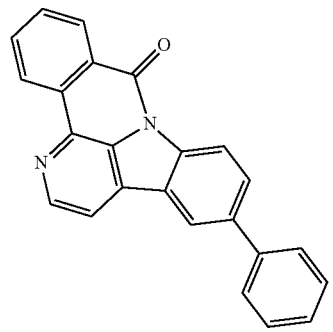
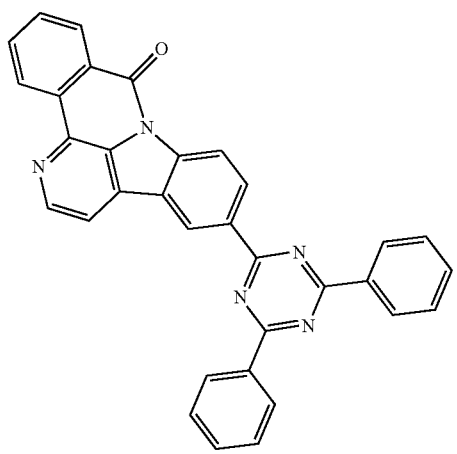
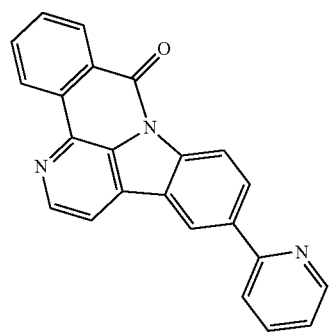
-continued
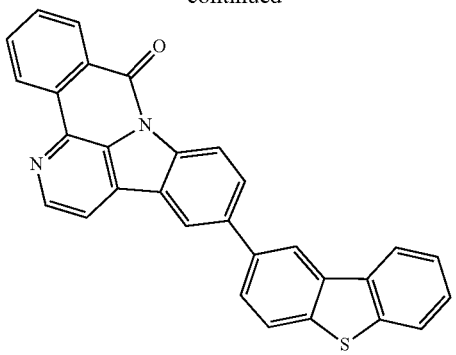
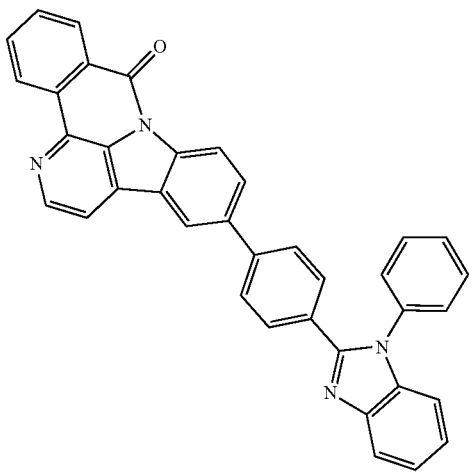
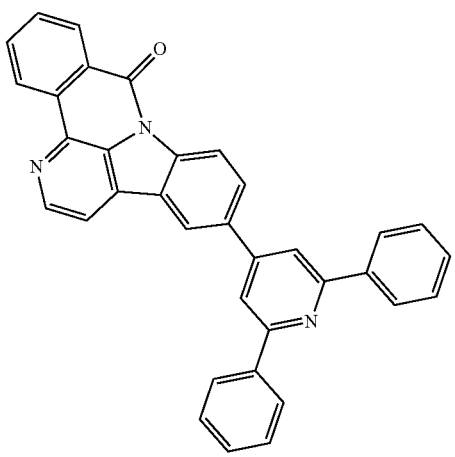

187
-continued
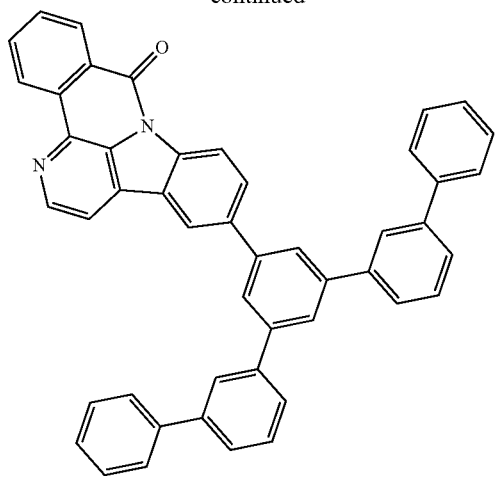
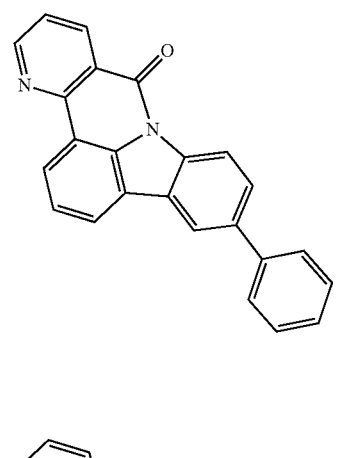
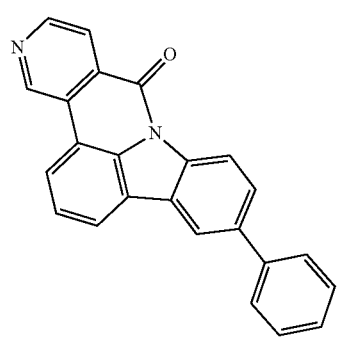
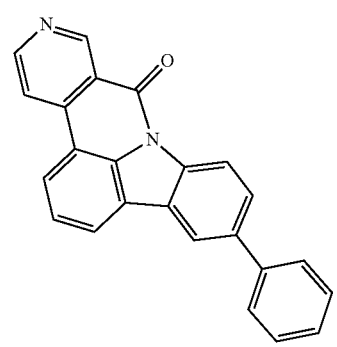
188
-continued
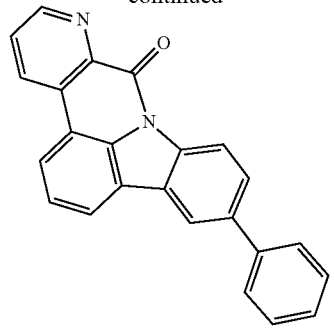
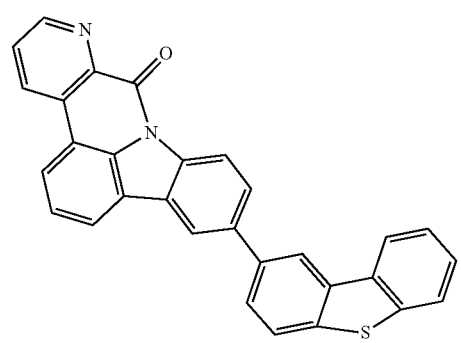
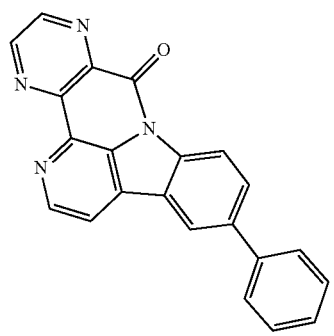
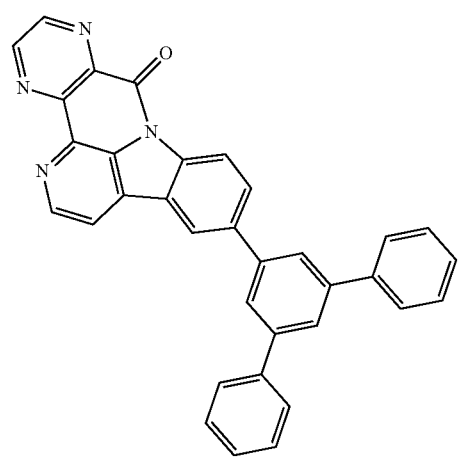

189
-continued
190
-continued
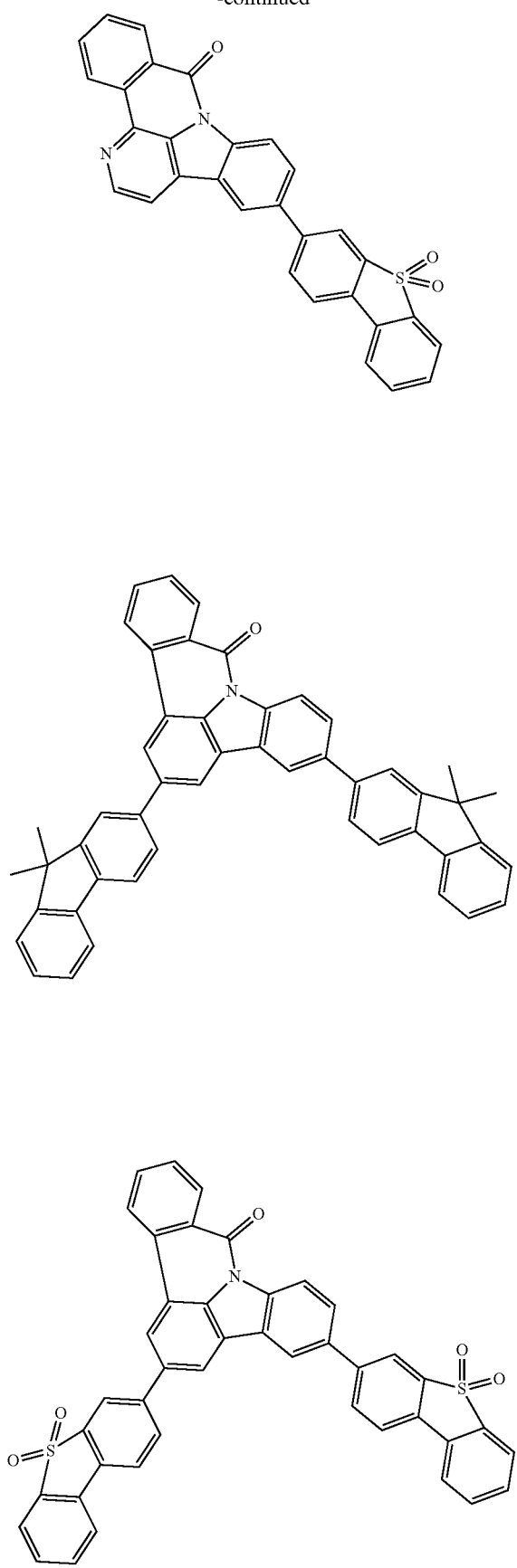
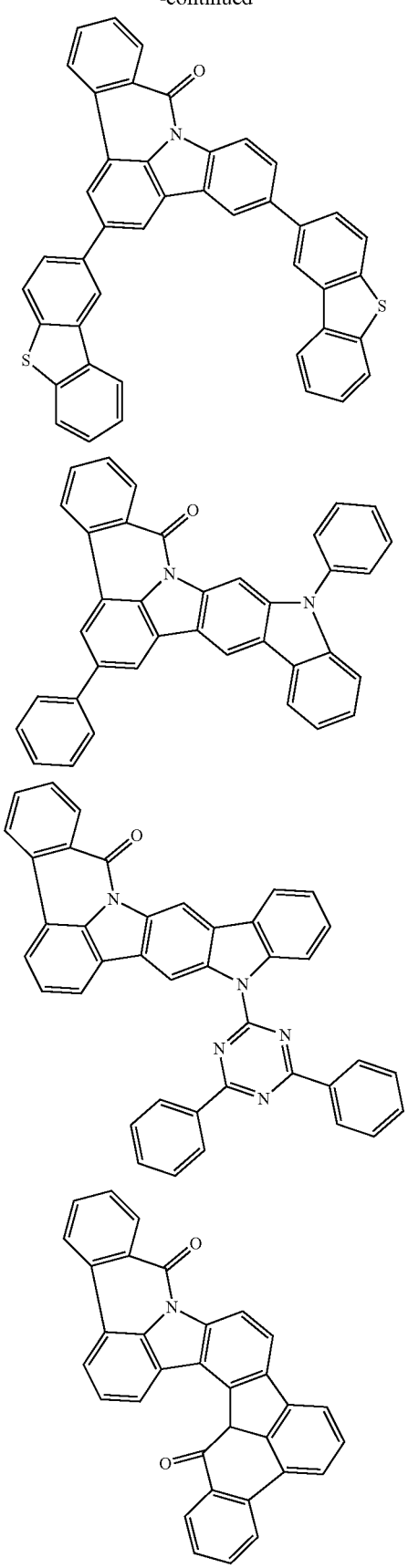

191
-continued
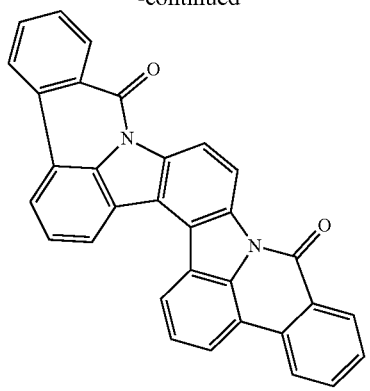
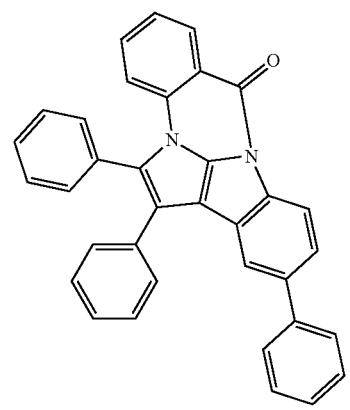
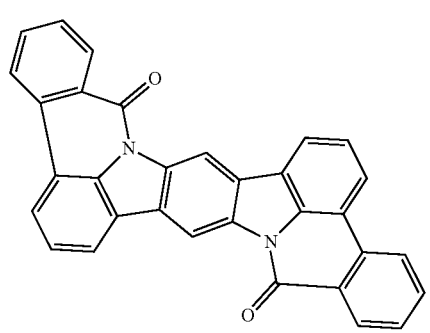
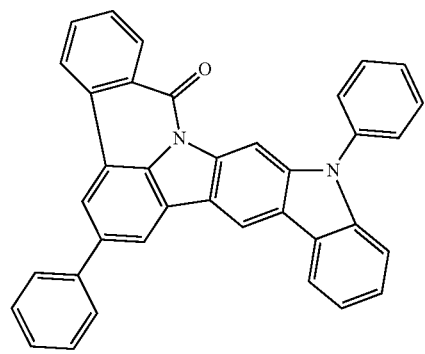
192
-continued
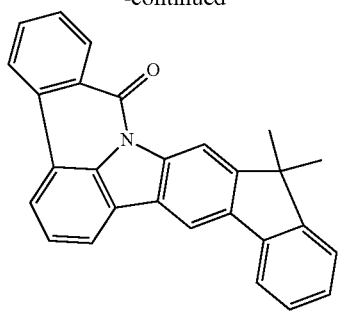
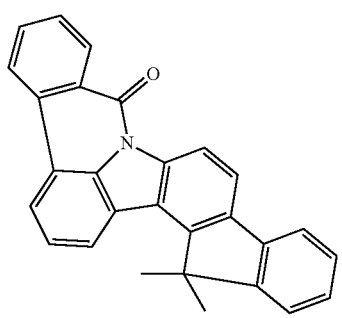
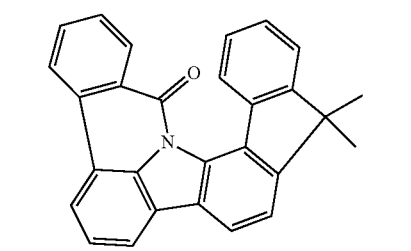
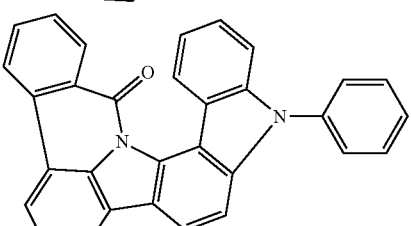
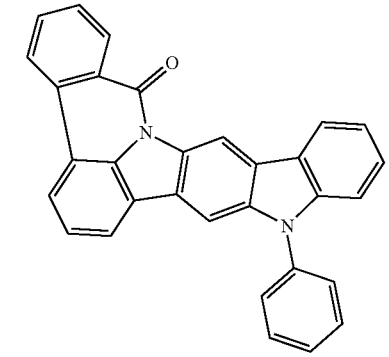

193
-continued
194
-continued
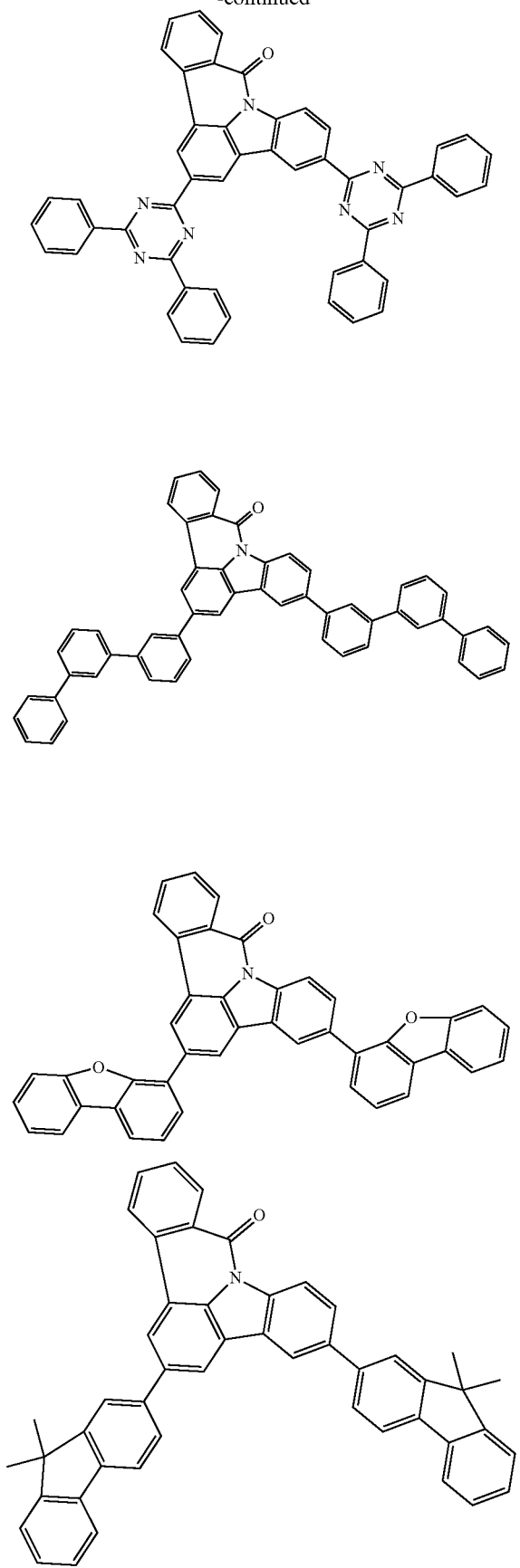
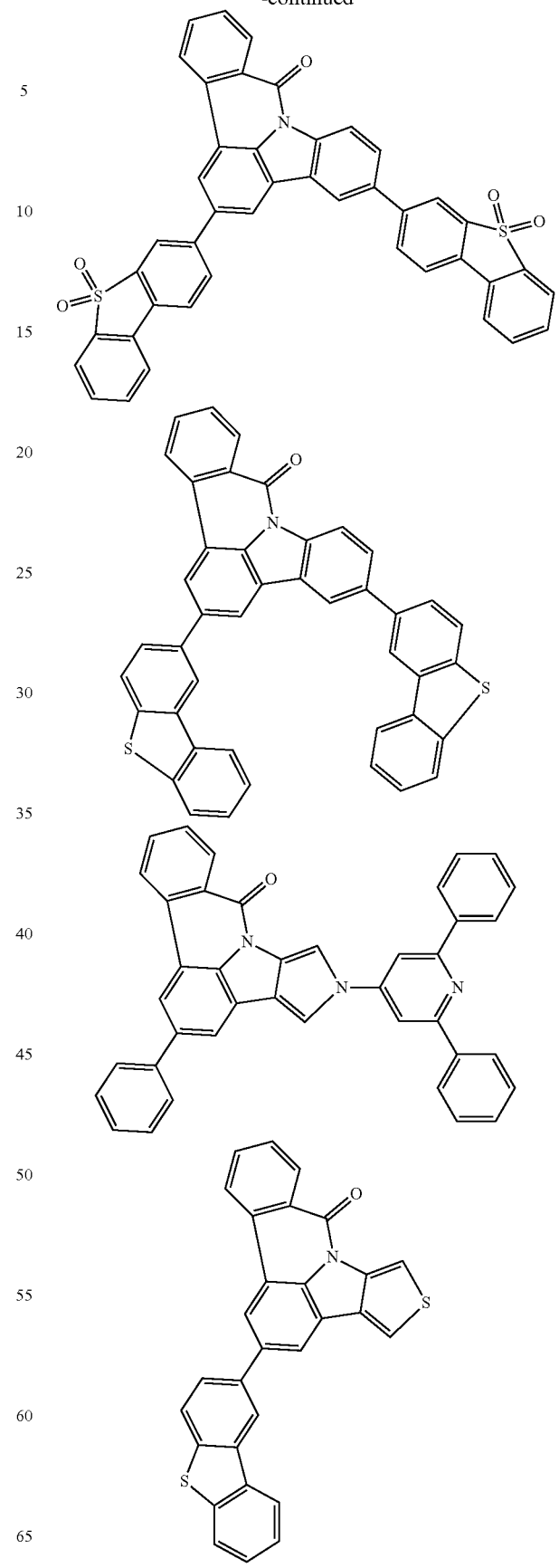

195
-continued
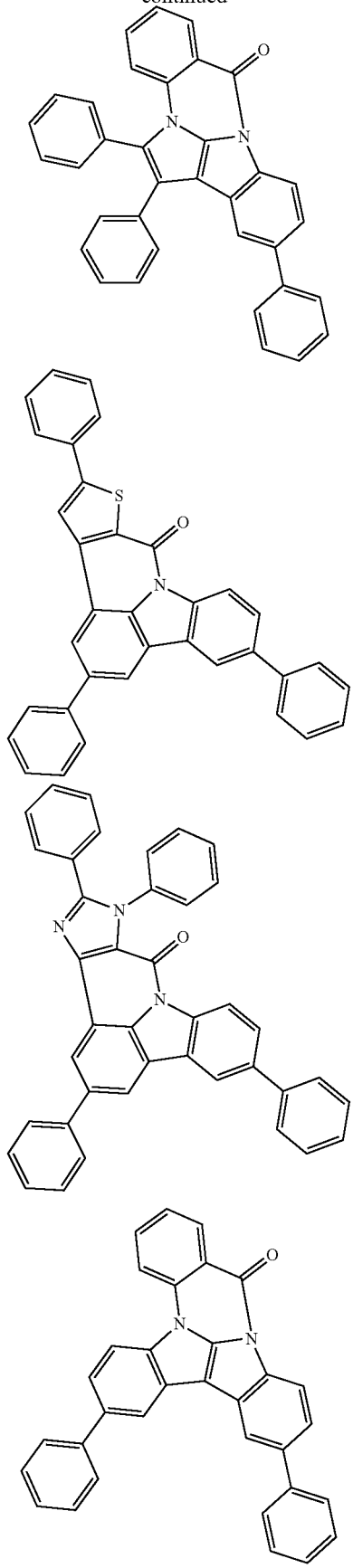
196
-continued
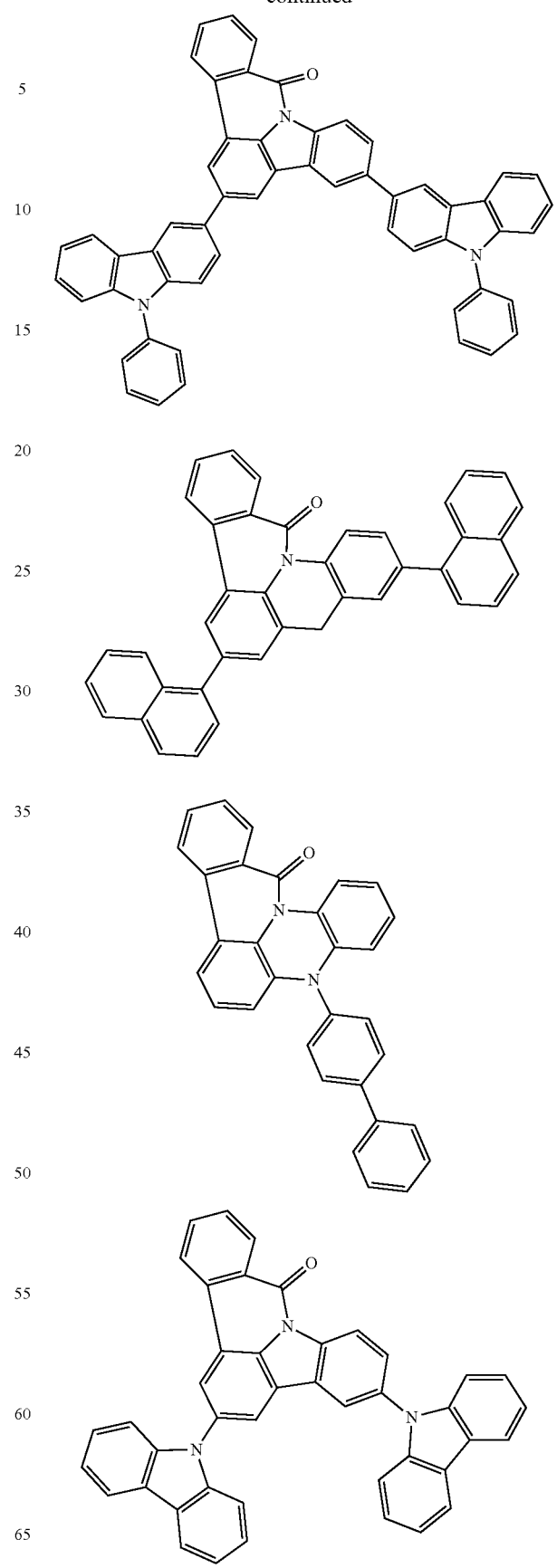

197
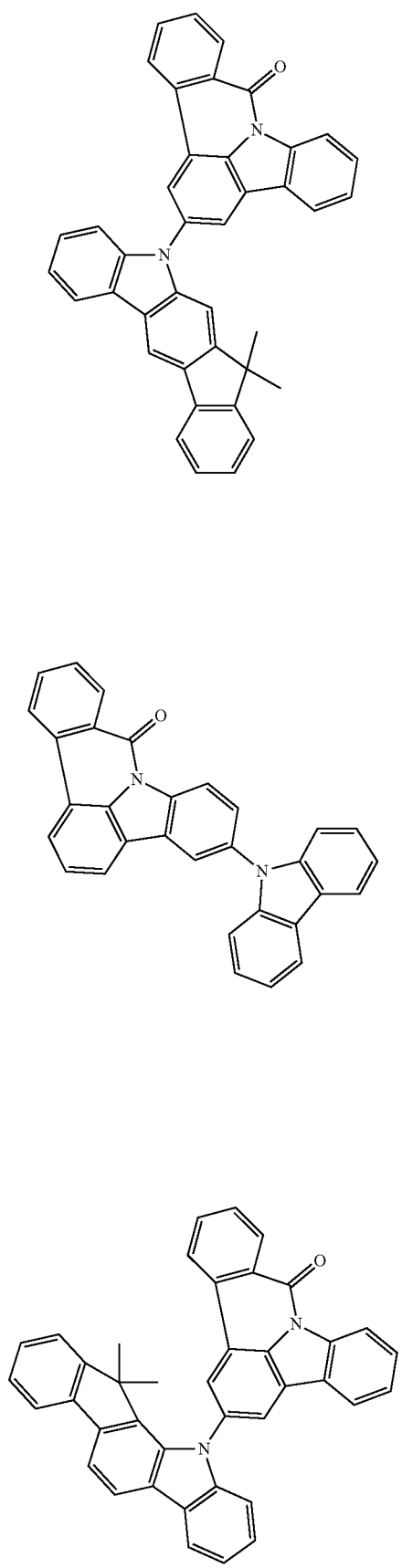
198
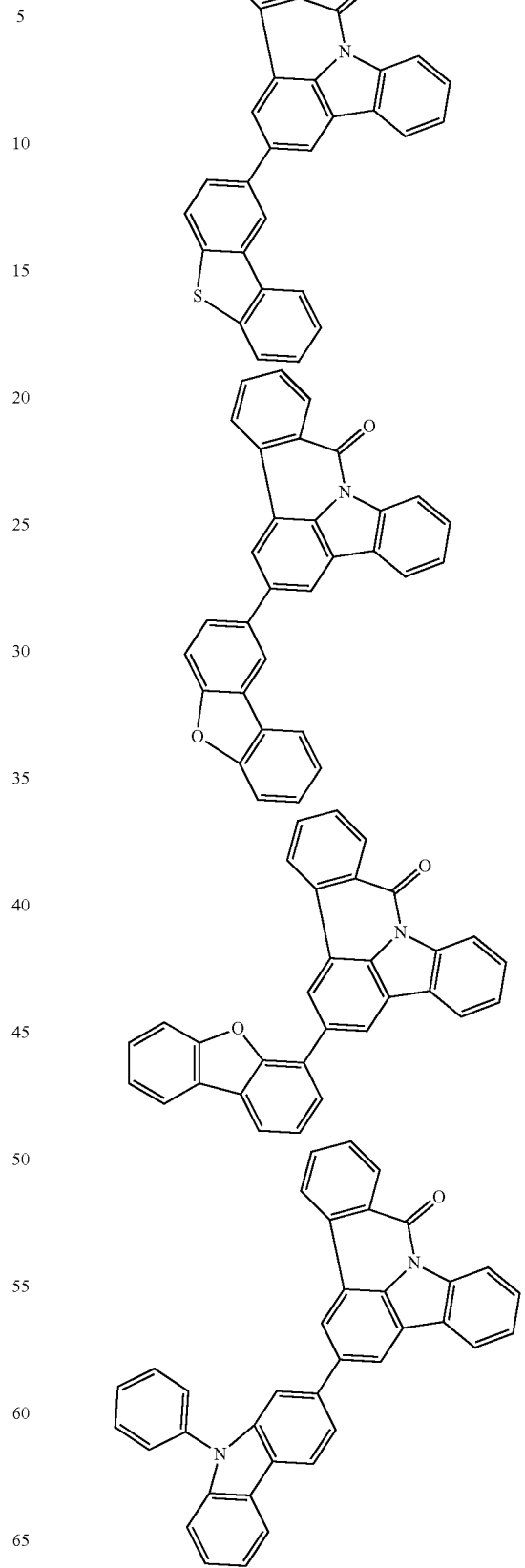

199
-continued
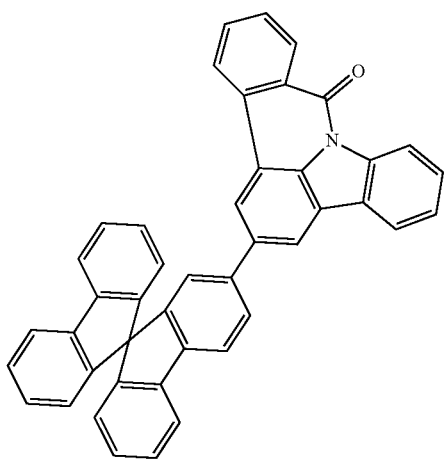
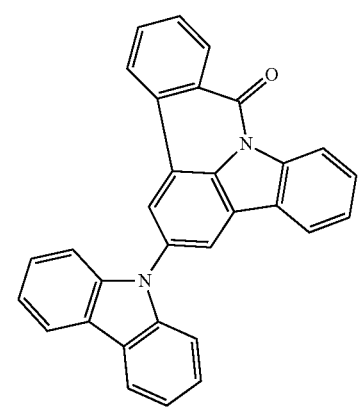
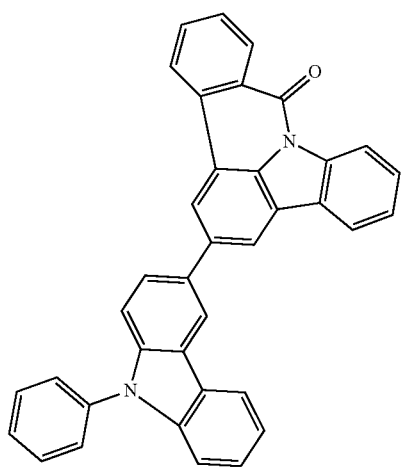
200
-continued
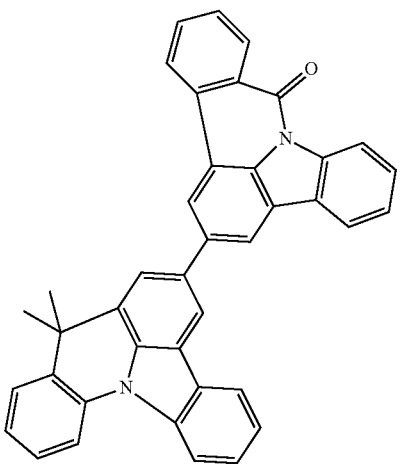
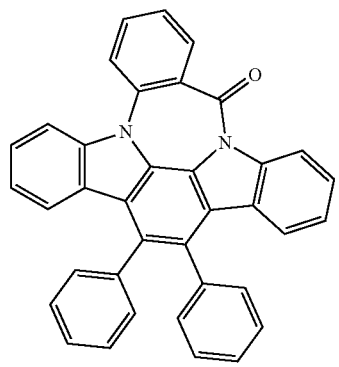
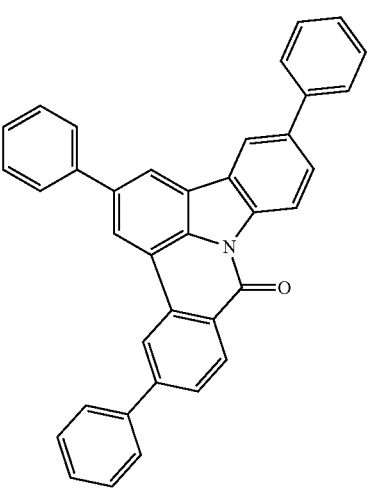
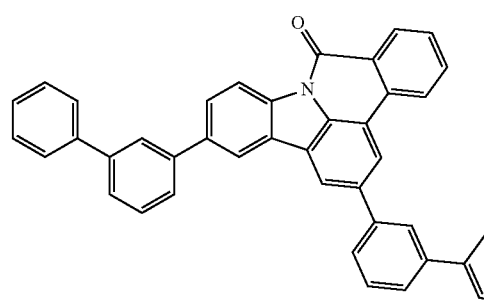

201
-continued
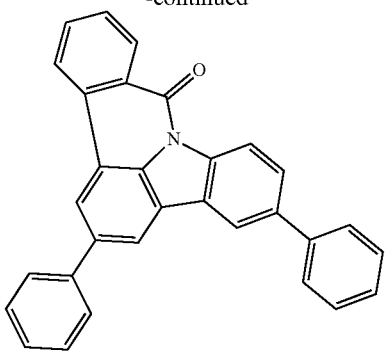
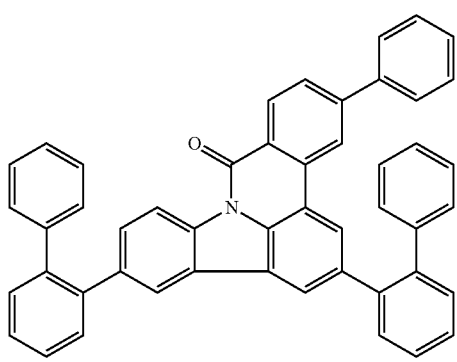
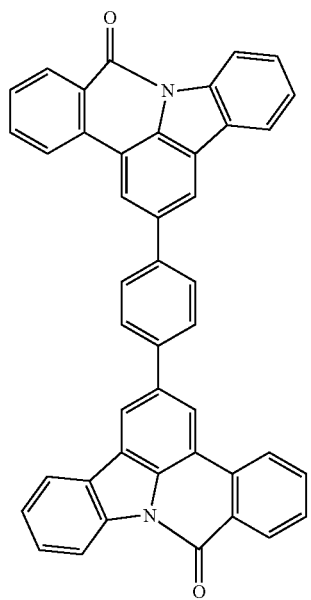
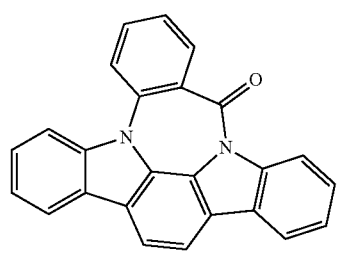
202
-continued
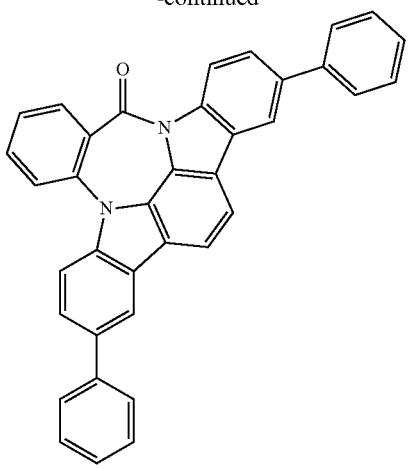
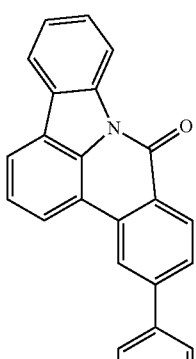
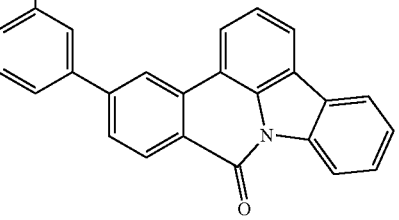
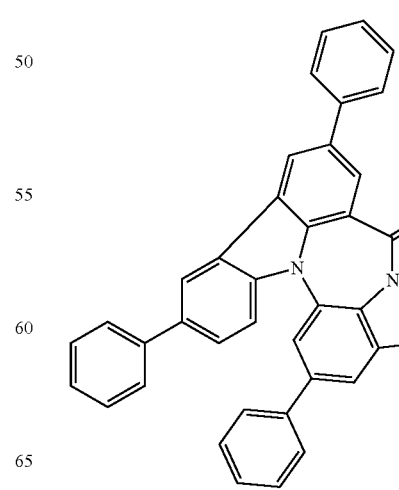

203
-continued
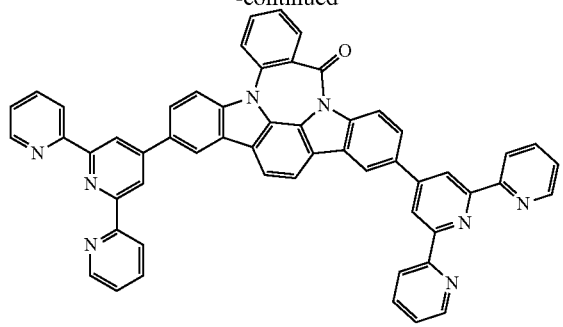
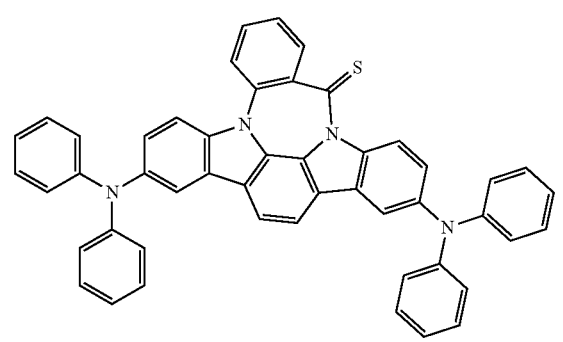
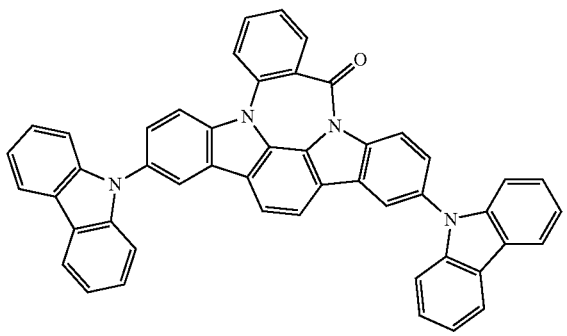
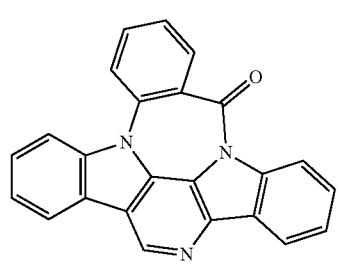
204
-continued
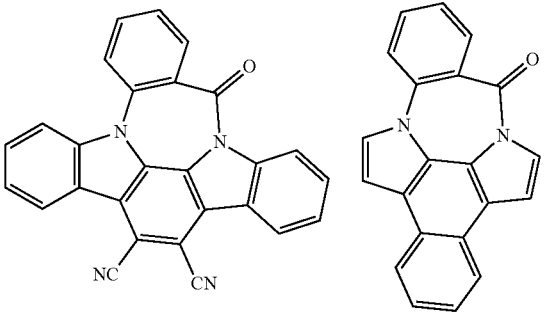
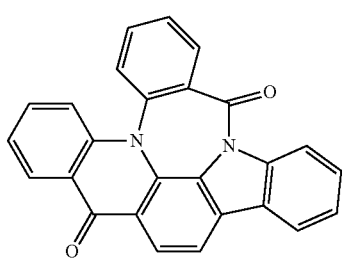
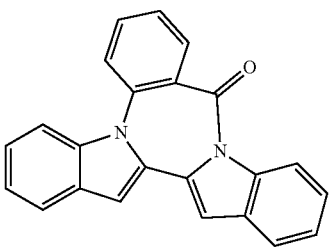
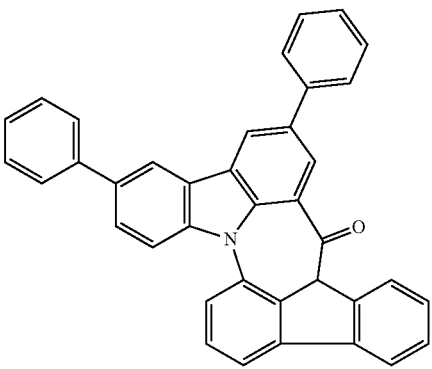

205
-continued
206
-continued
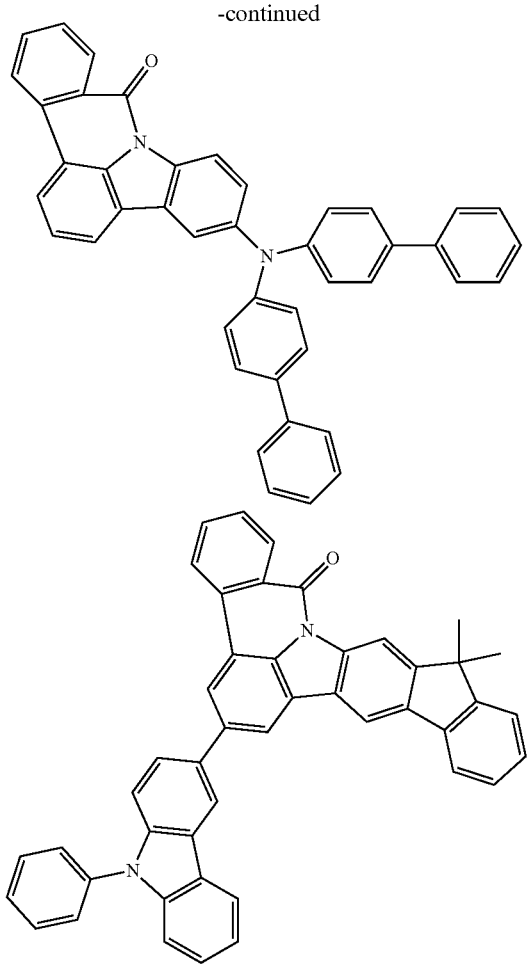
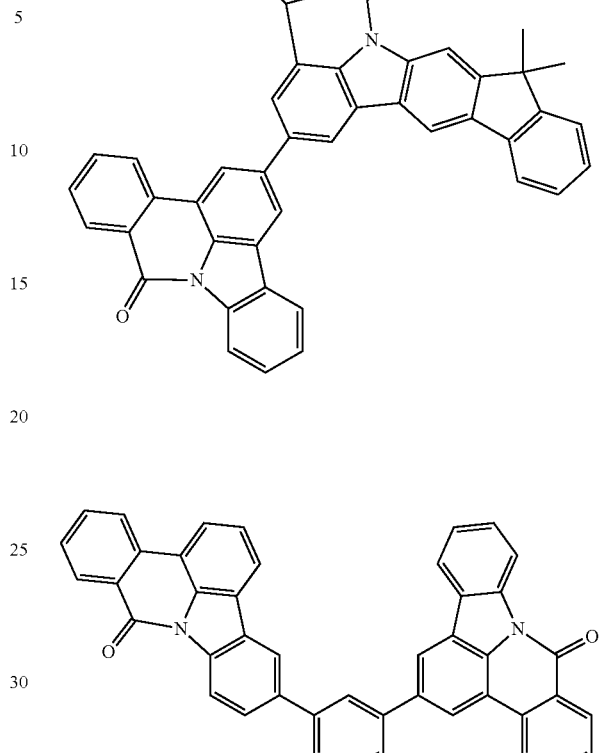
Examples of ketone derivatives which can be used as electron-transporting matrix materials are the following structures:
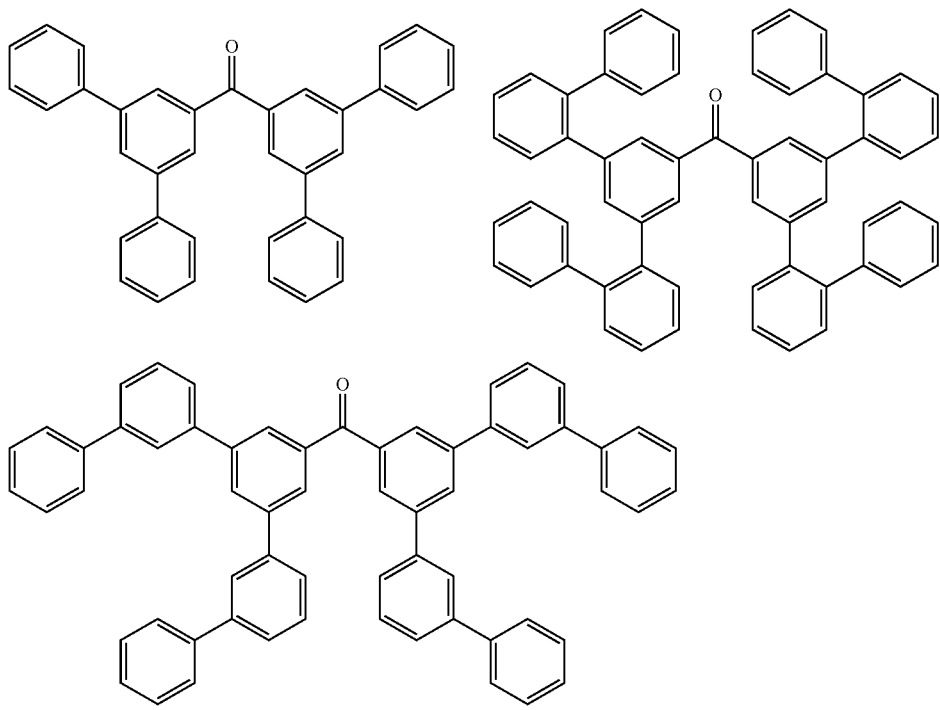

-continued
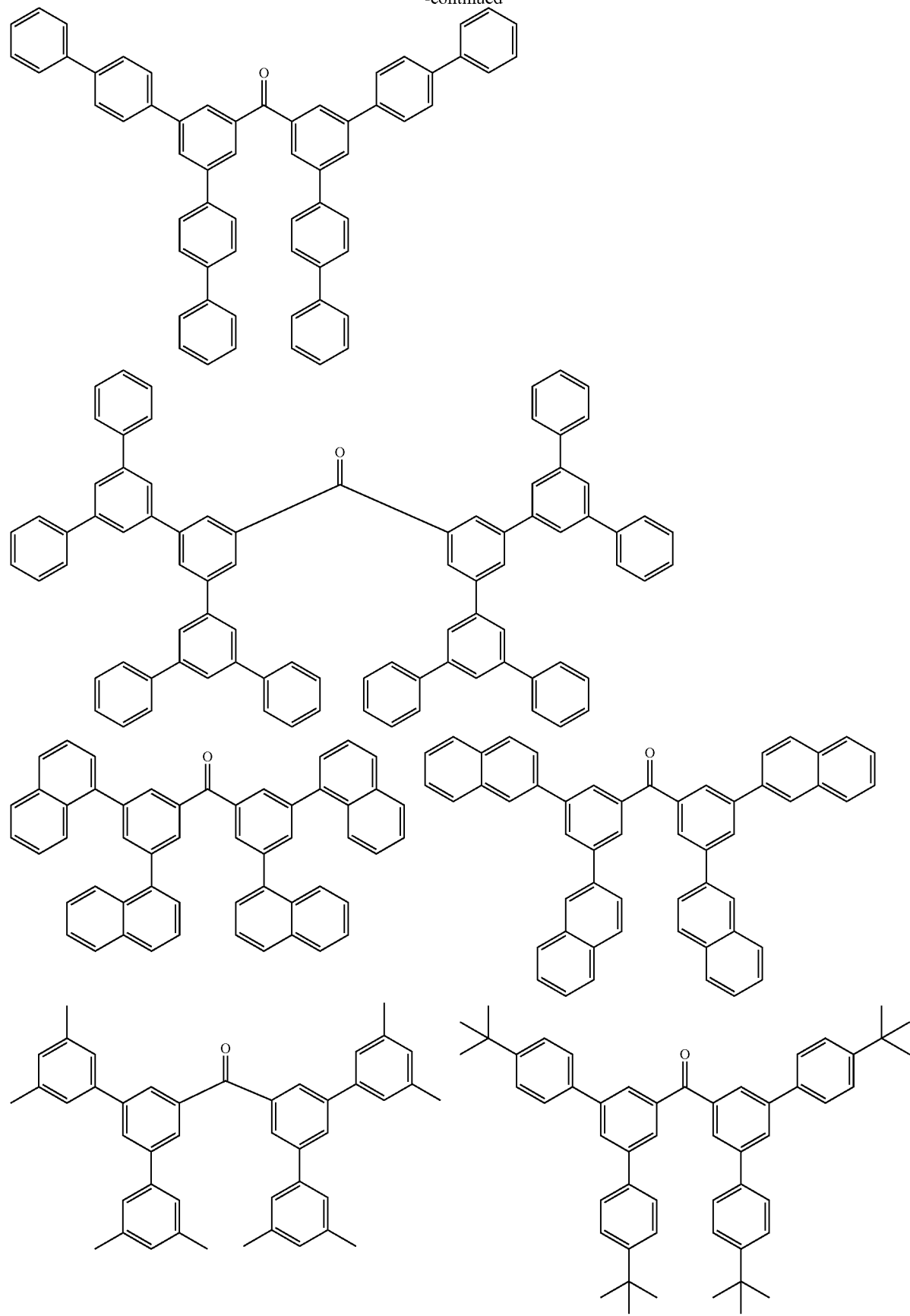

-continued
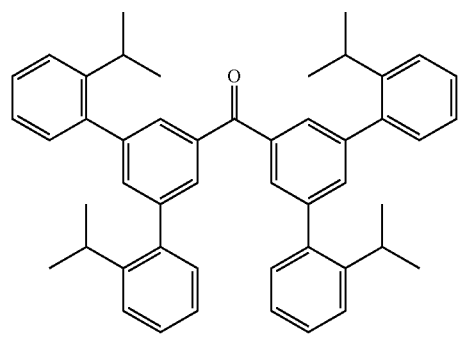
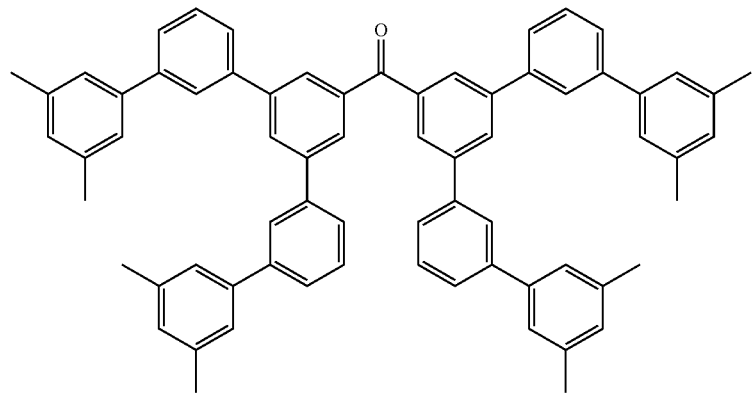
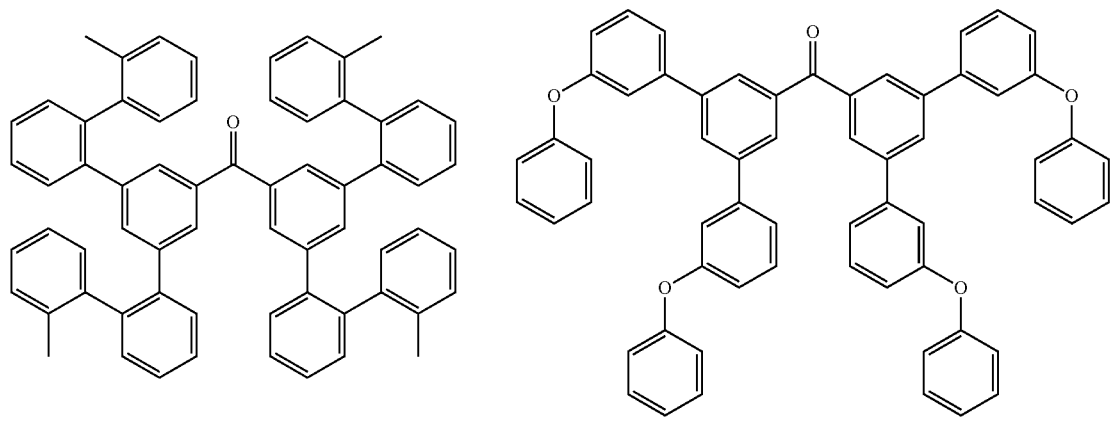
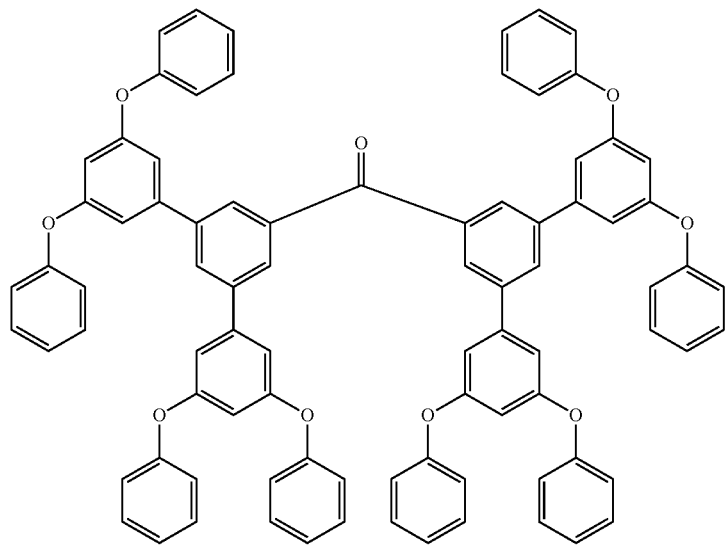

211
-continued
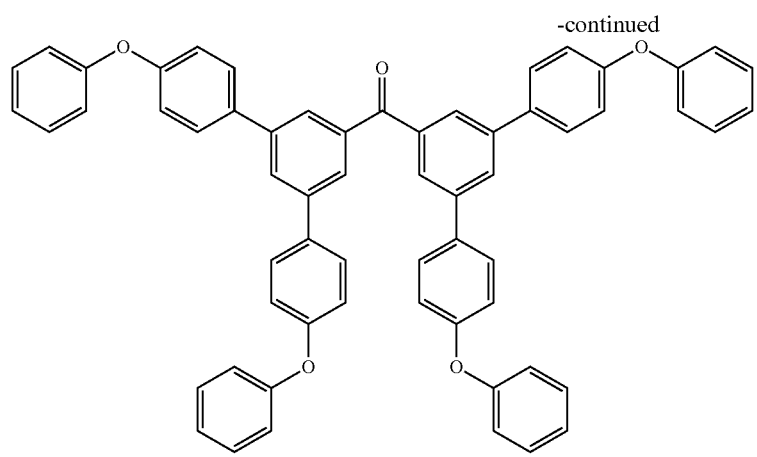
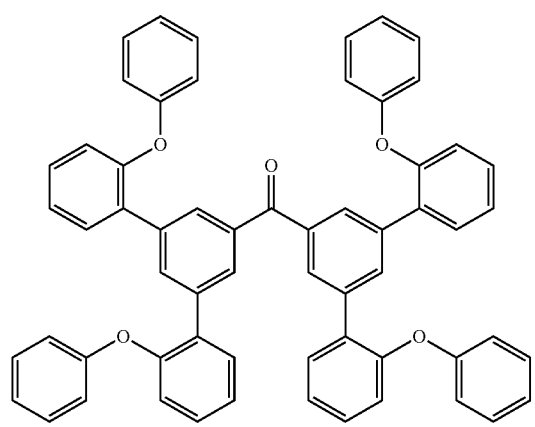
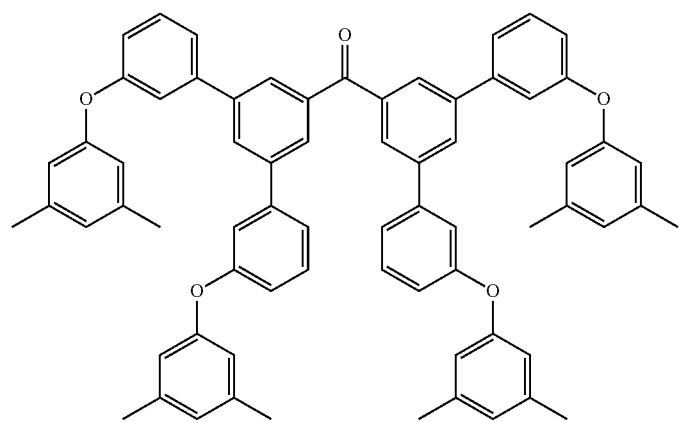
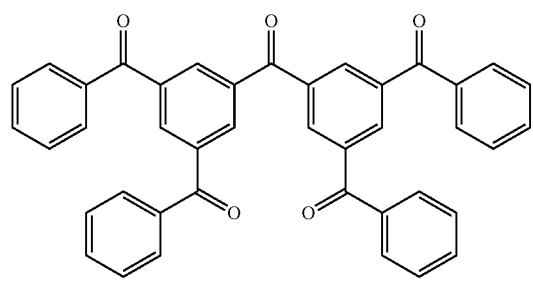
212

-continued
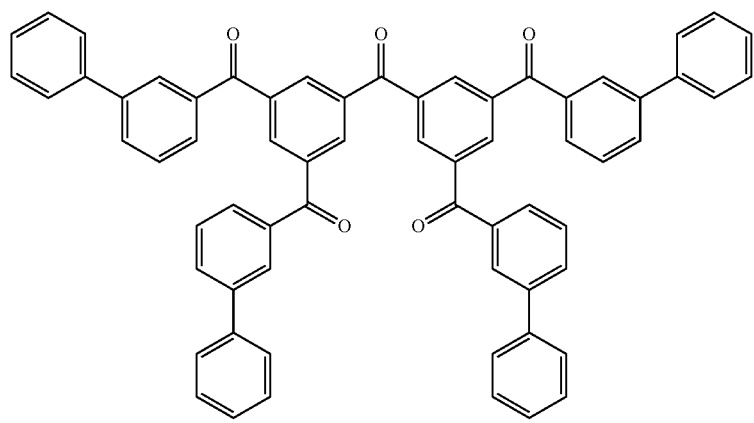
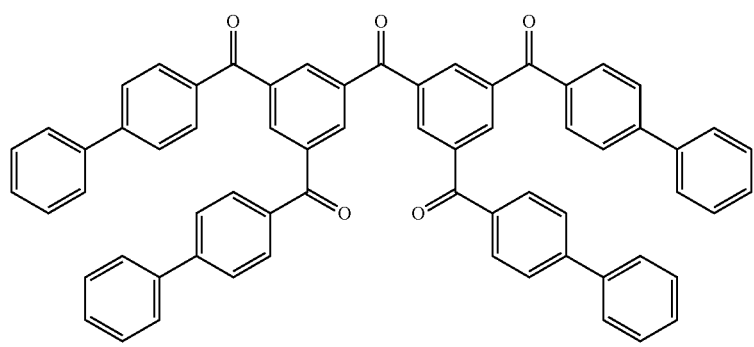
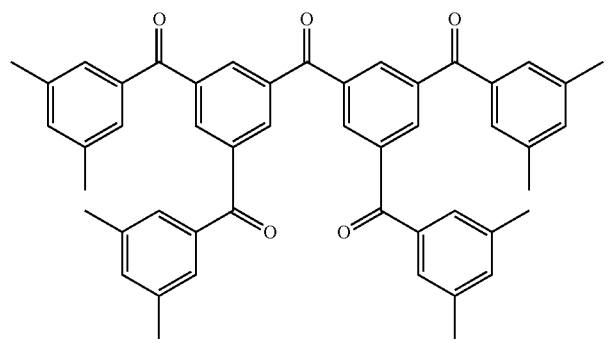
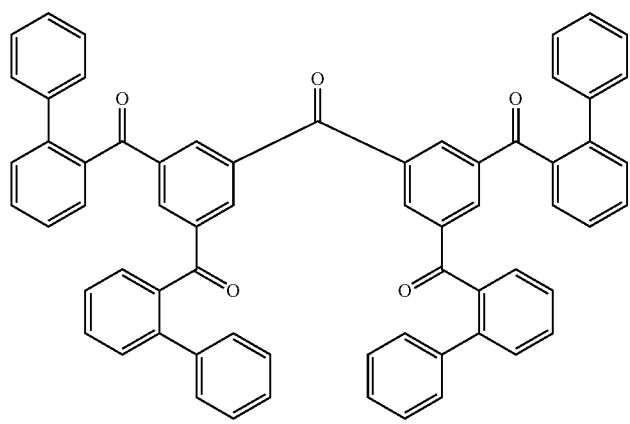

-continued
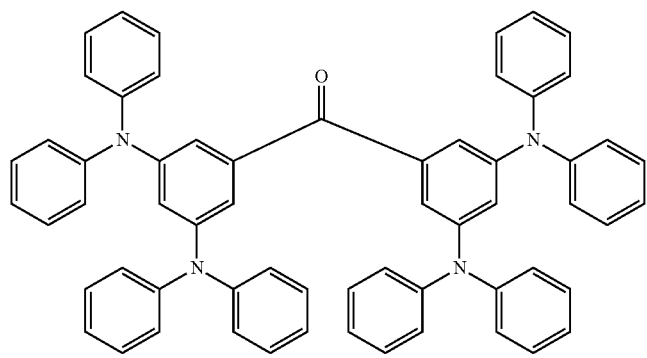
215
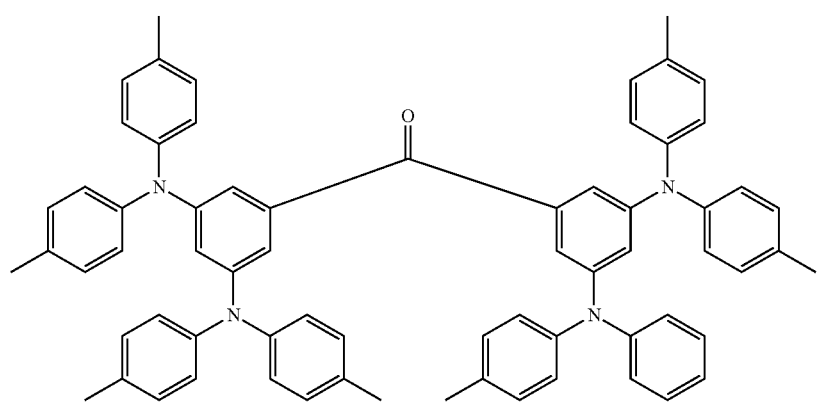
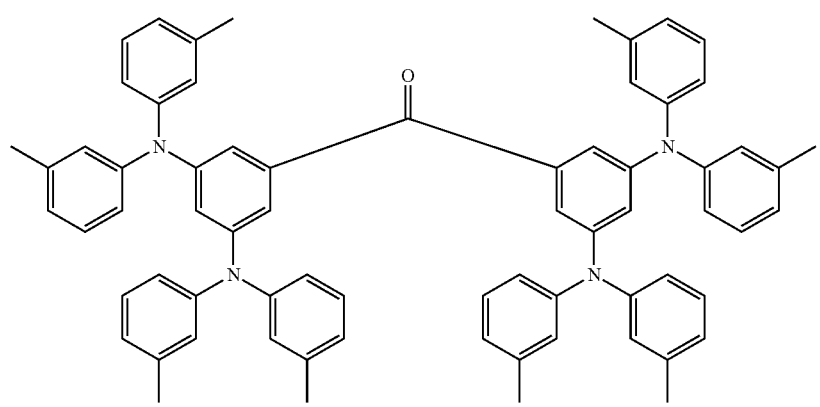
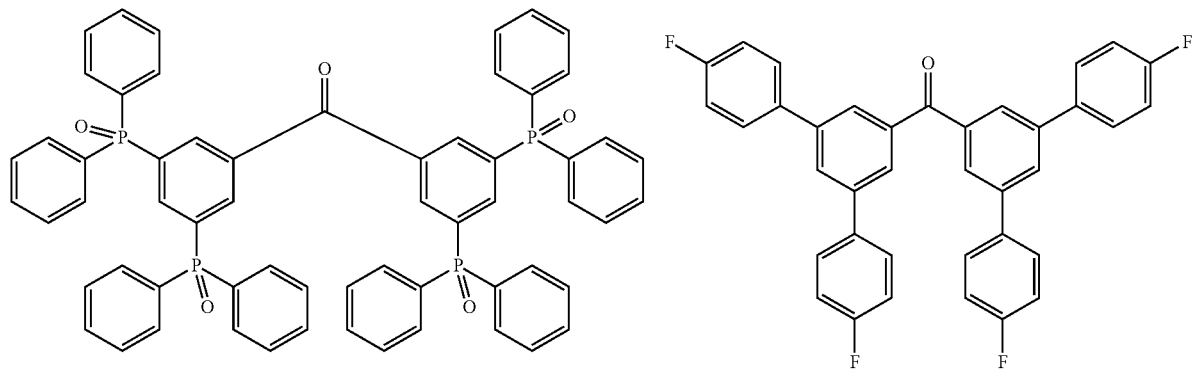
216

217 218
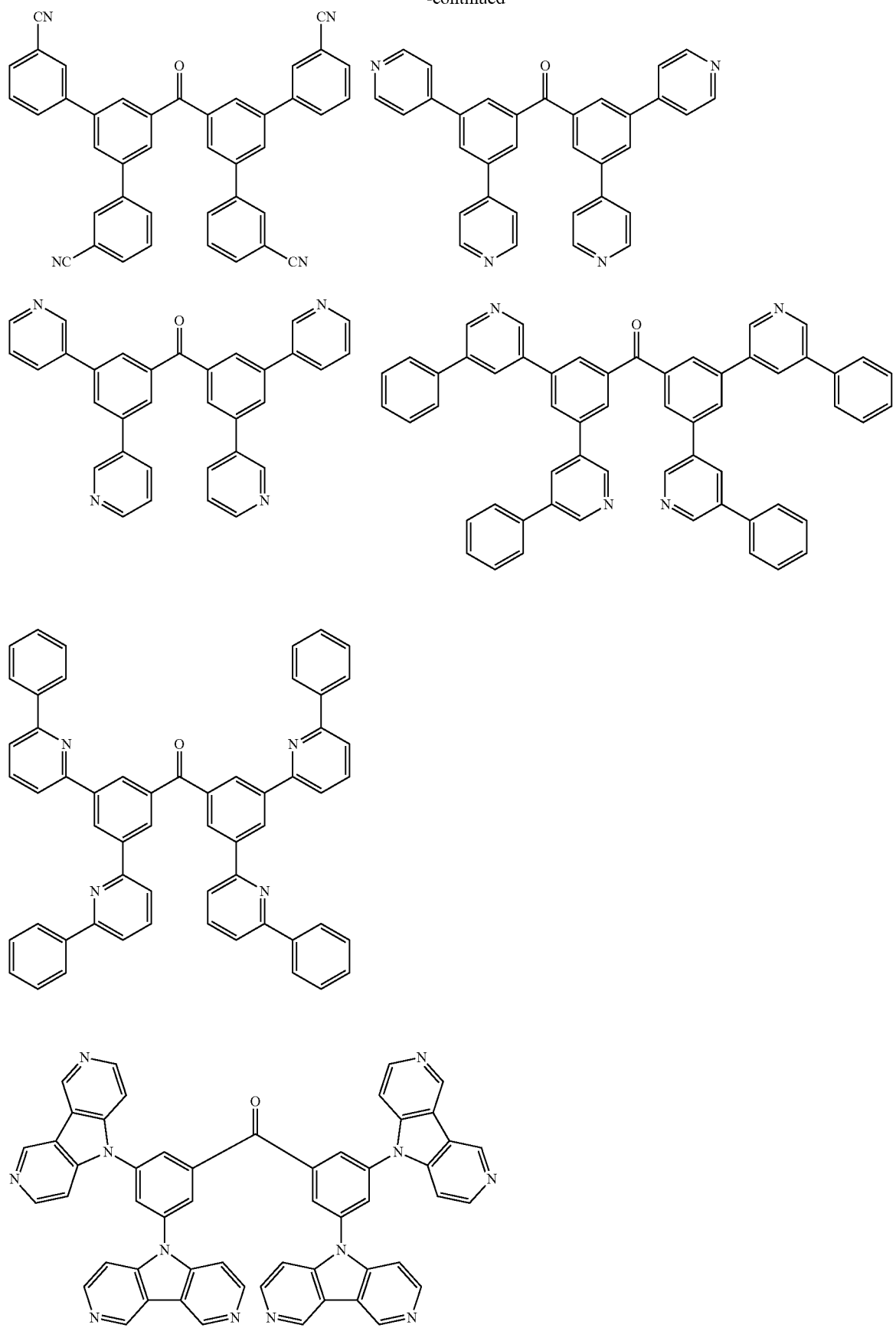

-continued
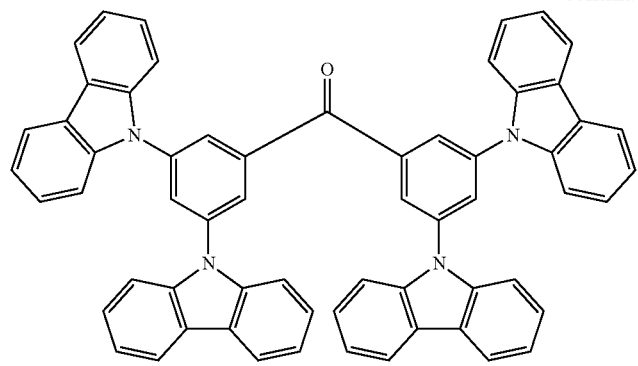
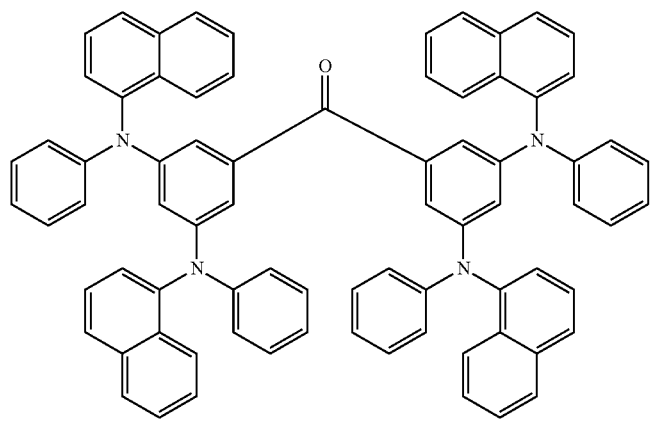
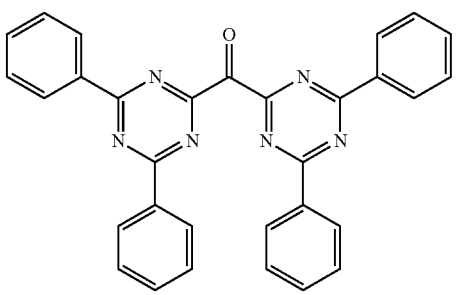
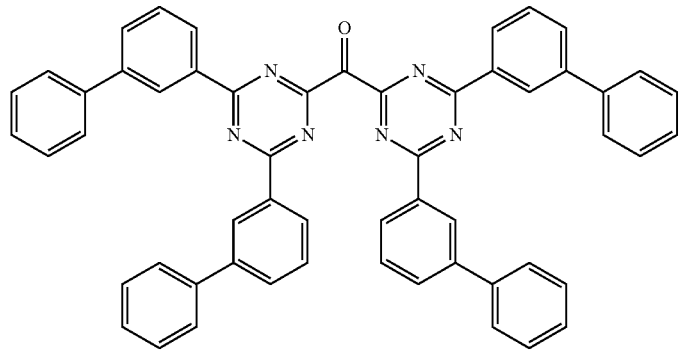
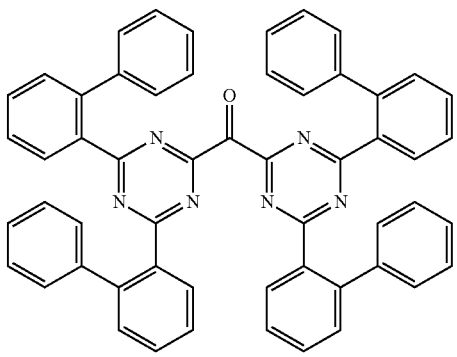
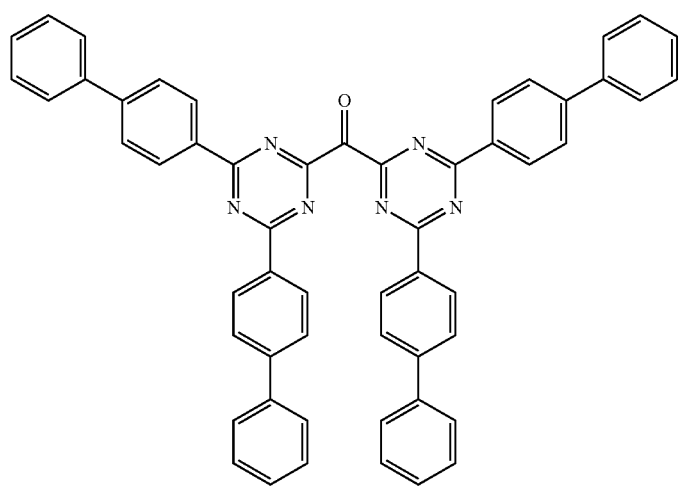

-continued
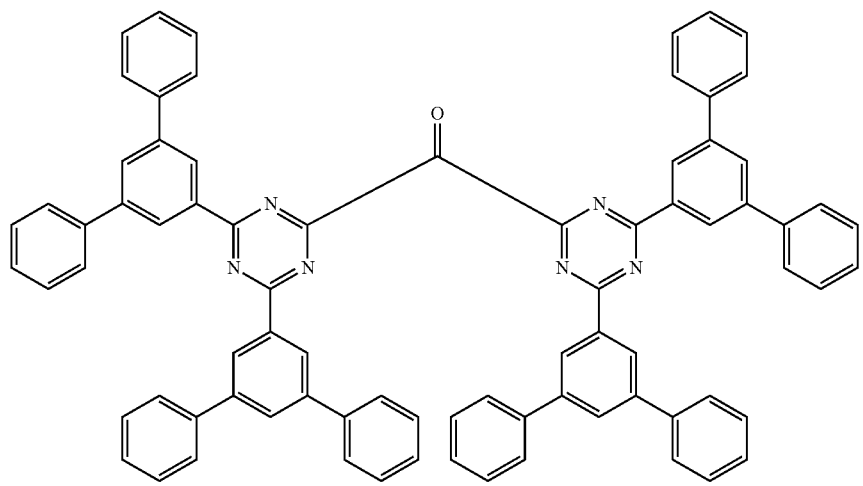
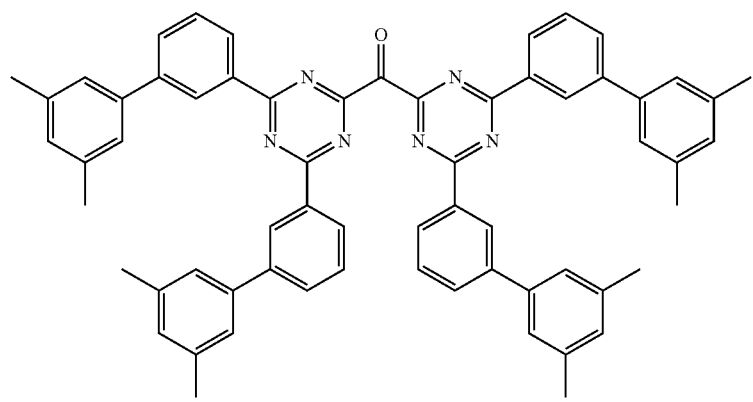
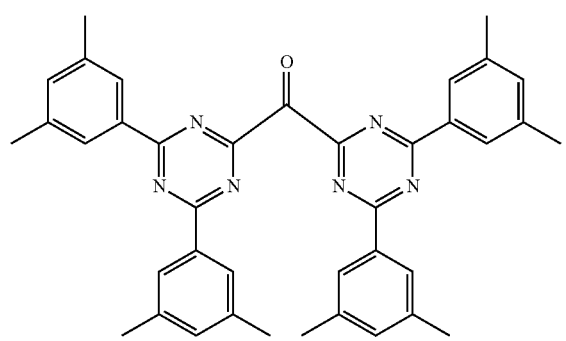
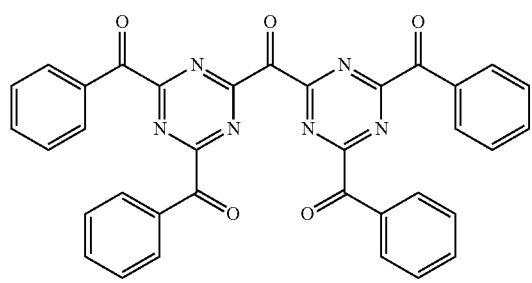

223
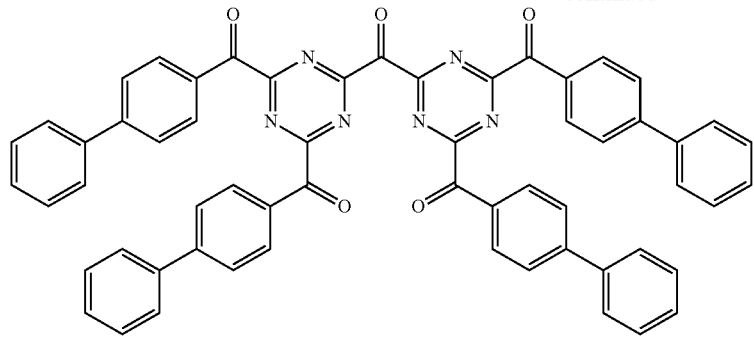
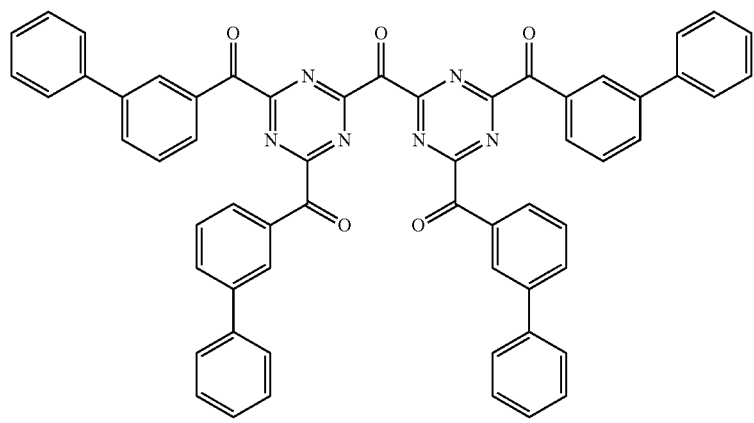
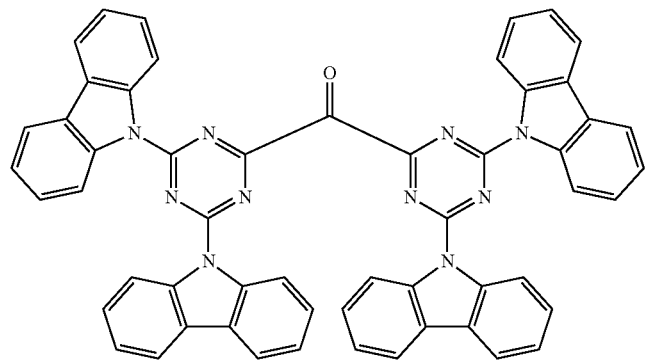
224
-continued
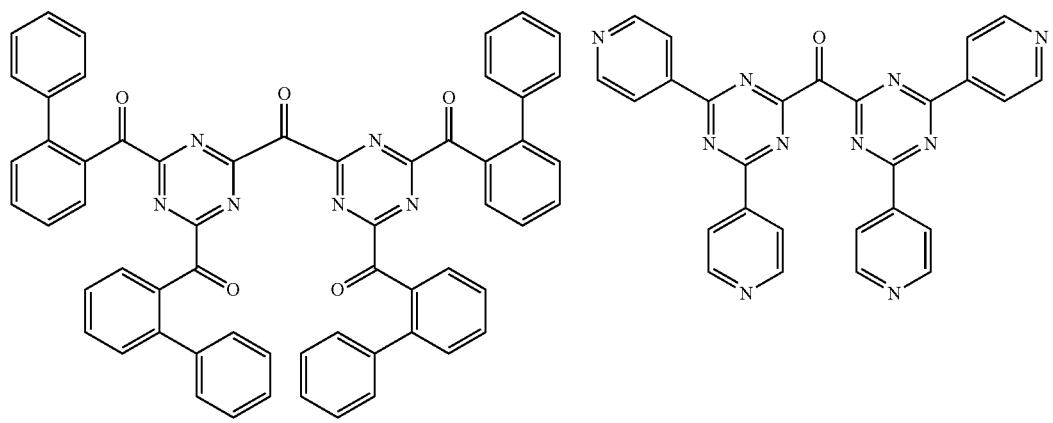

| 225 | 226 |
|---|---|
| 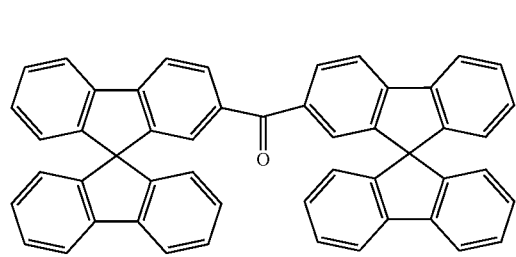 | 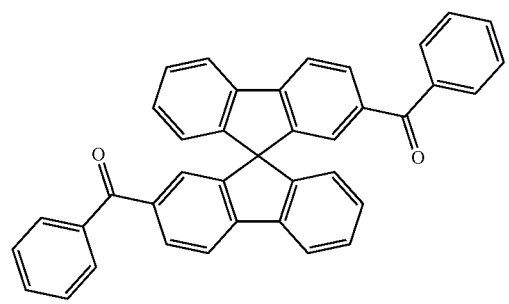 |
| 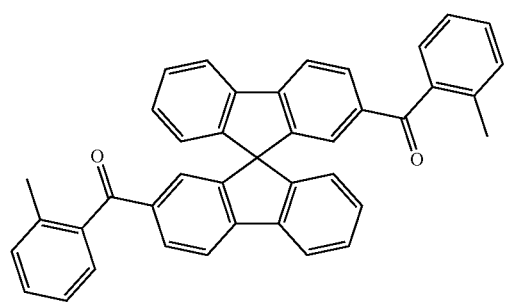 | 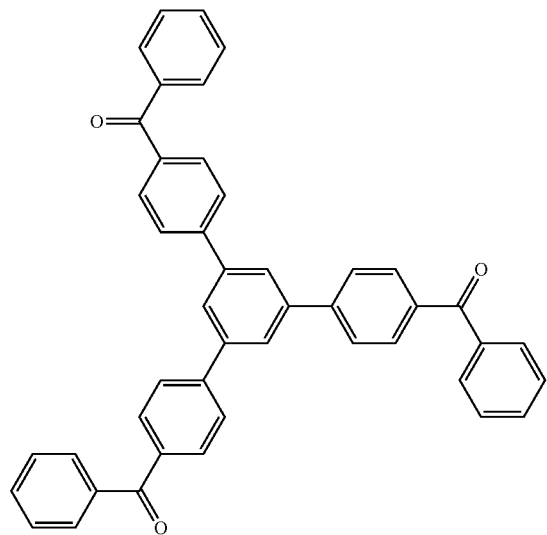 |
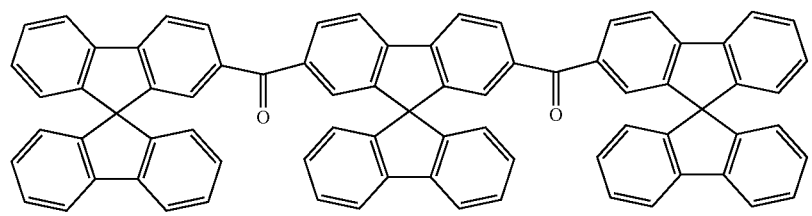
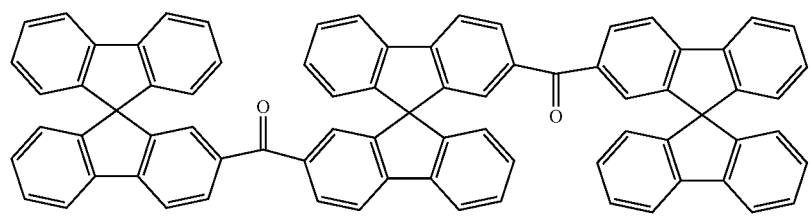

227
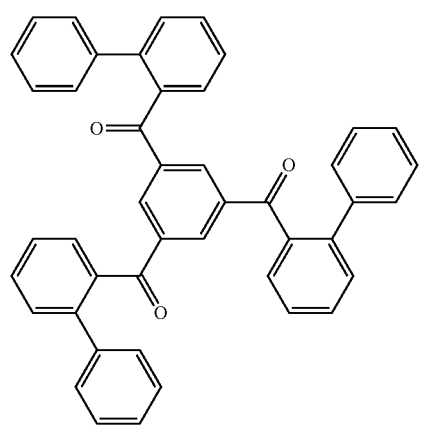
228
-continued
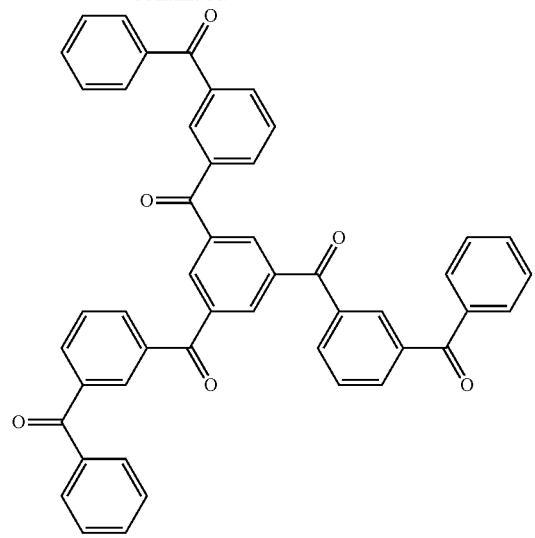
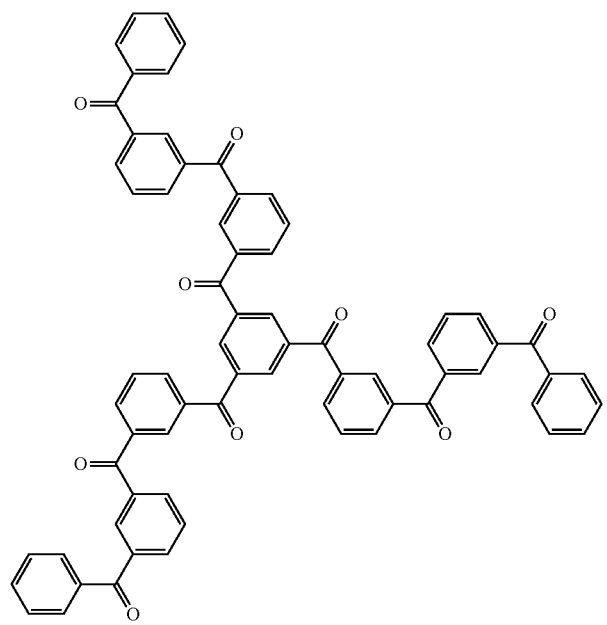
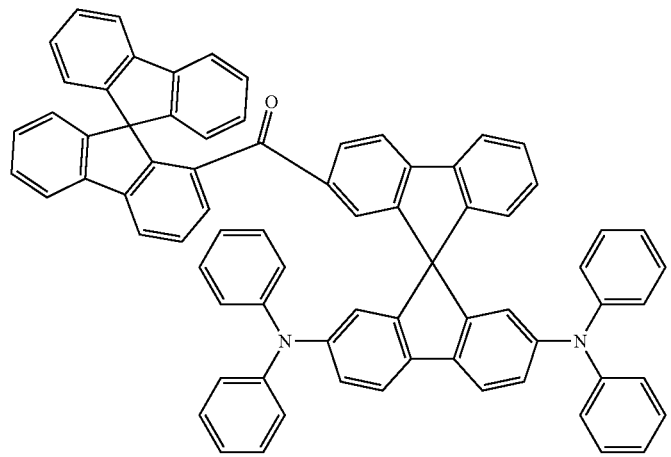

Examples of metal complexes which can be used as electron-transporting matrix materials are the following structures:
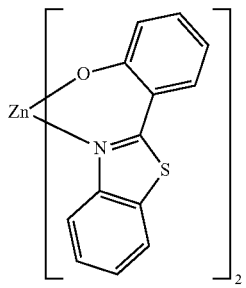
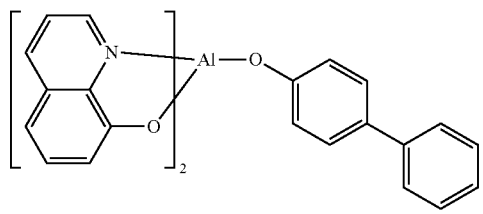
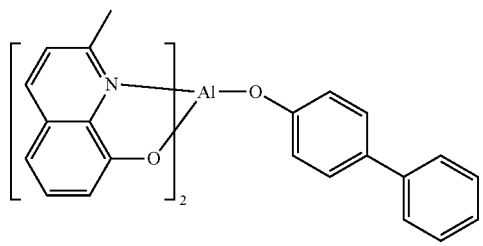
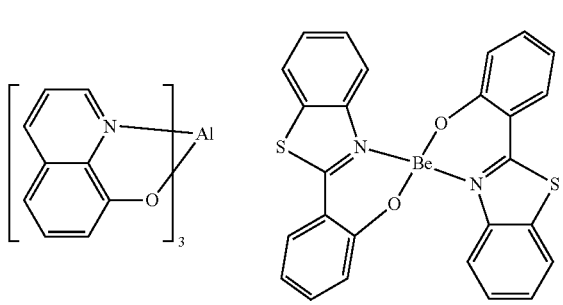
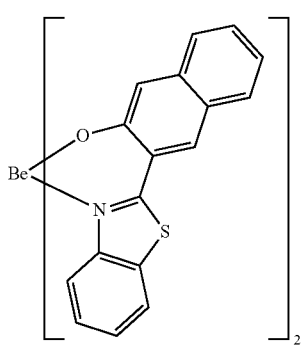
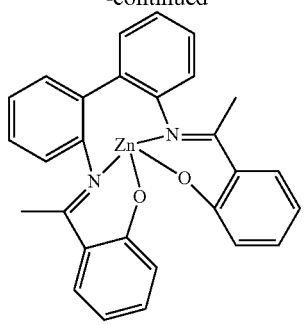
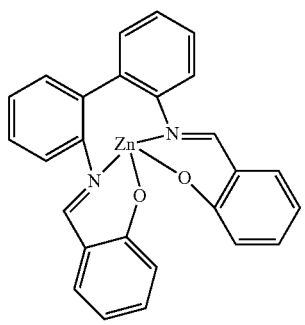
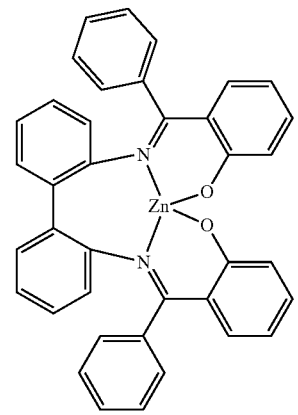
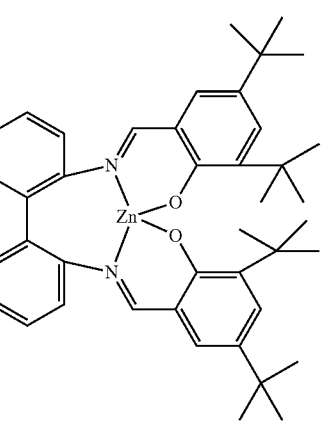
Examples of phosphine oxides which can be used as electron-transporting matrix materials:

231 232
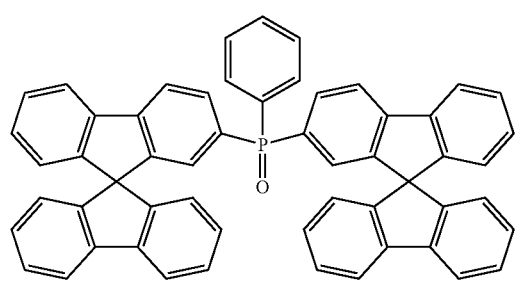
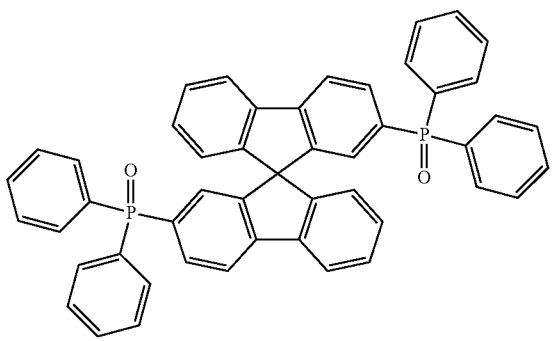
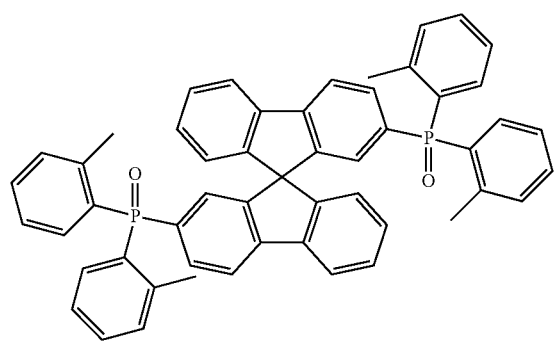
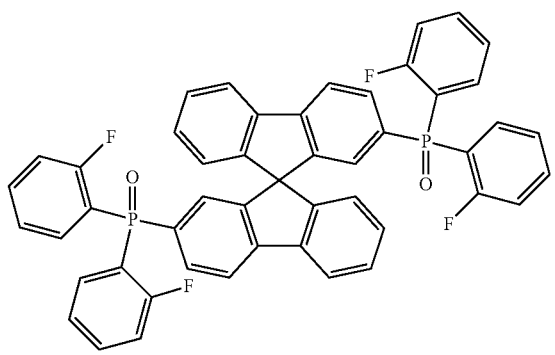
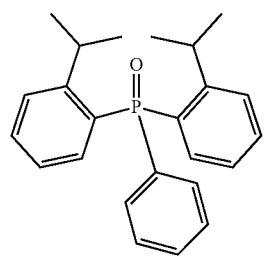
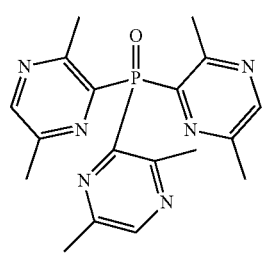
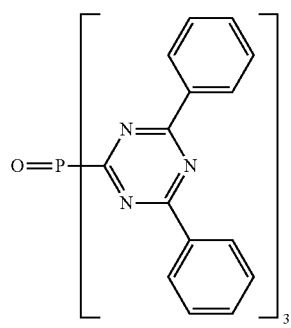
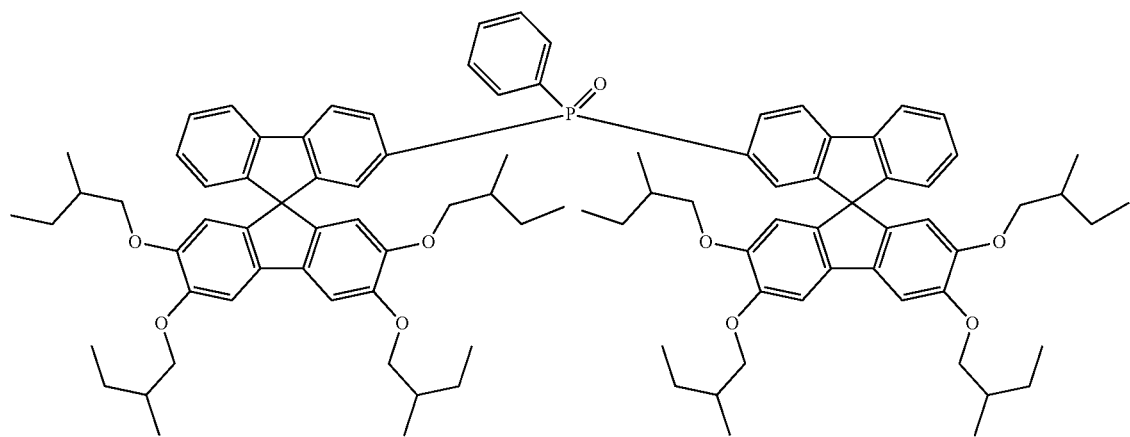

233
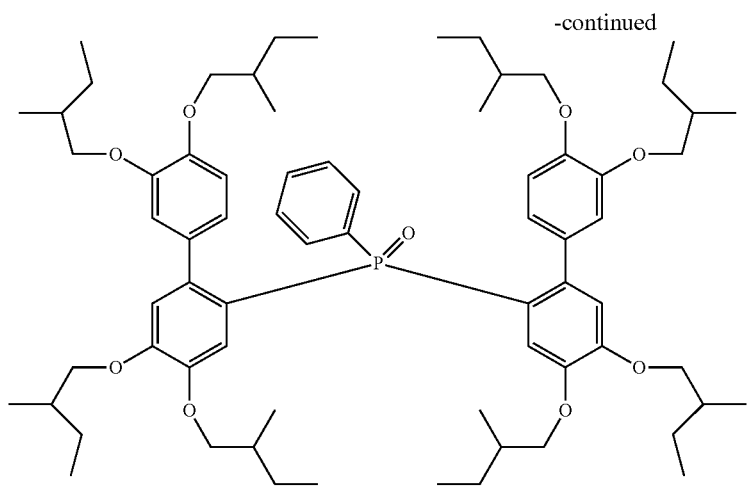
234
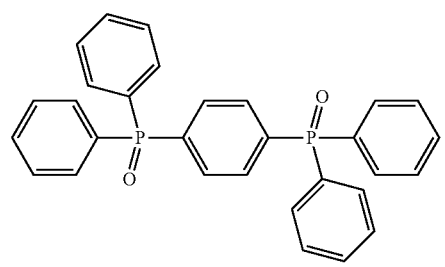
-continued
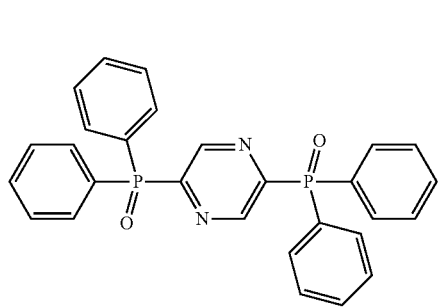
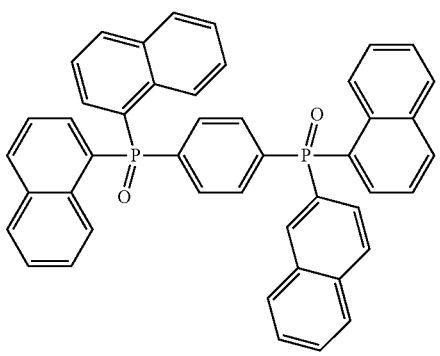
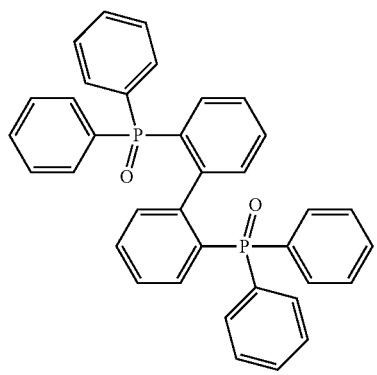
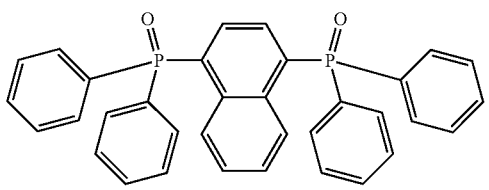
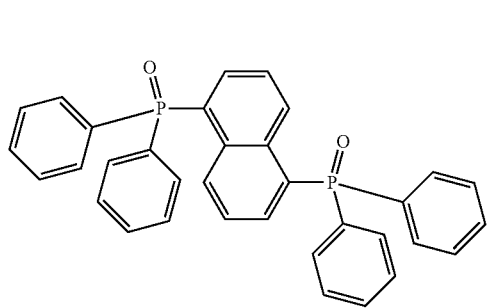
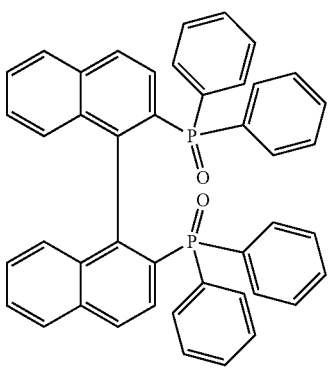

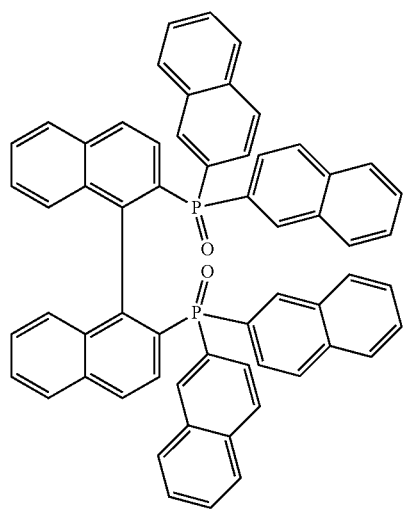
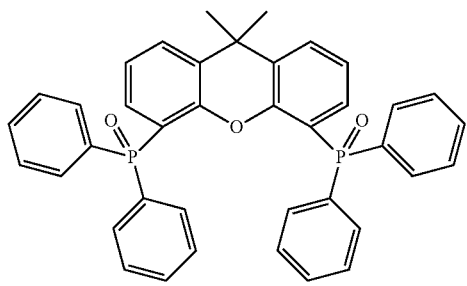
Examples of indolo- and indenocarbazole derivatives in the broadest sense which can be used as hole- or electron-transporting matrix materials according to the substitution pattern are the following structures:
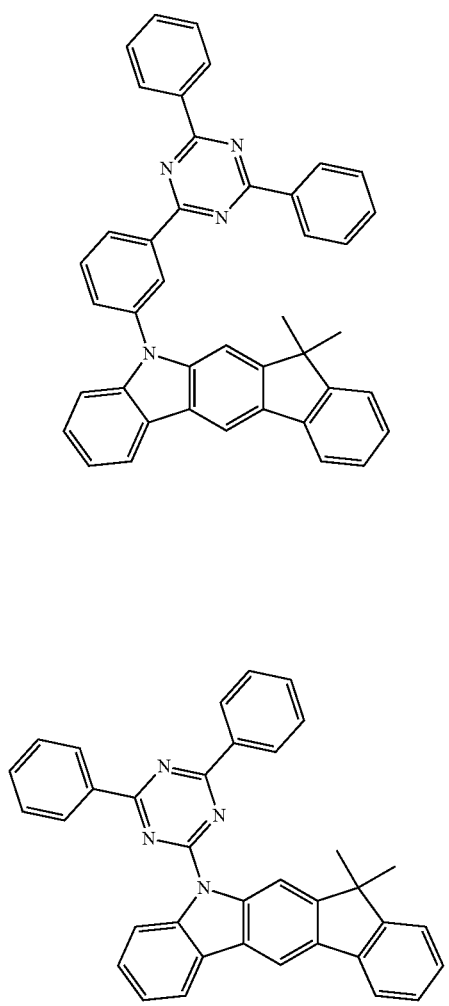
-continued
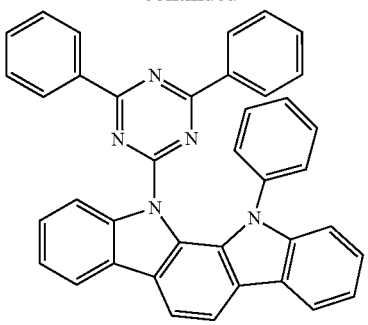
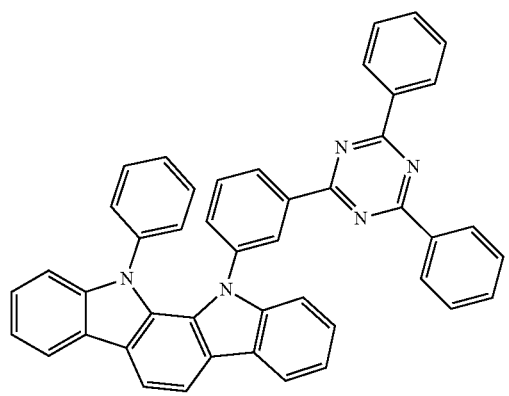
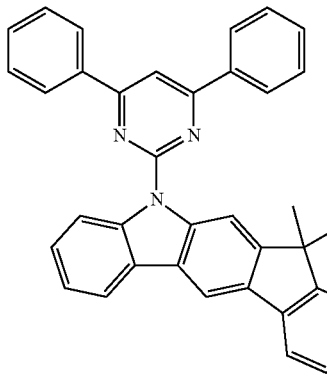

-continued
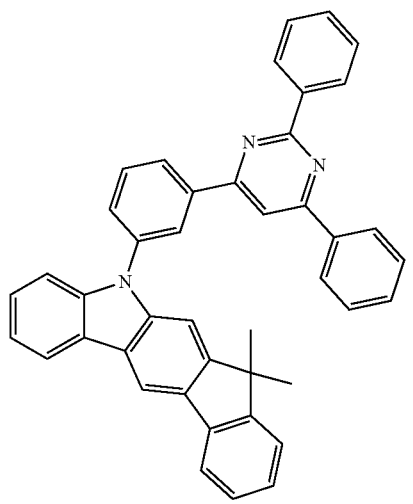
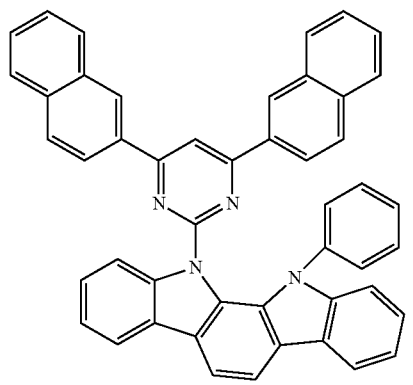
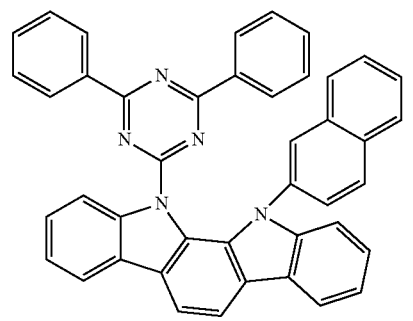
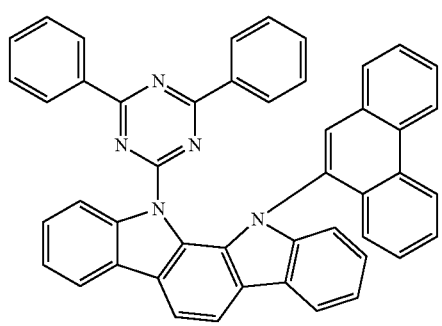
-continued
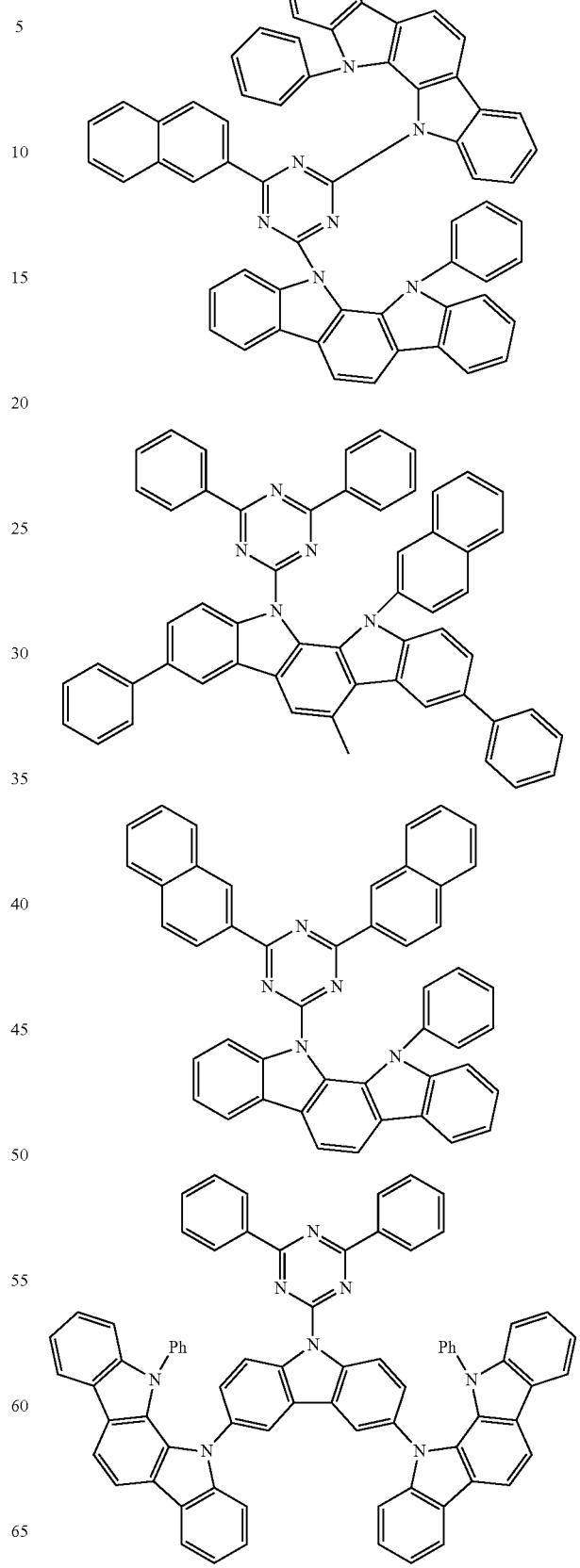

239
-continued
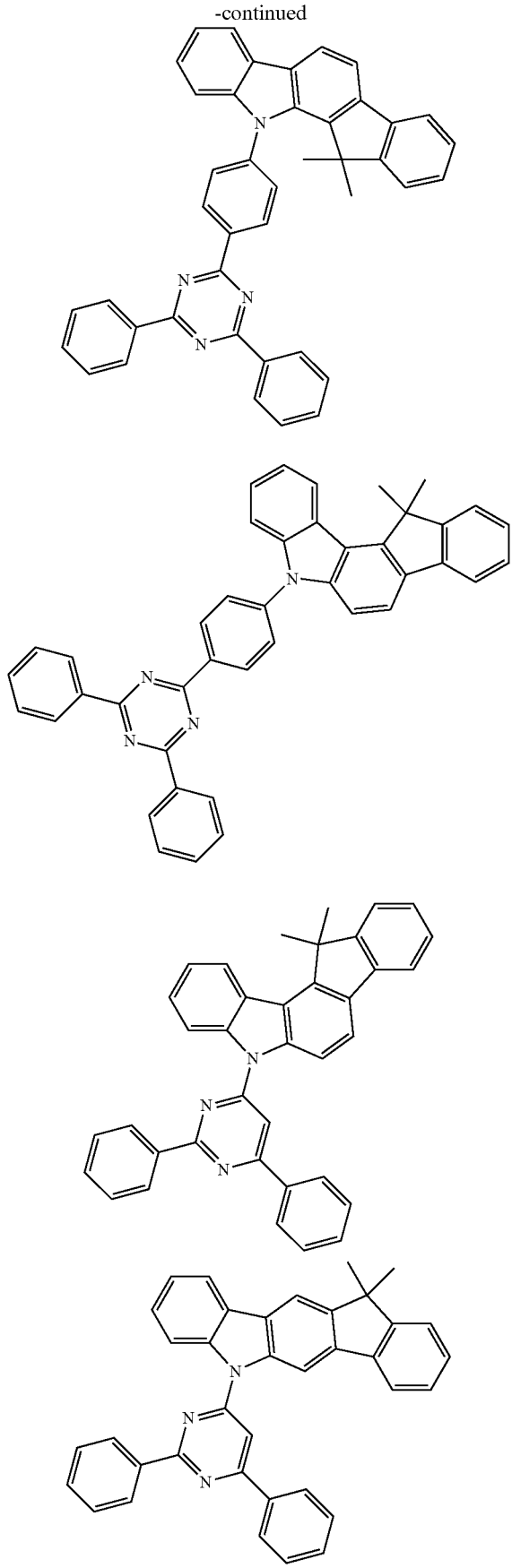
240
-continued
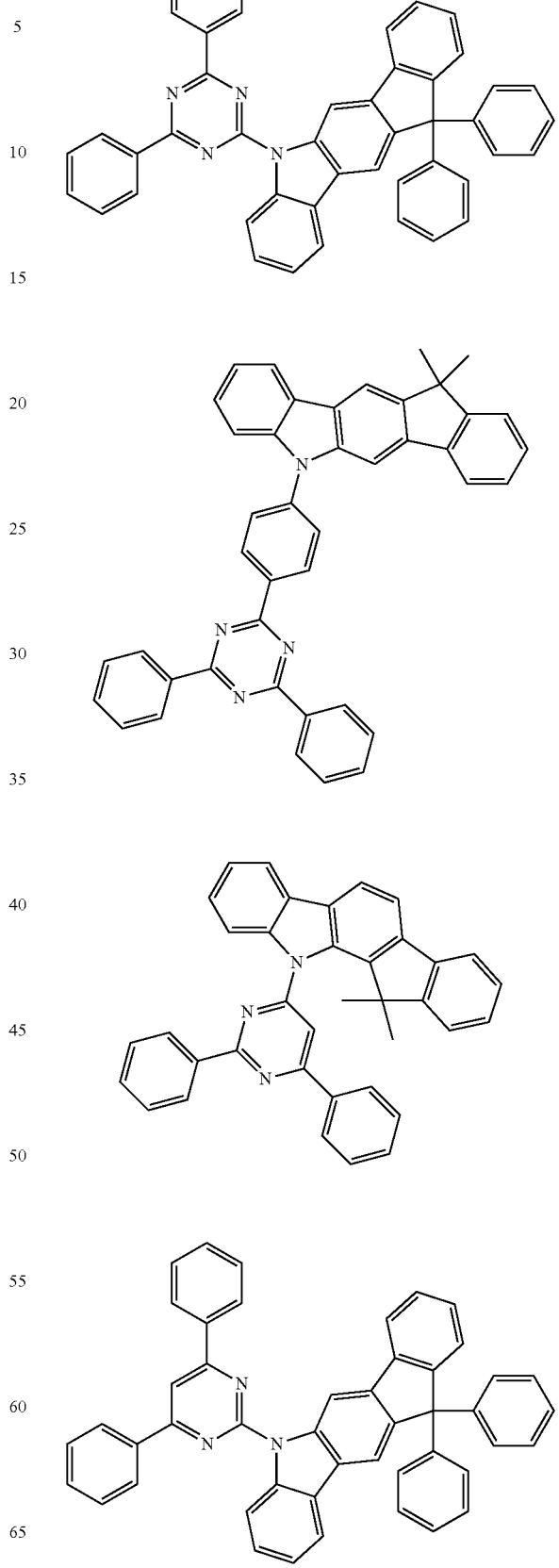

-continued
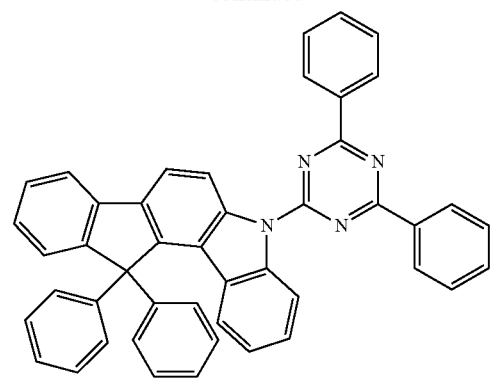
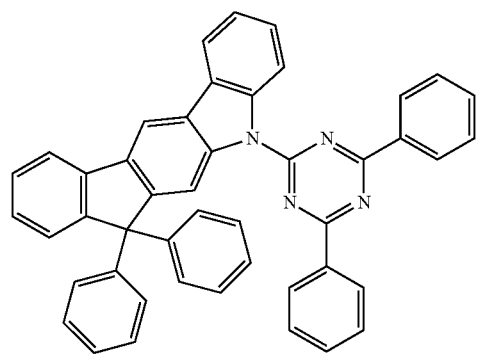
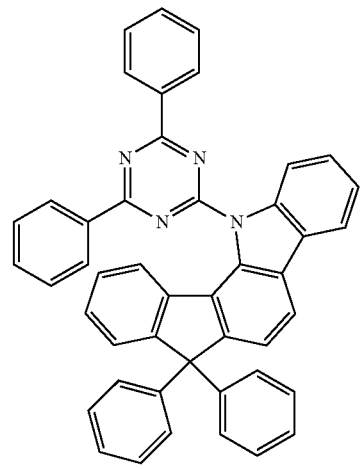
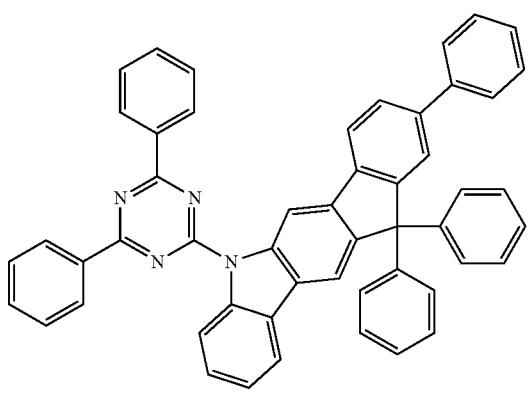
-continued
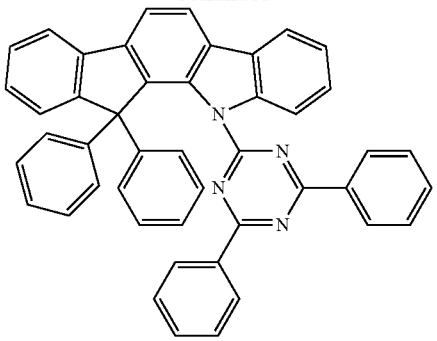
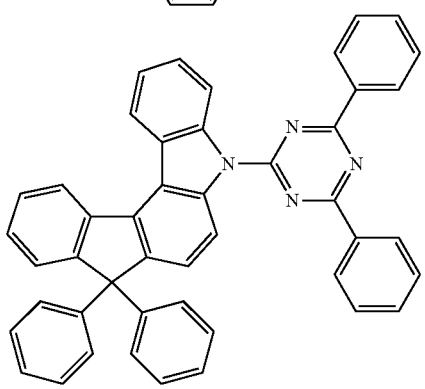
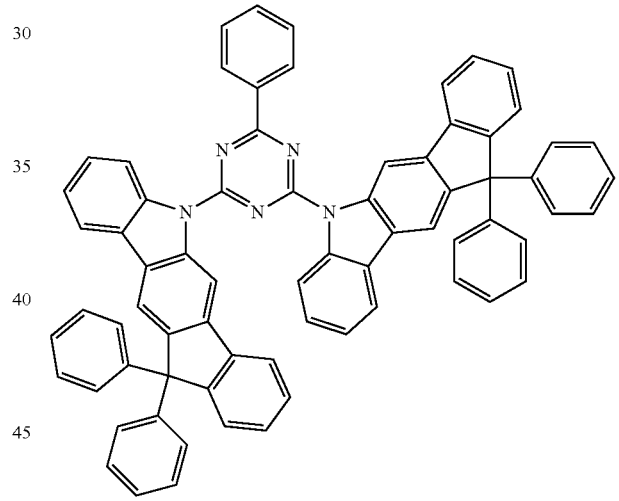
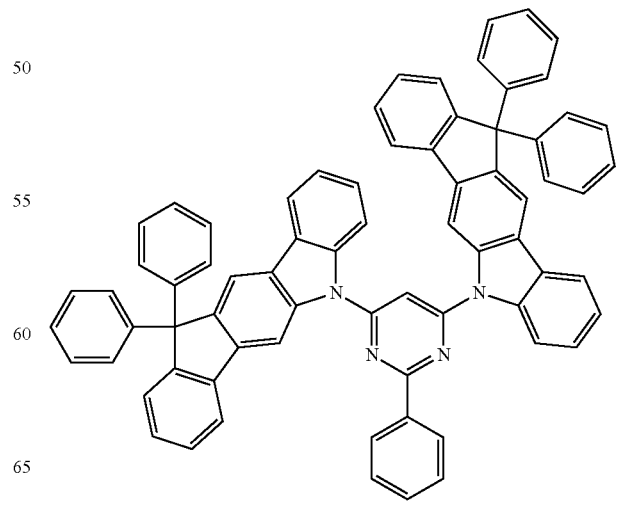

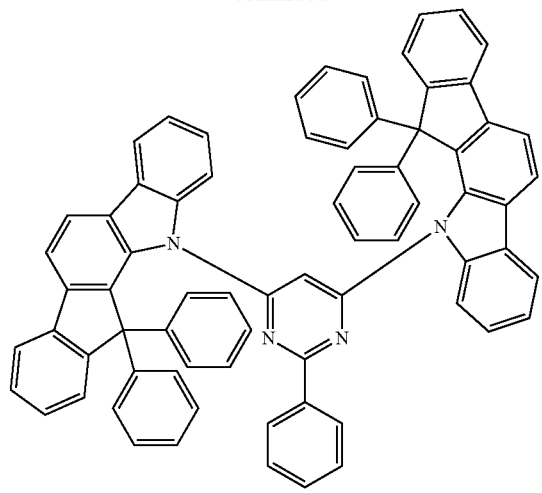
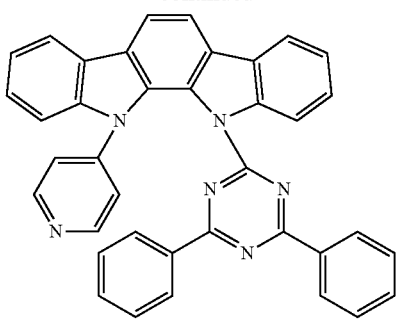
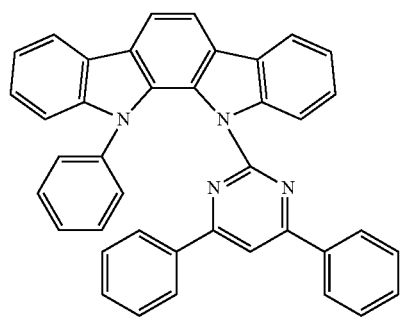
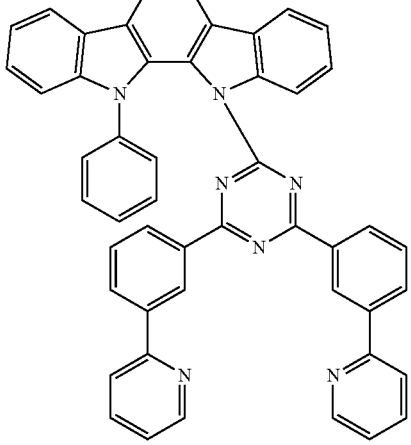
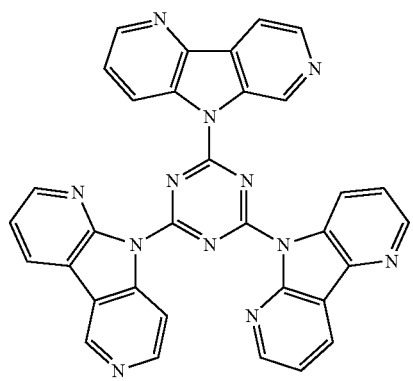
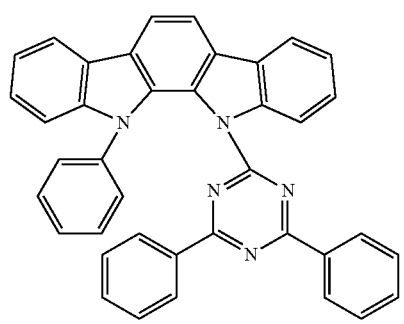
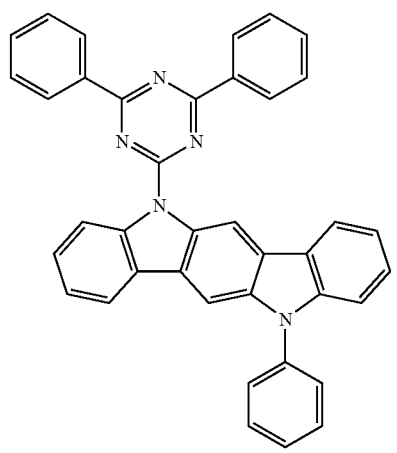

245
-continued
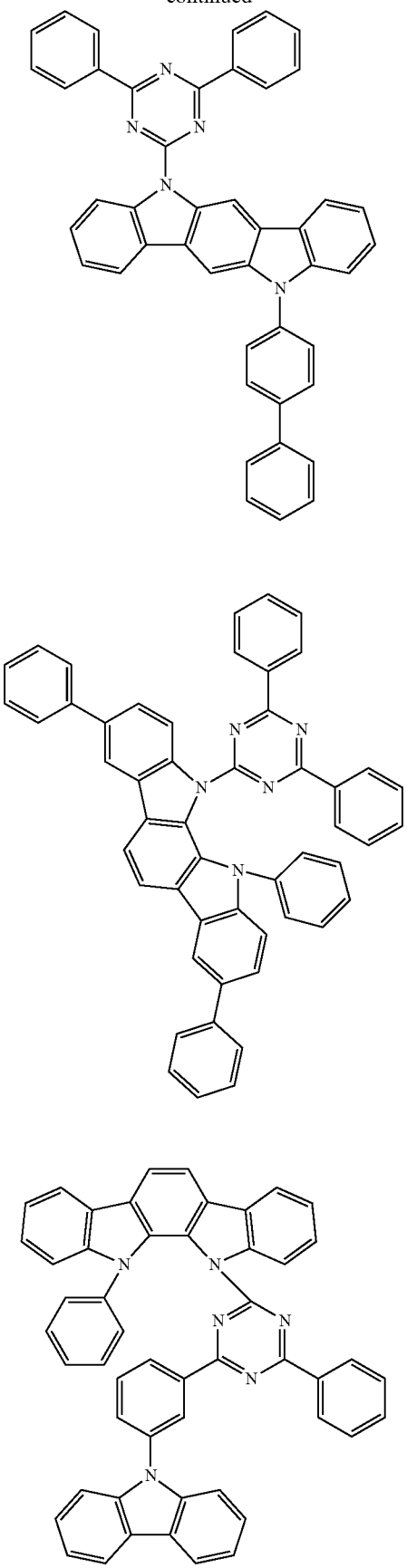
246
-continued
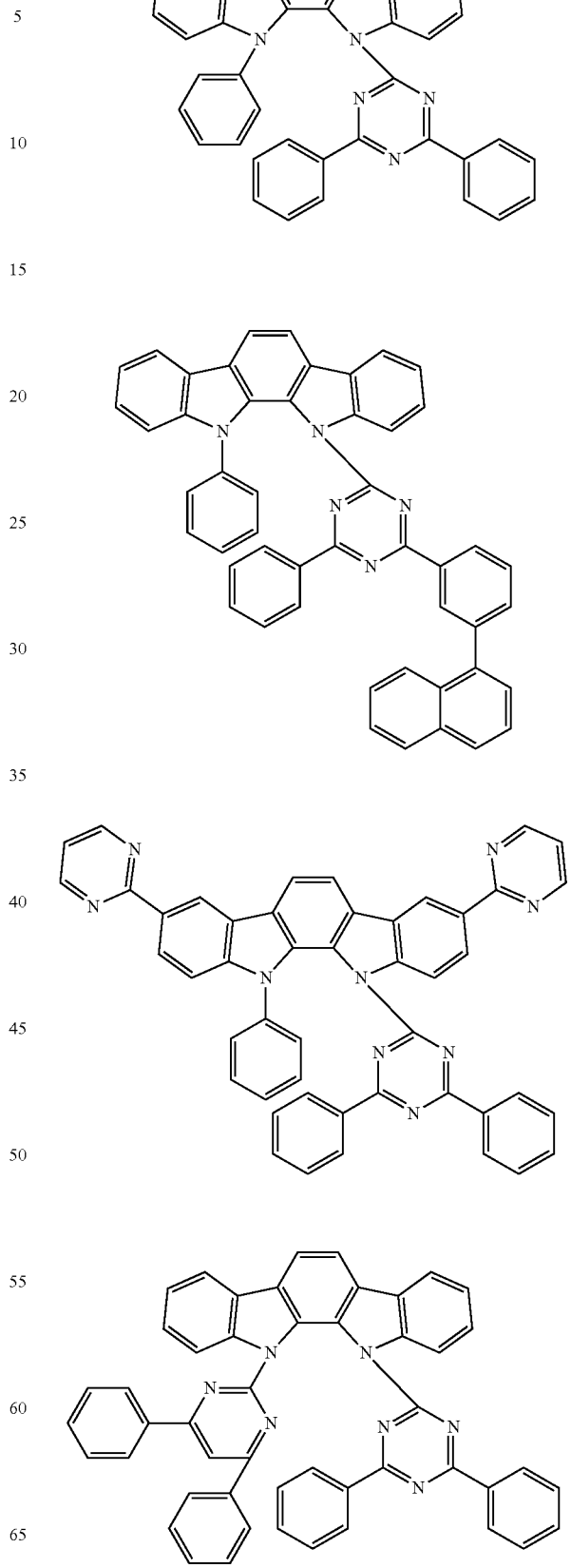

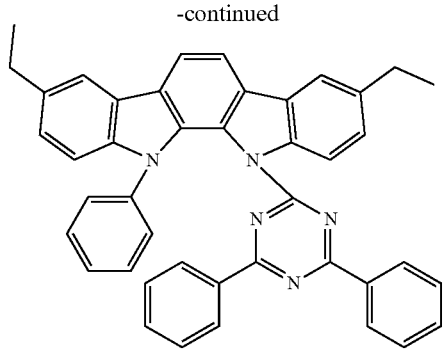
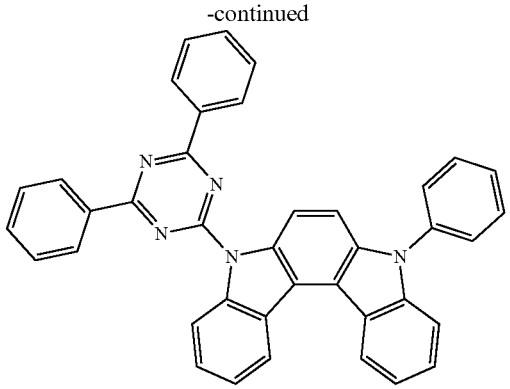
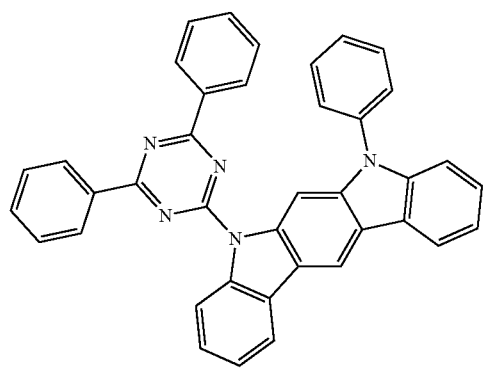
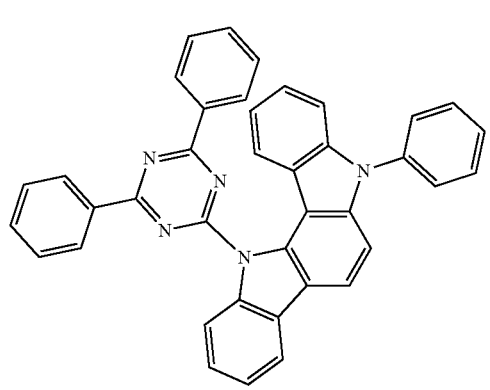
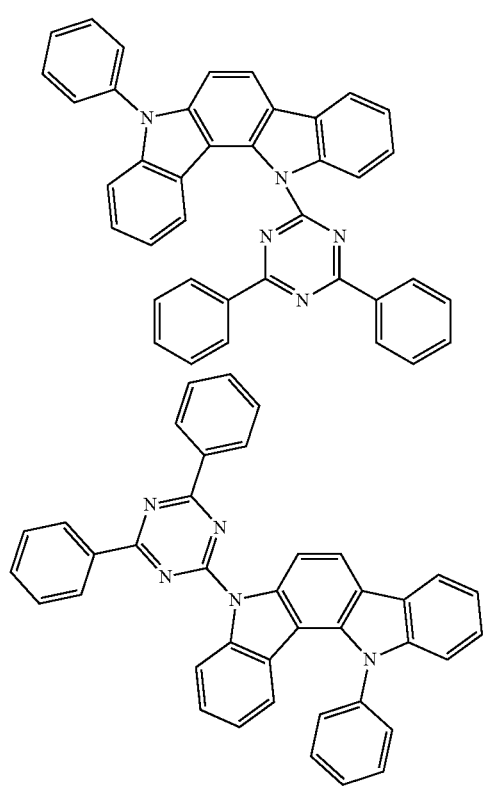
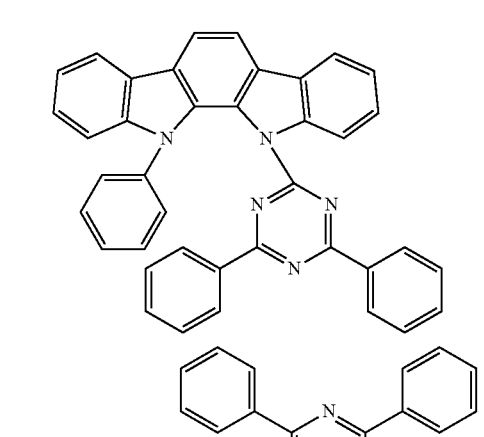
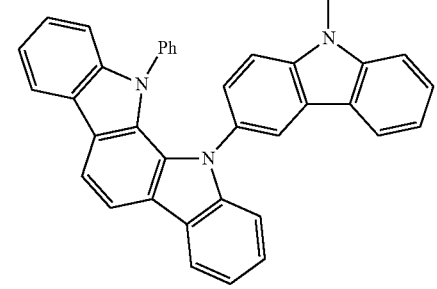

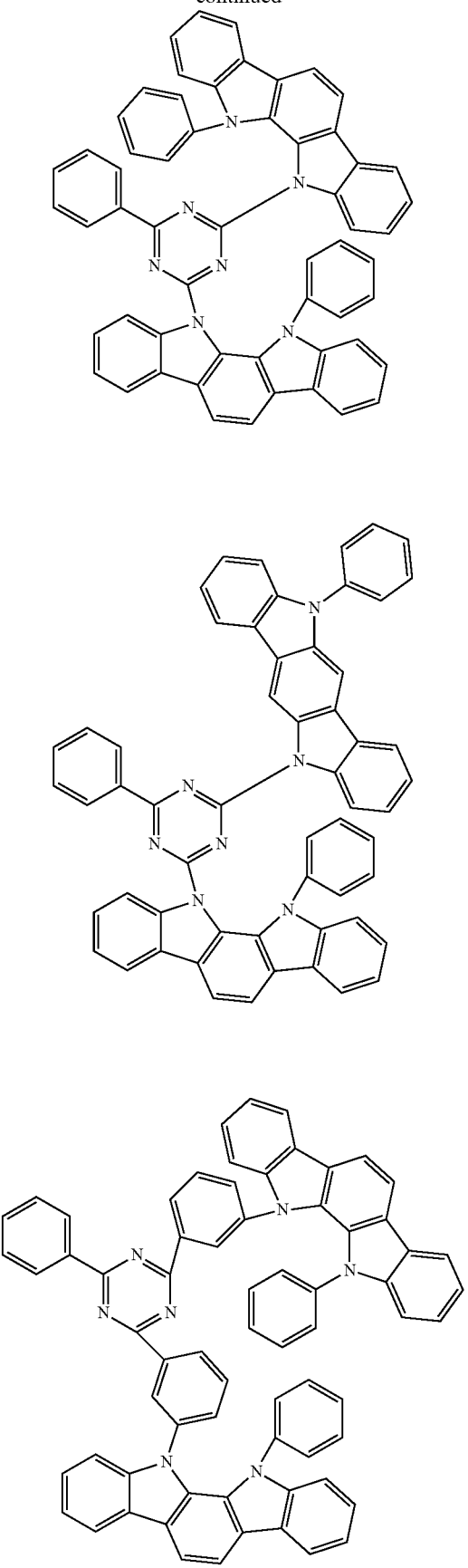

251
-continued
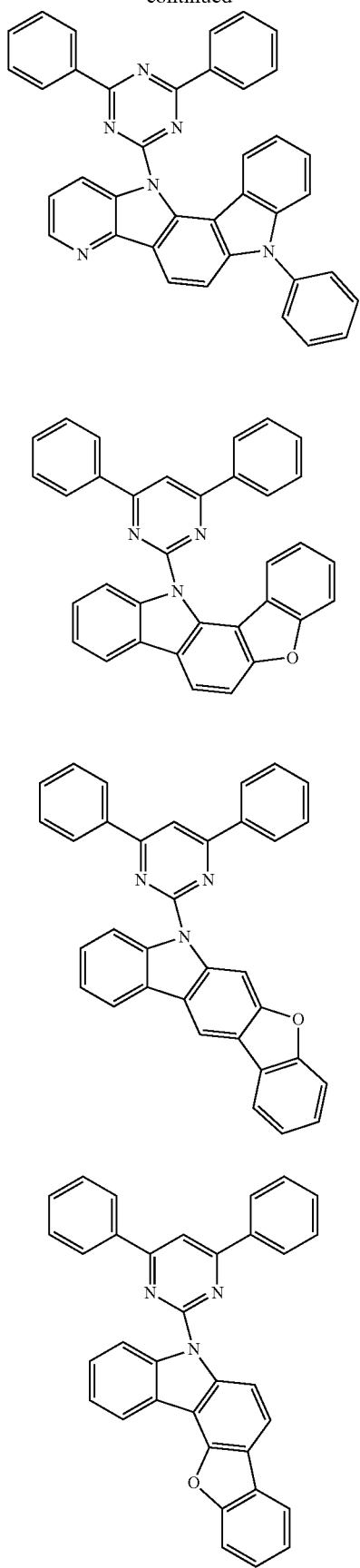
252
-continued
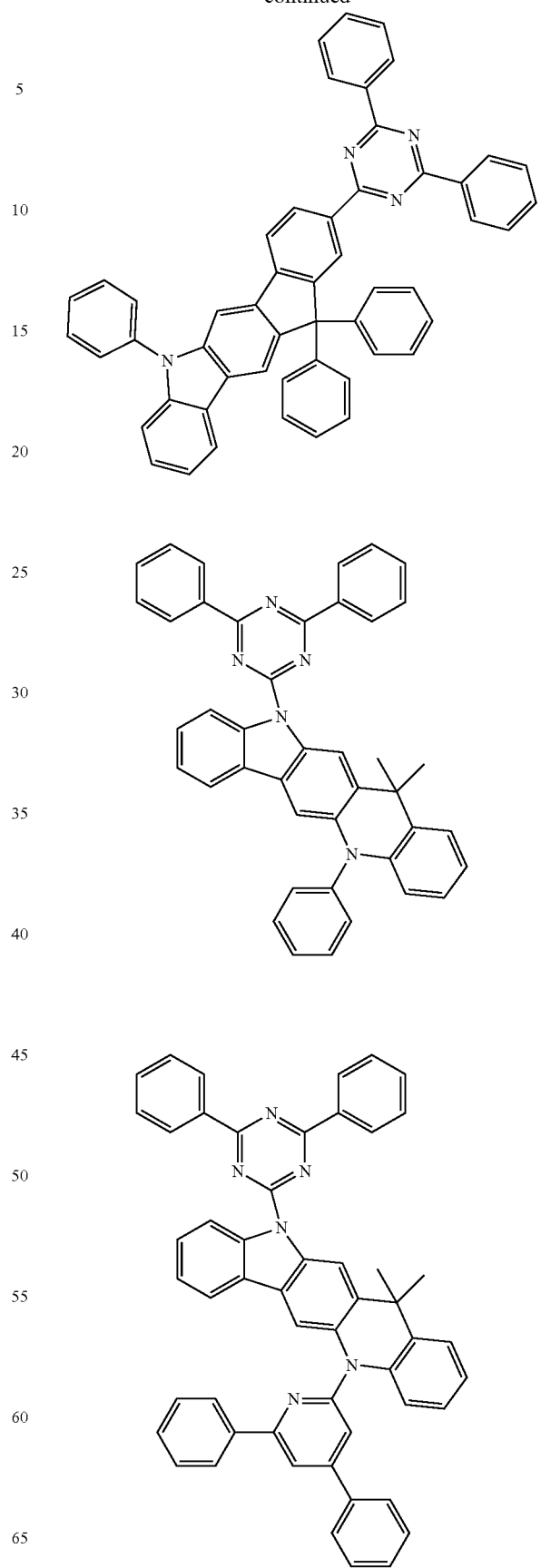

253
-continued
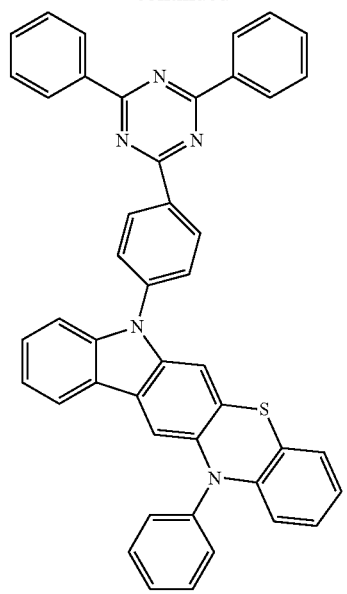
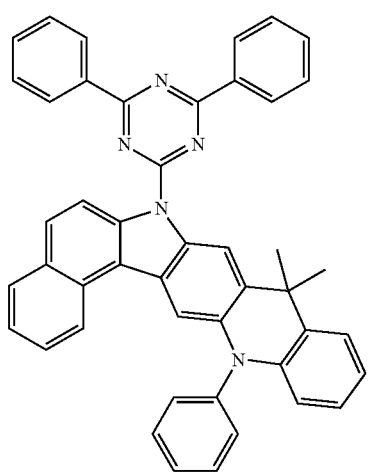
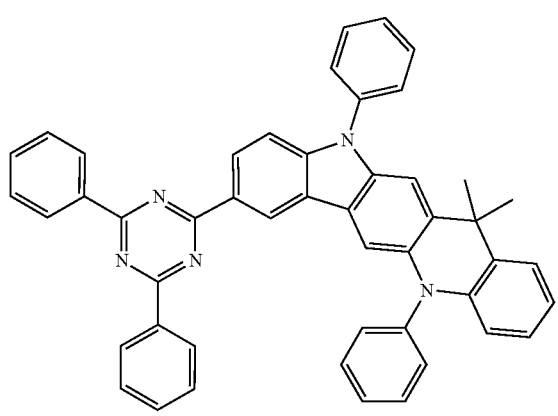
254
-continued
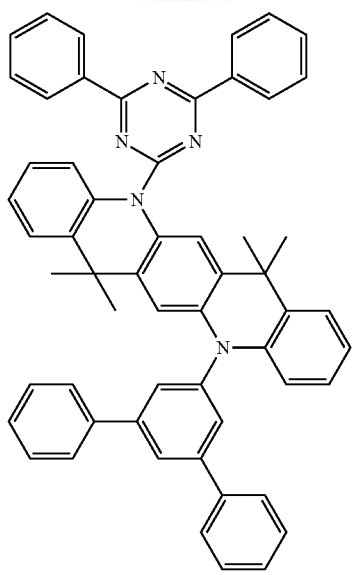
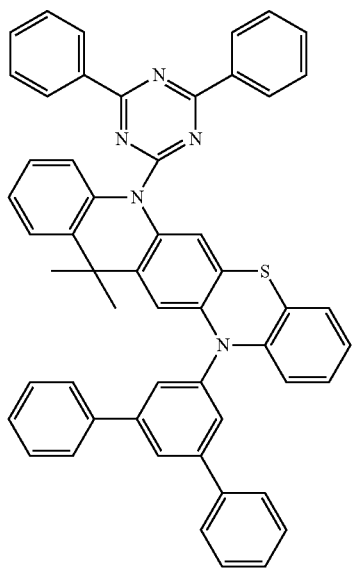
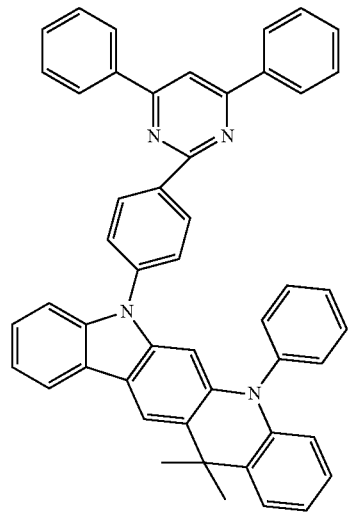

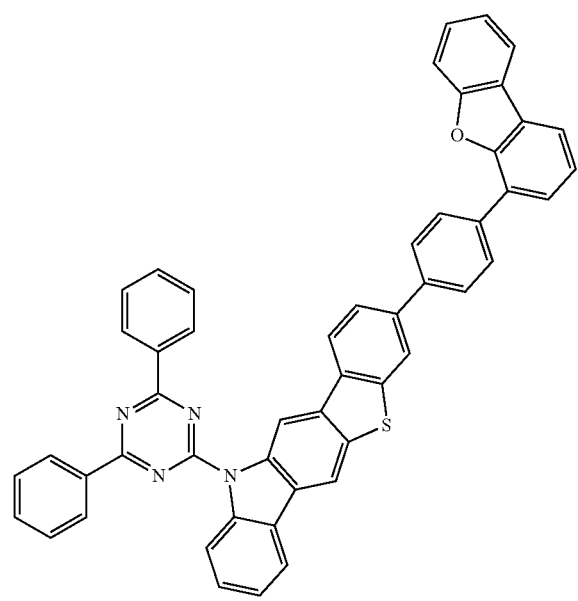
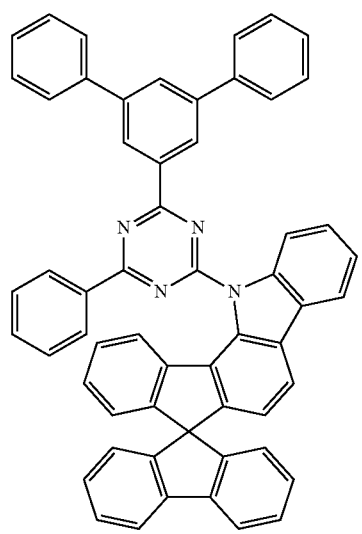
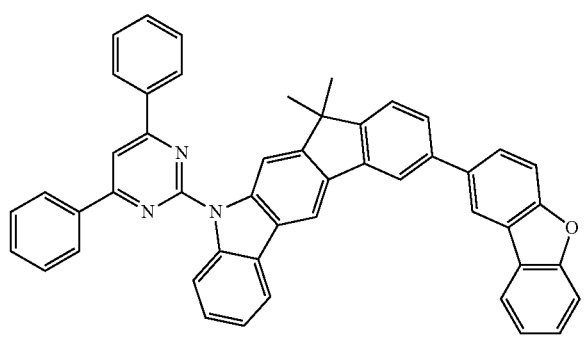

257
-continued
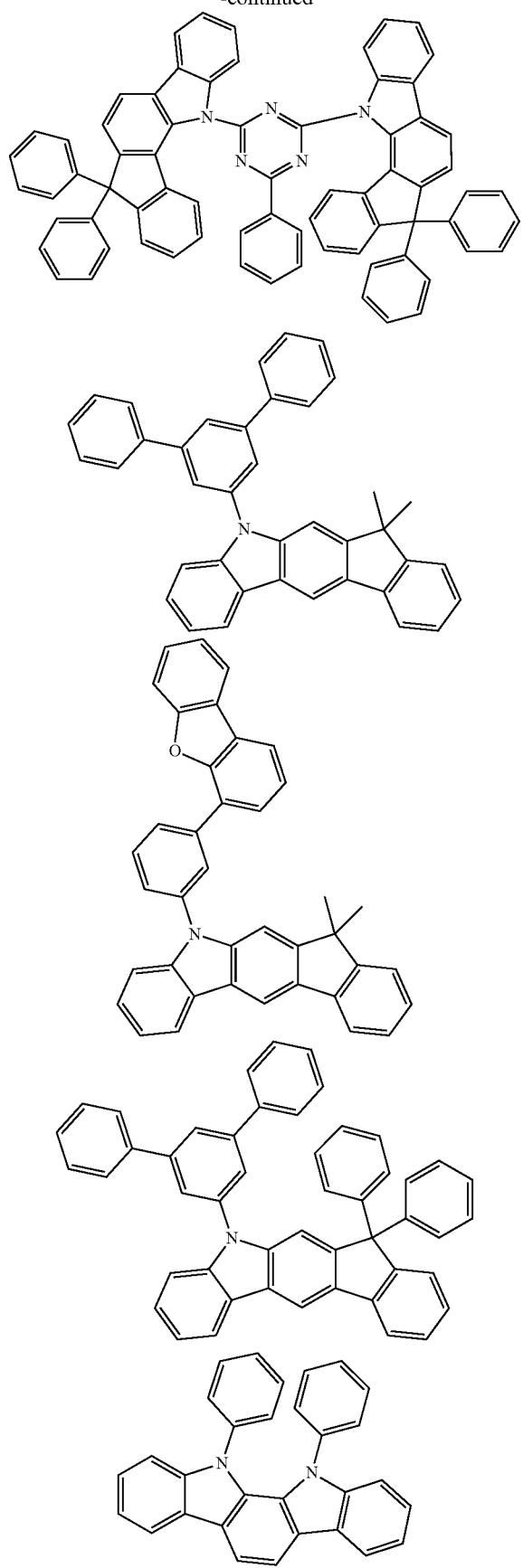
258
-continued
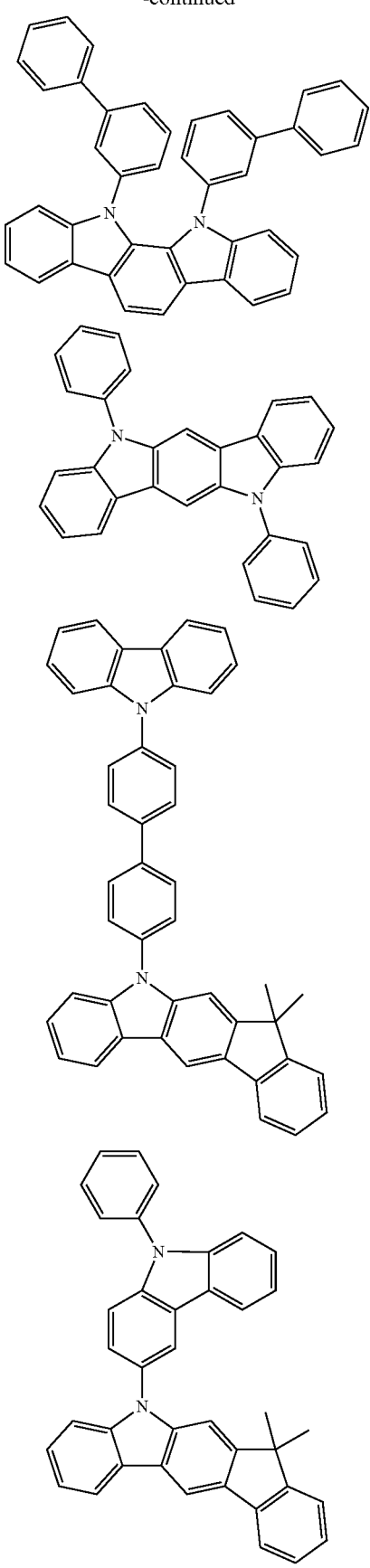

259
-continued
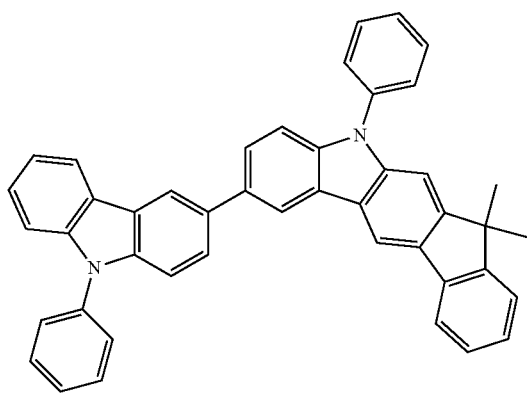
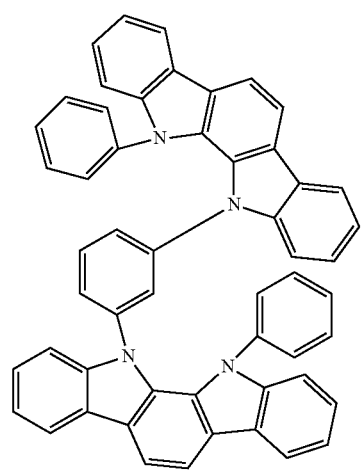
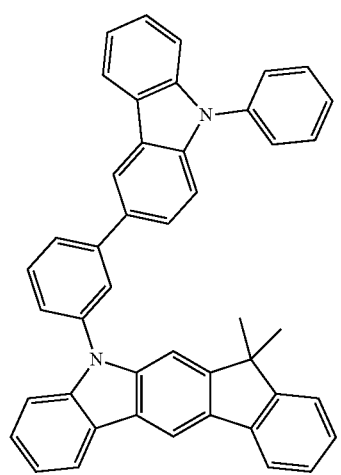
260
-continued
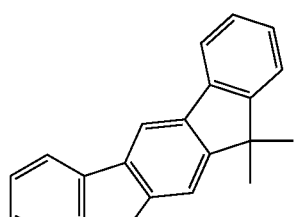
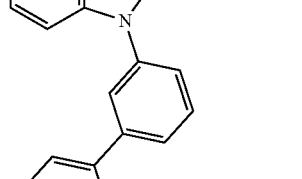
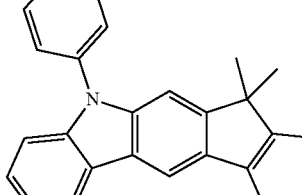
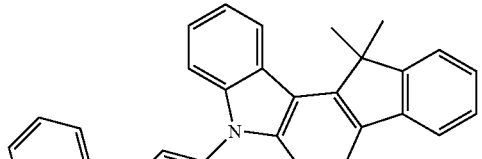
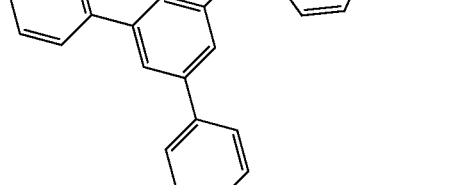
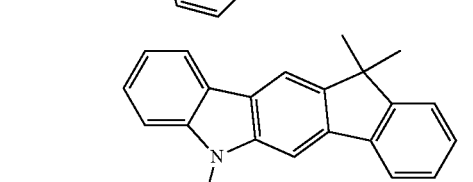
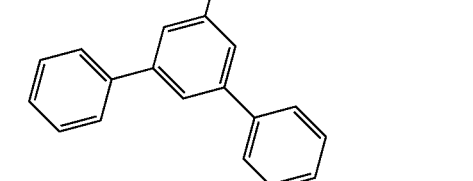
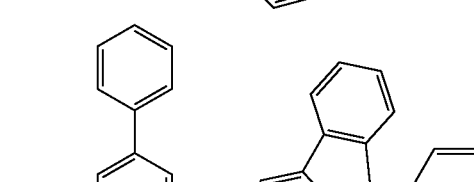
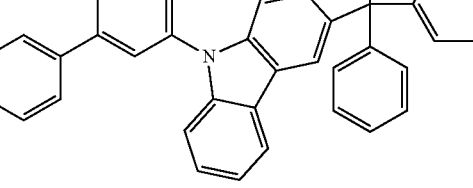

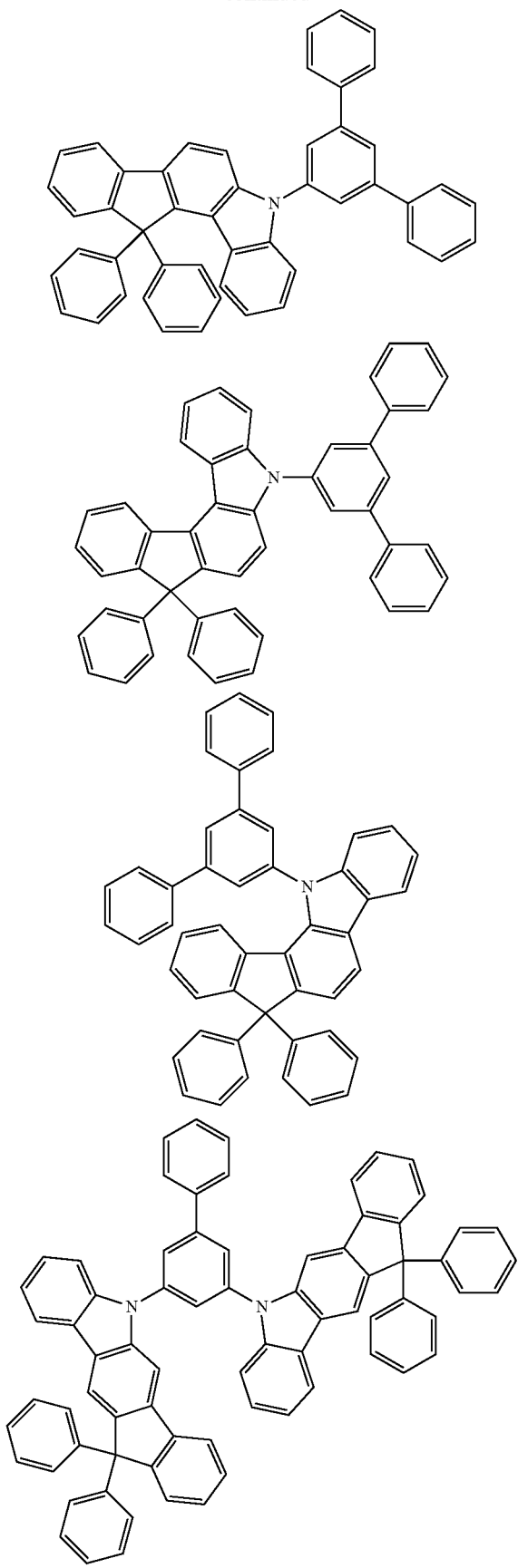
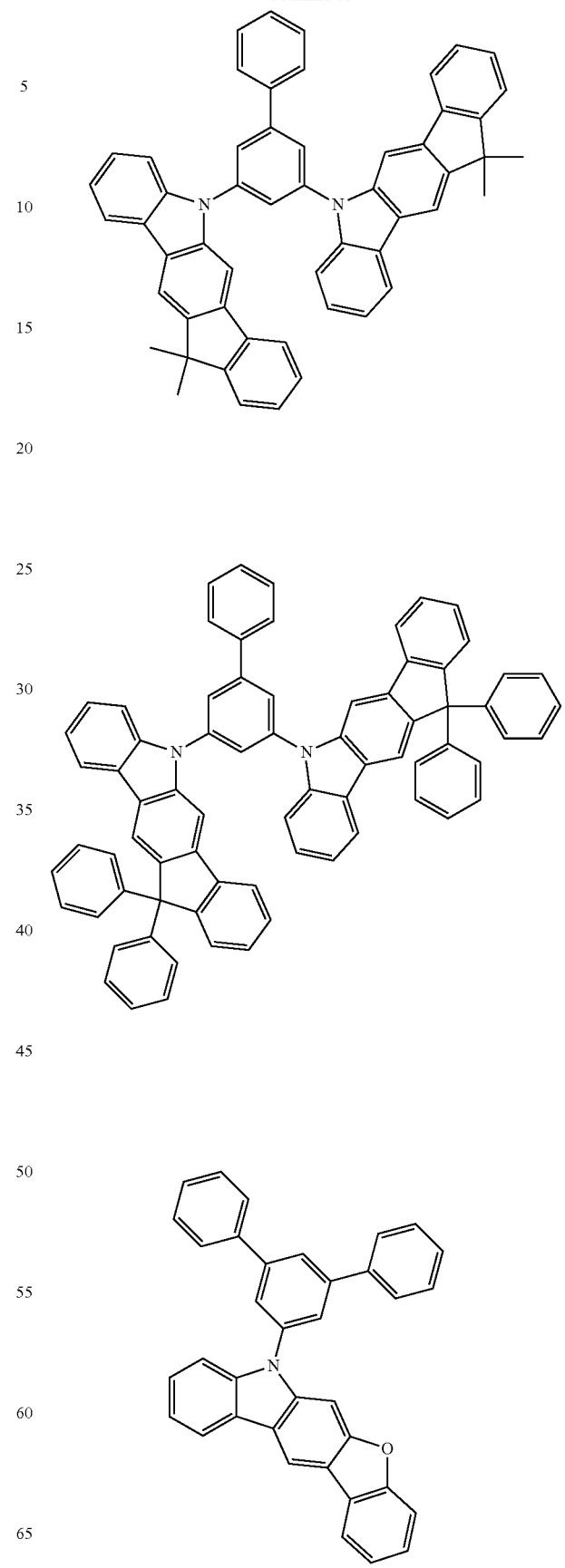

263
-continued
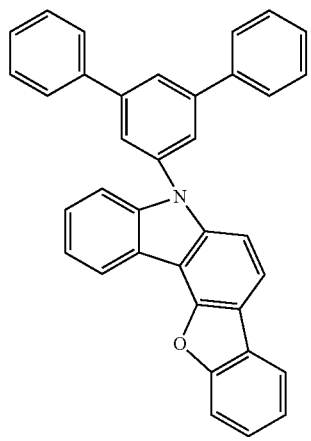
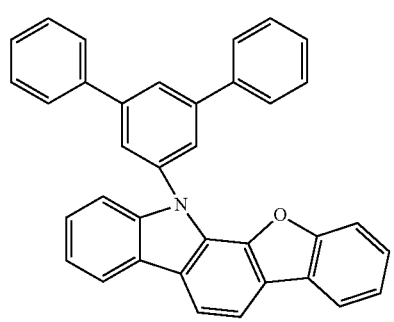
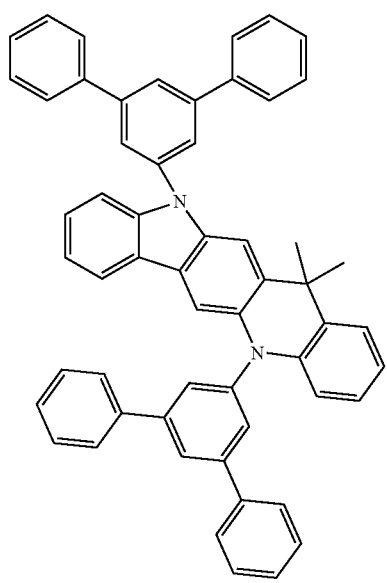
264
-continued
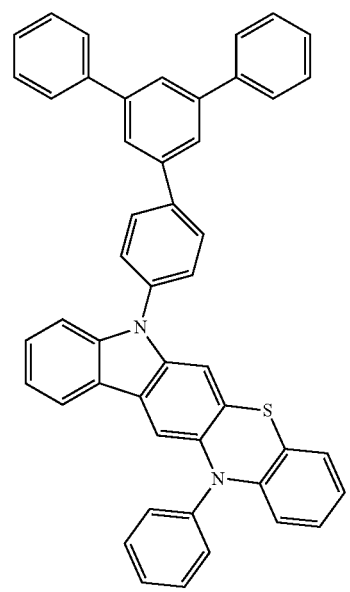
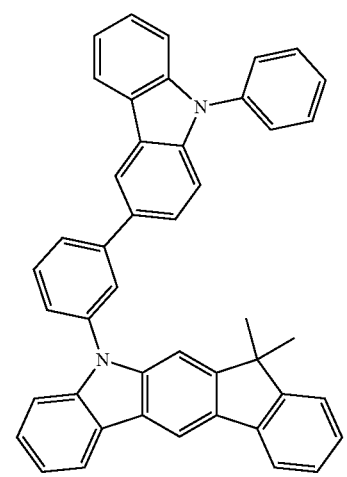
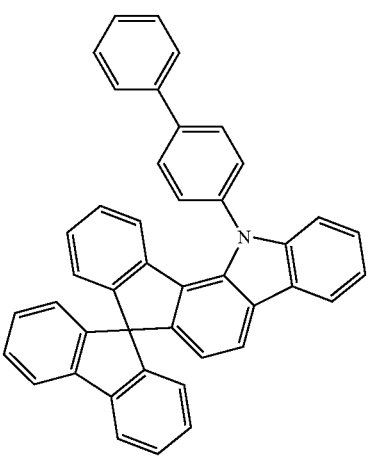

-continued
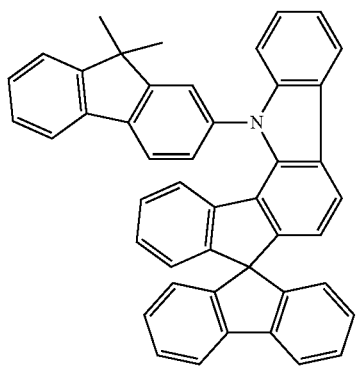 [SMILES: CC1(C)c2ccccc2-c2ccc(-n3c4ccccc4c4ccc5c(c43)-c3ccccc3C53c4ccccc4-c4ccccc43)cc21]
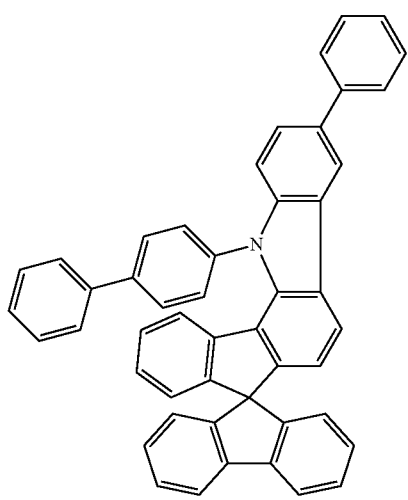
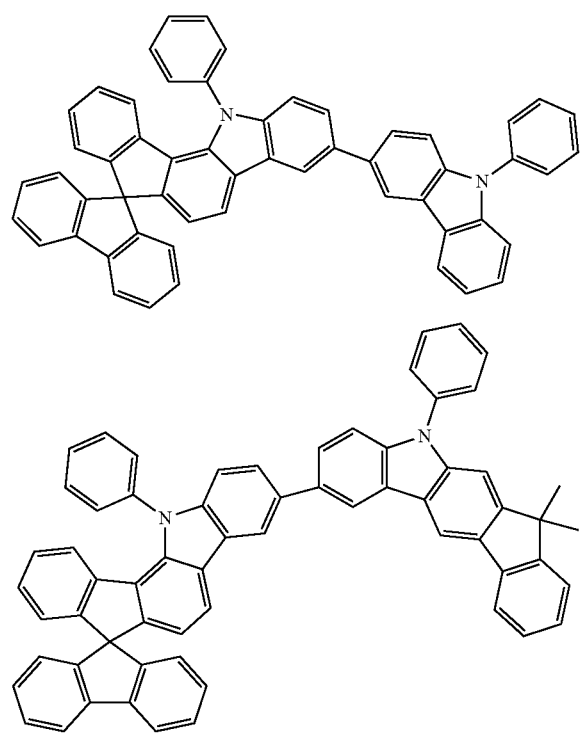
-continued
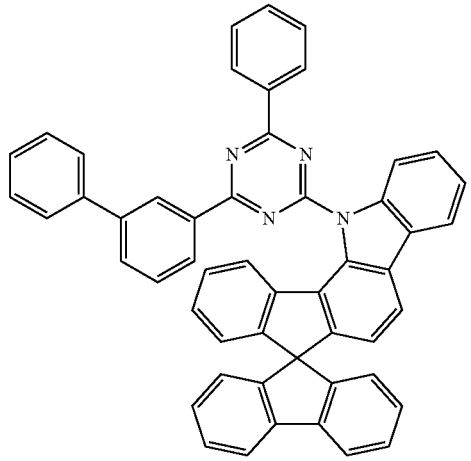
Examples of carbazole derivatives which can be used as hole- or electron-transporting matrix materials according to the substitution pattern are the following structures:
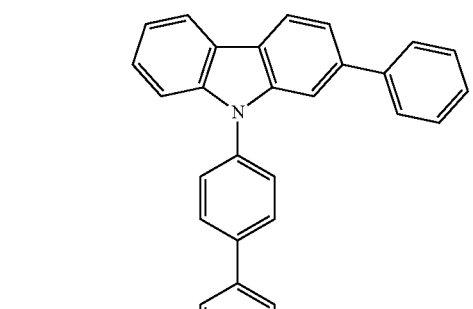
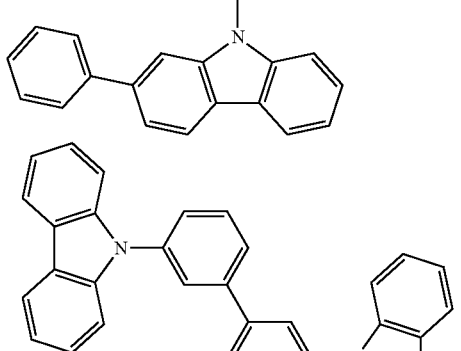
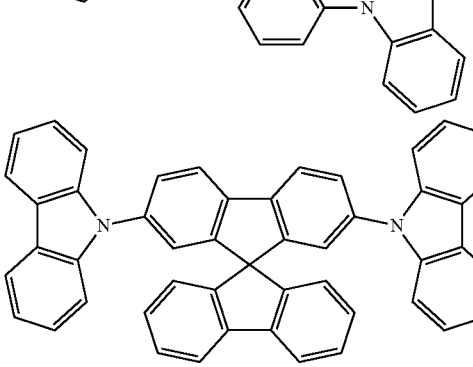

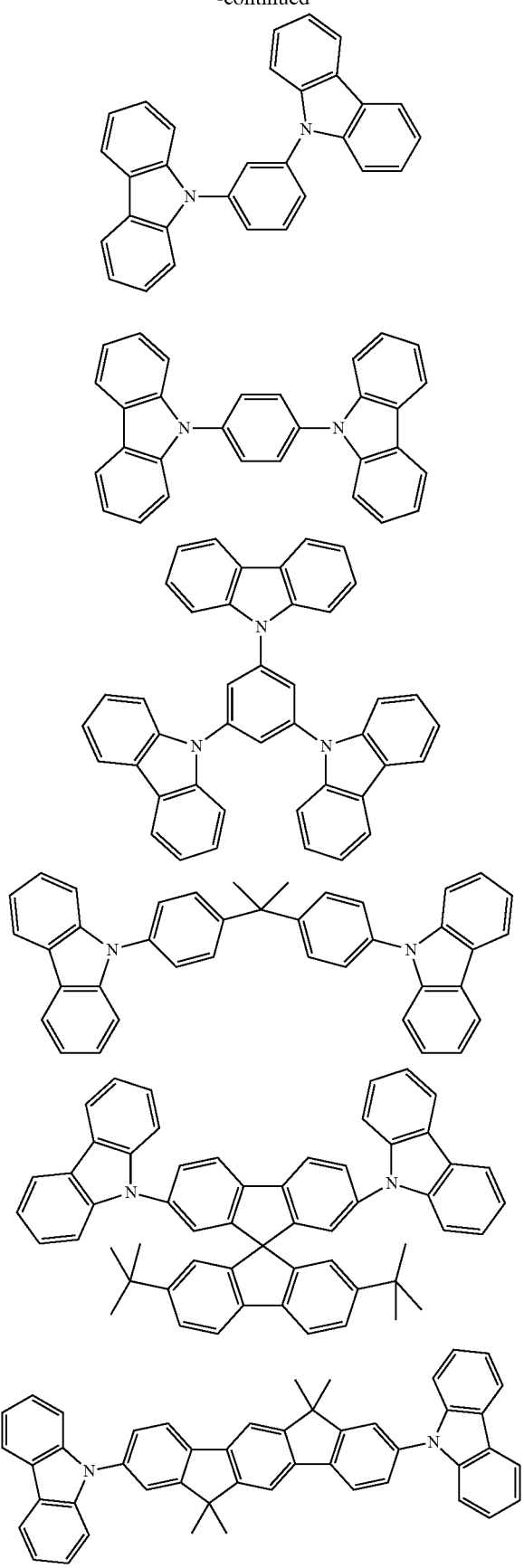

269
-continued
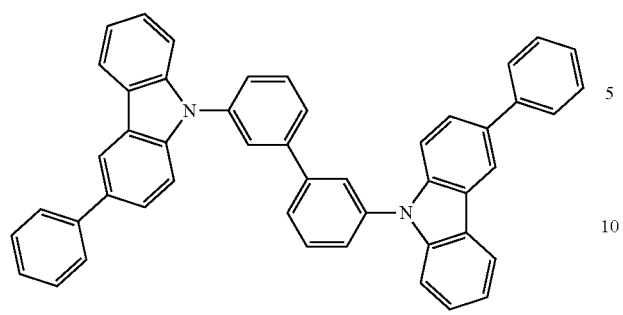
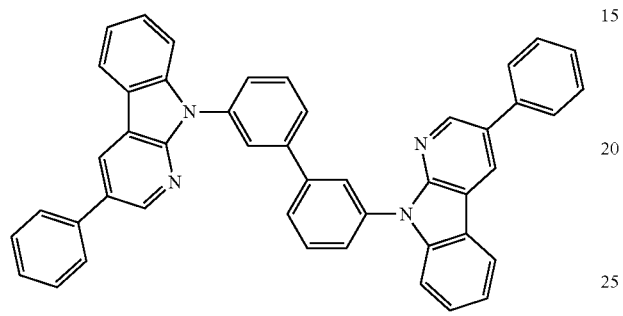
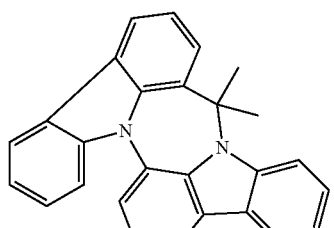
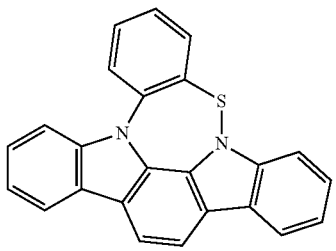
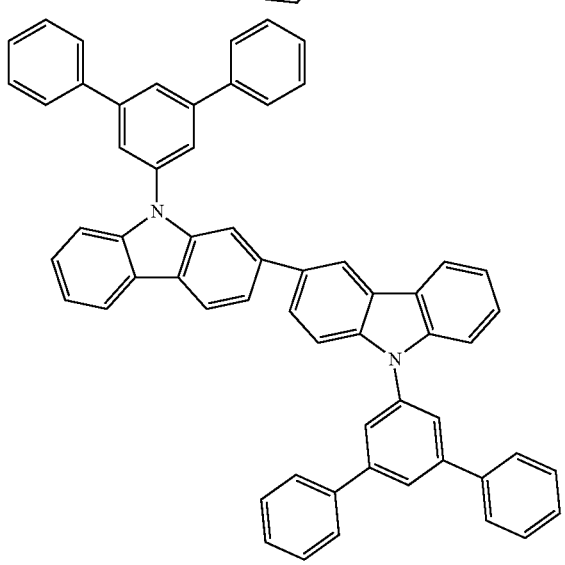
270
-continued
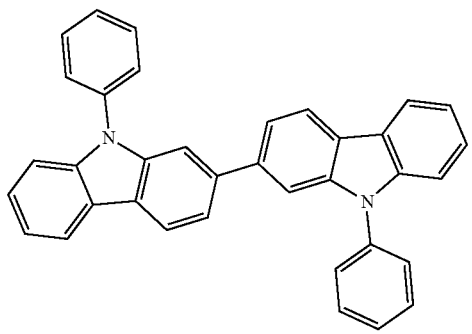
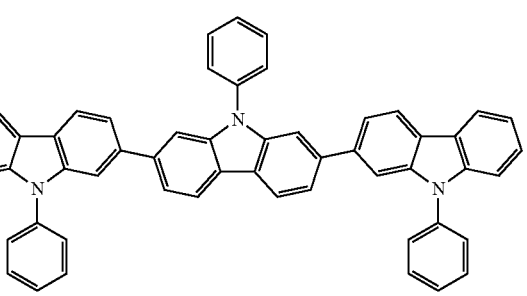
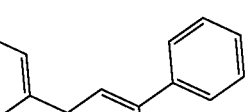
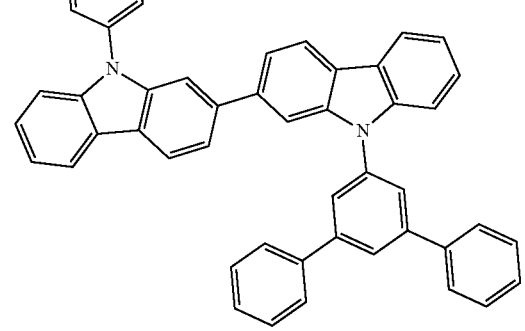

271
-continued
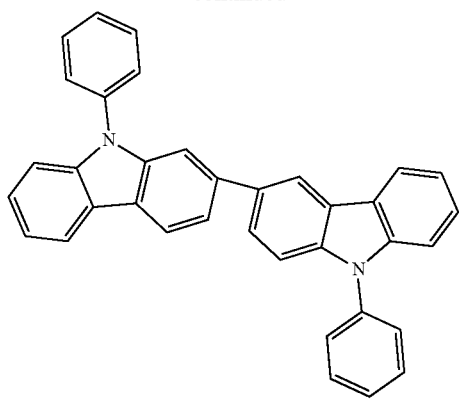
272
-continued
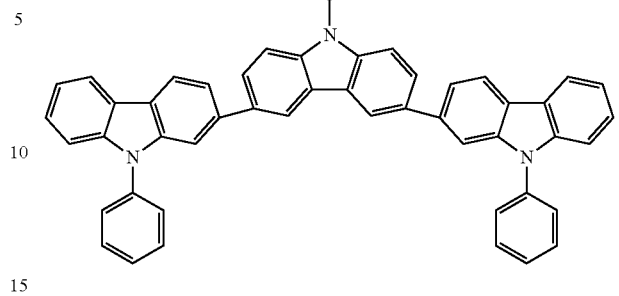
Examples of bridged carbazole derivatives which can be used as hole-transporting matrix materials:
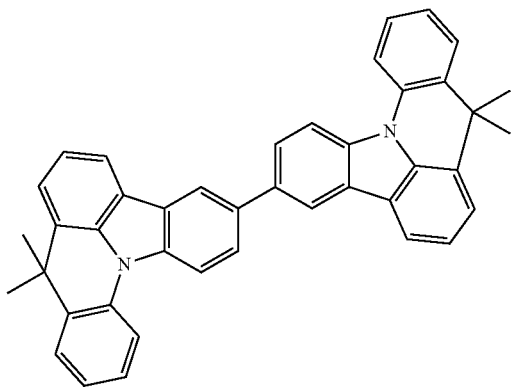
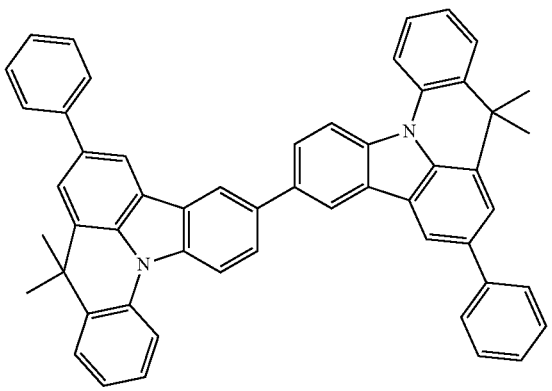
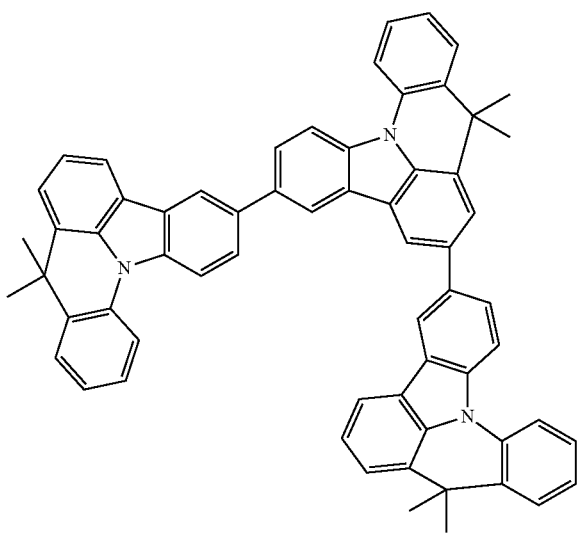
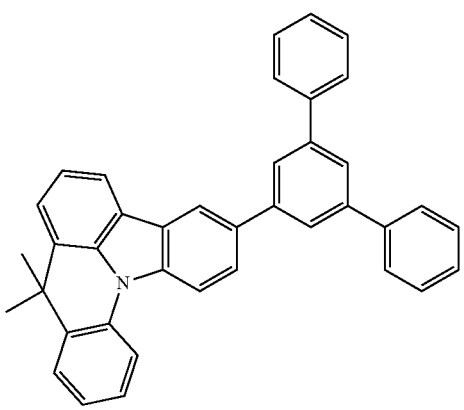

-continued
273
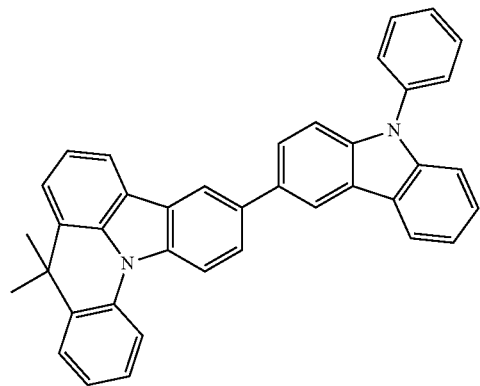
274
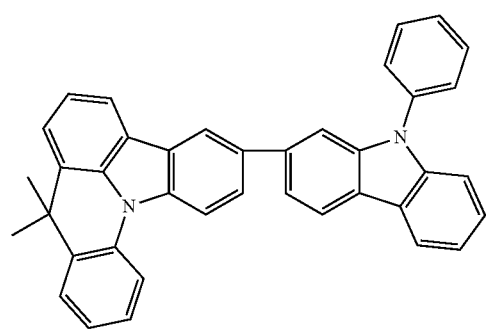
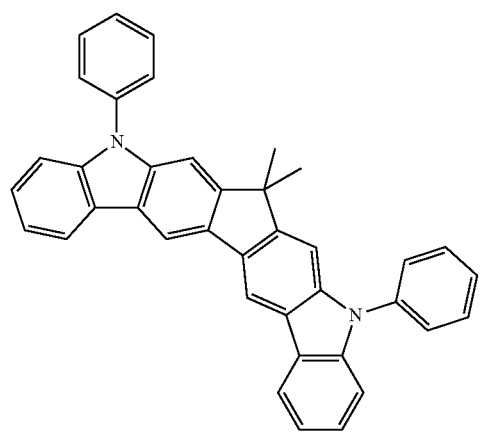
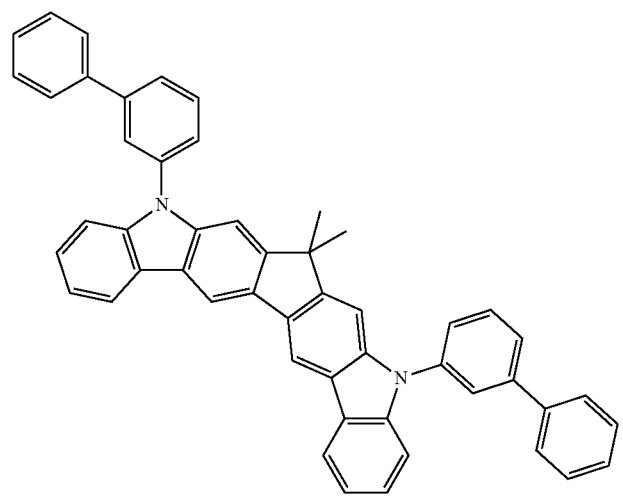
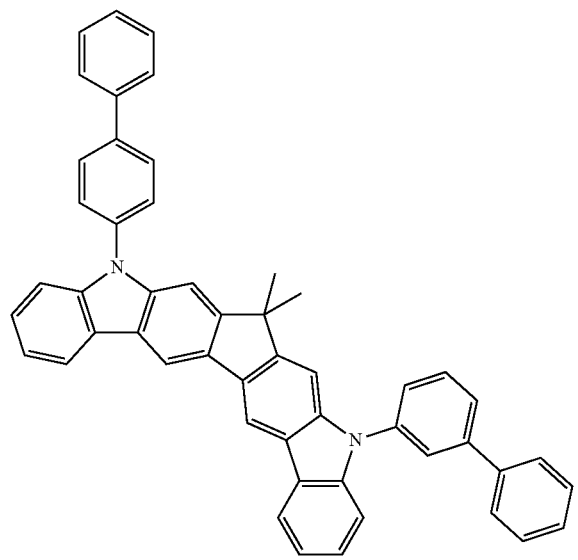
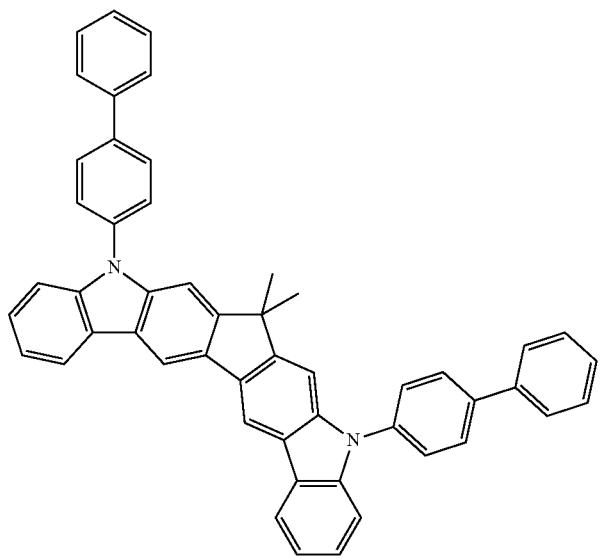

-continued
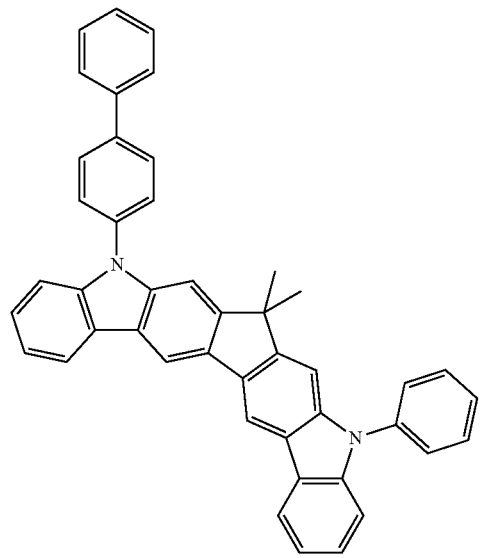
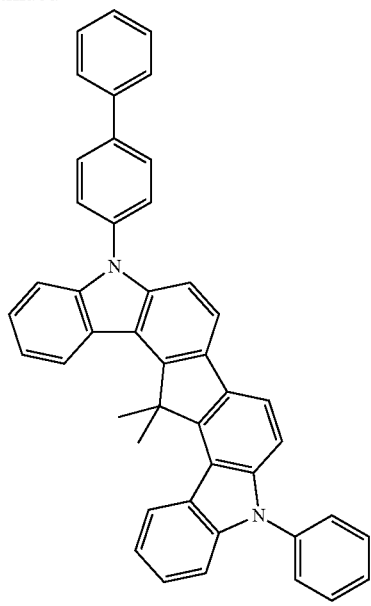
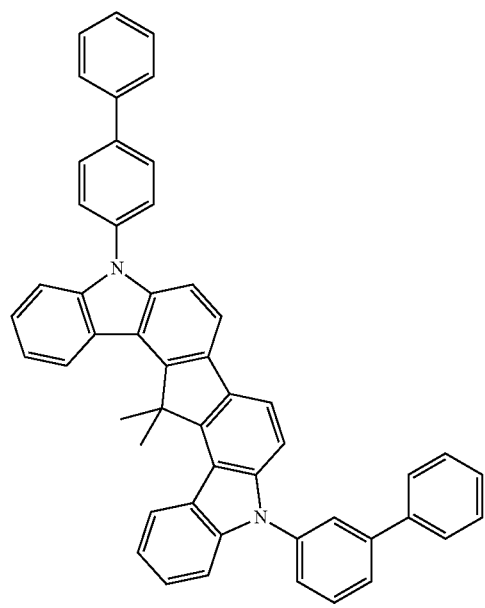
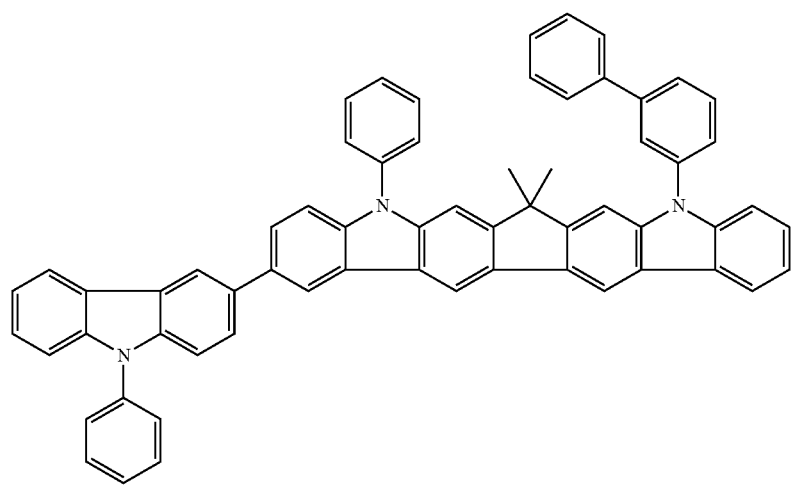

-continued
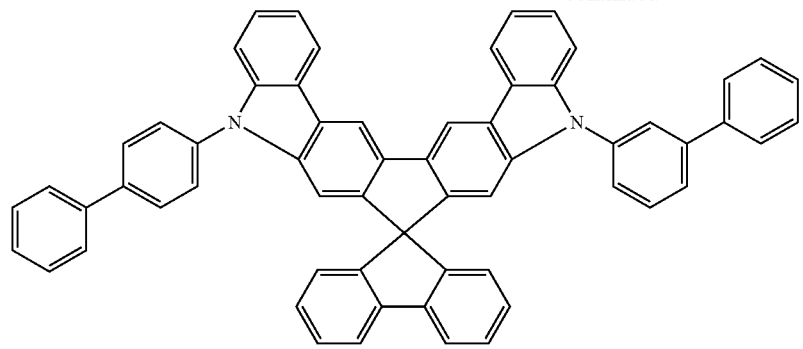
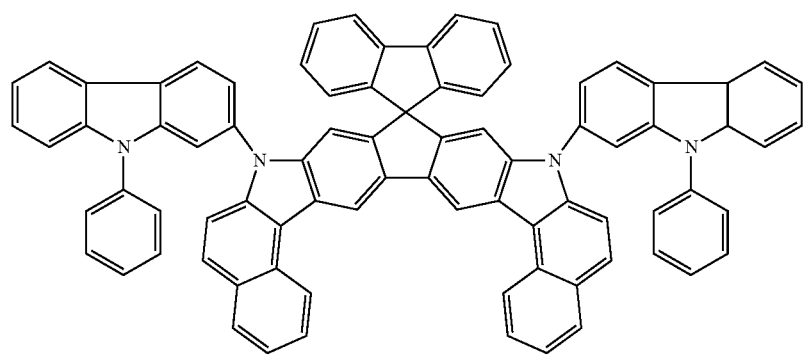
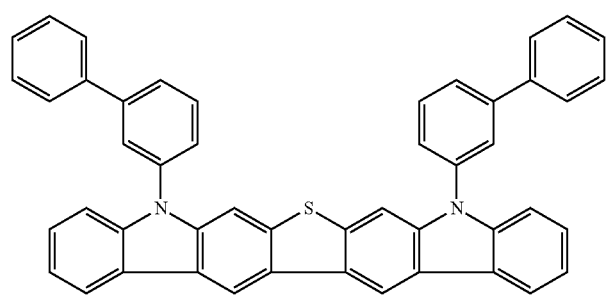
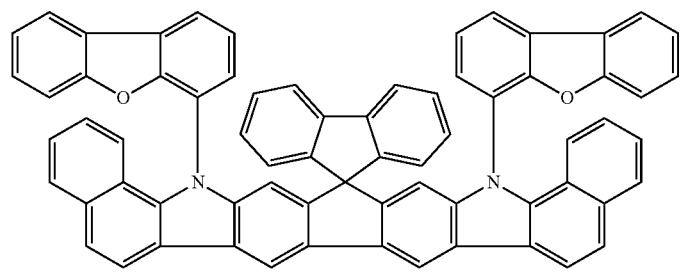
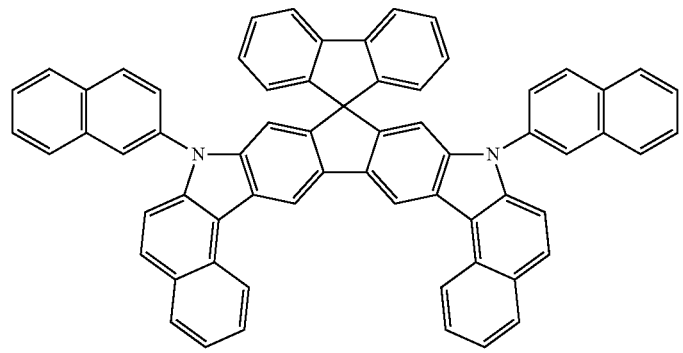

-continued
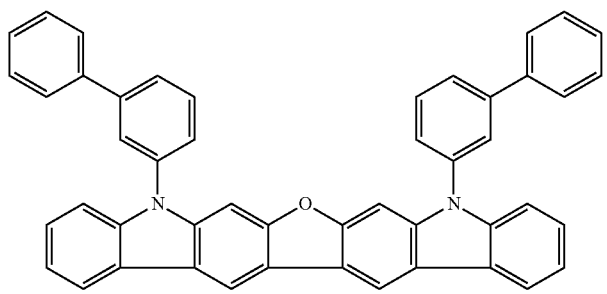
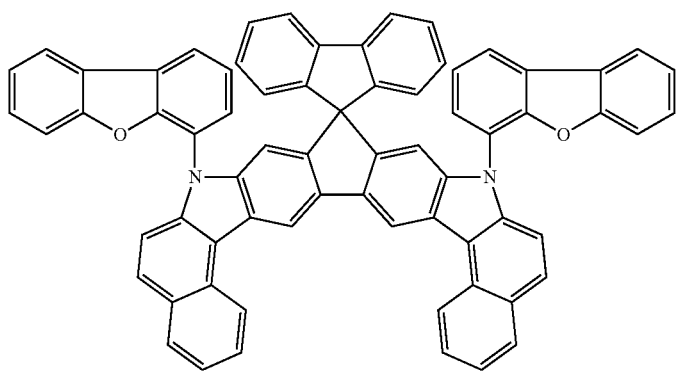
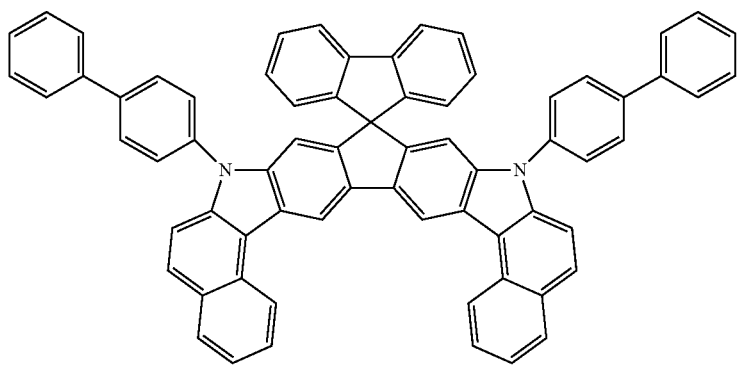
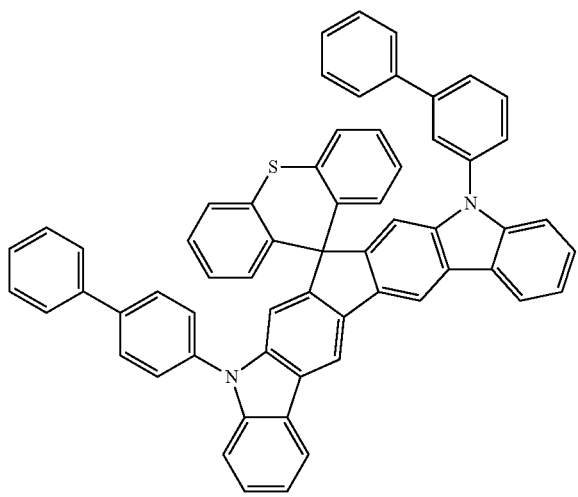

-continued
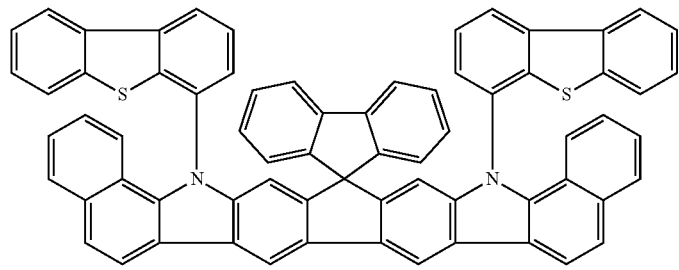
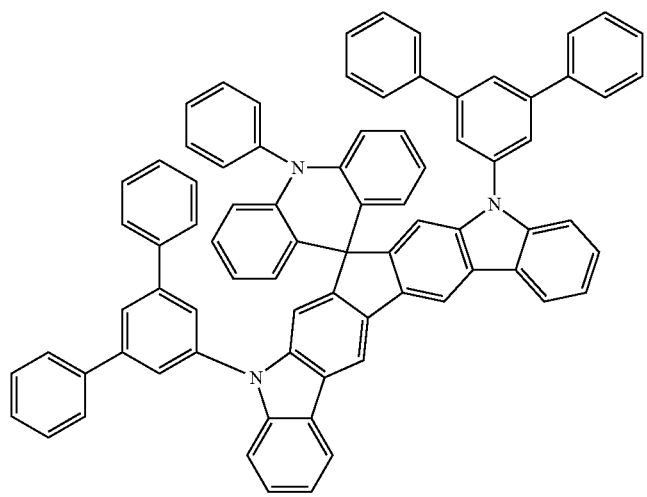
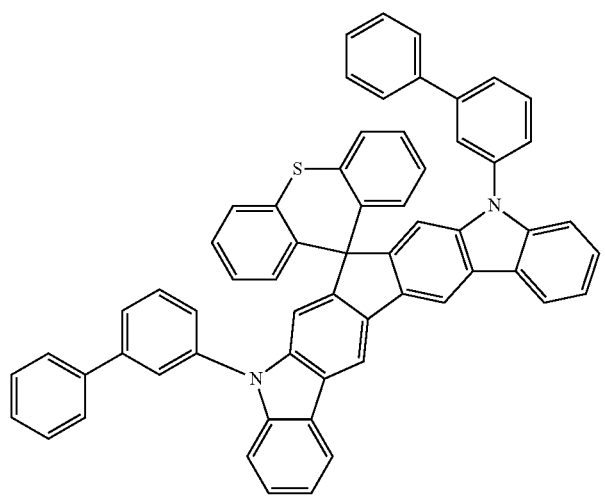
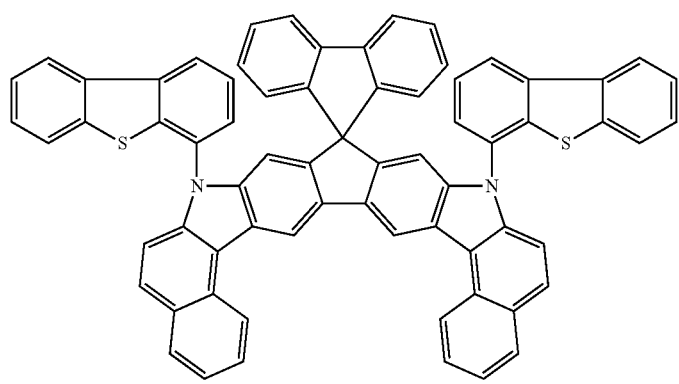

-continued
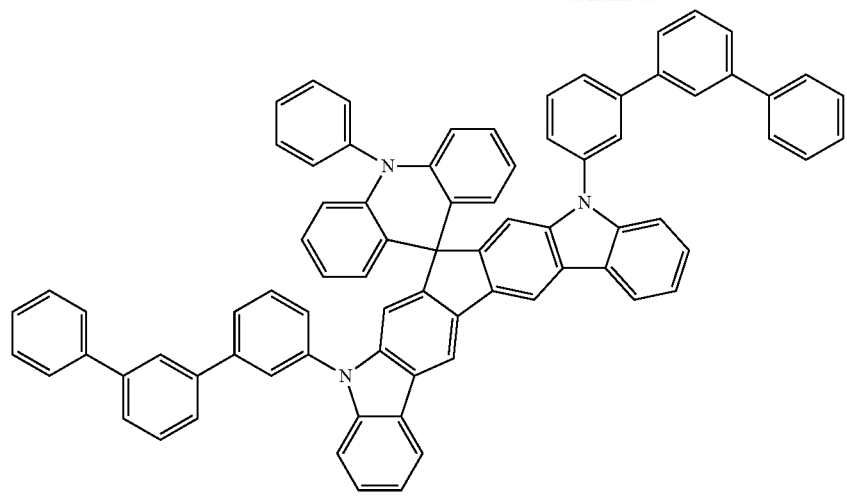
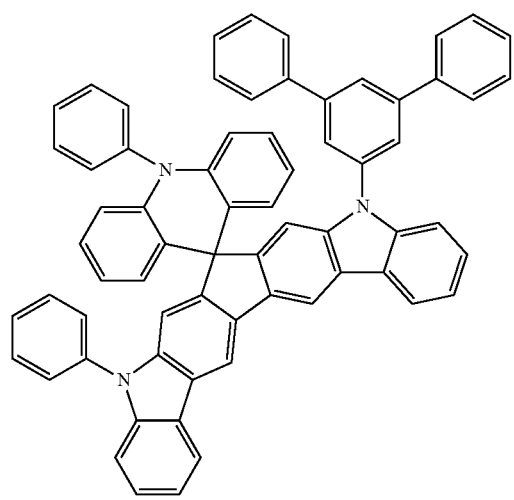
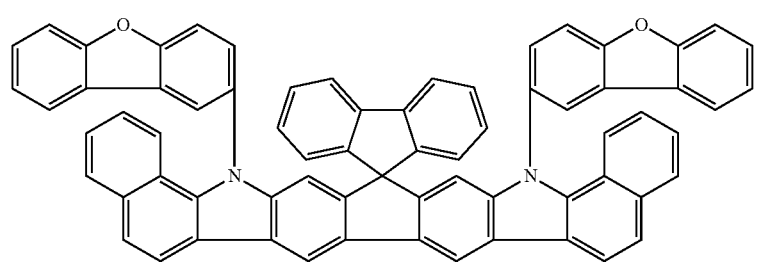

-continued
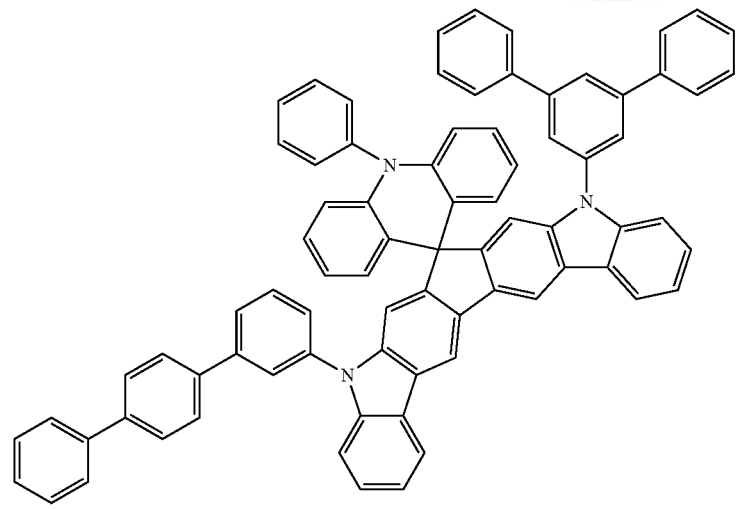
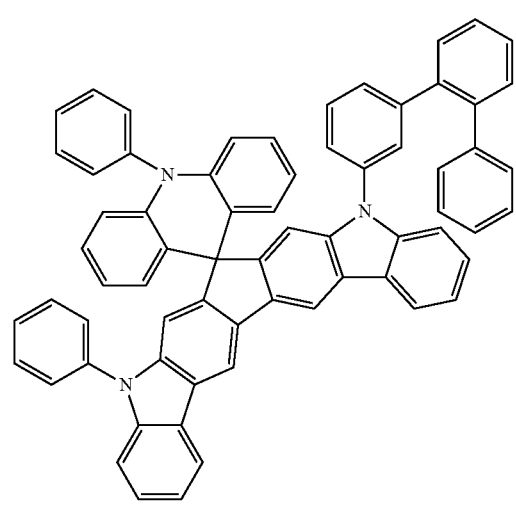
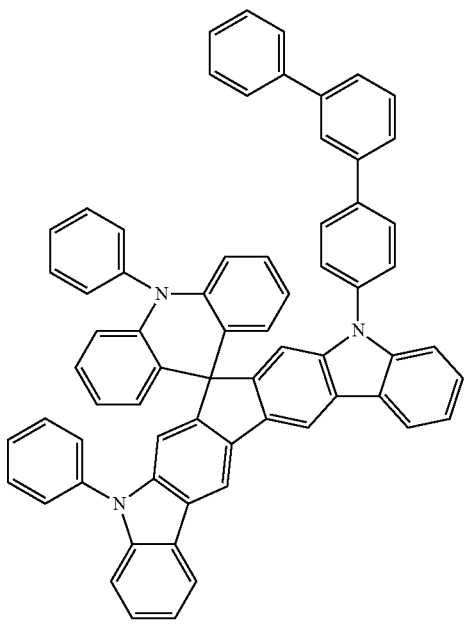
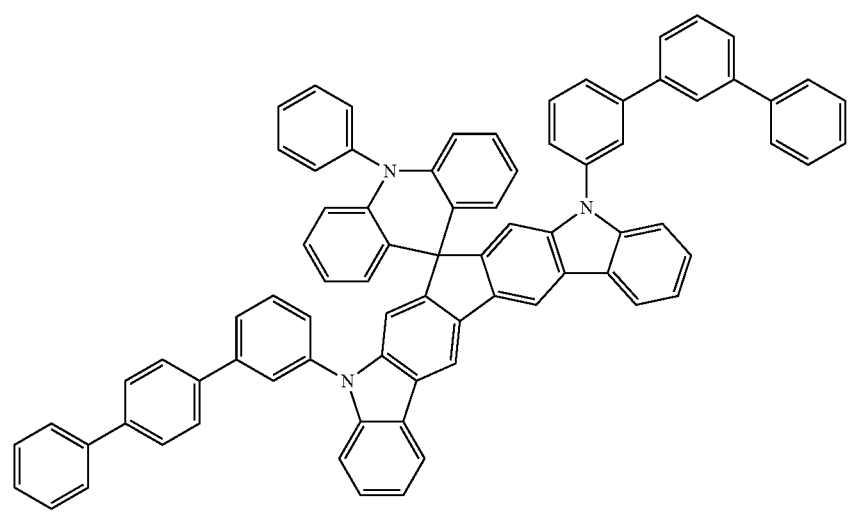

287 288
-continued
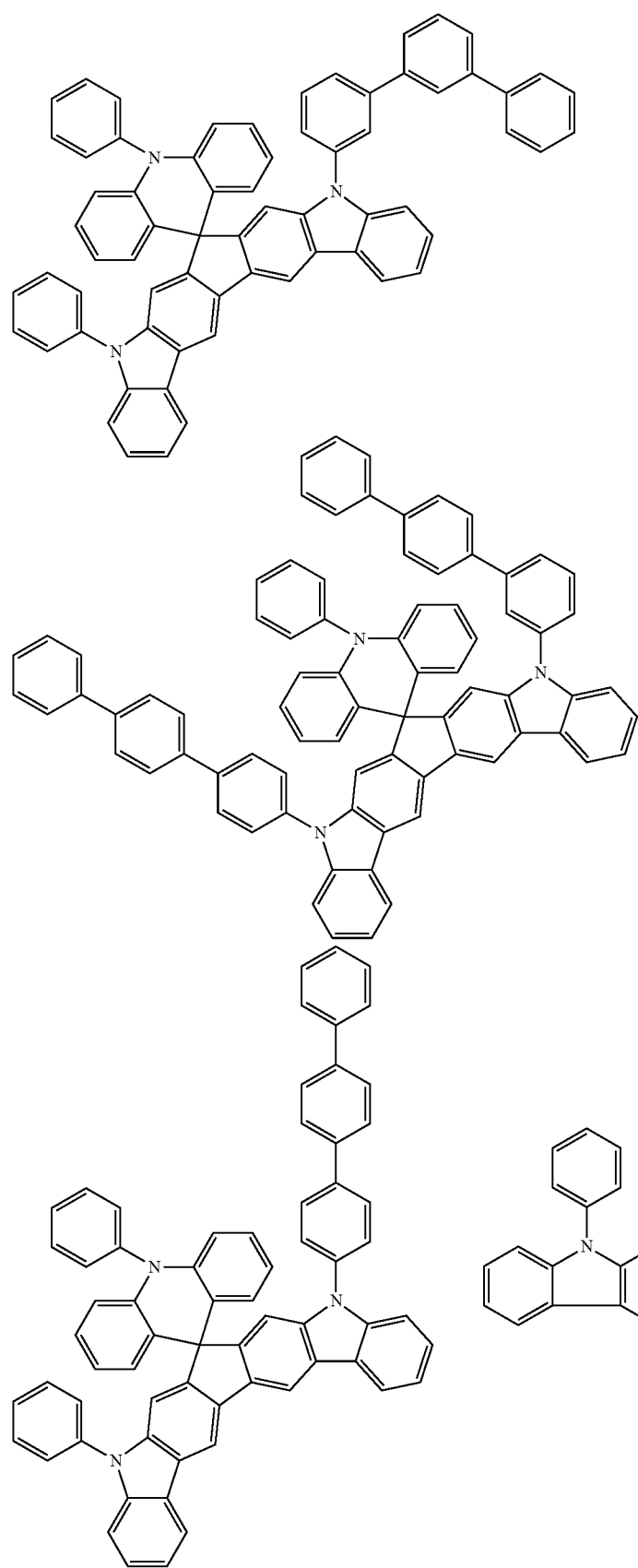
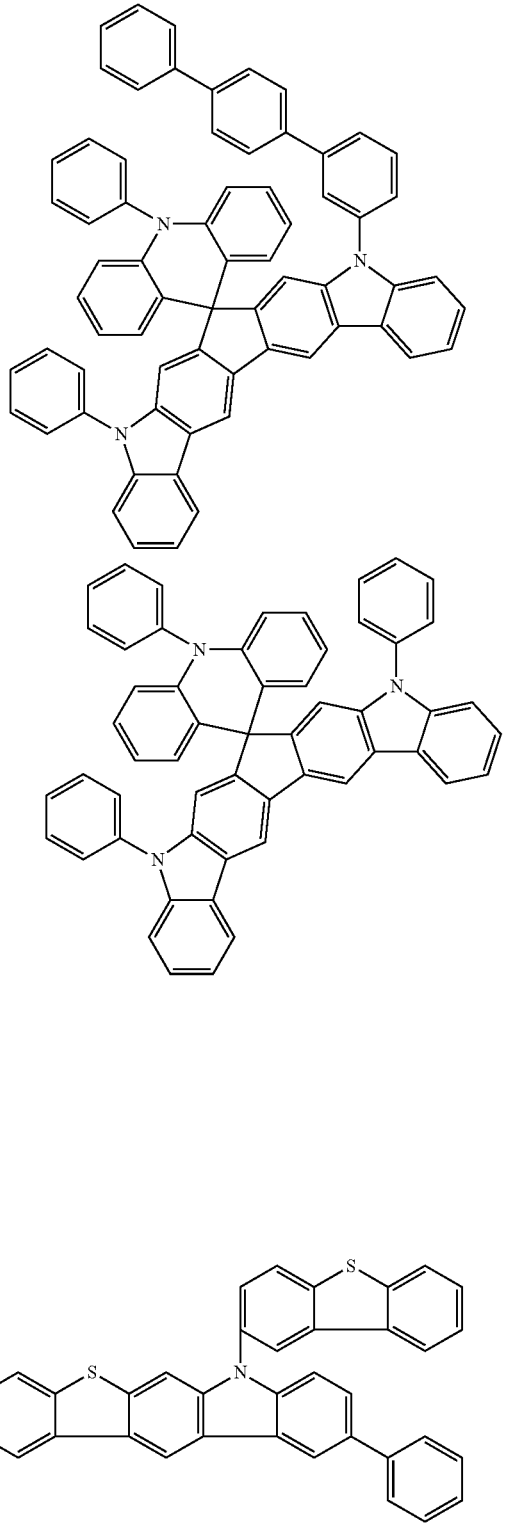

289
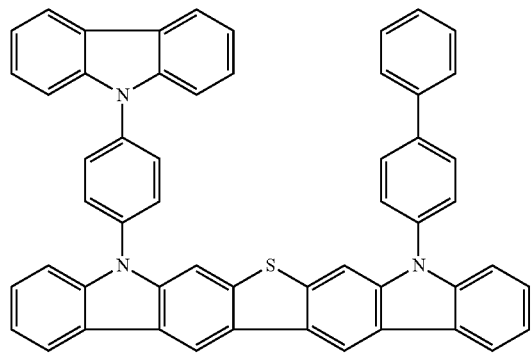
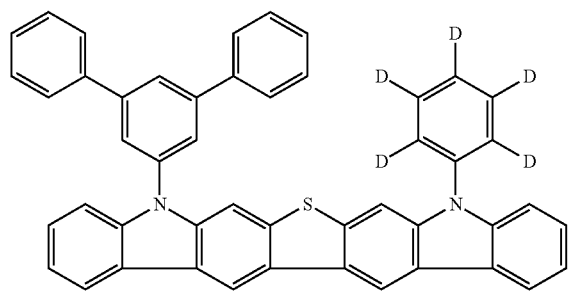
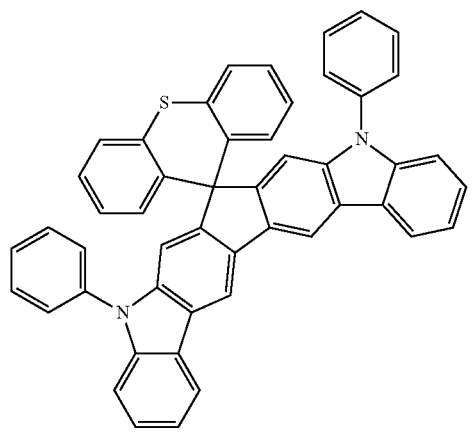
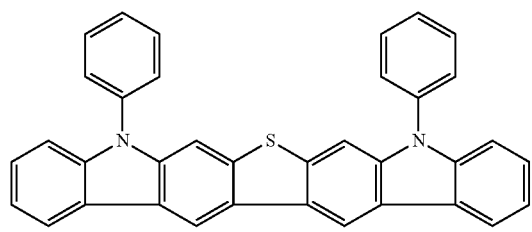
290
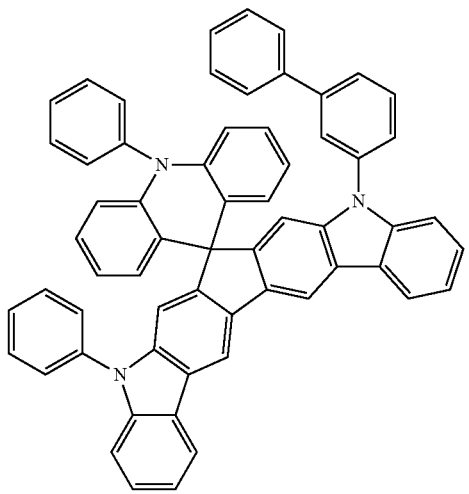
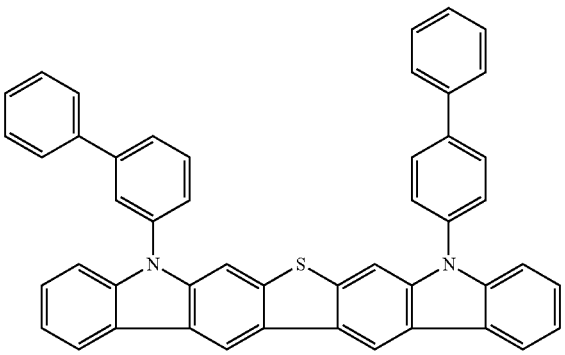
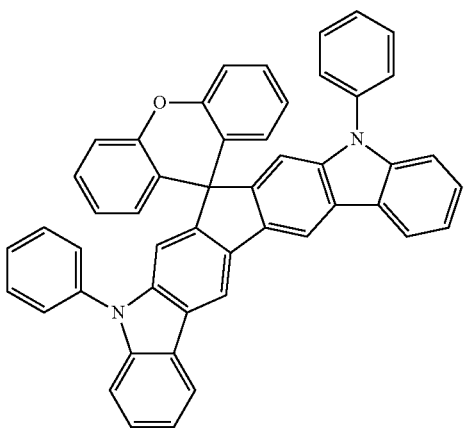
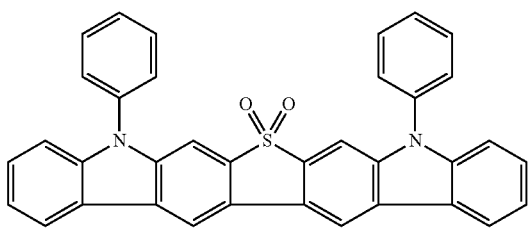

291 292
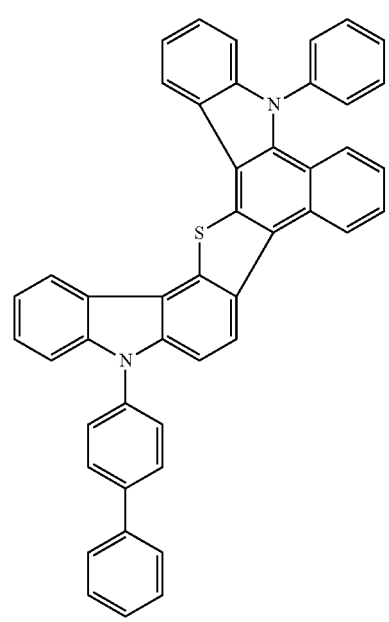 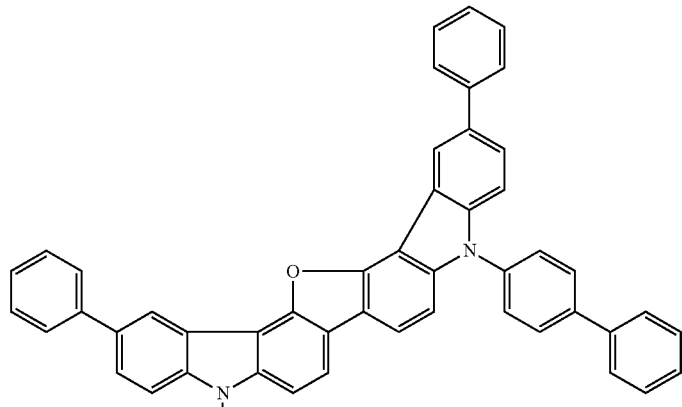
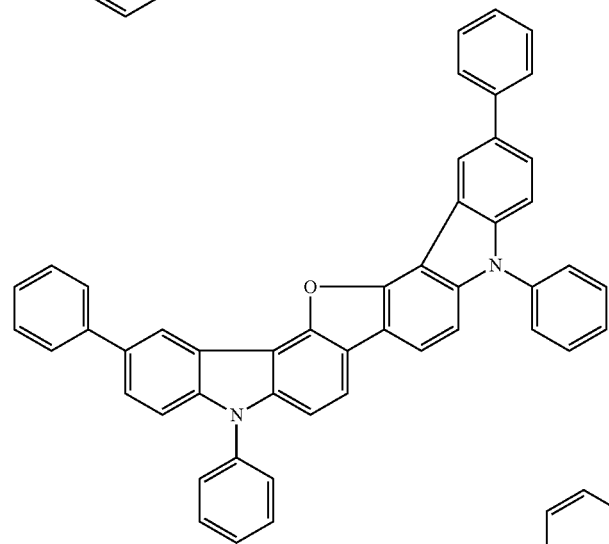 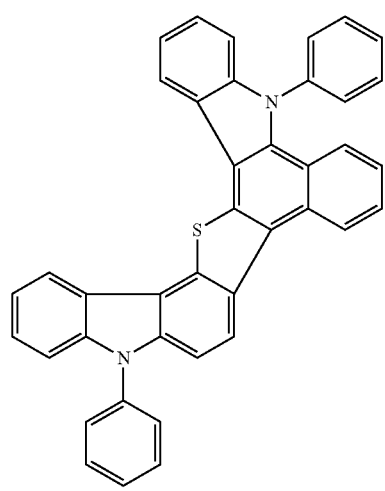
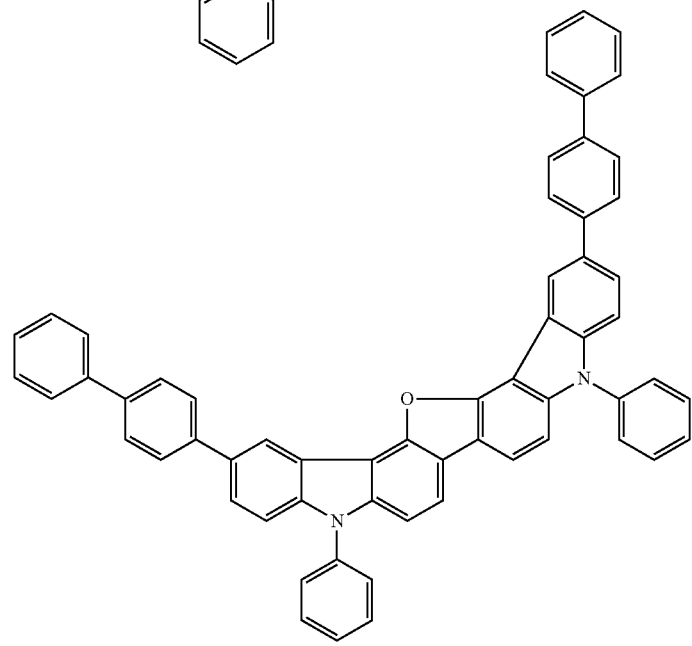

293 294
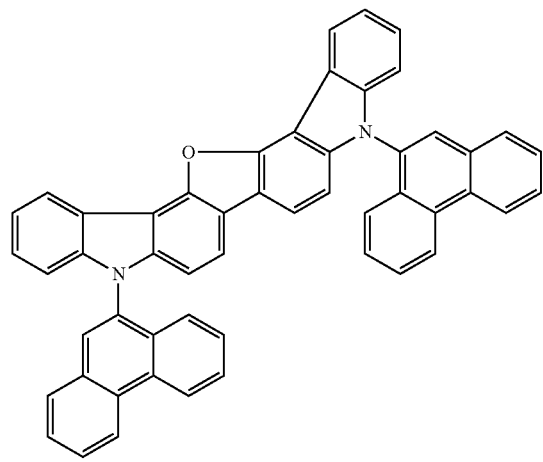
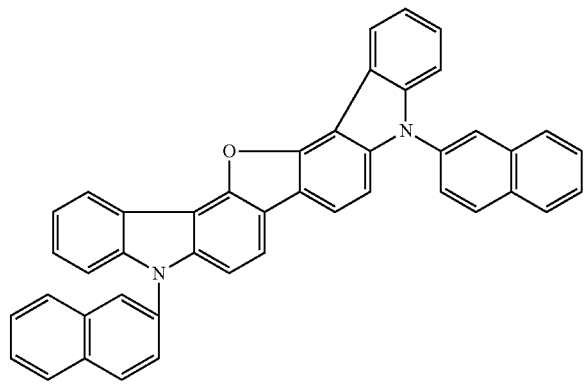
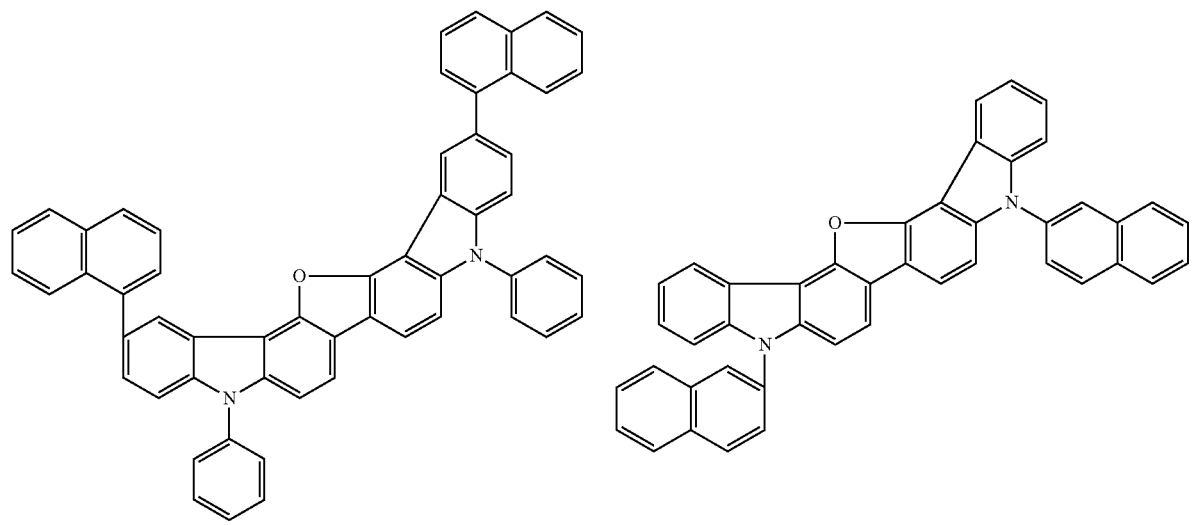
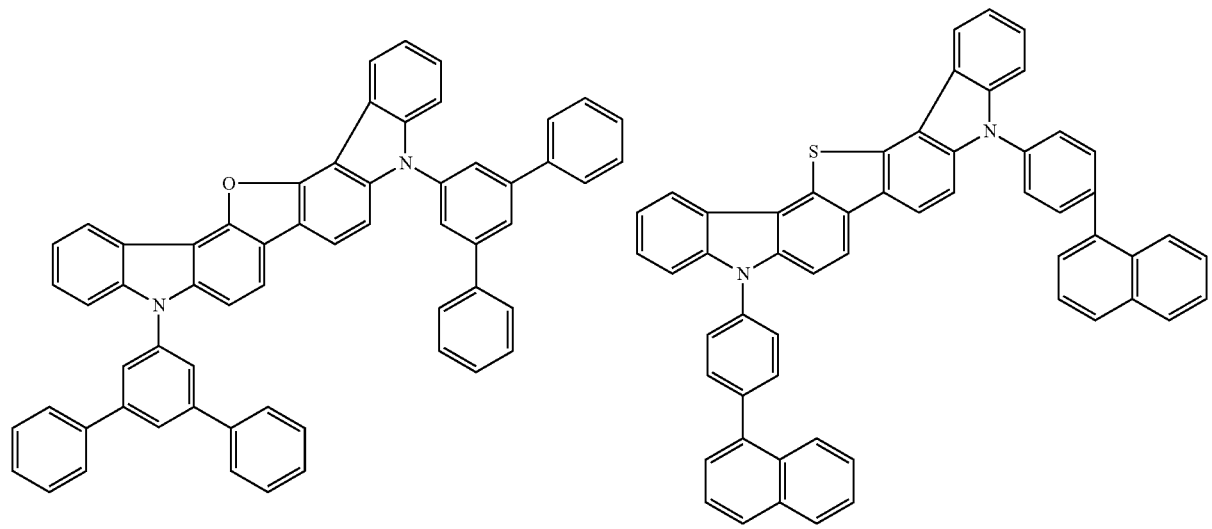

-continued
295 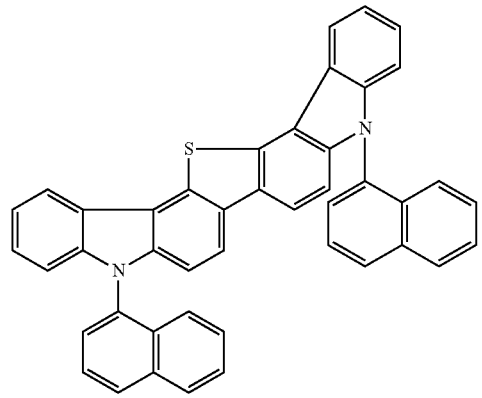
296 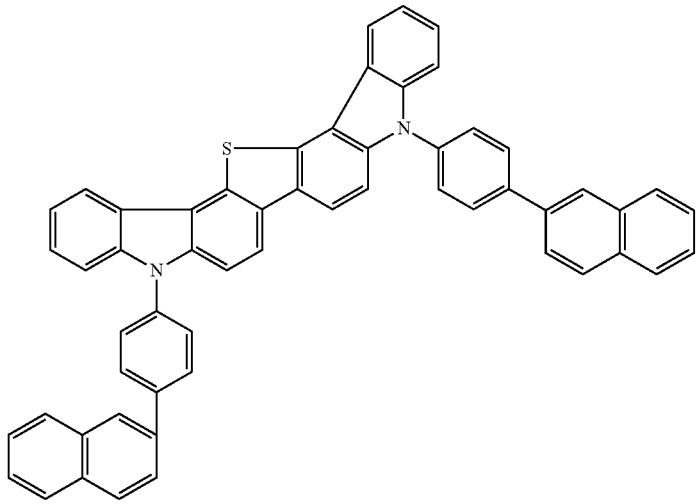
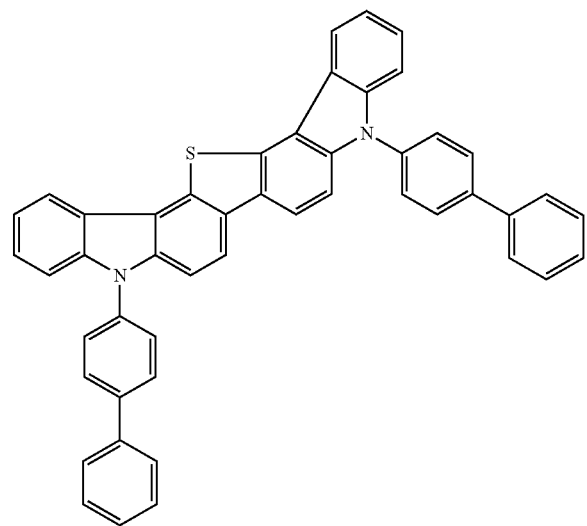
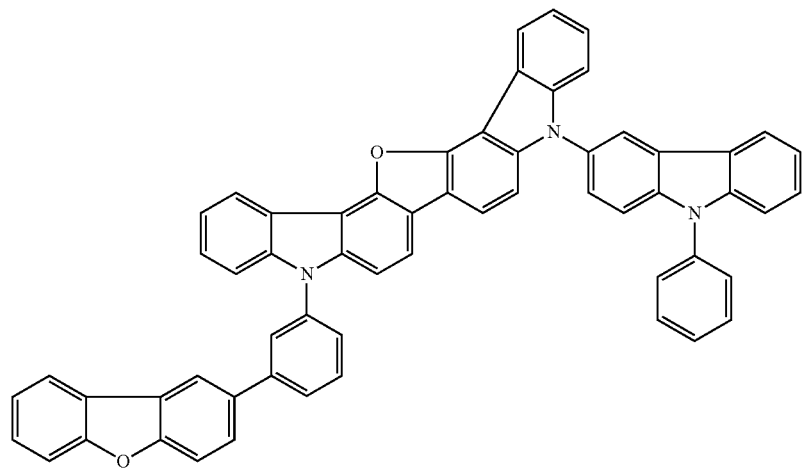

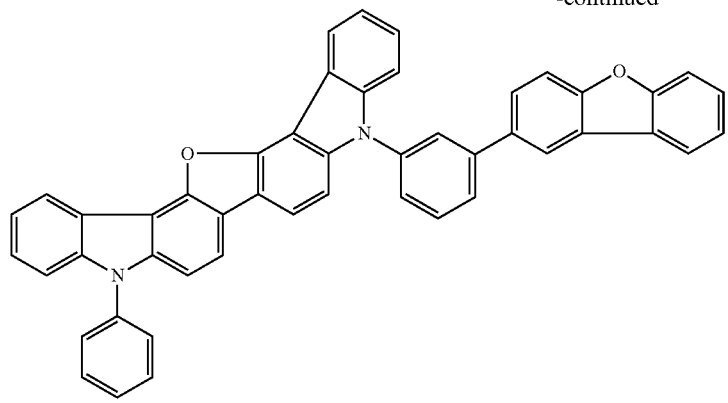
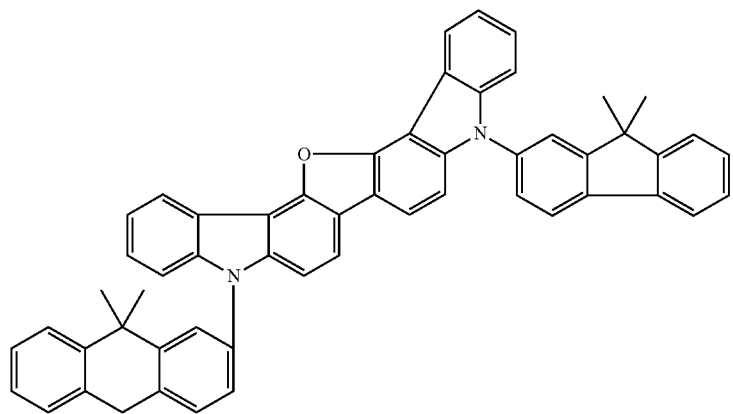
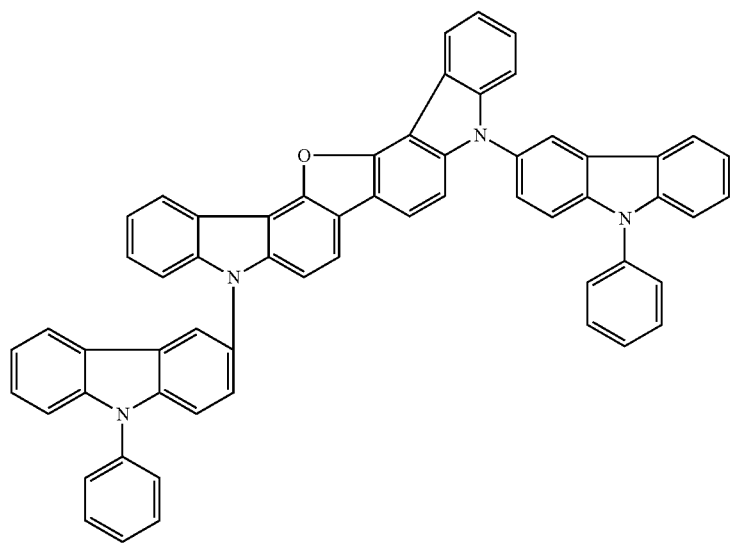

Examples of biscarbazole derivatives which can be used as hole-transporting matrix materials:
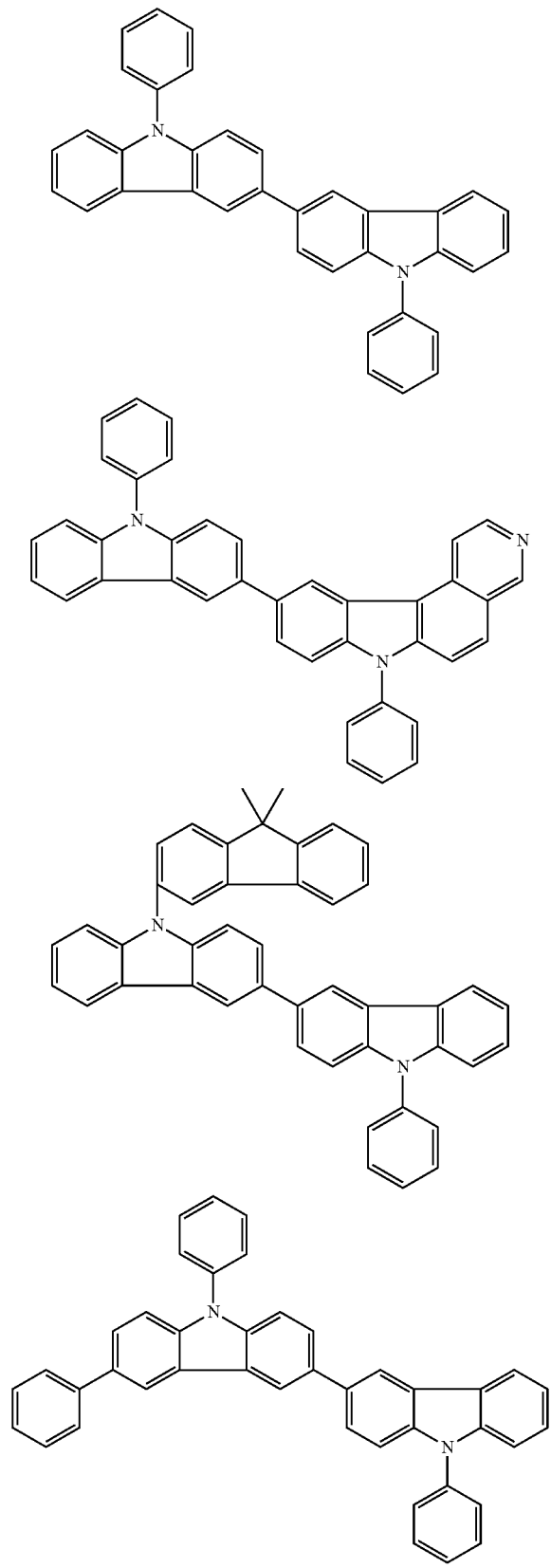
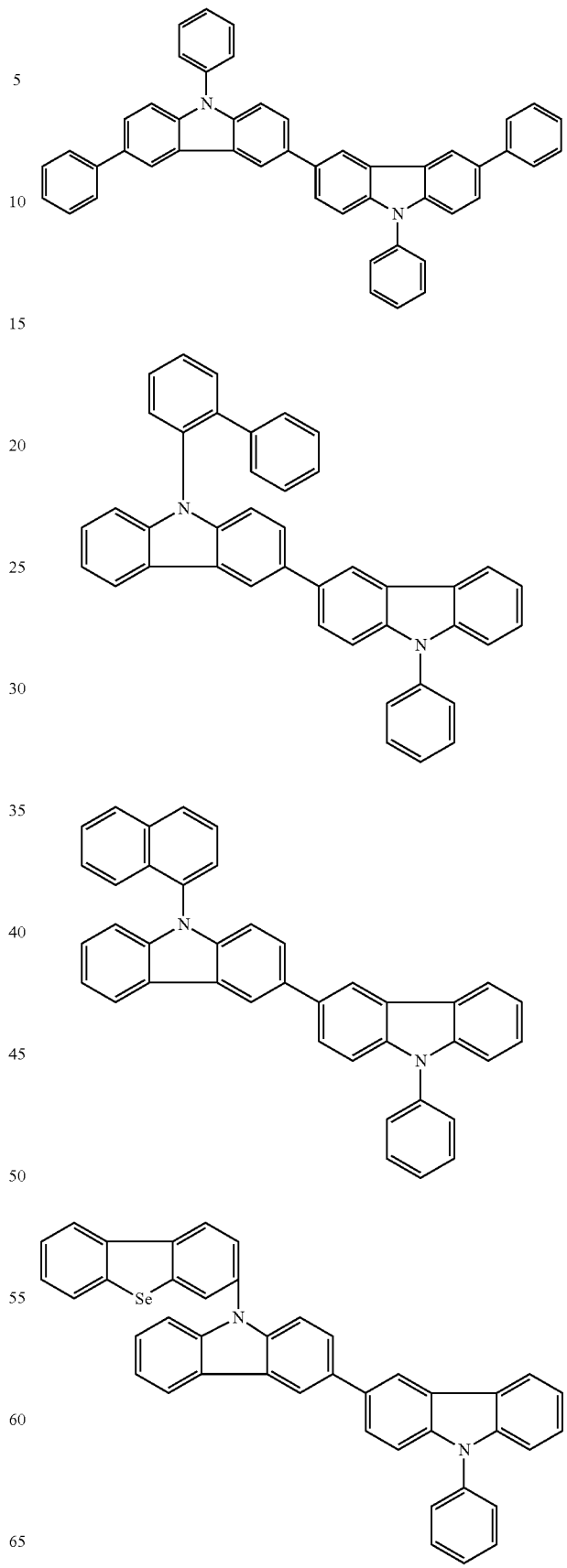

301
-continued
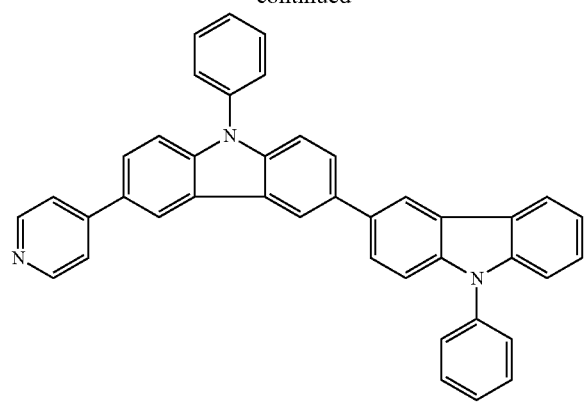
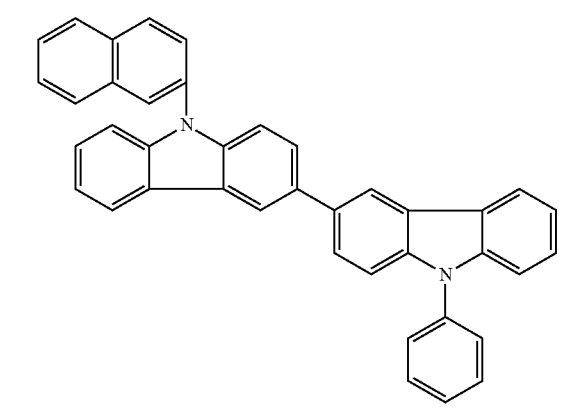
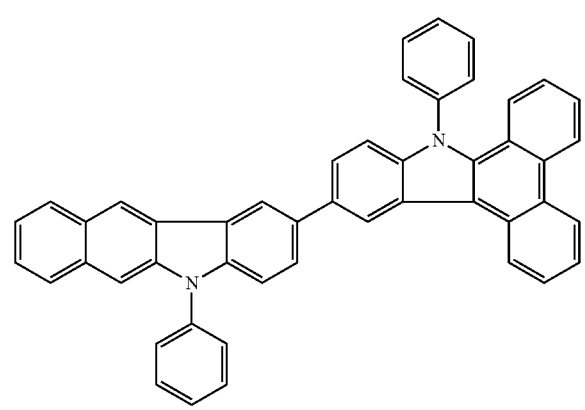
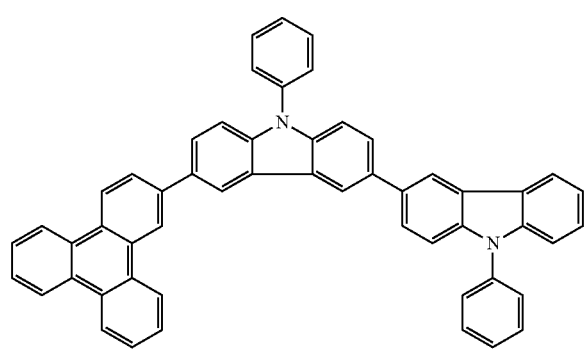
302
-continued
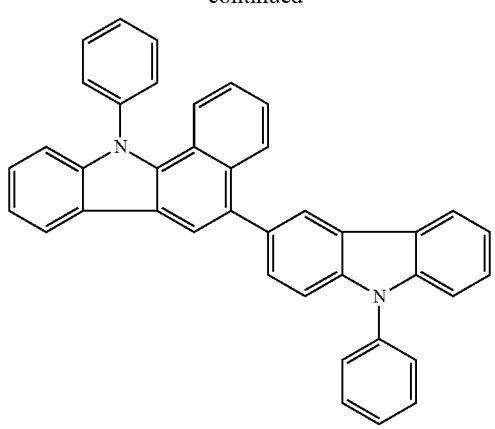
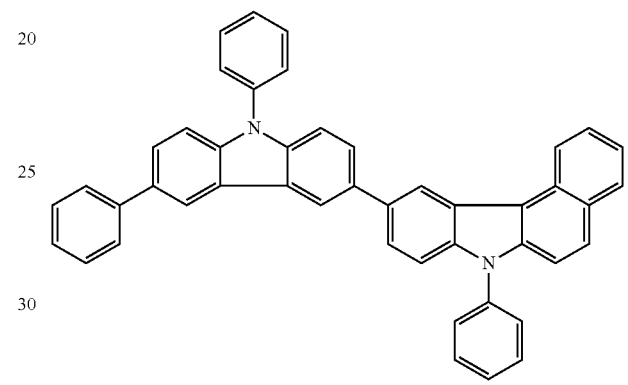
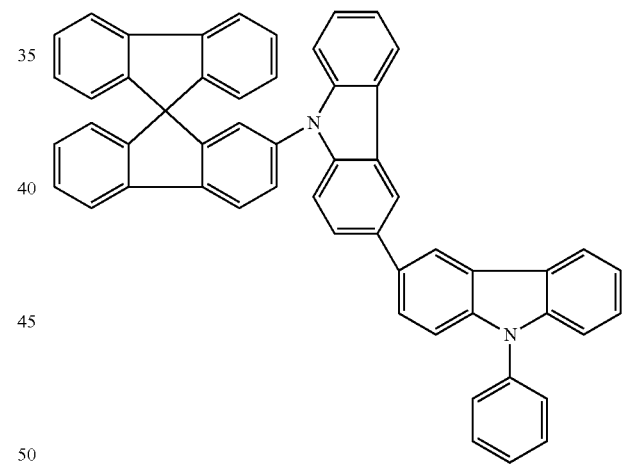
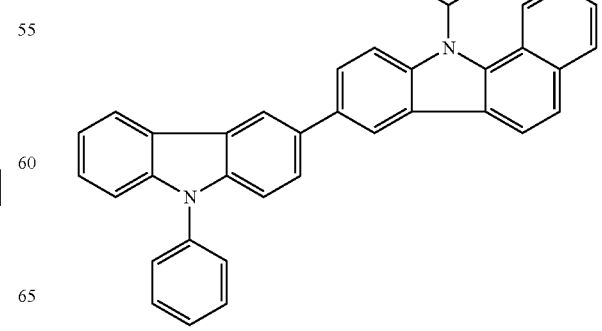

303
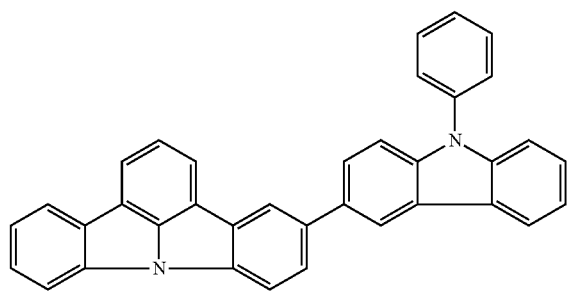
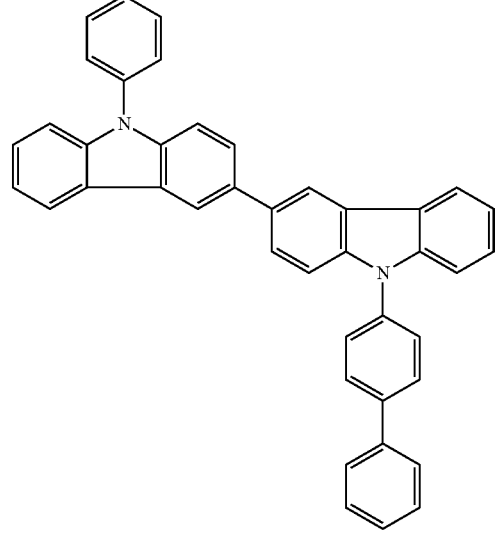
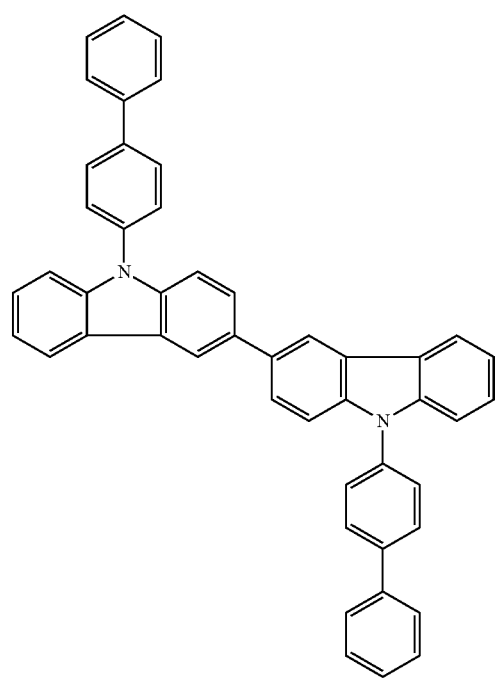
304
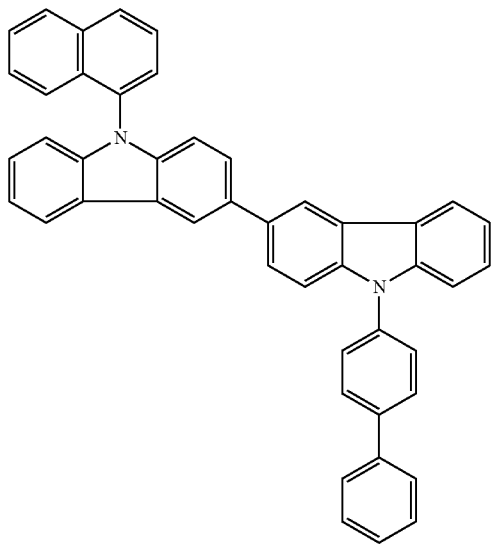
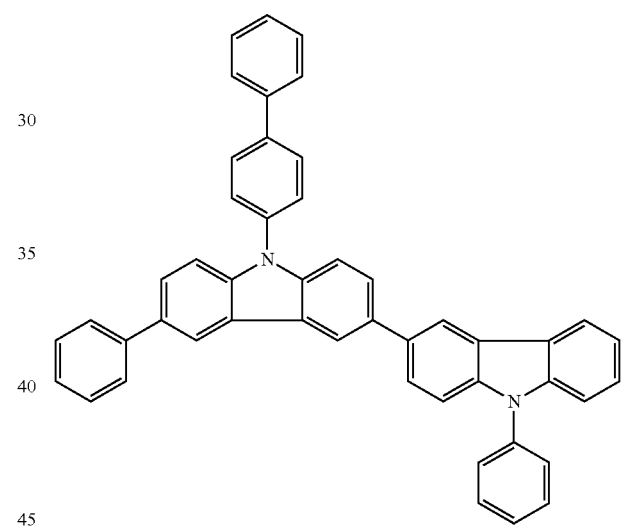
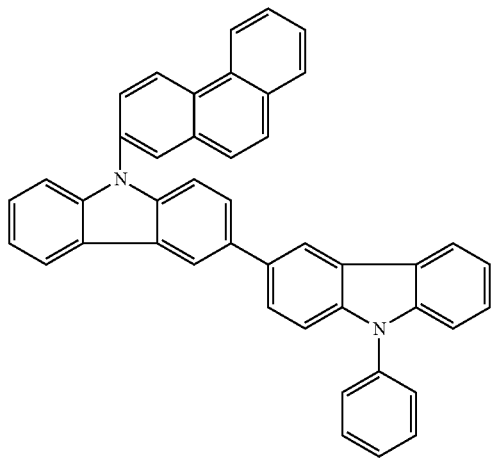

305
-continued
306
-continued
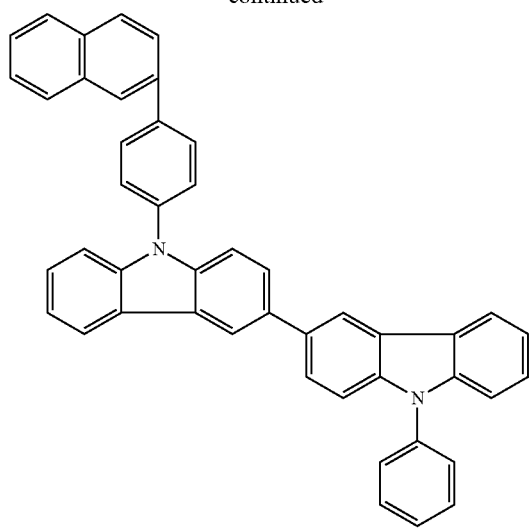
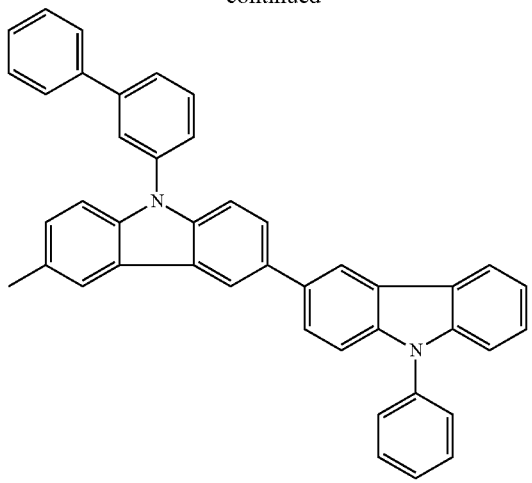
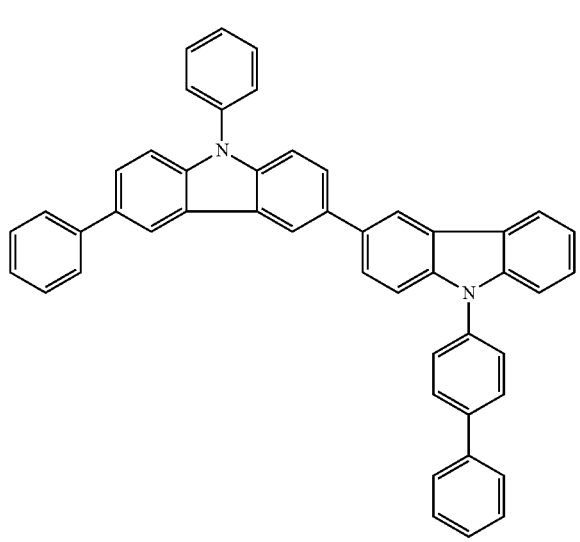
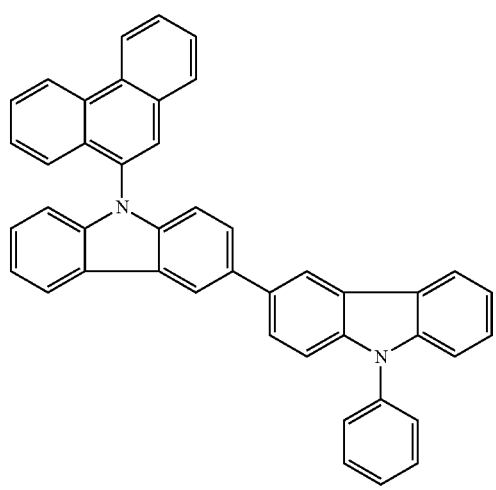
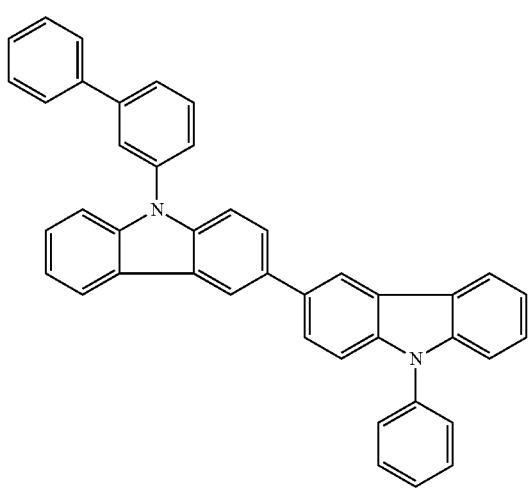

307
-continued
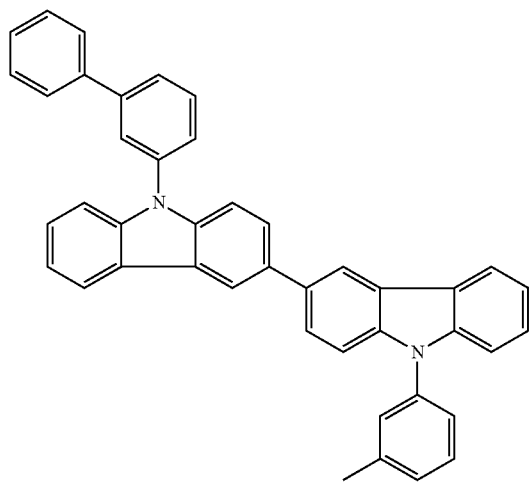
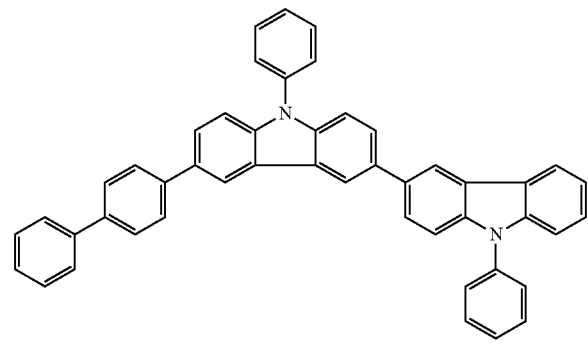
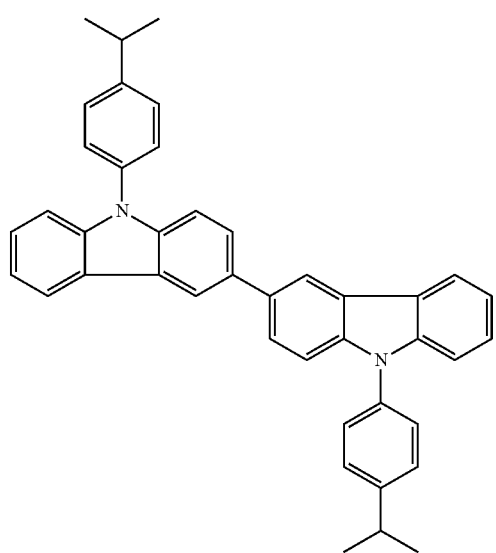
308
-continued
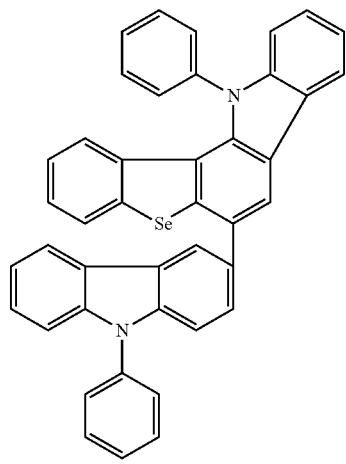
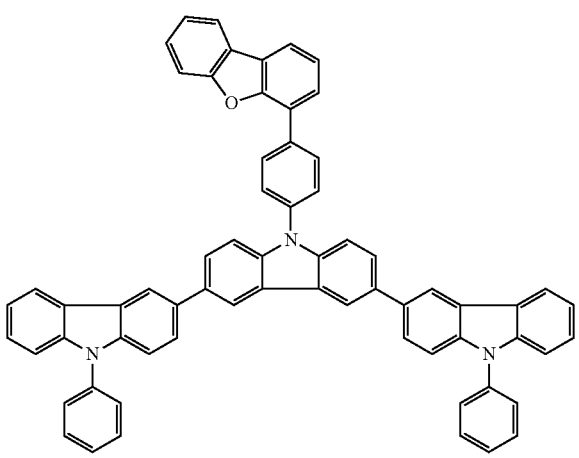
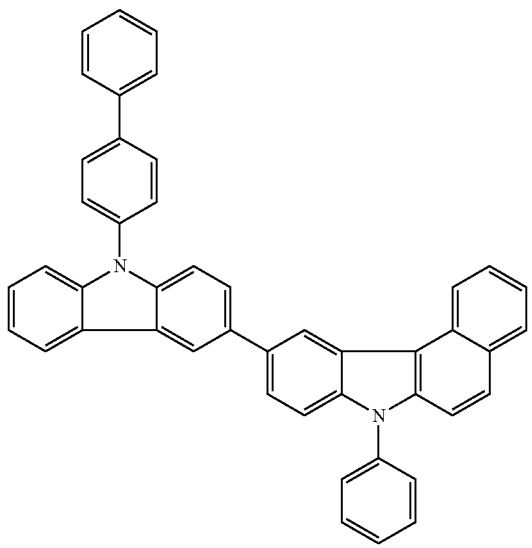

309
-continued
310
-continued
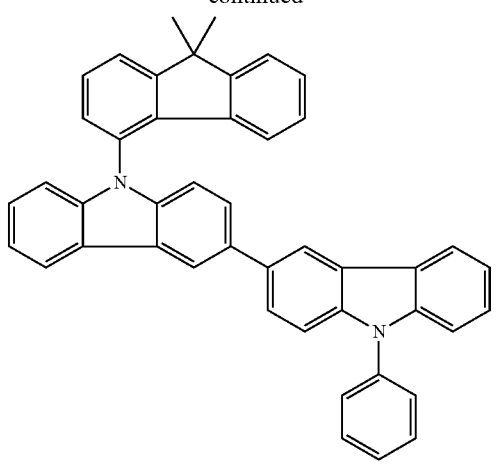
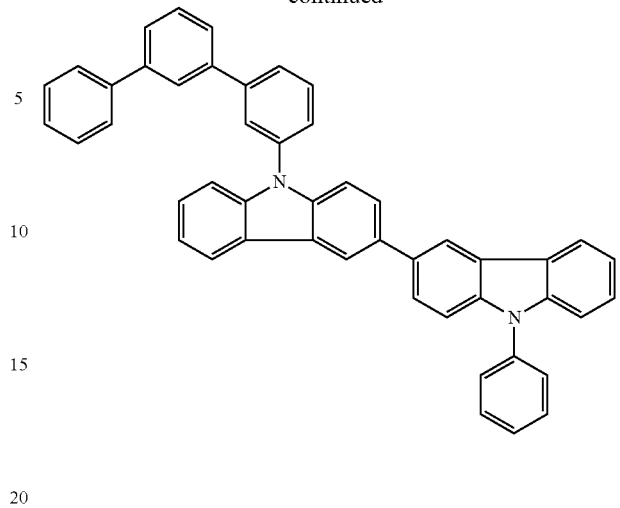
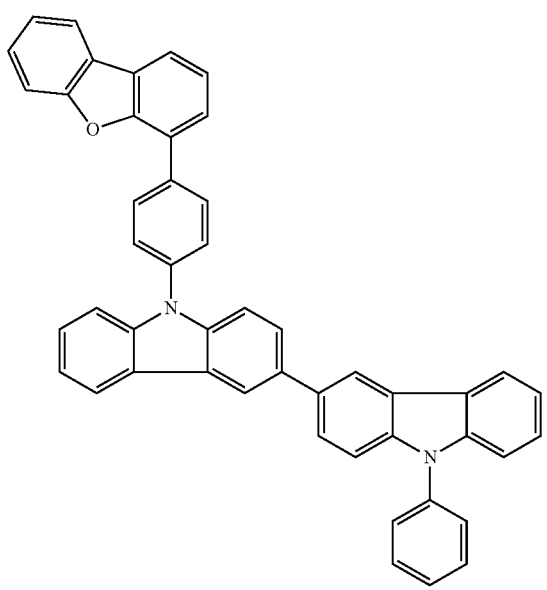
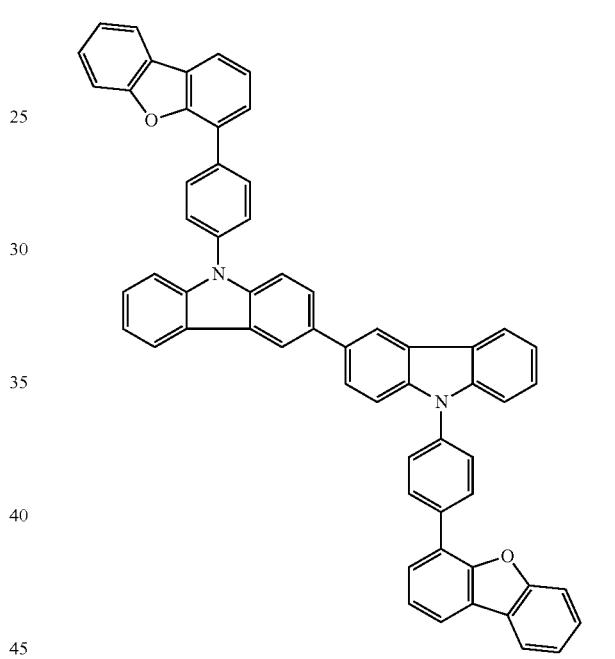
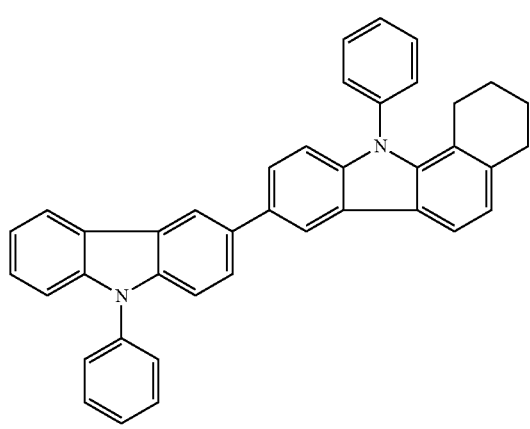
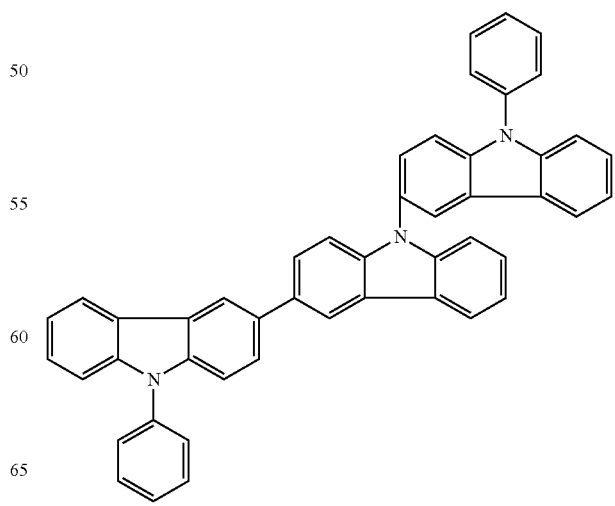

311
-continued
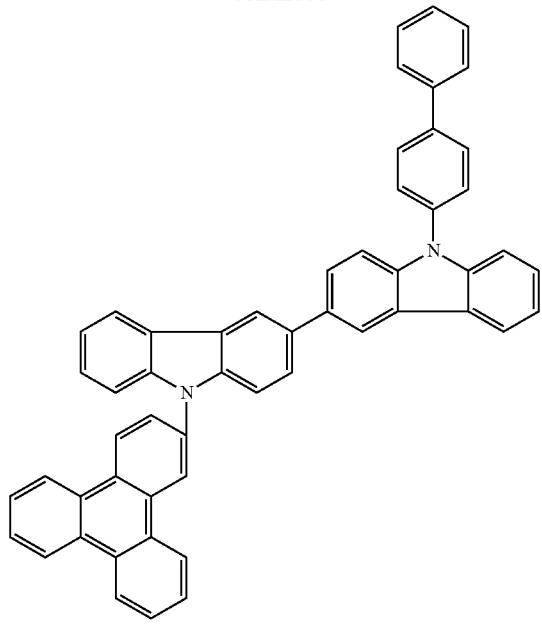
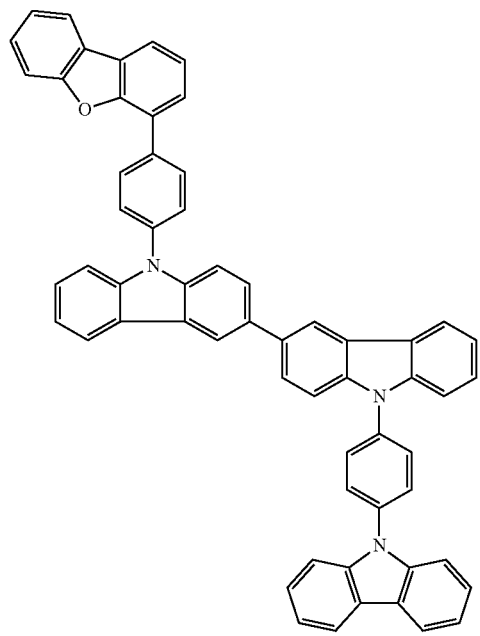
312
-continued
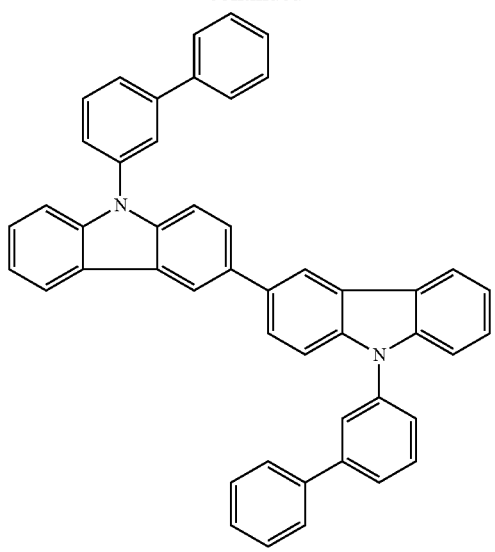
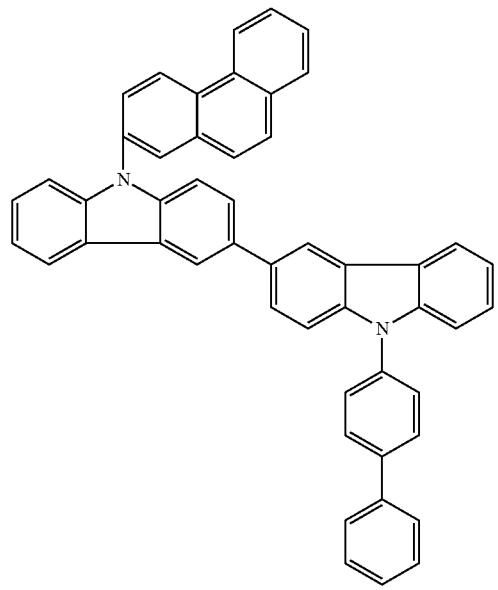

313
-continued
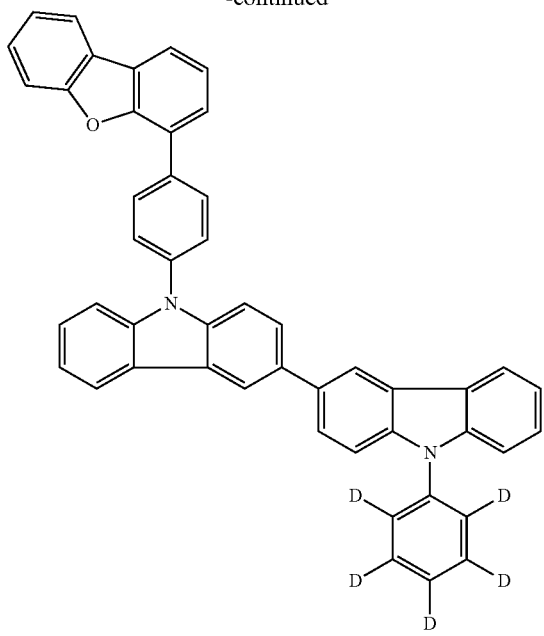
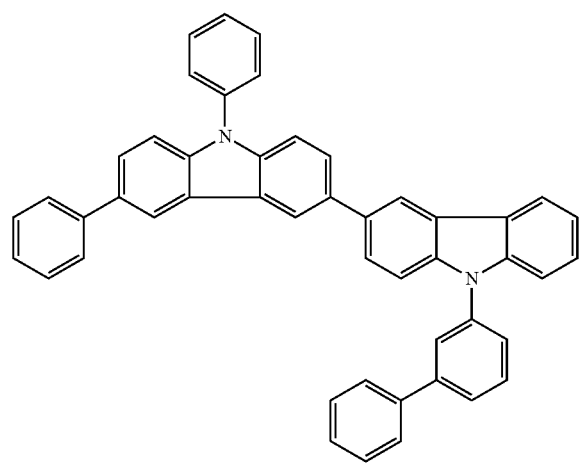
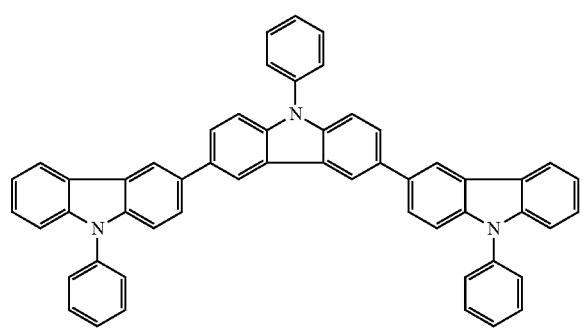
314
-continued
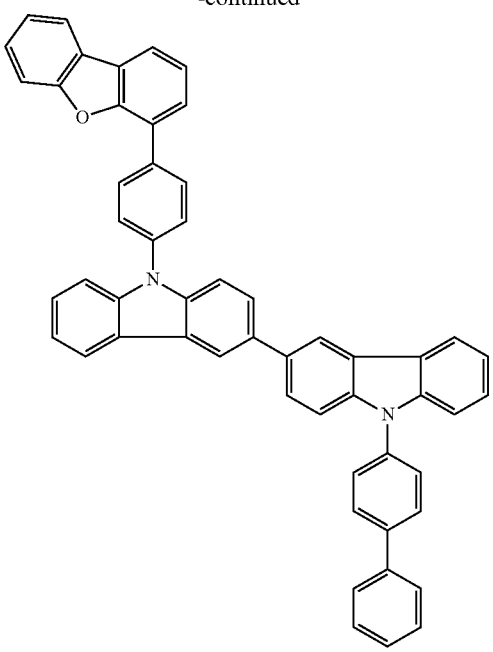
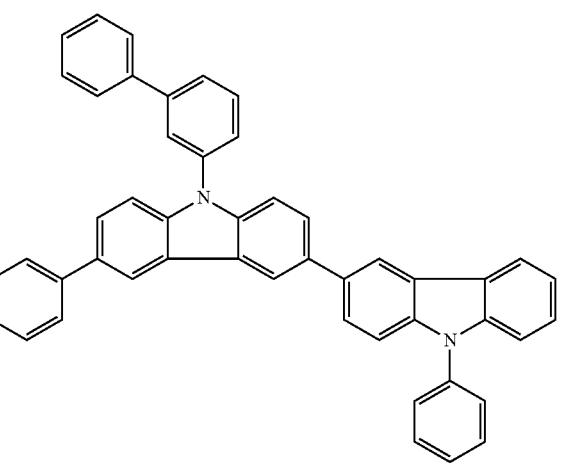
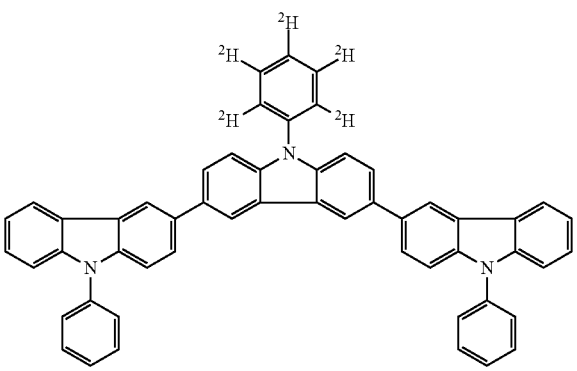

315
-continued
316
-continued
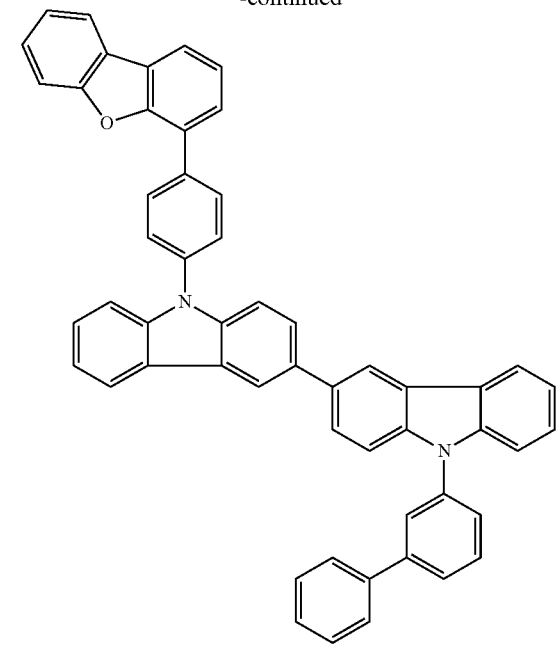
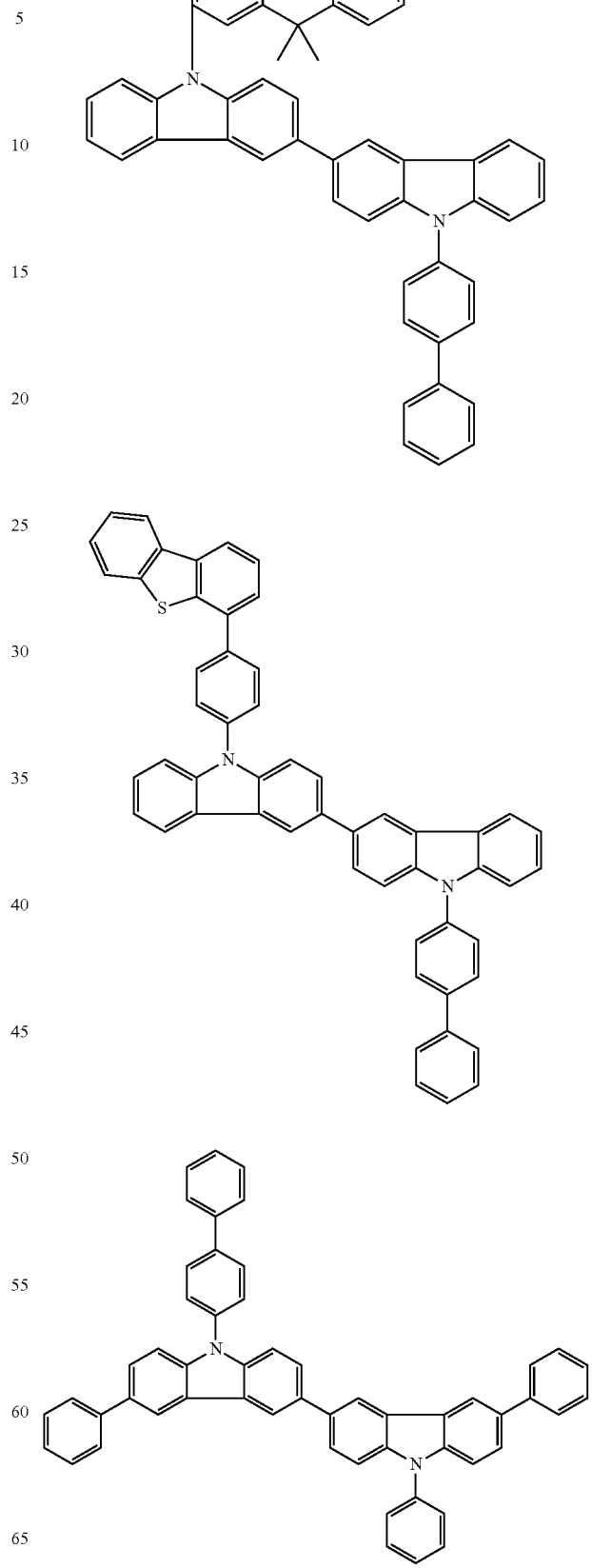

317
-continued
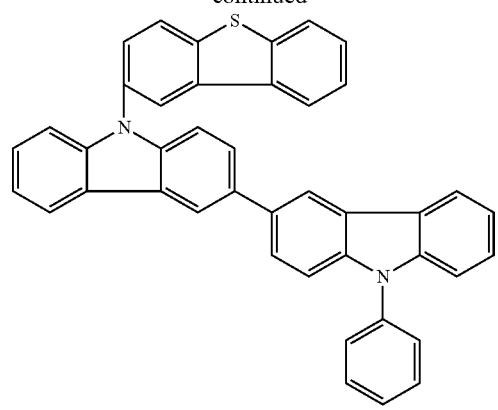
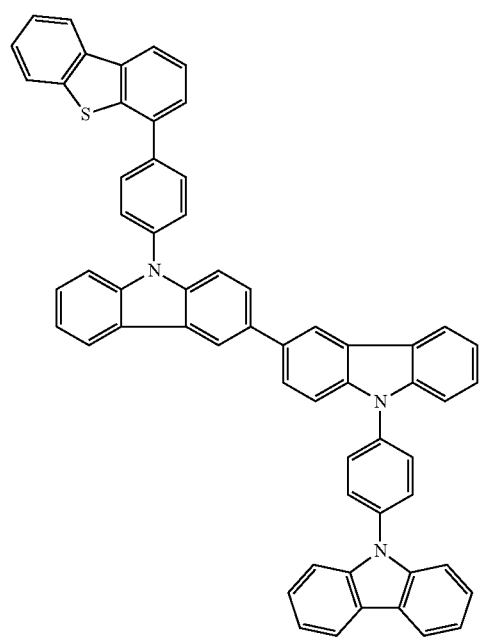
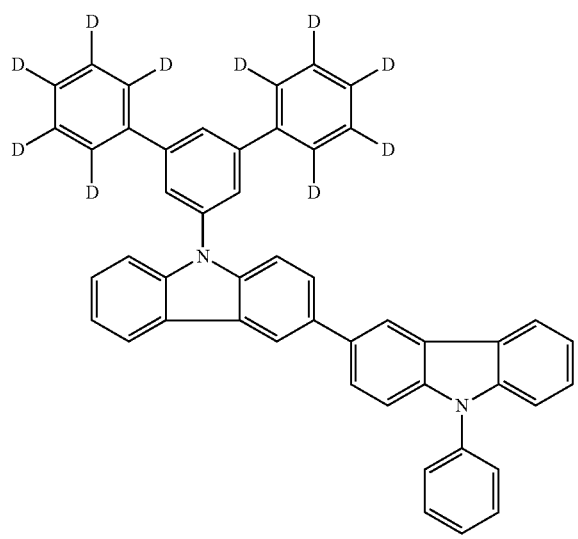
318
-continued
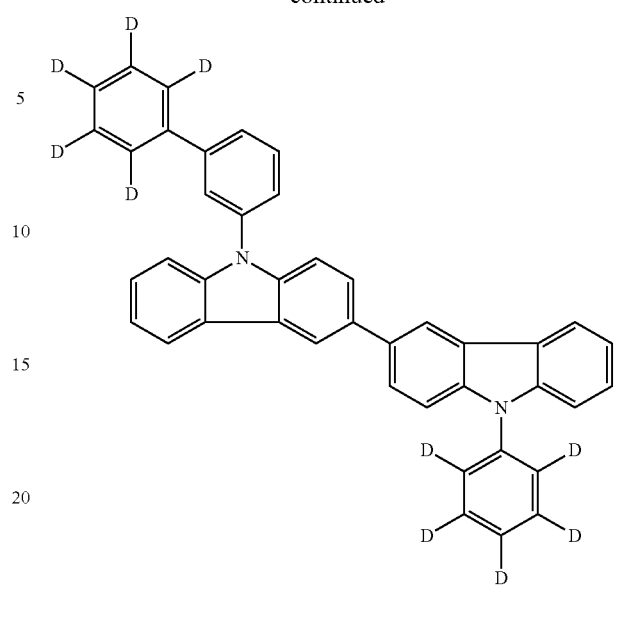
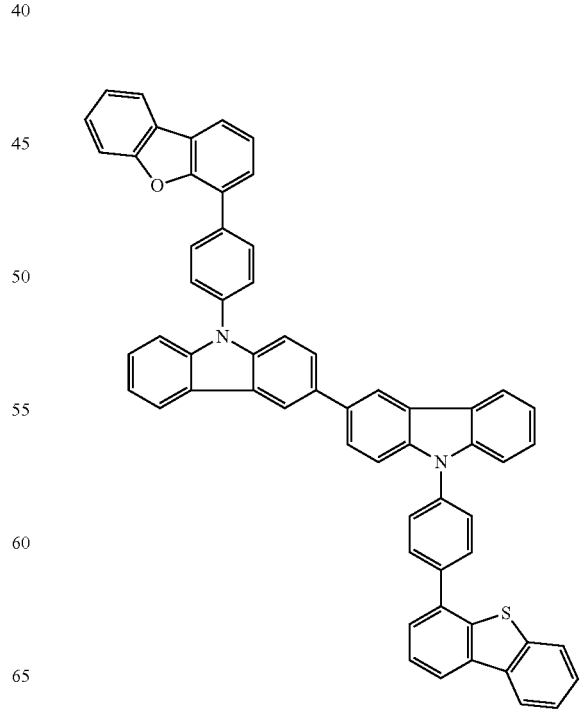

319
-continued
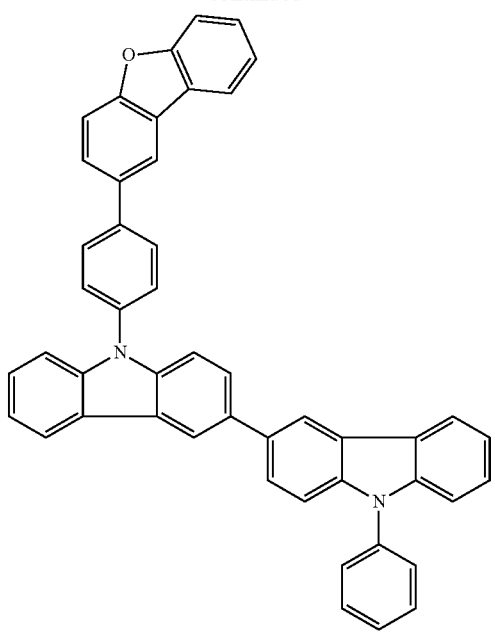
320
-continued
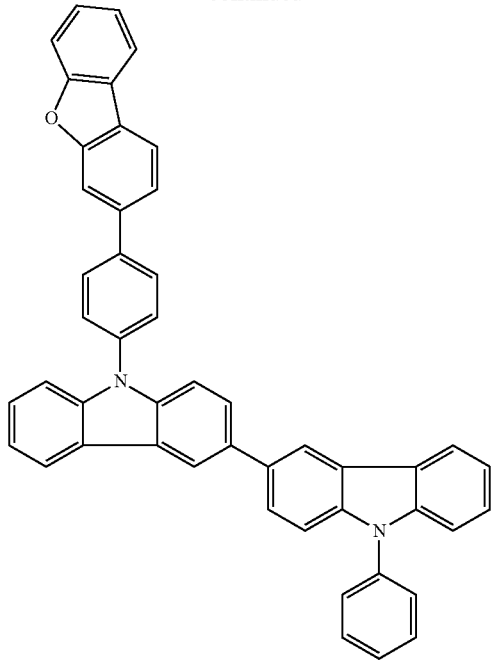
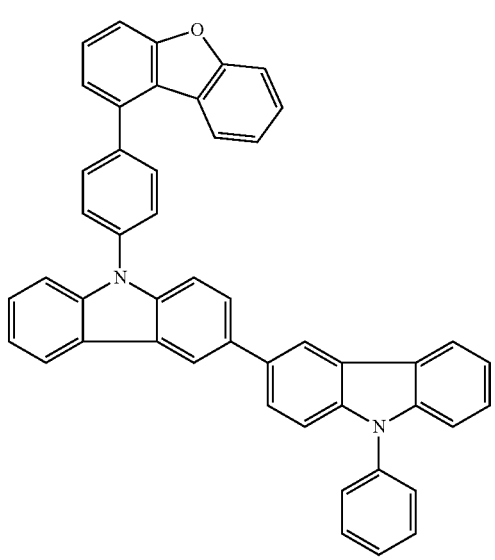
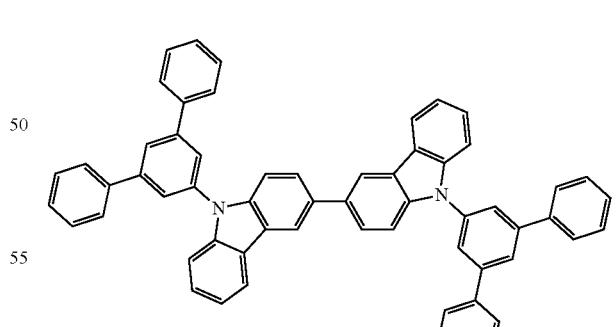
Examples of amines which can be used as hole-transporting matrix materials:

321
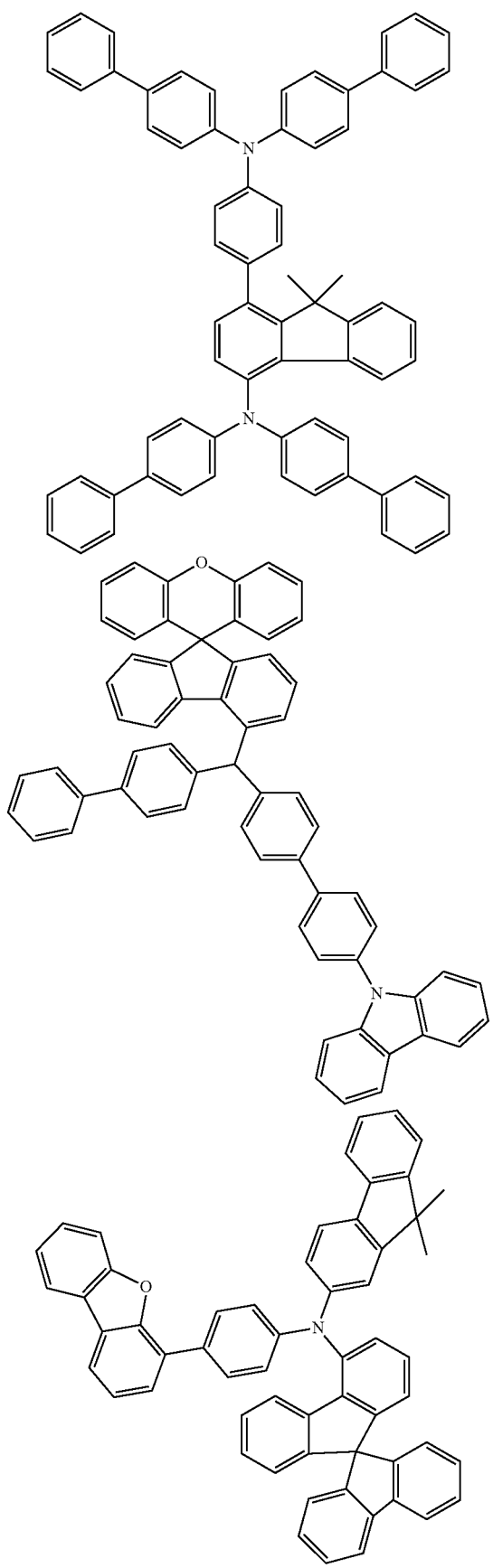
322
-continued
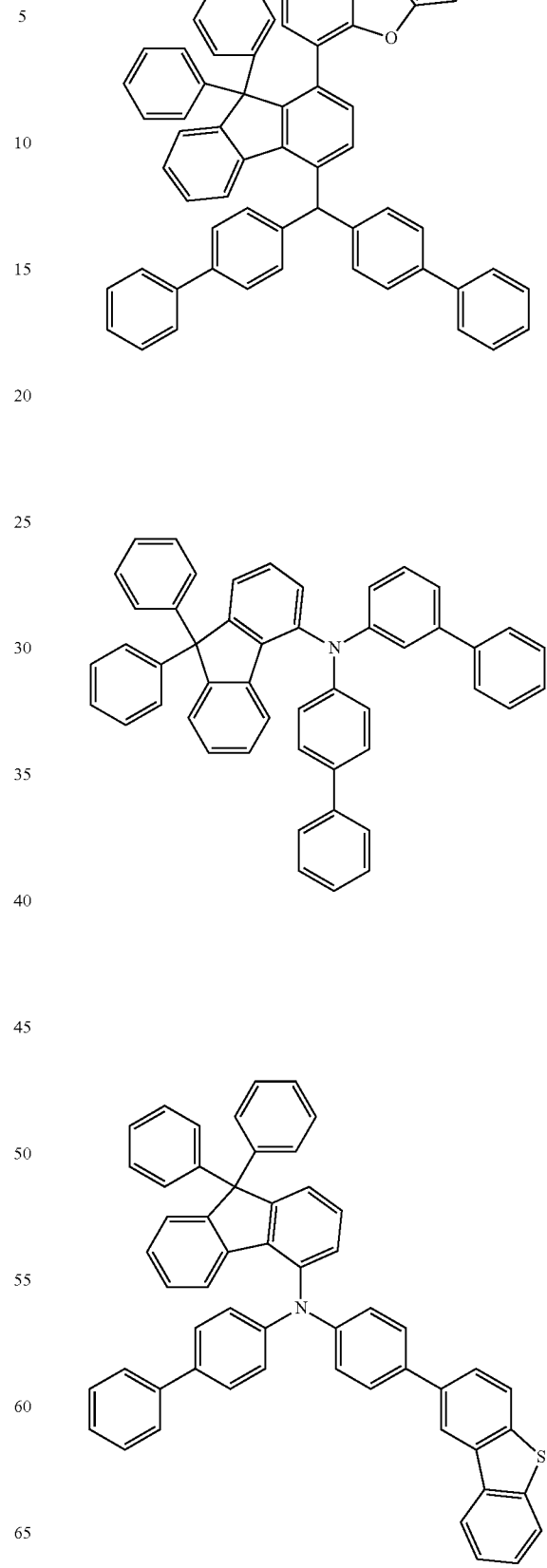

323
-continued
324
-continued
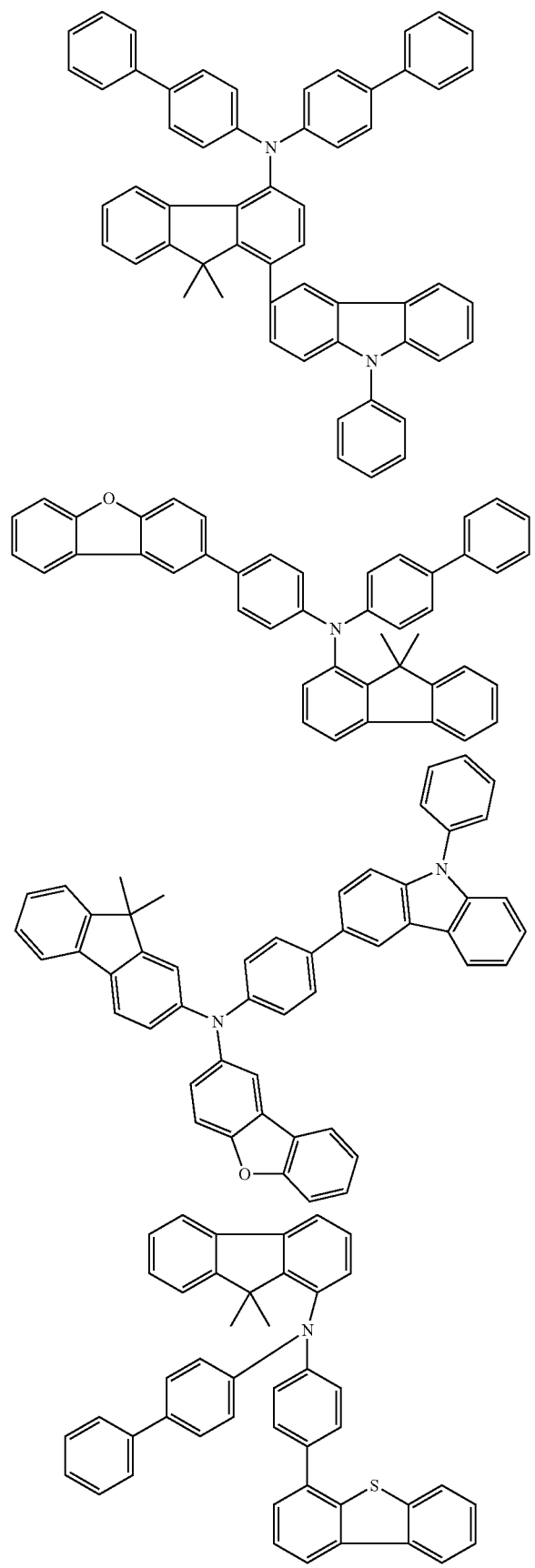
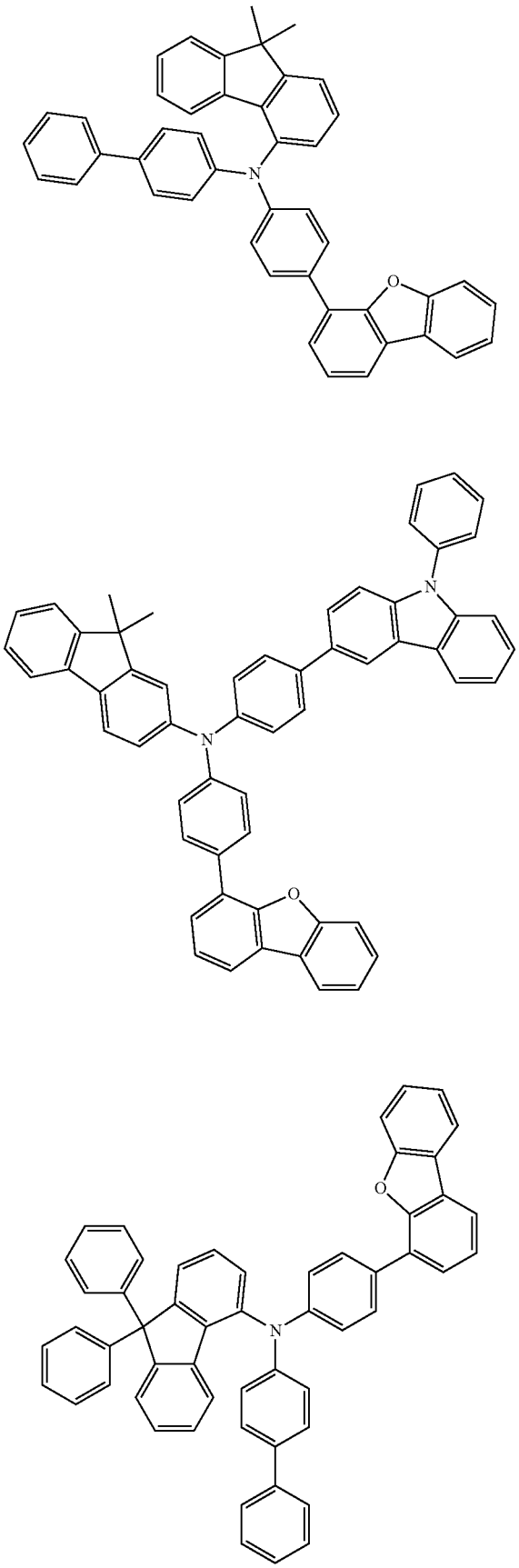

325
-continued
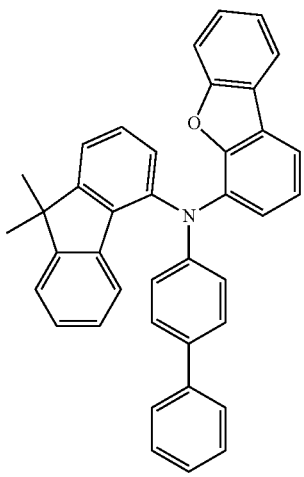
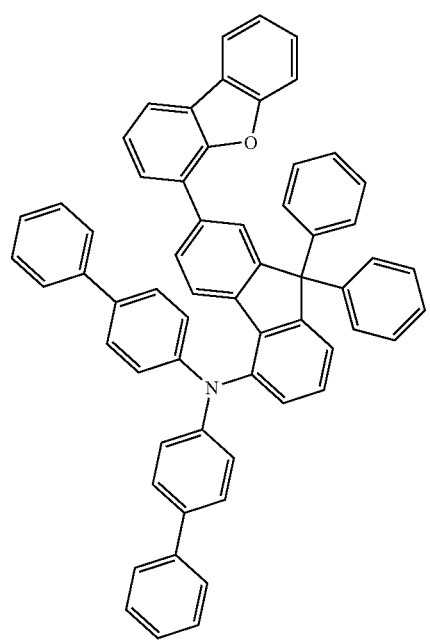
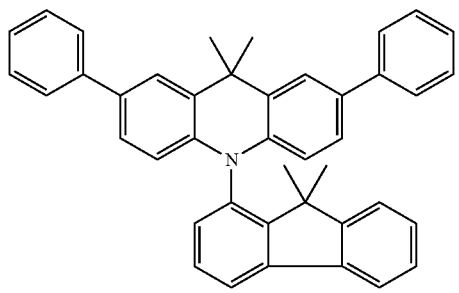
326
-continued
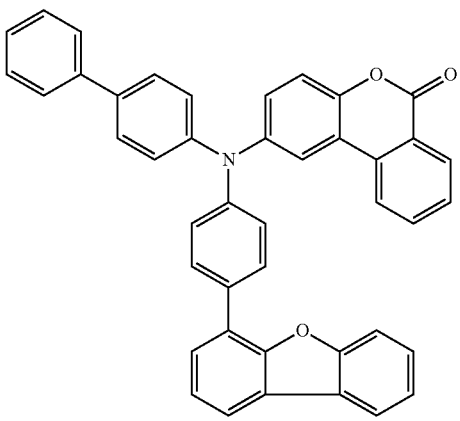
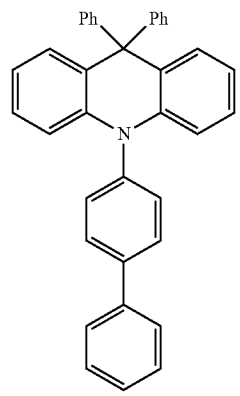
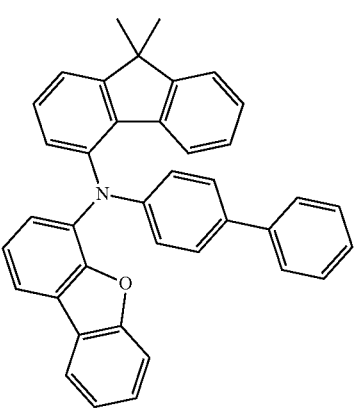

327
-continued
328
-continued
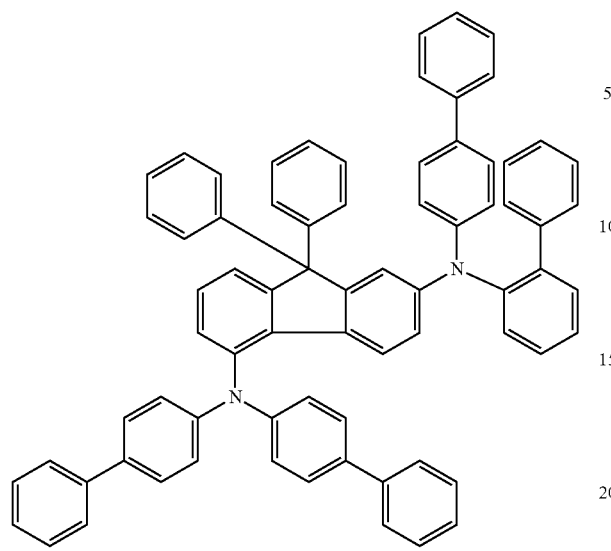
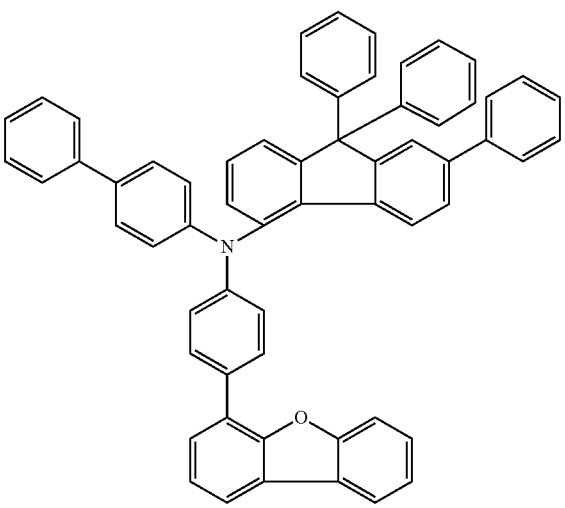
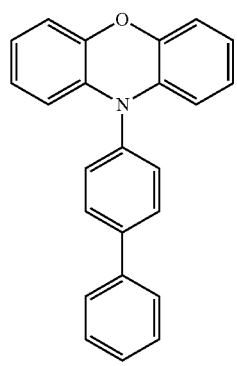
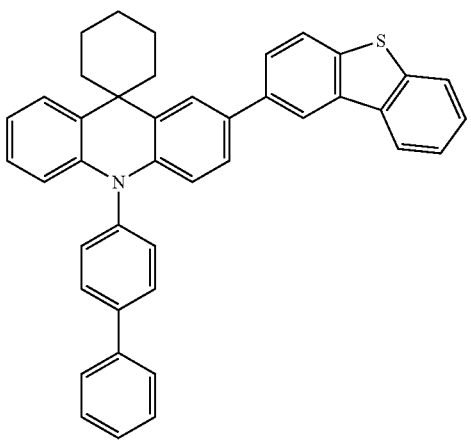 [SMILES: c1ccc(-c2ccc(N3c4ccccc4C4(CCCCC4)c4cc(-c5ccc6sc7ccccc7c6c5)ccc43)cc2)cc1]
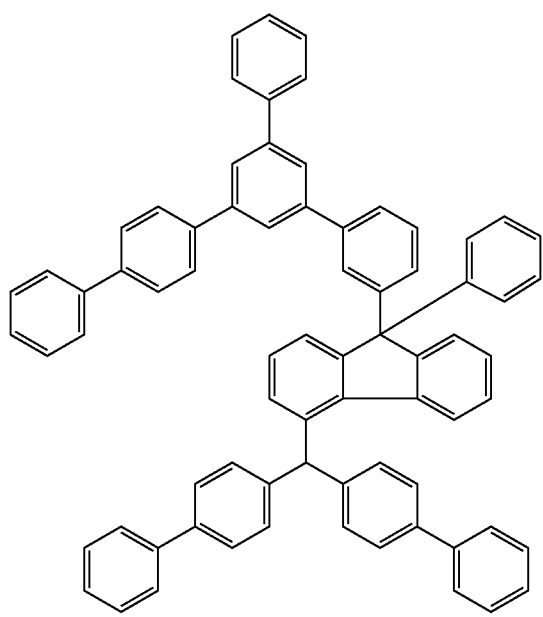
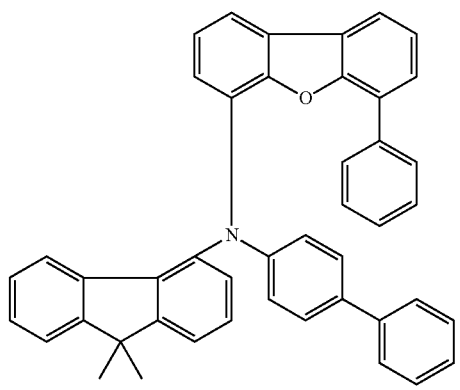

| 329 -continued | 330 -continued |
|---|---|
| 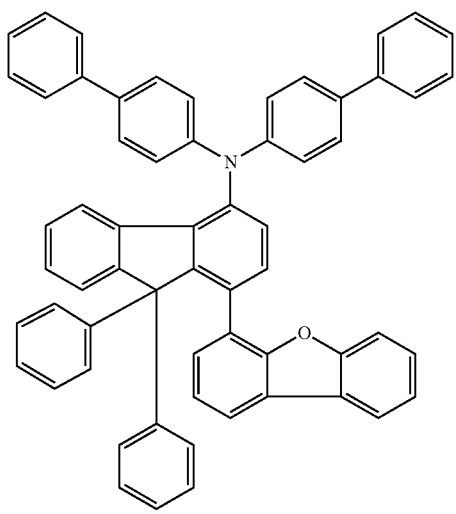 | 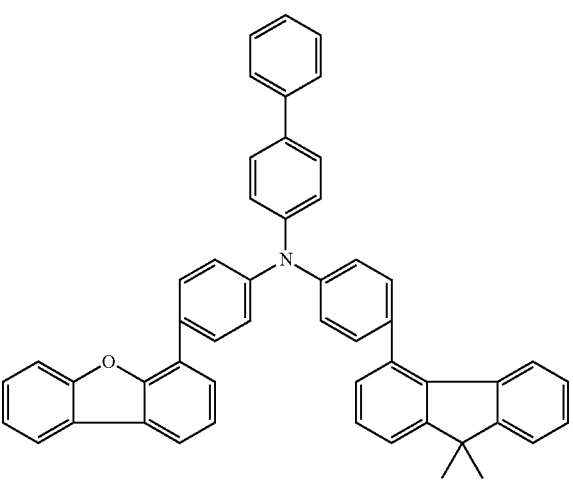 |
| 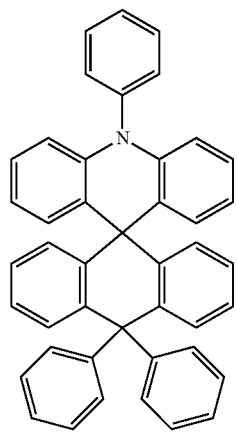 | 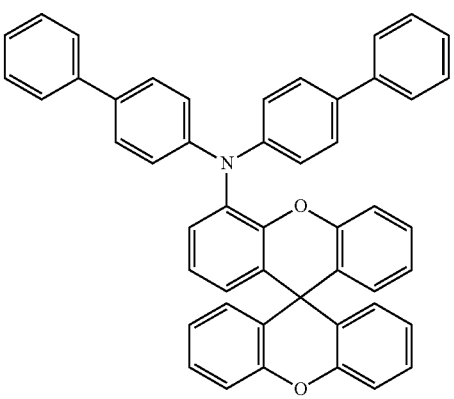 |
| 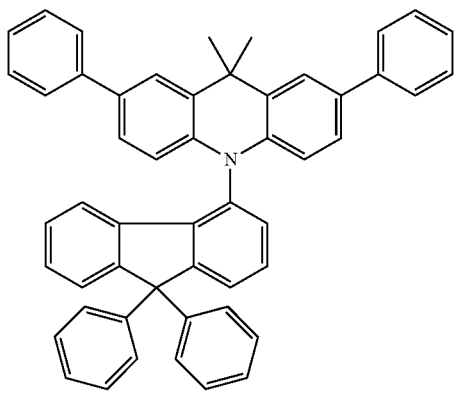 | 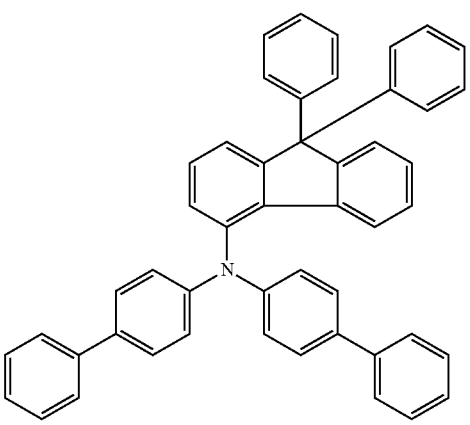 |

331
-continued
332
-continued
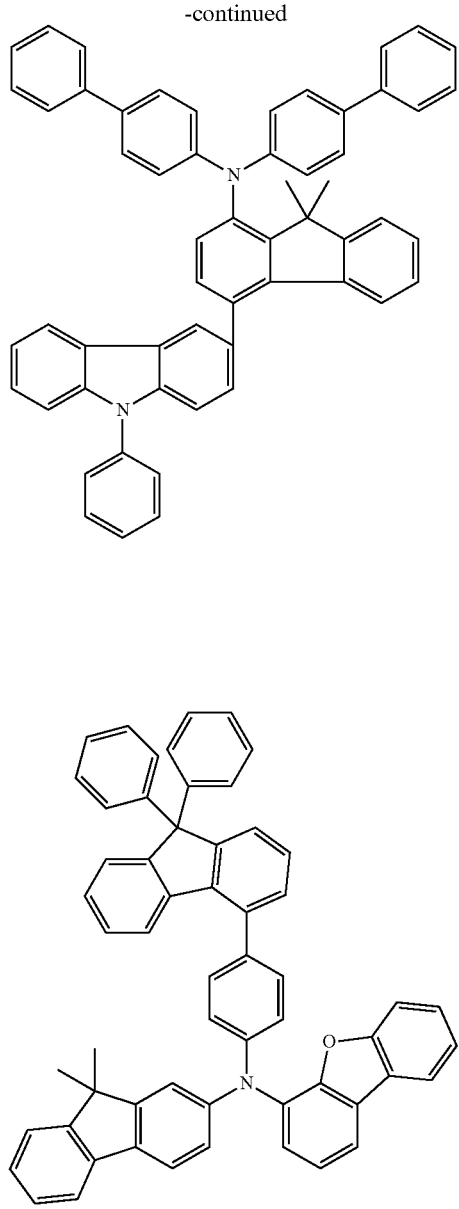
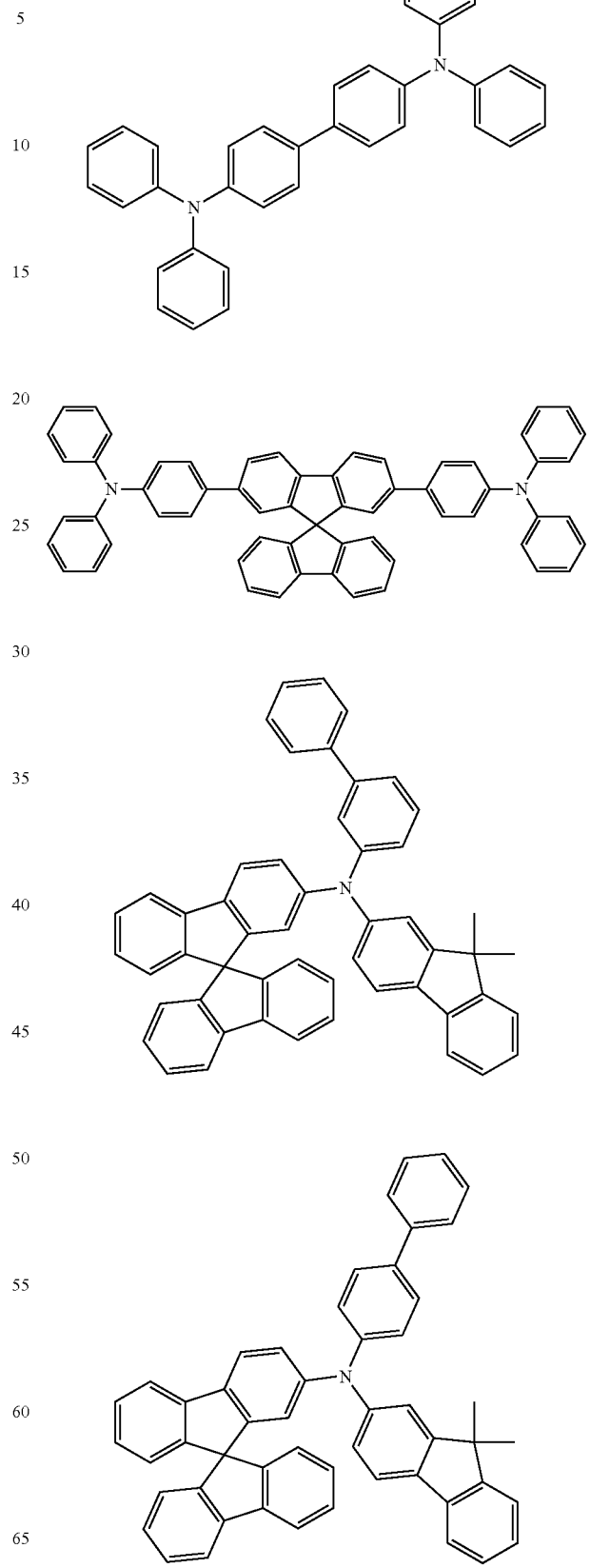

333
-continued
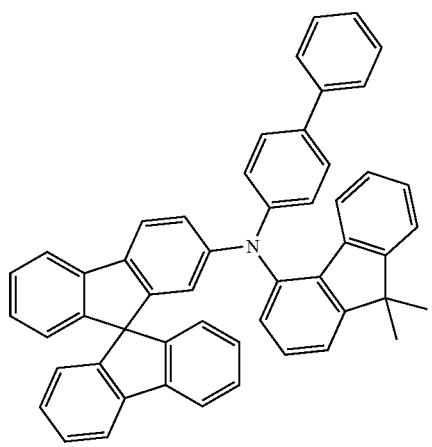
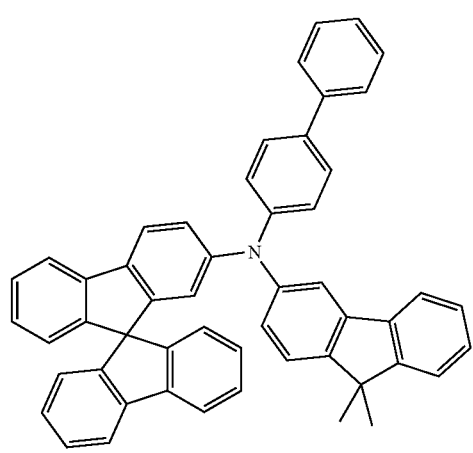
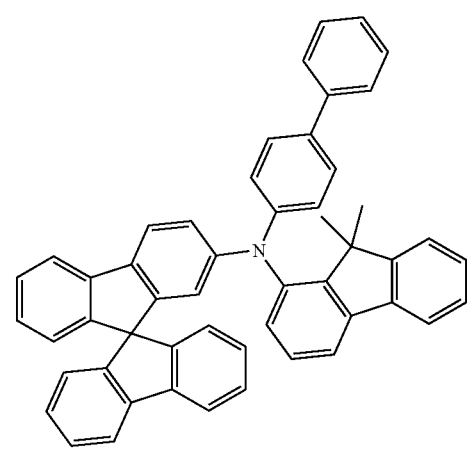
334
-continued
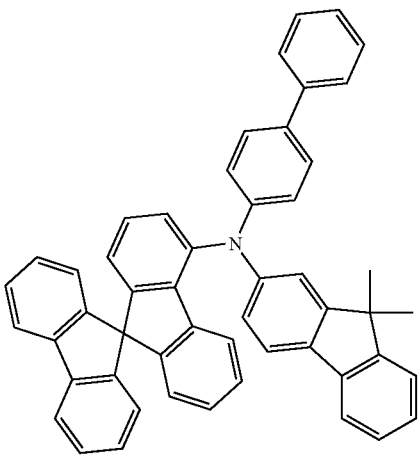
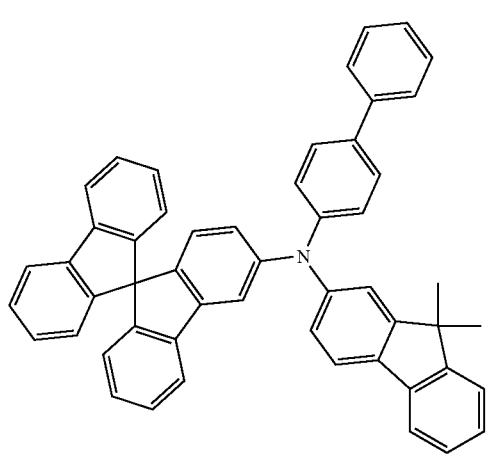
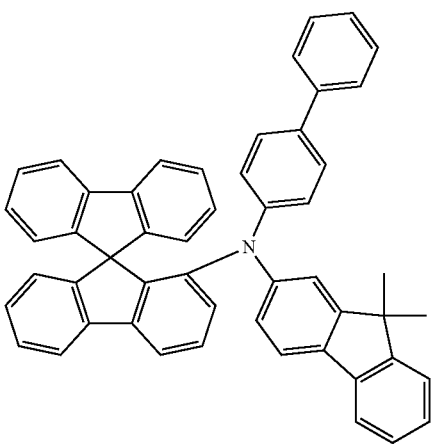

335
-continued
336
-continued
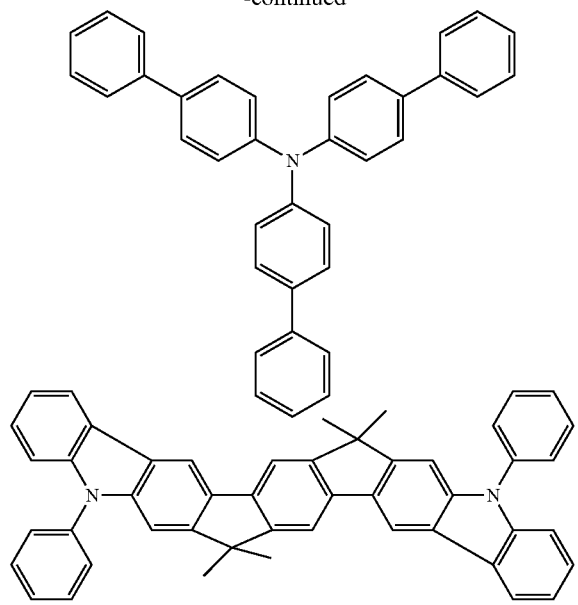
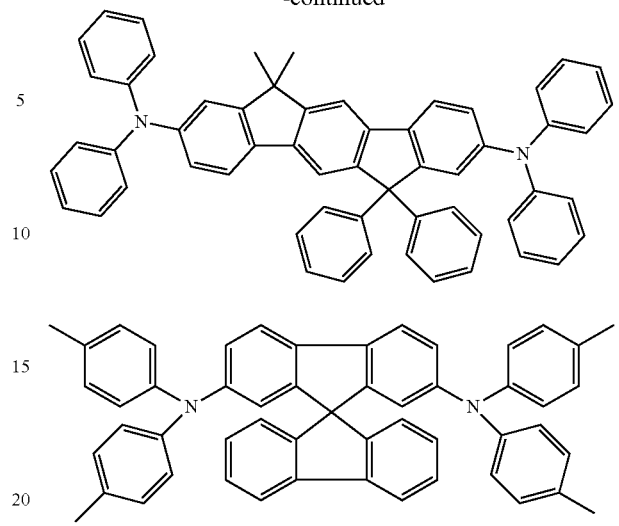
Examples of materials which can be used as wide band-gap matrix materials:
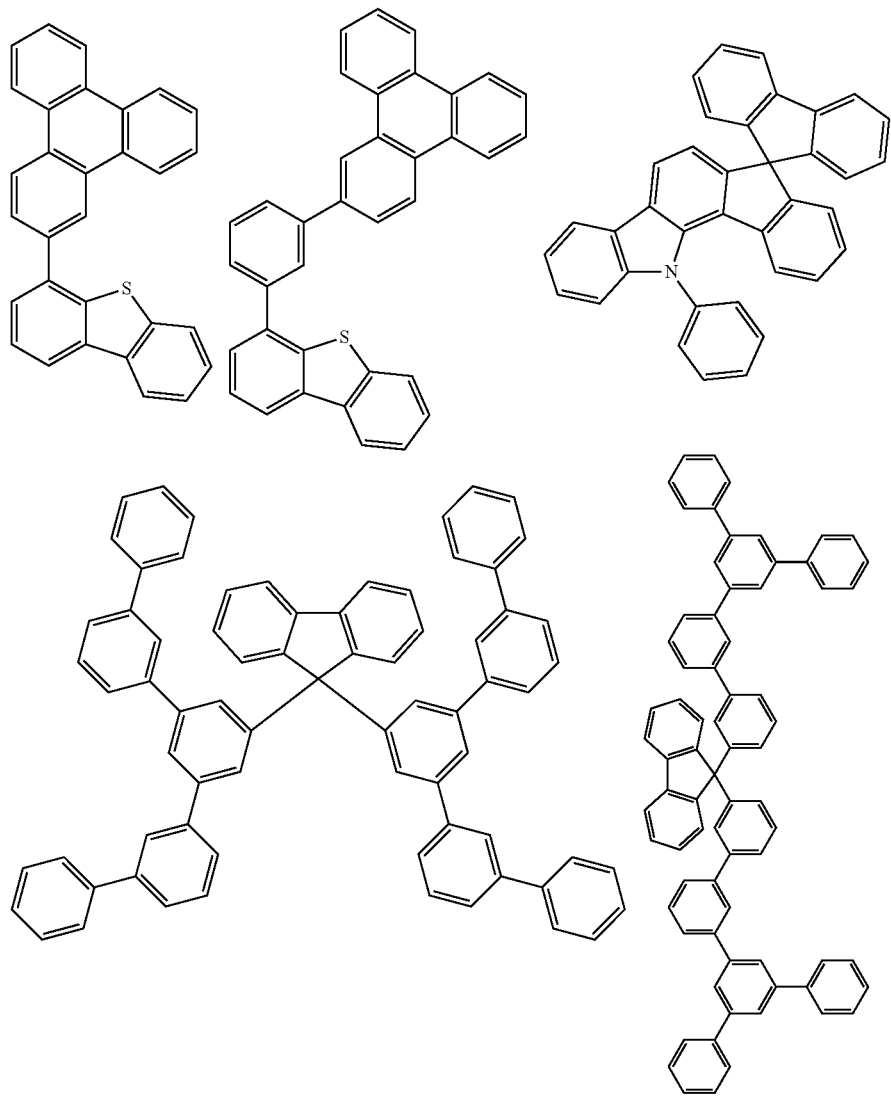

-continued
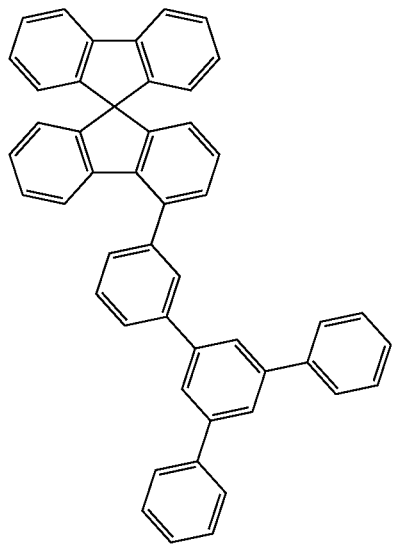
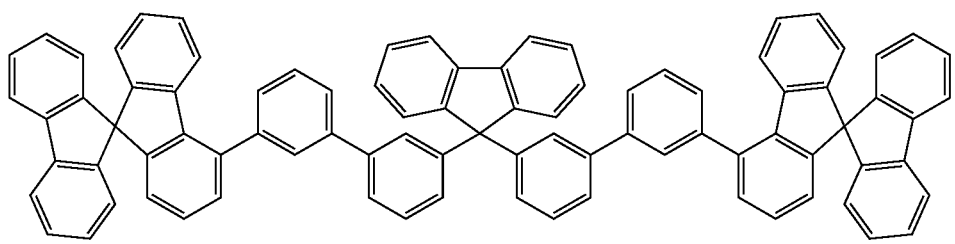
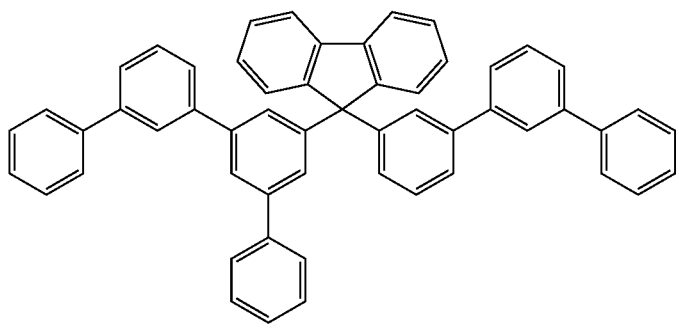
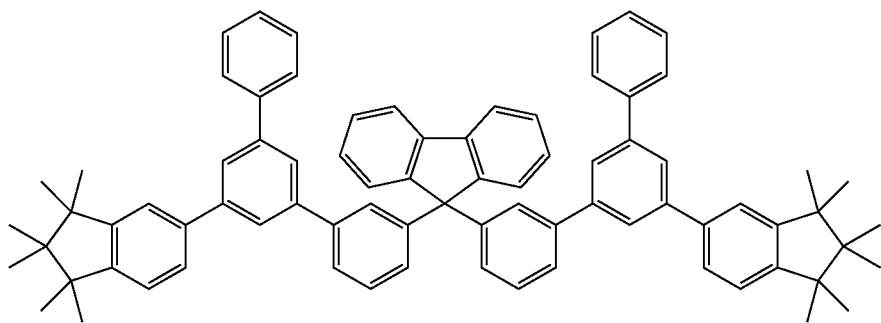

-continued

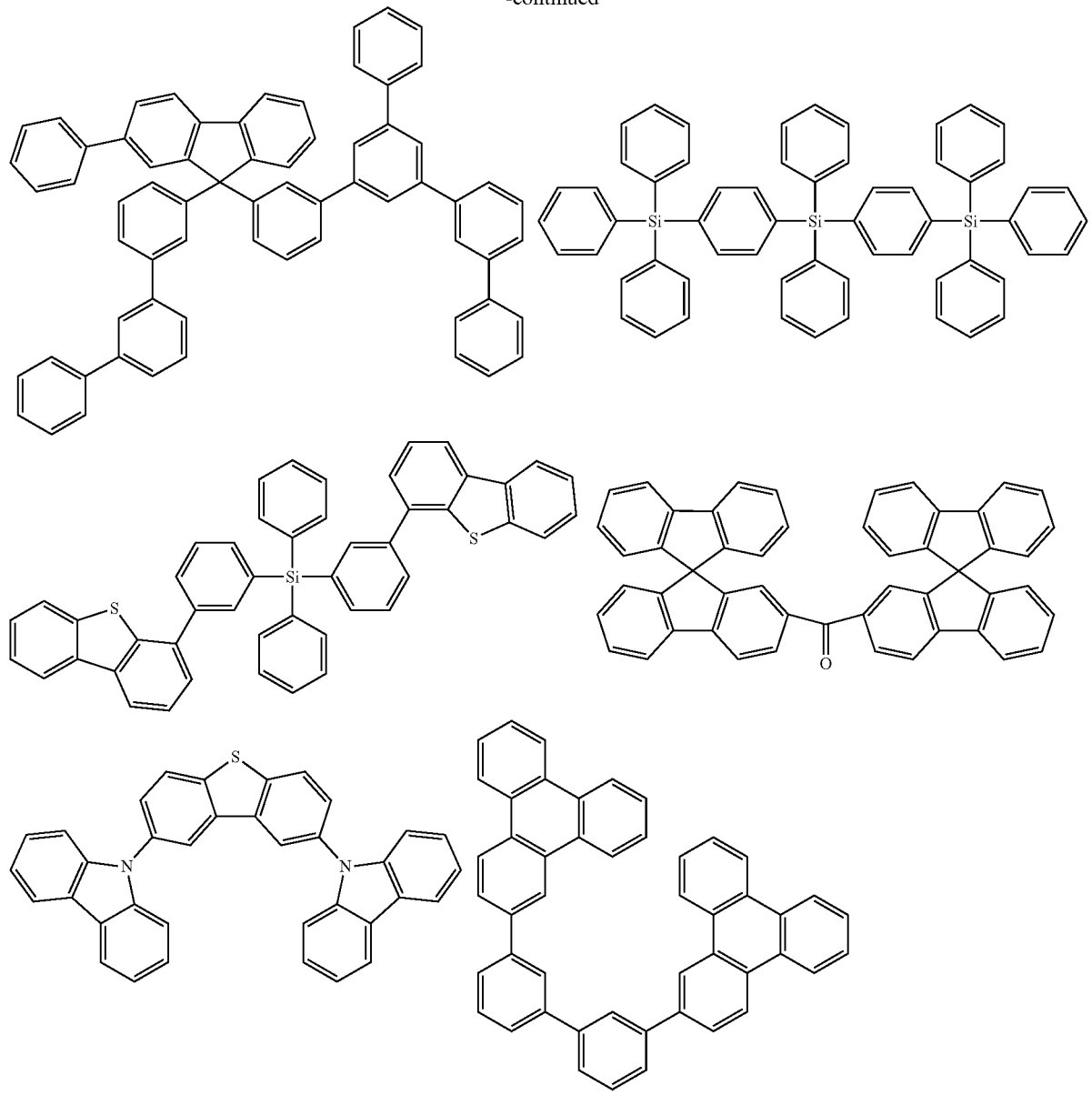

It is further preferable to use a mixture of two or more triplet emitters, especially two or three triplet emitters, together with one or more matrix materials. In this case, the triplet emitter having the shorter-wave emission spectrum serves as co-matrix for the triplet emitter having the longer-wave emission spectrum. For example, the metal complexes of the invention can be combined with a metal complex emitting at shorter wavelength, for example a blue-, green- or yellow-emitting metal complex, as co-matrix. For example, it is also possible to use the metal complexes of the invention as co-matrix for triplet emitters that emit at longer wavelength, for example for red-emitting triplet emitters. In this case, it may also be preferable when both the shorter-wave- and the longer-wave-emitting metal complex is a compound of the invention. A preferred embodiment in the case of use of three triplet emitters is when two are used as co-host and one as emitting material. These triplet emitters preferably have the emission colours of green, yellow and red or blue, green and orange.

A preferred mixture in the emitting layer comprises an electron-transporting host material, what is called a "wide bandgap" host material which, owing to its electronic properties, is not involved to a significant degree, if at all, in the charge transport in the layer, a co-dopant which is a triplet emitter which emits at a shorter wavelength than the compound of the invention, and a compound of the invention.

A further preferred mixture in the emitting layer comprises an electron-transporting host material, what is called a "wide bandgap" host material which, owing to its electronic properties, is not involved to a significant degree, if at all, in the charge transport in the layer, a hole-transporting host material, a co-dopant which is a triplet emitter which emits at a shorter wavelength than the compound of the invention, and a compound of the invention.

The compounds of the invention can also be used in other functions in the electronic device, for example as hole transport material in a hole injection or transport layer, as charge generation material, as electron blocker material, as hole blocker material or as electron transport material, for example in an electron transport layer. It is likewise possible to use the compounds of the invention as matrix material for other phosphorescent metal complexes in an emitting layer.

Preferred cathodes are metals having a low work function, metal alloys or multilayer structures composed of various metals, for example alkaline earth metals, alkali metals, main group metals or lanthanoids (e.g. Ca, Ba, Mg, Al, In, Mg, Yb, Sm, etc.). Additionally suitable are alloys composed of an alkali metal or alkaline earth metal and silver, for example an alloy composed of magnesium and silver. In the case of multilayer structures, in addition to the metals mentioned, it is also possible to use further metals having a relatively high work function, for example Ag, in which case combinations of the metals such as Mg/Ag, Ca/Ag or Ba/Ag, for example, are generally used. It may also be preferable to introduce a thin interlayer of a material having a high dielectric constant between a metallic cathode and the organic semiconductor. Examples of useful materials for this purpose are alkali metal or alkaline earth metal fluorides, but also the corresponding oxides or carbonates (e.g. LiF, $Li_2O$, $BaF_2$, MgO, NaF, CsF, $Cs_2CO_3$, etc.). Likewise useful for this purpose are organic alkali metal complexes, e.g. Liq (lithium quinolinate). The layer thickness of this layer is preferably between 0.5 and 5 nm.

Preferred anodes are materials having a high work function. Preferably, the anode has a work function of greater than 4.5 eV versus vacuum. Firstly, metals having a high redox potential are suitable for this purpose, for example Ag, Pt or Au. Secondly, metal/metal oxide electrodes (e.g. Al/Ni/$NiO_x$, Al/$PtO_x$) may also be preferred. For some applications, at least one of the electrodes has to be transparent or partly transparent in order to enable either the irradiation of the organic material (O-SC) or the emission of light (OLED/PLED, O-laser). Preferred anode materials here are conductive mixed metal oxides. Particular preference is given to indium tin oxide (ITO) or indium zinc oxide (IZO). Preference is further given to conductive doped organic materials, especially conductive doped polymers, for example PEDOT, PANI or derivatives of these polymers. It is further preferable when a p-doped hole transport material is applied to the anode as hole injection layer, in which case suitable p-dopants are metal oxides, for example $MoO_3$ or $WO_3$, or (per)fluorinated electron-deficient aromatic systems. Further suitable p-dopants are HAT-CN (hexacyanohexaazatriphenylene) or the compound NPD9 from Novaled. Such a layer simplifies hole injection into materials having a low HOMO, i.e. a large HOMO in terms of magnitude.

In the further layers, it is generally possible to use any materials as used according to the prior art for the layers, and the person skilled in the art is able, without exercising inventive skill, to combine any of these materials with the materials of the invention in an electronic device.

Suitable charge transport materials as usable in the hole injection or hole transport layer or electron blocker layer or in the electron transport layer of the organic electroluminescent device of the invention are, for example, the compounds disclosed in Y. Shirota et al., Chem. Rev. 2007, 107(4), 953-1010, or other materials as used in these layers according to the prior art. Preferred hole transport materials which can be used in a hole transport, hole injection or electron blocker layer in the electroluminescent device of the invention are indenofluorenamine derivatives (for example according to WO 06/122630 or WO 06/100896), the amine derivatives disclosed in EP 1661888, hexaazatriphenylene derivatives (for example according to WO 01/049806), amine derivatives having fused aromatic systems (for example according to U.S. Pat. No. 5,061,569), the amine derivatives disclosed in WO 95/09147, monobenzoindenofluorenamines (for example according to WO 08/006449), dibenzoindenofluorenamines (for example according to WO 07/140847), spirobifluorenamines (for example according to WO 2012/034627, WO2014/056565), fluorenamines (for example according to EP 2875092, EP 2875699 and EP 2875004), spirodibenzopyranamines (e.g. EP 2780325) and dihydroacridine derivatives (for example according to WO 2012/150001).

The device is correspondingly (according to the application) structured, contact-connected and finally hermetically sealed, since the lifetime of such devices is severely shortened in the presence of water and/or air.

Additionally preferred is an organic electroluminescent device, characterized in that one or more layers are coated by a sublimation process. In this case, the materials are applied by vapour deposition in vacuum sublimation systems at an initial pressure of typically less than $10^{-5}$ mbar, preferably less than $10^{-6}$ mbar. It is also possible that the initial pressure is even lower or even higher, for example less than $10^{-7}$ mbar.

Preference is likewise given to an organic electroluminescent device, characterized in that one or more layers are coated by the OVPD (organic vapour phase deposition) method or with the aid of a carrier gas sublimation. In this case, the materials are applied at a pressure between $10^{-5}$ mbar and 1 bar. A special case of this method is the OVJP (organic vapour jet printing) method, in which the materials are applied directly by a nozzle and thus structured (for example M. S. Arnold et al., Appl. Phys. Lett. 2008, 92, 053301).

Preference is additionally given to an organic electroluminescent device, characterized in that one or more layers are produced from solution, for example by spin-coating, or by any printing method, for example screen printing, flexographic printing, offset printing or nozzle printing, but more preferably LITI (light-induced thermal imaging, thermal transfer printing) or inkjet printing. For this purpose, soluble compounds are needed, which are obtained, for example, through suitable substitution.

The organic electroluminescent device can also be produced as a hybrid system by applying one or more layers from solution and applying one or more other layers by vapour deposition. For example, it is possible to apply an emitting layer comprising a metal complex of the invention and a matrix material from solution, and to apply a hole blocker layer and/or an electron transport layer thereto by vapour deposition under reduced pressure.

These methods are known in general terms to those skilled in the art and can be applied by those skilled in the art without difficulty to organic electroluminescent devices comprising compounds of formula (1) or the above-detailed preferred embodiments.

The electronic devices of the invention, especially organic electroluminescent devices, are notable for one or more of the following surprising advantages over the prior art:

1. The metal complexes of the invention can be synthesized in very high yield and very high purity with exceptionally short reaction times and at comparatively low reaction temperatures.
2. The metal complexes of the invention have excellent thermal stability, which is also manifested in the sublimation of the complexes. In particular, the complexes of the invention show a lower sublimation temperature than similar polypodal complexes having three ortho-metallated ligands. The compounds of the invention are therefore of very good suitability for processing by vacuum vapour deposition.
3. The metal complexes of the invention have very good hydrolysis stability. In particular, hydrolysis stability is much better than in the case of complexes containing acetylacetonate derivatives as ligands, but in which the ligands do not have polypodal bridging. The compounds of the invention are therefore also of very good suitability for processing from solution.
4. Organic electroluminescent devices comprising the metal complexes of the invention as emitting materials have a very good lifetime. This is particularly true even in simple OLEDs in which the metal complex of the invention is incorporated into a single matrix—i.e. a matrix and host material.
5. Organic electroluminescent devices comprising the metal complexes of the invention as emitting materials have excellent efficiency and show oriented emission.

These abovementioned advantages are not accompanied by a deterioration in the further electronic properties.

The invention is illustrated in more detail by the examples which follow, without any intention of restricting it thereby. The person skilled in the art will be able to use the details given, without exercising inventive skill, to produce further electronic devices of the invention and hence to execute the invention over the entire scope claimed.

EXAMPLES

The syntheses which follow, unless stated otherwise, are conducted under a protective gas atmosphere in dried solvents. The metal complexes are additionally handled with exclusion of light or under yellow light. The solvents and reagents can be purchased, for example, from Sigma-ALDRICH or ABCR. The respective figures in square brackets or the numbers quoted for individual compounds relate to the CAS numbers of the compounds known from the literature. In the case of compounds that can have multiple tautomeric forms, one tautomeric form is shown in a representative manner.

A: Synthesis of the Synthons S—Part 1

Example S1

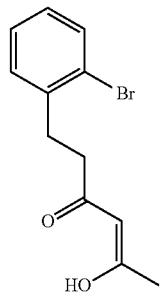

Preparation according to Casey, Brian M. et al., Beilstein Journal of Organic Chemistry, 9, 1472-1479, 2013.

To a suspension, cooled to 0° C., of 2.6 g (110 mmol) of NaH in 300 ml of THF are added dropwise, with good stirring, 10.3 g (100 mmol) of acetylacetone [123-54-6] (caution: evolution of hydrogen) and the mixture is stirred for a further 15 min. Then 42.0 ml (105 mmol) of n-BuLi, 2.5 M in n-hexane, are added dropwise and the mixture is stirred for another 15 min. Then a solution, cooled to 0° C., of 25.0 g (100 mmol) of 2-bromobenzyl bromide [3433-80-5] in 25 ml of THF is added all at once with very good stirring. The mixture is stirred for a further 10 min, the ice bath is removed, and the mixture is allowed to warm up to 15° C. over 30 min and hydrolysed by dropwise addition of 110 ml of 2N aqueous HCl. The aqueous phase is removed and extracted three times with 200 ml each time of ethyl acetate. The combined organic phases are washed twice with 300 ml each time of saturated sodium chloride solution and dried over magnesium sulfate. After the solvent has been removed under reduced pressure, the oily residue is chromatographed in an automatic column system (CombiFlash Torrent from A. Semrau). Yield: 12.4 g (46 mmol), 46%. Purity: about 97% by $^1$H NMR.

In an analogous manner, it is possible to prepare the following compounds:

| Ex. | Reactants | Product | Yield |
|---|---|---|---|
| S2 | [7307-03-1] [3433-80-5] | | 39% |
| S3 | [18362-64-4] [3433-80-5] | | 37% |

-continued
| Ex. | Reactants | Product | Yield |
|---|---|---|---|
| S4 | 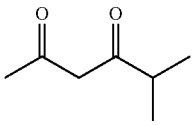<br>[7307-03-1]<br>[3433-80-5] | 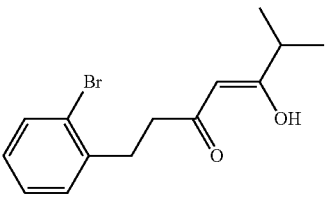 [SMILES: CC(C)/C(O)=C/C(=O)CCc1ccccc1Br] | 48% |
| S5 | 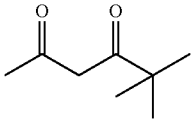<br>[7307-04-2]<br>[3433-80-5] | 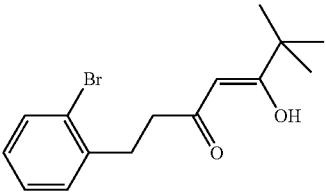 [SMILES: CC(C)(C)/C(O)=C/C(=O)CCc1ccccc1Br] | 64% |
| S6 | 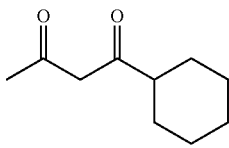<br>[15972-15-3]<br>[3433-80-5] | 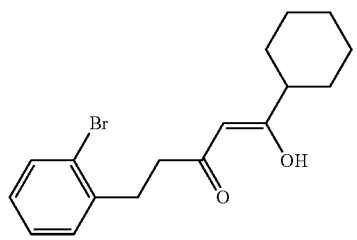 [SMILES: O=C(/C=C(\O)C1CCCCC1)CCc1ccccc1Br] | 50% |
| S7 | 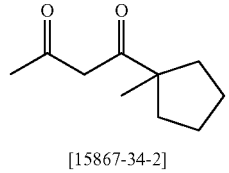<br>[15867-34-2]<br>[3433-80-5] | 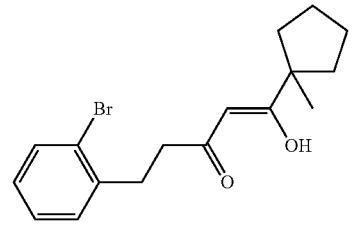 [SMILES: CC1(/C(O)=C/C(=O)CCc2ccccc2Br)CCCC1] | 61% |
| S8 | 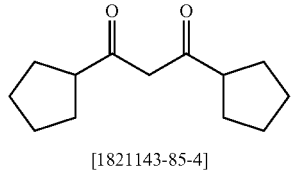<br>[1821143-85-4]<br>[3433-80-5] | 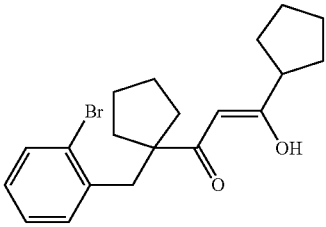 [SMILES: O=C(/C=C(\O)C1CCCC1)C1(Cc2ccccc2Br)CCCC1] | 48% |
| S9 | 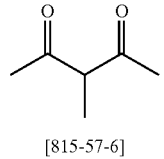<br>[815-57-6]<br>[3433-80-5] | 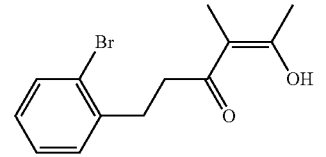 [SMILES: C/C(O)=C(\C)C(=O)CCc1ccccc1Br] | 50% |
| S10 | 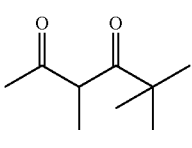<br>[60600-51-3]<br>[3433-80-5] | 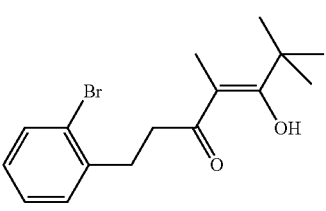 [SMILES: C/C(C(=O)CCc1ccccc1Br)=C(/O)C(C)(C)C] | 63% |

-continued
| Ex. | Reactants | Product | Yield |
|---|---|---|---|
| S11 | 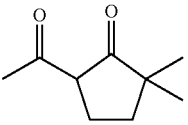 [2570-70-8] [3433-80-5] | 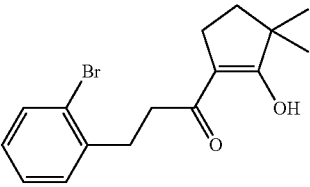 [SMILES: CC1(C)CCC(C(=O)CCc2ccccc2Br)=C1O] | 59% |
| S12 | 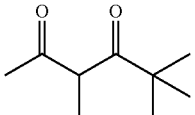 [111239-32-8] [3433-80-5] | 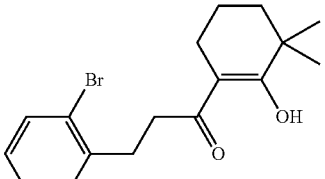 | 63% |
| S13 | 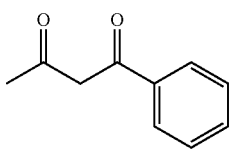 [3318-61-4] [3433-80-5] | 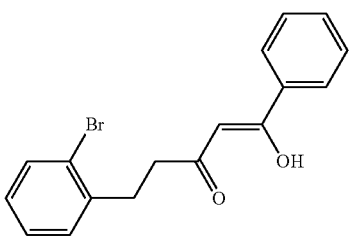 [SMILES: O=C(/C=C(\O)c1ccccc1)CCc1ccccc1Br] | 60% |
| S14 | 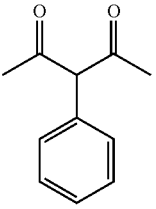 [5910-25-8] [3433-80-5] | 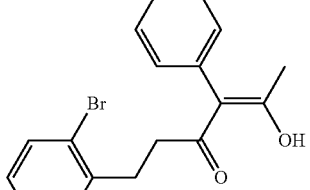 | 55% |
| S15 | 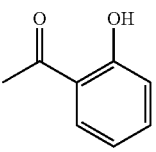 [118-93-4] [3433-80-5] | 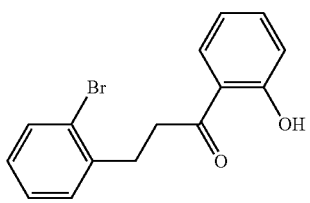 [SMILES: O=C(CCc1ccccc1Br)c1ccccc1O] | 49% |
| S16 | 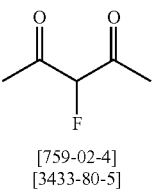 [759-02-4] [3433-80-5] | 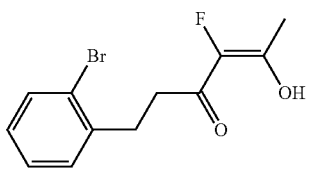 [SMILES: C/C(O)=C(\F)C(=O)CCc1ccccc1Br] | 29% |
| S17 | 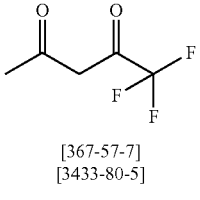 [367-57-7] [3433-80-5] | 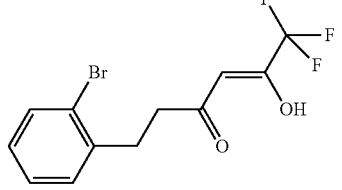 | 46% |

-continued
| Ex. | Reactants | Product | Yield |
|---|---|---|---|
| S18 | [123-54-6] 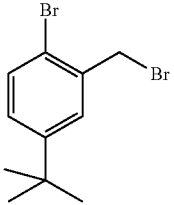 [875664-32-7] | 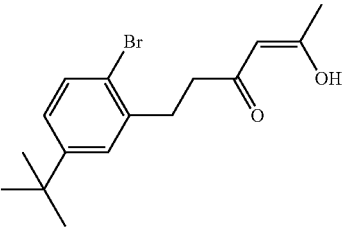 [SMILES: C/C(O)=C/C(=O)CCc1cc(C(C)(C)C)ccc1Br] | 55% |
| S19 | [123-54-6] 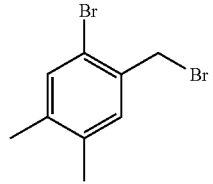 [2090556-71-9] | 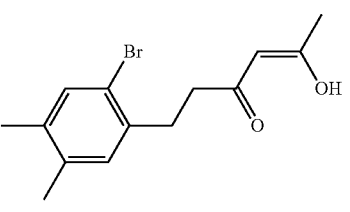 [SMILES: C/C(O)=C/C(=O)CCc1cc(C)c(C)cc1Br] | 57% |
| S20 | [123-54-6] 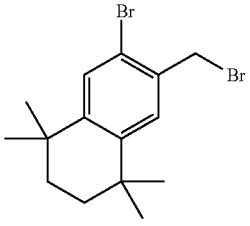 [410528-62-0] | 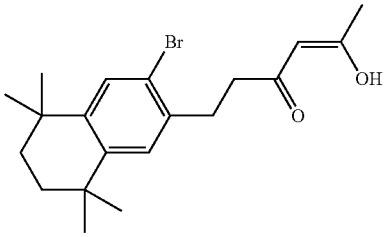 [SMILES: C/C(O)=C/C(=O)CCc1cc2c(cc1Br)C(C)(C)CCC2(C)C] | 61% |
| S21 | [123-54-6] 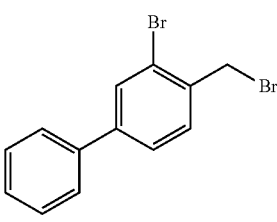 [1396865-04-5] | 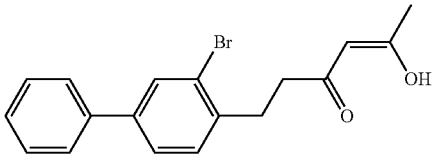 [SMILES: C/C(O)=C/C(=O)CCc1ccc(-c2ccccc2)cc1Br] | 56% |

| Ex. | Reactants | Product | Yield |
|---|---|---|---|
| S22 | [123-54-6]<br>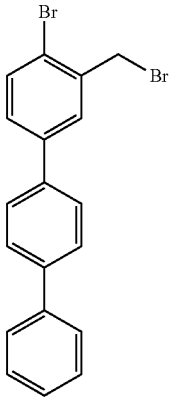<br>[1422181-28-9] | 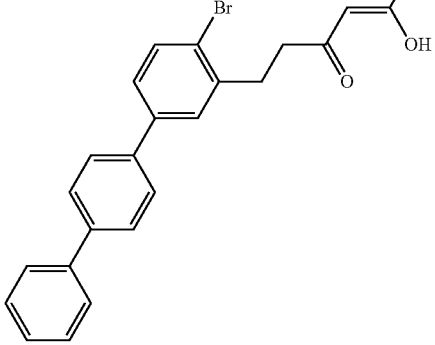 | 53% |
| S23 | [123-54-6]<br>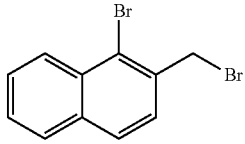<br>[37763-43-2] | 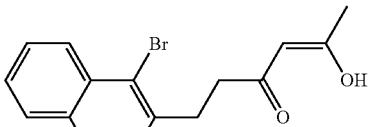 | 46% |

Example S50

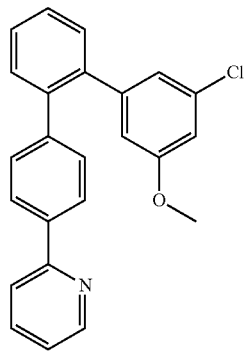 [SMILES: COc1cc(Cl)cc(-c2ccccc2-c2ccc(-c3ccccn3)cc2)c1]

A mixture of 26.9 g (100 mmol) of 2-(3-chloro-5-methoxyphenyl)-4,4,5,5-tetramethyl-1,3,2-dioxaborolane [929626-16-4], 31.0 g (100 mmol) of 2-(2'-bromo[1,1'-biphenyl]-4-yl)pyridine [1374202-35-3], 21.2 g (200 mmol) of sodium carbonate, 788 mg (3 mmol) of triphenylphosphine, 225 mg (1 mmol) of palladium(II) acetate, 300 ml of toluene, 100 ml of ethanol and 300 ml of water is heated under reflux for 48 h. After cooling, the mixture is extended with 300 ml of toluene, and the organic phase is removed, washed once with 500 ml of water and once with 500 ml of saturated sodium chloride solution, and dried over magnesium sulfate. After the solvent has been removed, the residue is chromatographed on silica gel (n-heptane/ethyl acetate, 2:1 v/v). Yield: 28.4 g (76 mmol), 76%. Purity: about 97% by $^1$H NMR.

In an analogous manner, it is possible to prepare the following compounds:

| Ex. | Reactants | Product | Yield |
|---|---|---|---|
| S51 | 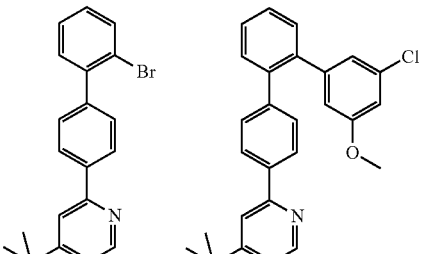 [1989597-33-2] | | 80% |
| S52 | 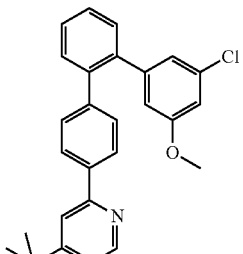 [1989597-43-4] | | 73% |
| S53 | 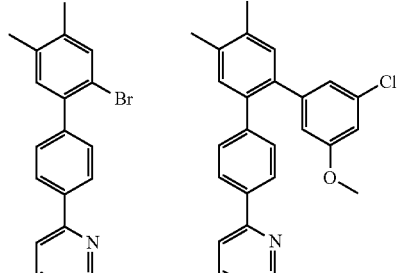 [1989597-34-3] | | 75% |
| S54 | 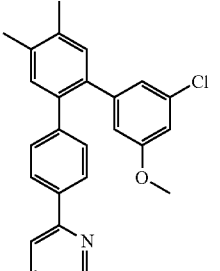 [1989597-41-2] | | 80% |
| S55 | 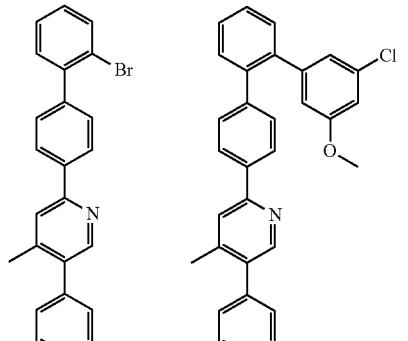 [1989597-44-5] | | 77% |
| S56 | 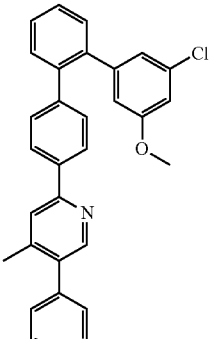 [2088182-36-7] | | 71% |

Example S100

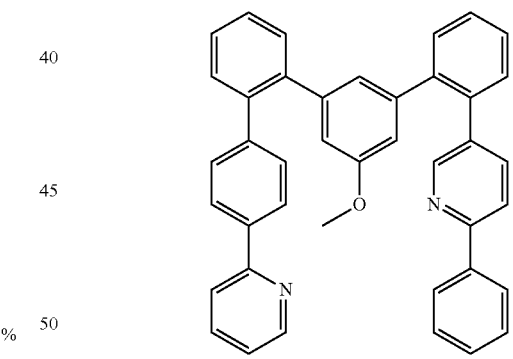

A mixture of 37.2 g (100 mmol) of S50, 31.0 g (100 mmol) of 5-(2-bromophenyl)-2-phenylpyridine [1989597-29-6], 21.2 g (200 mmol) of sodium carbonate, 1.23 g (3 mmol) of SPhos, 449 mg (2 mmol) of palladium(II) acetate, 300 ml of toluene, 100 ml of ethanol and 300 ml of water is heated under reflux for 16 h. After cooling, the mixture is extended with 300 ml of toluene, and the organic phase is removed, washed once with 500 ml of water and once with 500 ml of saturated sodium chloride solution, and dried over magnesium sulfate. After the solvent has been removed, the residue is chromatographed on silica gel (n-heptane/ethyl acetate, 2:1 v/v). Yield: 40.3 g (71 mmol), 71%. Purity: about 97% by $^1$H NMR.

In an analogous manner, it is possible to prepare the following compounds:

| Ex. | Reactants | Product | Yield |
|---|---|---|---|
| S101 | 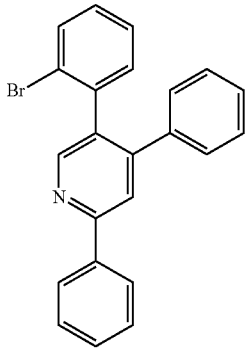<br>[1989597-32-1]<br>S50 | 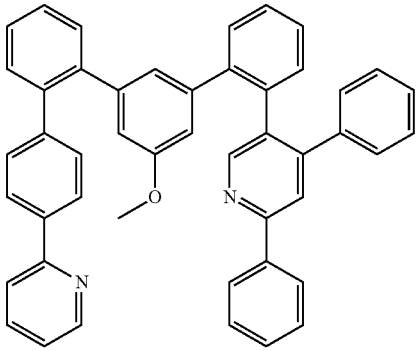 [SMILES: COc1cc(-c2ccccc2-c2ccc(-c3ccccn3)cc2)cc(-c2ccccc2-c2cnc(-c3ccccc3)cc2-c2ccccc2)c1] | 68% |
| S102 | 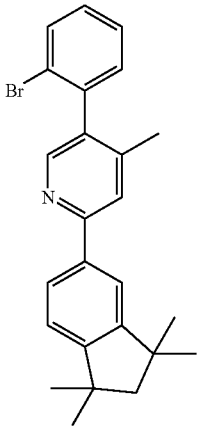<br>[2088182-35-6]<br>S51 | 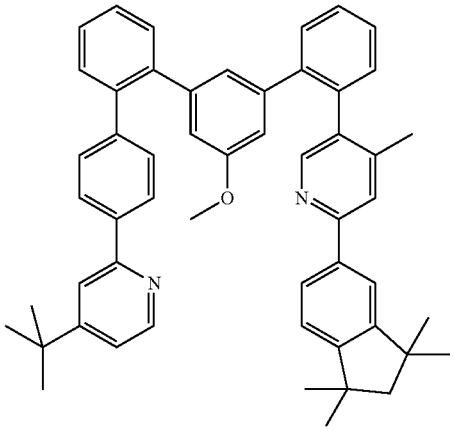 [SMILES: COc1cc(-c2ccccc2-c2ccc(-c3cc(C(C)(C)C)ccn3)cc2)cc(-c2ccccc2-c2cnc(-c3ccc4c(c3)C(C)(C)CC4(C)C)cc2C)c1] | 70% |
| S103 | 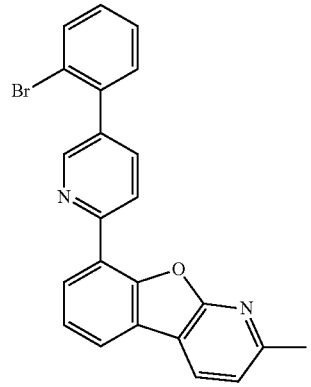<br>[1989597-42-3]<br>S52 | 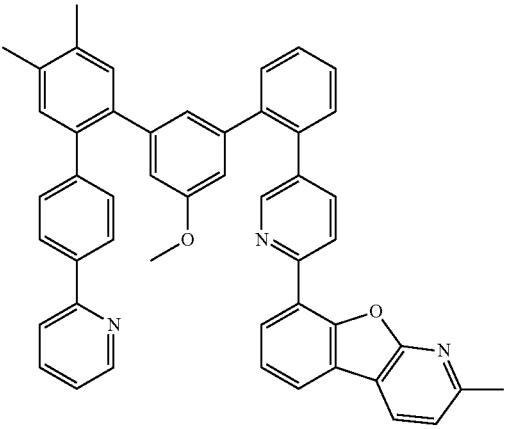 | 74% |

| Ex. | Reactants | Product | Yield |
|---|---|---|---|
| S104 | 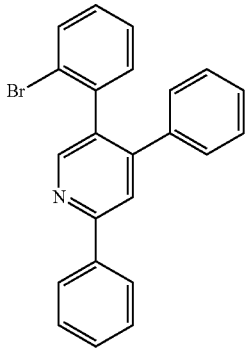 [1989597-32-1] S53 | 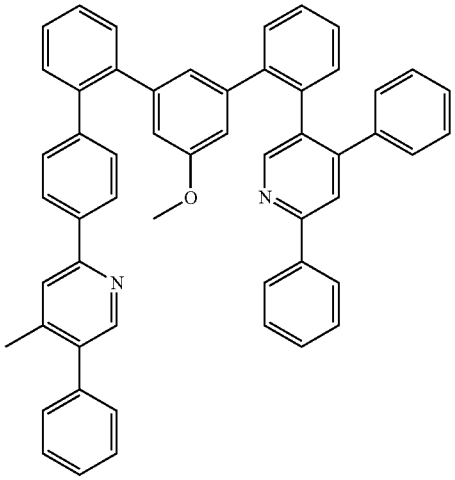 [SMILES: COc1cc(-c2ccccc2-c2ccc(-c3cc(C)c(-c4ccccc4)cn3)cc2)cc(-c2ccccc2-c2cnc(-c3ccccc3)cc2-c2ccccc2)c1] | 69% |
| S105 | 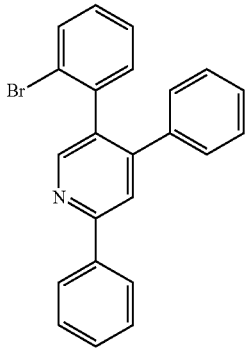 [1989597-32-1] S54 | 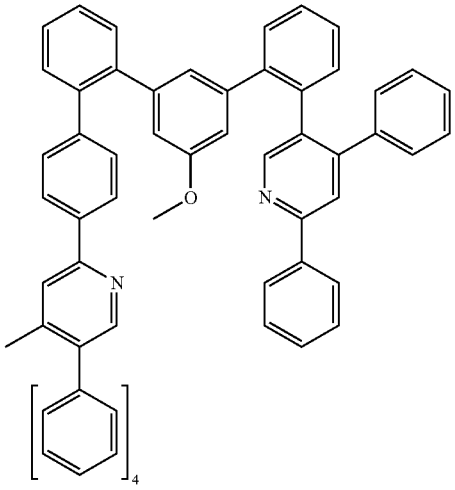 | 75% |
| S106 | 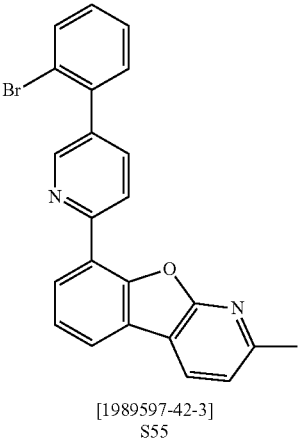 [SMILES: Cc1ccc2c(n1)oc1c(-c3ccc(-c4ccccc4Br)cn3)cccc12] [1989597-42-3] S55 | 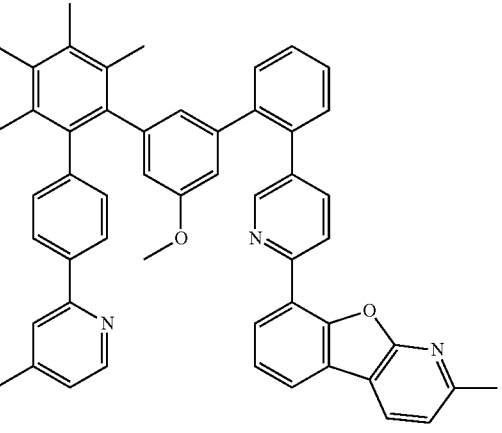 | 73% |

| Ex. | Reactants | Product | Yield |
|---|---|---|---|
| S107 | [1989597-42-3] S56 | | 67% |
| S108 | [1989597-32-1] S56 | | 70% |

Example S200

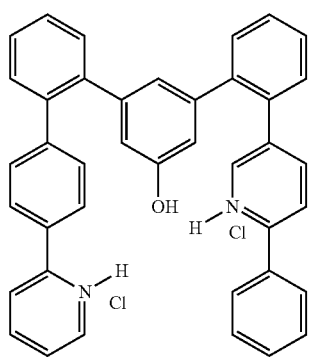

A mixture of 55.6 g (100 mmol) of S100 and 115.6 g (1 mol) of pyridinium hydrochloride [628-13-7] is heated to 200° C. on a water separator for 3 h, discharging the distillate from time to time. After cooling, 1000 ml of ice-water are added to the reaction mixture, crystallizing the product. The mixture is left to stand in a refrigerator overnight, and the crystals are filtered off with suction, washed with a little ice-water and dried under reduced pressure. Yield: 55.0 g (87 mmol), 87%; purity: about 97% by $^1$H NMR.

In an analogous manner, it is possible to prepare the following compounds:

| Ex. | Reactant | Product | Yield |
|---|---|---|---|
| S201 | S101 | 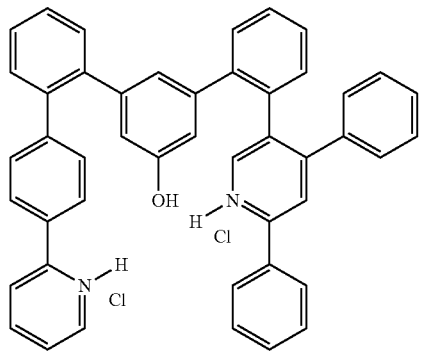 | 90% |
| S202 | S102 | 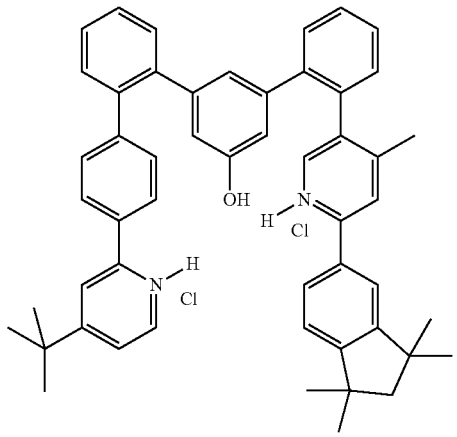 | 88% |
| S203 | S103 | 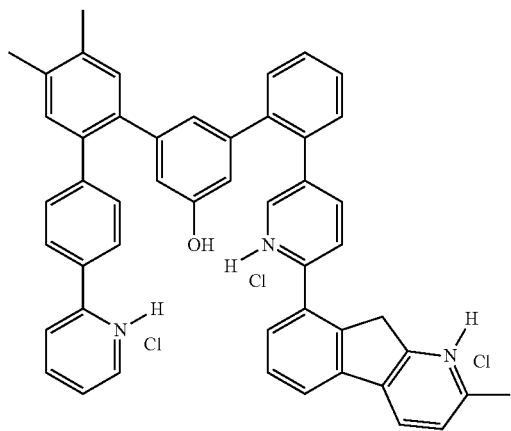 | 85% |

-continued
| Ex. | Reactant | Product | Yield |
|---|---|---|---|
| S204 | S104 | 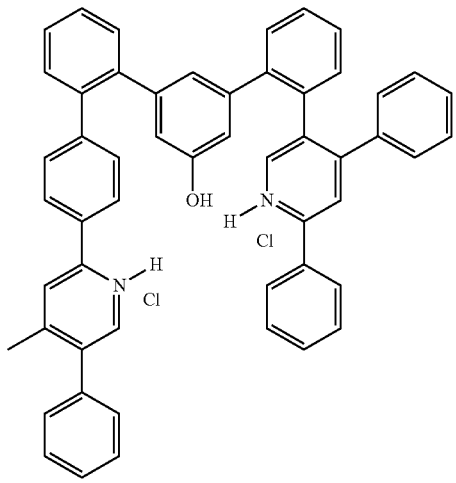 | 85% |
| S205 | S105 | 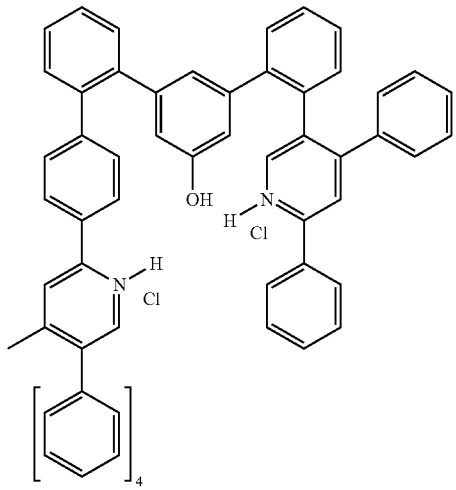 | 91% |
| S206 | S106 | 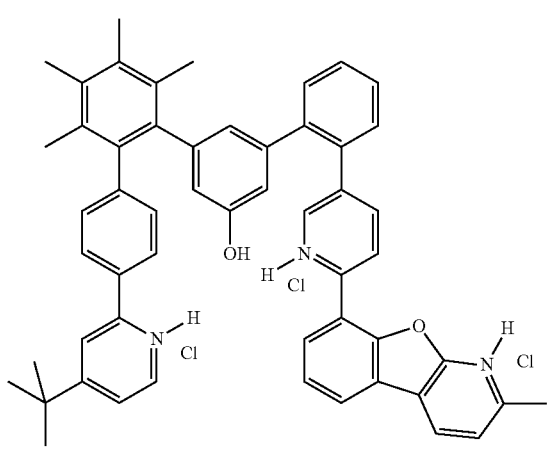 | 90% |

| Ex. | Reactant | Product | Yield |
|---|---|---|---|
| S207 | S107 | 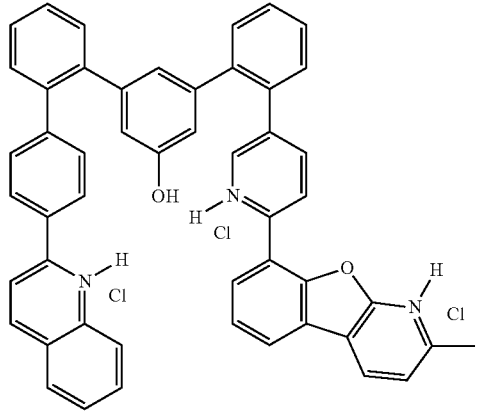 | 86% |
| S208 | S108 | 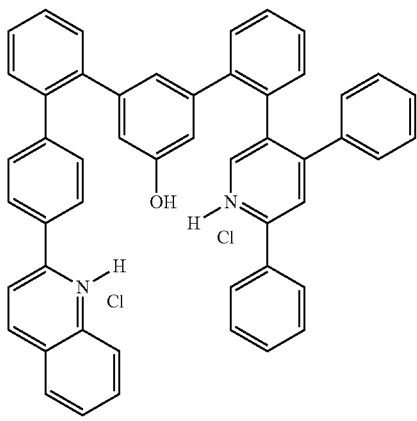 | 88% |

Example S300

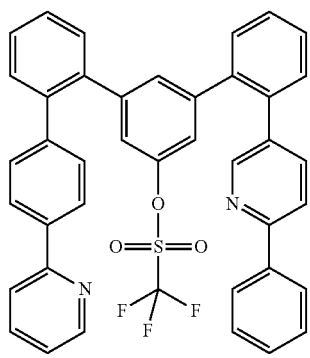 [SMILES: O=S(=O)(Oc1cc(-c2ccccc2-c2ccc(-c3ccccn3)cc2)cc(-c2ccccc2-c2ccc(-c3ccccc3)nc2)c1)C(F)(F)F]

To a solution, cooled to 0° C., of 55.6 g (100 mmol) of S200 in a mixture of 500 ml of dichloromethane and 100 ml of pyridine are added dropwise, with good stirring, 34 ml (200 mmol) of trifluoromethanesulfonic anhydride [358-23-6]. The reaction mixture is allowed to warm up to room temperature and stirred for a further 16 h, poured onto 1000 ml of ice-water while stirring and stirred for a further 10 min, the organic phase is removed and the aqueous phase is extracted three times with 300 ml each time of dichloromethane. The combined organic phases are washed twice with 300 ml each time of ice-water and once with 500 ml of saturated NaCl solution and dried over sodium sulfate. The wax obtained after removal of the dichloromethane under reduced pressure is recrystallized from acetonitrile. Yield: 60.5 g (88 mmol), 88%; purity: about 95% by $^1$H NMR.

In an analogous manner, it is possible to prepare the following compounds:

| Ex. | Reactant | Product | Yield |
|---|---|---|---|
| S301 | S201 | 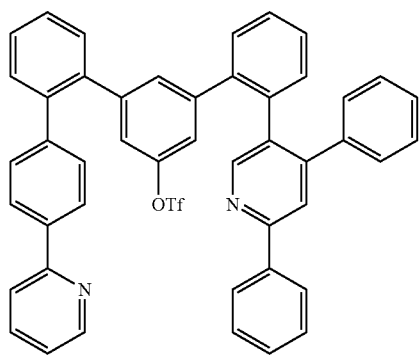 [SMILES: O=S(=O)(Oc1cc(-c2ccccc2-c2ccc(-c3ccccn3)cc2)cc(-c2ccccc2-c2cnc(-c3ccccc3)cc2-c2ccccc2)c1)C(F)(F)F] | 90% |
| S302 | S202 | 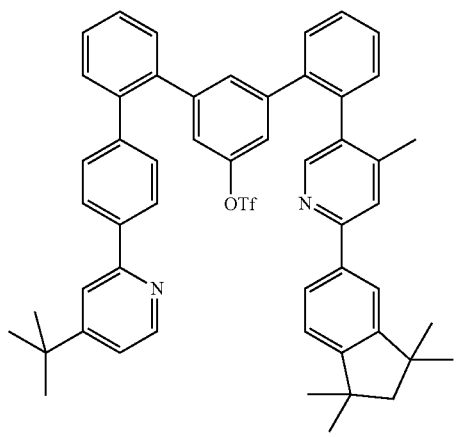 [SMILES: Cc1cc(-c2ccc3c(c2)C(C)(C)CC3(C)C)ncc1-c1ccccc1-c1cc(OS(=O)(=O)C(F)(F)F)cc(-c2ccccc2-c2ccc(-c3cc(C(C)(C)C)ccn3)cc2)c1] | 81% |
| S303 | S203 | 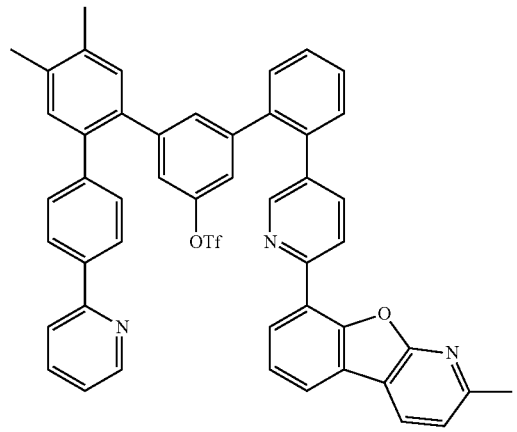 | 83% |

-continued

| Ex. | Reactant | Product | Yield |
|---|---|---|---|
| S304 | S204 | | 81% |
| S305 | S205 | | 83% |
| S306 | S206 | | 77% |

-continued

| Ex. | Reactant | Product | Yield |
|---|---|---|---|
| S307 | S207 | | 79% |
| S308 | S208 | | 85% |

Example S400

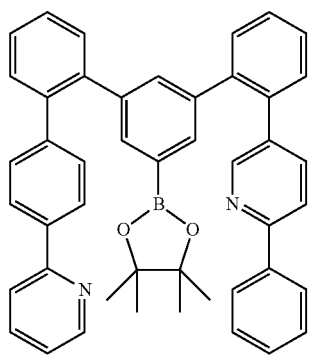 [SMILES: CC1(C)OB(c2cc(-c3ccccc3-c3ccc(-c4ccccn4)cc3)cc(-c3ccccc3-c3ccc(-c4ccccc4)nc3)c2)OC1(C)C]

To a solution of 68.5 g (100 mmol) of S300 and bis(diphenylphosphino)palladium(II) dichloride x DCM in 500 ml of dioxane are added, with good stirring, 41.8 ml (300 mmol) triethylamine and then, in a dropwise manner, 29.0 ml (200 mmol) of 4,4,5,5-tetramethyl-[1,3,2]-dioxaborolane, and the mixture is heated under reflux for 16 h. After cooling, the mixture is concentrated to dryness under reduced pressure, and the oil is taken up in 500 ml of ethyl acetate, washed three times with 300 ml each time of water and once with 300 ml of saturated sodium chloride solution, and dried over magnesium sulfate, and the desiccant is filtered off using a silica gel bed in an ethyl acetate slurry. The solvent is removed under reduced pressure and the residue is recrystallized twice from acetonitrile with addition of a little ethyl acetate. Yield: 49.7 g (75 mmol), 75%; purity: about 95% by $^1$H NMR.

In an analogous manner, it is possible to prepare the following compounds:

| Ex. | Reactant | Product | Yield |
|---|---|---|---|
| S401 | S301 | 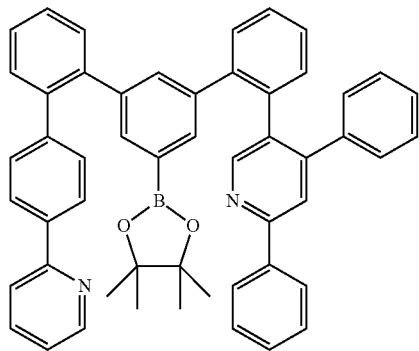 [SMILES: CC1(C)OB(c2cc(-c3ccccc3-c3ccc(-c4ccccn4)cc3)cc(-c3ccccc3-c3cnc(-c4ccccc4)cc3-c3ccccc3)c2)OC1(C)C] | 73% |
| S402 | S302 | 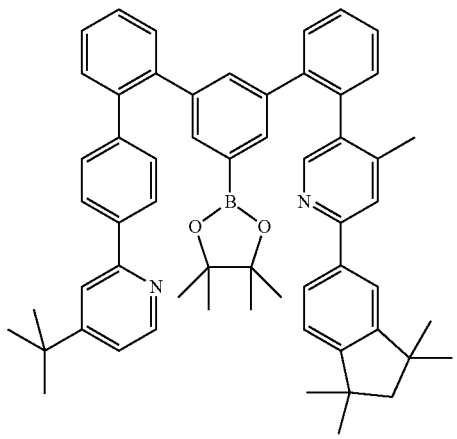 [SMILES: Cc1cc(-c2ccc3c(c2)C(C)(C)CC3(C)C)ncc1-c1ccccc1-c1cc(B2OC(C)(C)C(C)(C)O2)cc(-c2ccccc2-c2ccc(-c3cc(C(C)(C)C)ccn3)cc2)c1] | 69% |
| S403 | S303 | 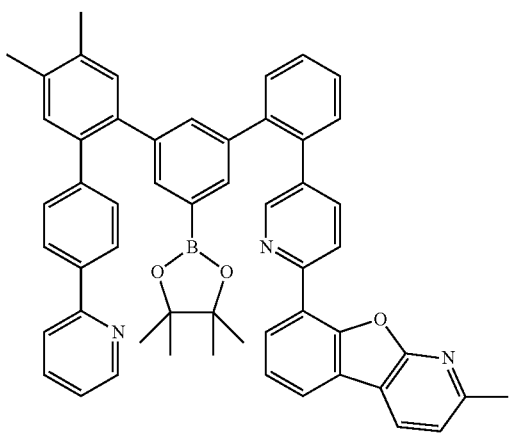 | 67% |

-continued
| Ex. | Reactant | Product | Yield |
|---|---|---|---|
| S404 | S304 | 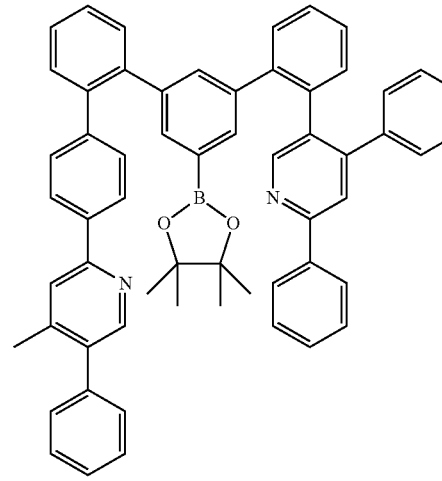 | 70% |
| S405 | S305 | 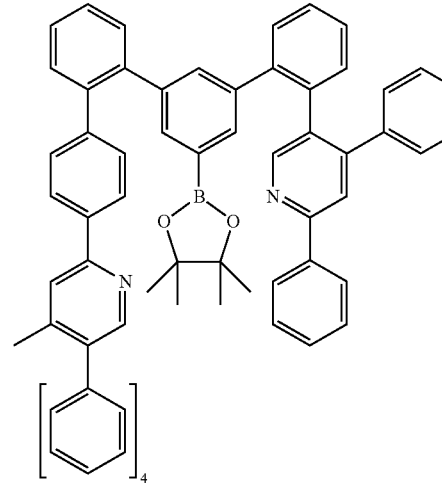 | 74% |
| S406 | S306 | 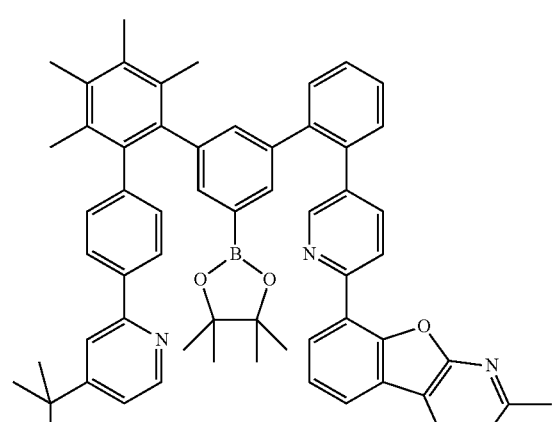 | 68% |

| Ex. | Reactant | Product | Yield |
|---|---|---|---|
| S407 | S307 | | 70% |
| S408 | S308 | | 67% |

B: Synthesis of the Ligands L

Example L1

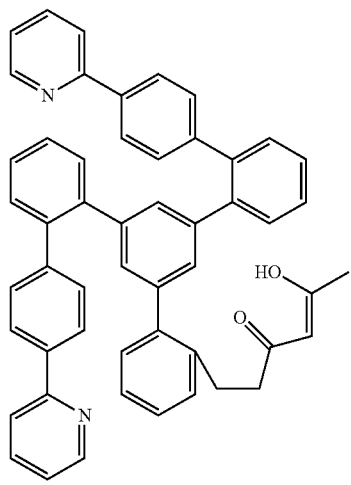 [SMILES: C/C(O)=C/C(=O)CCc1ccccc1-c1cc(-c2ccccc2-c2ccc(-c3ccccn3)cc2)cc(-c2ccccc2-c2ccc(-c3ccccn3)cc2)c1]

A mixture of 66.3 g (100 mmol) of 2,2'-[5"-(4,4,5,5-tetramethyl-1,3,2-dioxaborolan-2-yl)-[1,1':2',1":3",1'":2''',1''''-quinquephenyl]-4,4''''-diyl]bispyridine [1989597-72-9], 29.6 g (110 mmol) of S1, 31.8 g (300 mmol) of sodium carbonate, 1.23 g (3 mmol) of SPhos, 449 mg (2 mmol) of palladium(II) acetate, 300 ml of toluene, 100 ml of ethanol and 300 ml of water is heated under reflux for 18 h. After cooling, acetic acid is used to adjust the pH to 6-7, the organic phase is removed, the aqueous phase is extracted three times with 100 ml each time of toluene, and the combined organic phases are washed once with 300 ml of water and once with 500 ml of saturated sodium chloride solution and dried over sodium sulfate. After the solvent has been removed, the residue is chromatographed (CombiFlash Torrent from A. Semrau). Yield: 50.0 g (69 mmol), 69%; purity: about 97% by $^1$H NMR.

In an analogous manner, it is possible to prepare the following compounds:

| Ex. | Reactants | Product | Yield |
|---|---|---|---|
| L-Ref.1 | 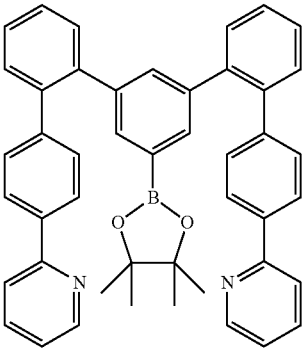 [1989597-72-9] 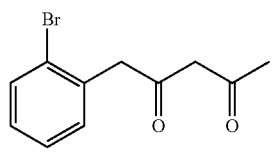 [473758-02-0] | 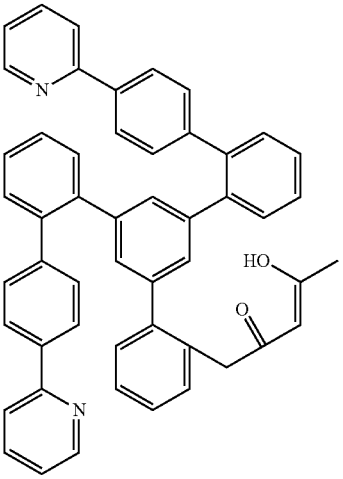 [SMILES: C/C(O)=C/C(=O)Cc1ccccc1-c1cc(-c2ccccc2-c2ccc(-c3ccccn3)cc2)cc(-c2ccccc2-c2ccc(-c3ccccn3)cc2)c1] | 58% |
| L2 | 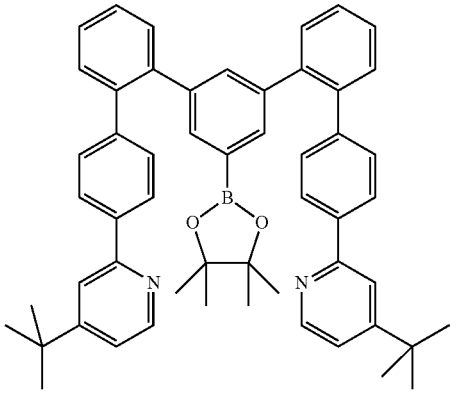 [1989597-75-2] S4 | 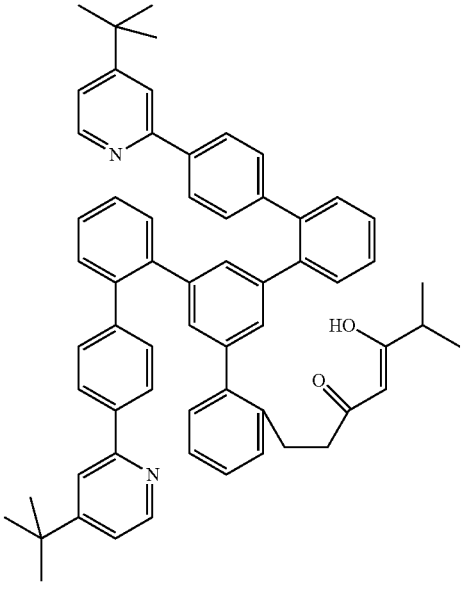 [SMILES: CC(C)/C(O)=C/C(=O)CCc1ccccc1-c1cc(-c2ccccc2-c2ccc(-c3cc(C(C)(C)C)ccn3)cc2)cc(-c2ccccc2-c2ccc(-c3cc(C(C)(C)C)ccn3)cc2)c1] | 70% |

| Ex. | Reactants | Product | Yield |
|---|---|---|---|
| L3 | [1989597-72-9] S22 | 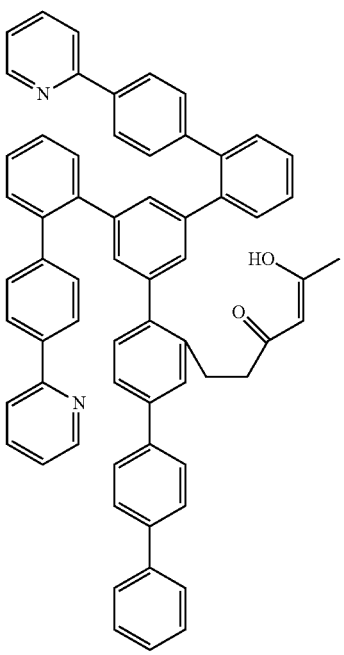 [SMILES: C/C(O)=C/C(=O)CCc1cc(-c2ccc(-c3ccccc3)cc2)ccc1-c1cc(-c2ccccc2-c2ccc(-c3ccccn3)cc2)cc(-c2ccccc2-c2ccc(-c3ccccn3)cc2)c1] | 64% |

Example L100

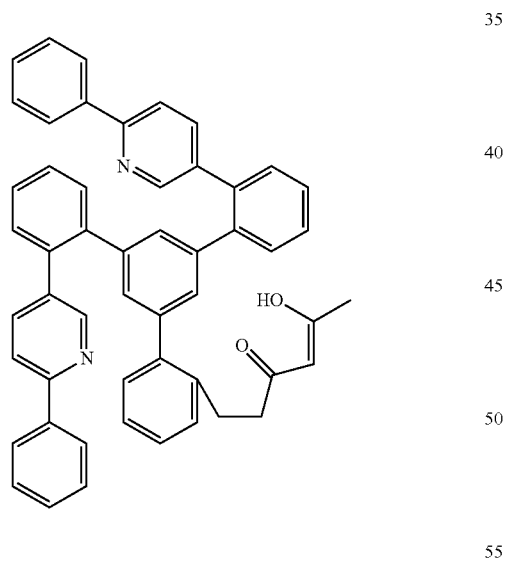

Procedure analogous to example L1, except that, rather than 2,2'-[5"-(4,4,5,5-tetramethyl-1,3,2-dioxaborolan-2-yl)-[1,1':2',1":3",1'":2'",1''''-quinquephenyl]-4,4''''-diyl]bispyridine [1989597-72-9], 3,3'-[5'-(4,4,5,5-tetramethyl-1,3,2-dioxaborolan-2-yl)-[1,1':3',1''-terphenyl]-2,2''-diyl]bis[6-phenylpyridine] [1989597-70-7] is used. Yield: 53.2 g (73 mmol), 73%; purity: about 97% by $^1$H NMR.

In an analogous manner, it is possible to prepare the following compounds:

| Ex. | Reactants | Product | Yield |
|---|---|---|---|
| L-Ref.2 | 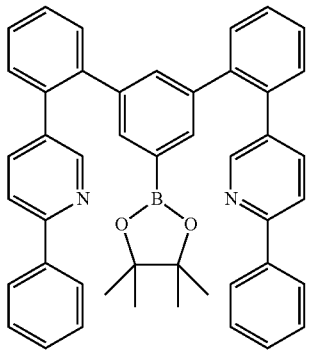 [1989597-70-7]<br>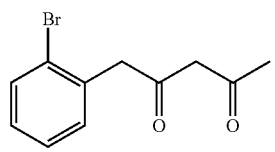 [473758-02-0] | 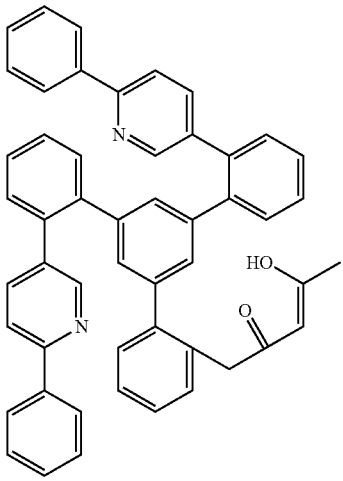 [SMILES: C/C(O)=C/C(=O)Cc1ccccc1-c1cc(-c2ccccc2-c2ccc(-c3ccccc3)nc2)cc(-c2ccccc2-c2ccc(-c3ccccc3)nc2)c1] | 54% |
| L101 | [1989597-70-7]<br>S7 | 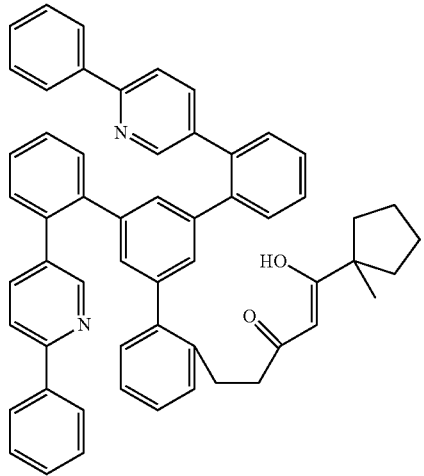 [SMILES: CC1(/C(O)=C/C(=O)CCc2ccccc2-c2cc(-c3ccccc3-c3ccc(-c4ccccc4)nc3)cc(-c3ccccc3-c3ccc(-c4ccccc4)nc3)c2)CCCC1] | 65% |
| L102 | 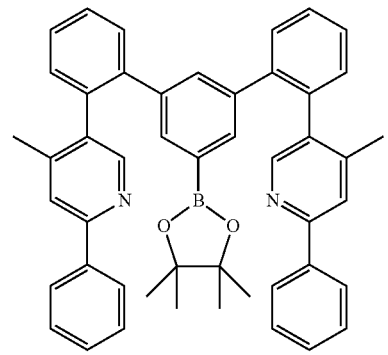 [1989597-71-8]<br>S20 | 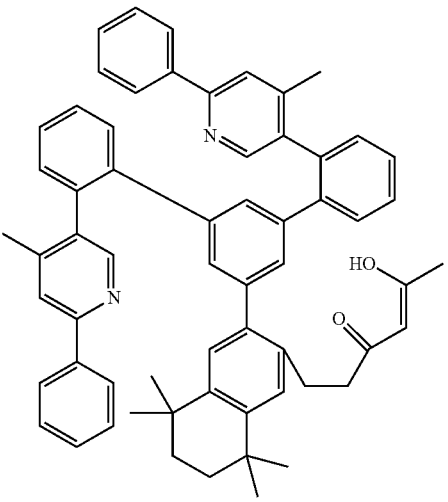 [SMILES: C/C(O)=C/C(=O)CCc1cc2c(cc1-c1cc(-c3ccccc3-c3cnc(-c4ccccc4)cc3C)cc(-c3ccccc3-c3cnc(-c4ccccc4)cc3C)c1)C(C)(C)CCC2(C)C] | 68% |

| Ex. | Reactants | Product | Yield |
|---|---|---|---|
| L103 | 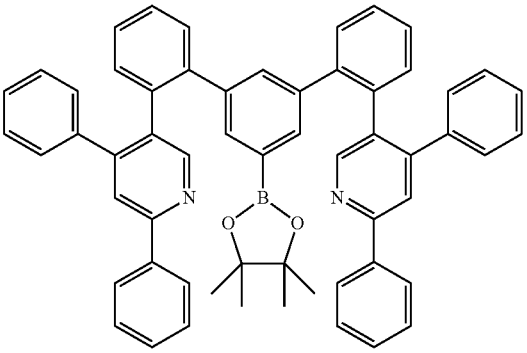 [1989597-74-1] S12 | 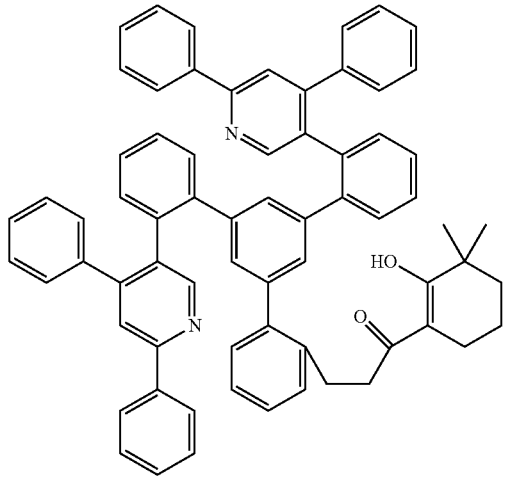 [SMILES: CC1(C)CCCC(C(=O)CCc2ccccc2-c2cc(-c3ccccc3-c3cnc(-c4ccccc4)cc3-c3ccccc3)cc(-c3ccccc3-c3cnc(-c4ccccc4)cc3-c3ccccc3)c2)=C1O] | 67% |
| L104 | 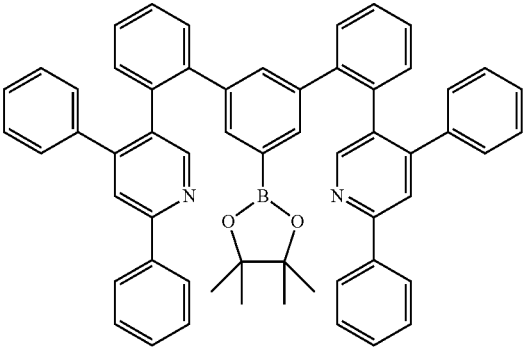 [1989597-74-1] S16 | 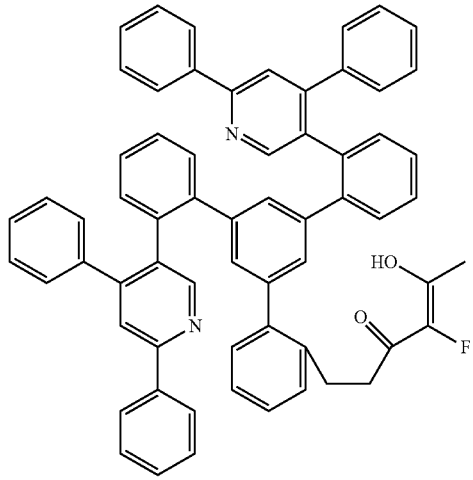 [SMILES: C/C(O)=C(\F)C(=O)CCc1ccccc1-c1cc(-c2ccccc2-c2cnc(-c3ccccc3)cc2-c2ccccc2)cc(-c2ccccc2-c2cnc(-c3ccccc3)cc2-c2ccccc2)c1] | 61% |

| Ex. | Reactants | Product | Yield |
|---|---|---|---|
| L105 | 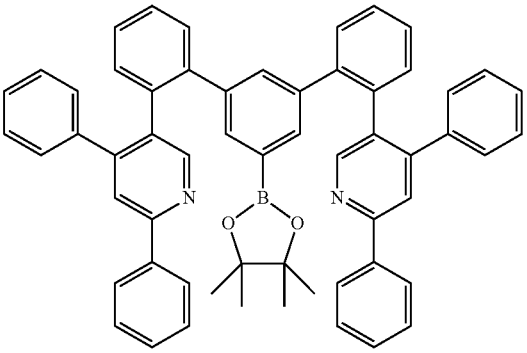<br>[1989597-74-1]<br>S17 | 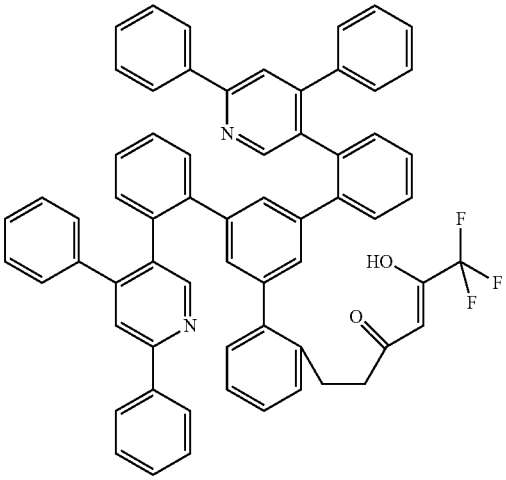 [SMILES: O=C(/C=C(\O)C(F)(F)F)CCc1ccccc1-c1cc(-c2ccccc2-c2cnc(-c3ccccc3)cc2-c2ccccc2)cc(-c2ccccc2-c2cnc(-c3ccccc3)cc2-c2ccccc2)c1] | 58% |
Example L200
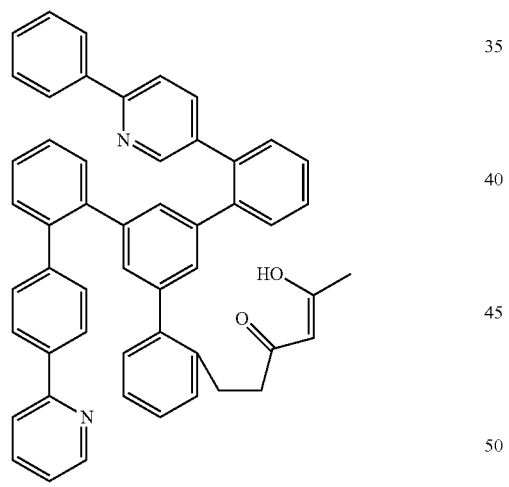
Procedure analogous to example L1, except that, rather than 2,2'-[5"-(4,4,5,5-tetramethyl-1,3,2-dioxaborolan-2-yl)-[1,1':2',1":3",1'":2'",1""-quinquephenyl]-4,4""-diyl]bispyridine [1989597-72-9], S400 is used. Yield: 53.0 g (72 mmol), 72%; purity: about 97% by $^1$H NMR.
In an analogous manner, it is possible to prepare the following compounds:

| Ex. | Reactants | Product | Yield |
|---|---|---|---|
| L-Ref.3 | S400 [473758-02-0] | 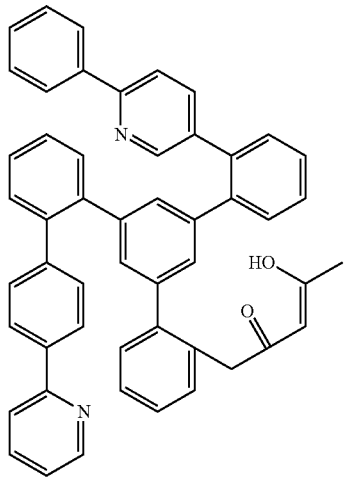 [SMILES: C/C(O)=C/C(=O)Cc1ccccc1-c1cc(-c2ccccc2-c2ccc(-c3ccccn3)cc2)cc(-c2ccccc2-c2ccc(-c3ccccc3)nc2)c1] | 56% |
| L201 | S401 S2 | 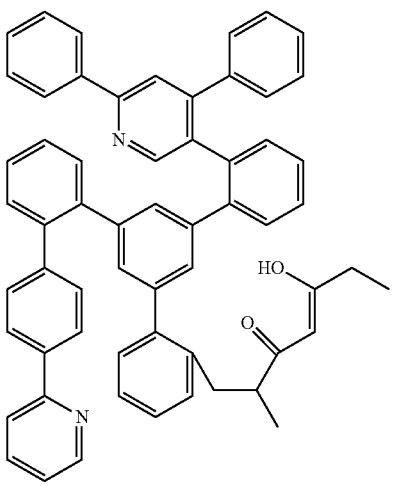 [SMILES: CC/C(O)=C/C(=O)C(C)Cc1ccccc1-c1cc(-c2ccccc2-c2ccc(-c3ccccn3)cc2)cc(-c2ccccc2-c2cnc(-c3ccccc3)cc2-c2ccccc2)c1] | 54% |
| L202 | S401 S3 | 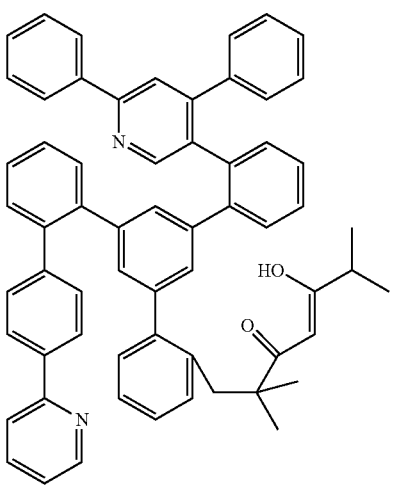 [SMILES: CC(C)/C(O)=C/C(=O)C(C)(C)Cc1ccccc1-c1cc(-c2ccccc2-c2ccc(-c3ccccn3)cc2)cc(-c2ccccc2-c2cnc(-c3ccccc3)cc2-c2ccccc2)c1] | 57% |

| Ex. | Reactants | Product | Yield |
|---|---|---|---|
| L203 | S402<br>S5 | 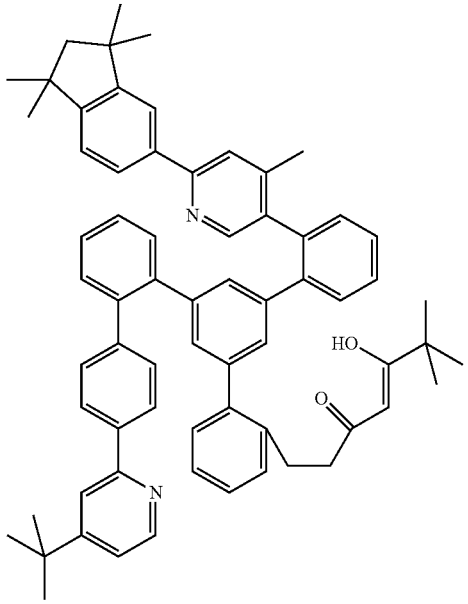 [SMILES: Cc1cc(-c2ccc3c(c2)C(C)(C)CC3(C)C)ncc1-c1ccccc1-c1cc(-c2ccccc2CCC(=O)/C=C(\O)C(C)(C)C)cc(-c2ccccc2-c2ccc(-c3cc(C(C)(C)C)ccn3)cc2)c1] | 65% |
| L204 | S402<br>S23 | 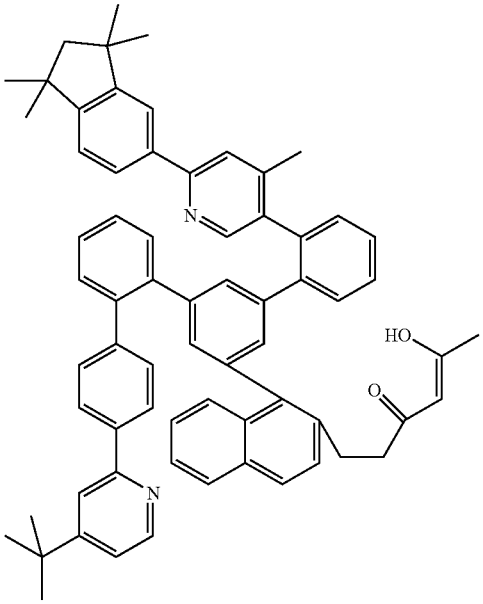 [SMILES: C/C(O)=C/C(=O)CCc1ccc2ccccc2c1-c1cc(-c2ccccc2-c2ccc(-c3cc(C(C)(C)C)ccn3)cc2)cc(-c2ccccc2-c2cnc(-c3ccc4c(c3)C(C)(C)CC4(C)C)cc2C)c1] | 67% |

| Ex. | Reactants | Product | Yield |
|---|---|---|---|
| L205 | S403<br>S8 | 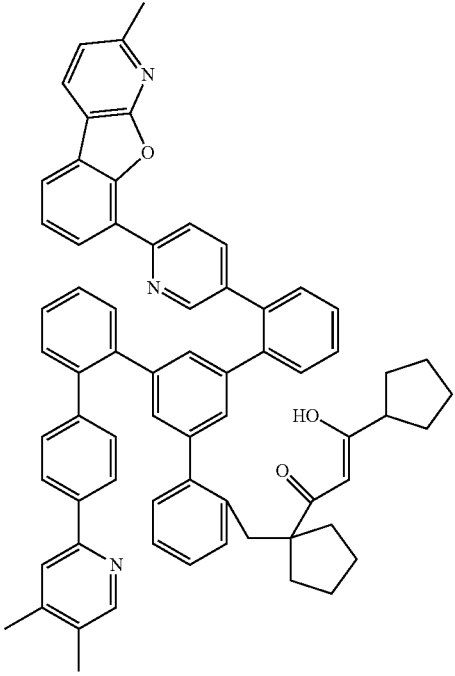 [SMILES: Cc1ccc2c(n1)oc1c(-c3ccc(-c4ccccc4-c4cc(-c5ccccc5CC5(C(=O)/C=C(\O)C6CCCC6)CCCC5)cc(-c5ccccc5-c5ccc(-c6cc(C)c(C)cn6)cc5)c4)cn3)cccc12] | 60% |
| L206 | S403<br>S19 | 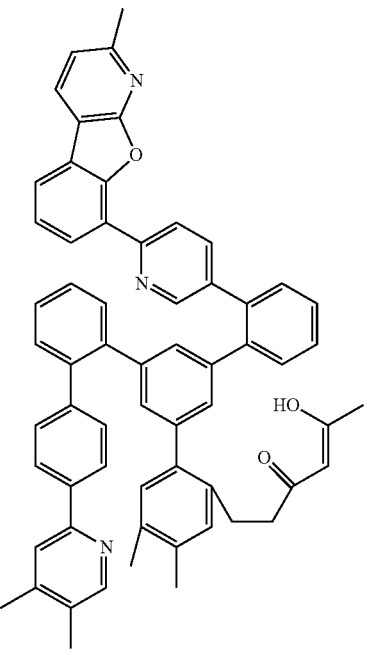 [SMILES: C/C(O)=C/C(=O)CCc1cc(C)c(C)cc1-c1cc(-c2ccccc2-c2ccc(-c3cc(C)c(C)cn3)cc2)cc(-c2ccccc2-c2ccc(-c3cccc4c3oc3nc(C)ccc34)nc2)c1] | 62% |

-continued

| Ex. | Reactants | Product | Yield |
|---|---|---|---|
| L207 | S403<br>S21 | | 66% |
| L208 | S404<br>S9 | | 65% |

| Ex. | Reactants | Product | Yield |
|---|---|---|---|
| L209 | S404<br>S10 | 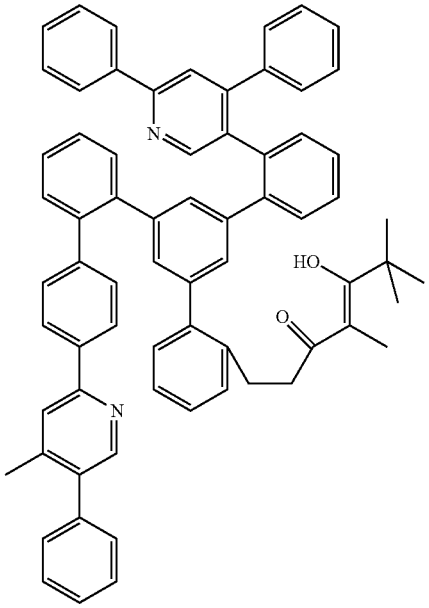 [SMILES: C/C(C(=O)CCc1ccccc1-c1cc(-c2ccccc2-c2ccc(-c3cc(C)c(-c4ccccc4)cn3)cc2)cc(-c2ccccc2-c2cnc(-c3ccccc3)cc2-c2ccccc2)c1)=C(/O)C(C)(C)C] | 60% |
| L210 | S405<br>S13 | 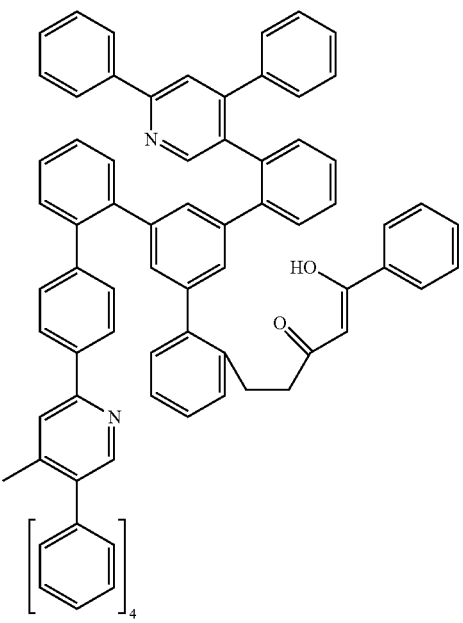 | 57% |

-continued
| Ex. | Reactants | Product | Yield |
|---|---|---|---|
| L211 | S405 S14 | 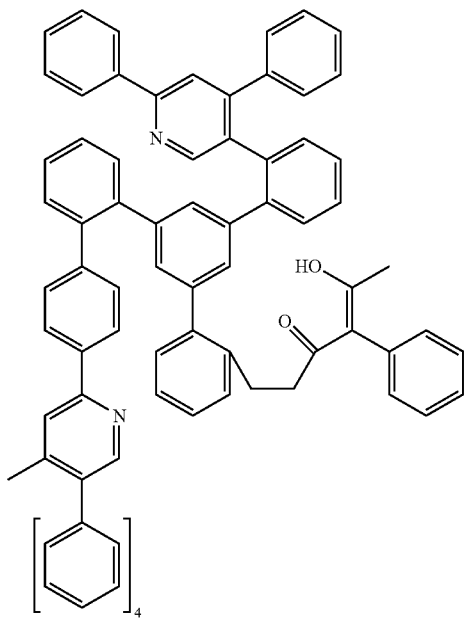 | 62% |
| L212 | S406 S15 | 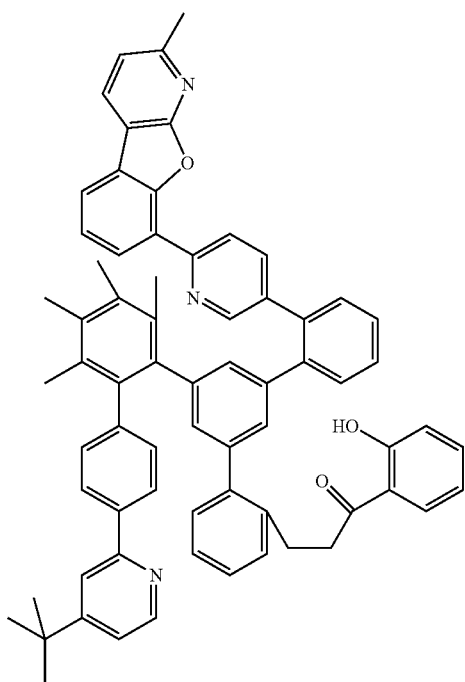 [SMILES: Cc1ccc2c(n1)oc1c(-c3ccc(-c4ccccc4-c4cc(-c5ccccc5CCC(=O)c5ccccc5O)cc(-c5c(C)c(C)c(C)c(C)c5-c5ccc(-c6cc(C(C)(C)C)ccn6)cc5)c4)cn3)cccc12] | 70% |

-continued
| Ex. | Reactants | Product | Yield |
|---|---|---|---|
| L213 | S407 S18 | 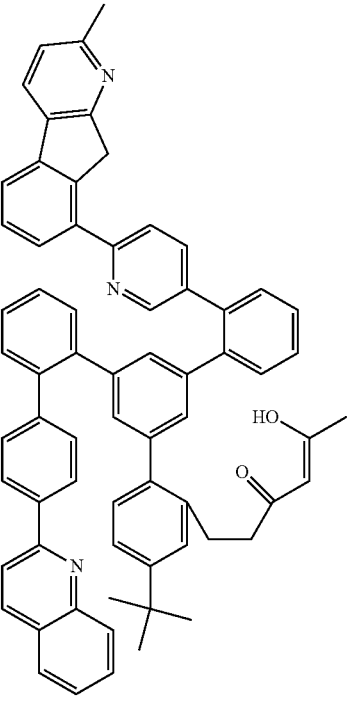 [SMILES: C/C(O)=C/C(=O)CCc1cc(C(C)(C)C)ccc1-c1cc(-c2ccccc2-c2ccc(-c3ccc4ccccc4n3)cc2)cc(-c2ccccc2-c2ccc(-c3cccc4c3Cc3nc(C)ccc3-4)nc2)c1] | 67% |
| L214 | S408 S19 | 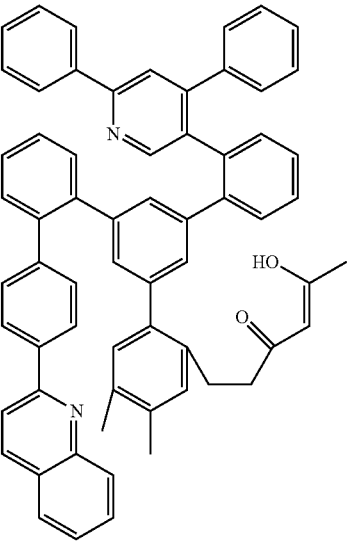 [SMILES: C/C(O)=C/C(=O)CCc1cc(C)c(C)cc1-c1cc(-c2ccccc2-c2ccc(-c3ccc4ccccc4n3)cc2)cc(-c2ccccc2-c2cnc(-c3ccccc3)cc2-c2ccccc2)c1] | 59% |

C: Preparation of the Metal Complexes

Example Ir(L1)

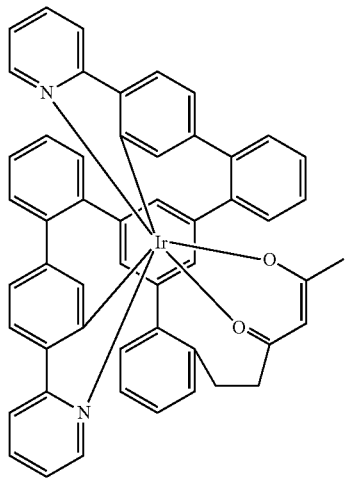

Variant A:

A mixture of 7.25 g (10 mmol) of ligand L1, 4.90 g (10 mmol) of trisacetylacetonatoiridium(III) [15635-87-7] and 120 g of hydroquinone [123-31-9] is initially charged in a 1000 ml two-neck round-bottom flask with a glass-sheathed magnetic bar. The flask is provided with a water separator (for media of lower density than water) and an air condenser with argon blanketing. The flask is placed in a metal heating bath. The apparatus is purged with argon from the top via the argon blanketing system for 15 min, allowing the argon to flow out of the side neck of the two-neck flask. Through the side neck of the two-neck flask, a glass-sheathed Pt-100 thermocouple is introduced into the flask and the end is positioned just above the magnetic stirrer bar. Then the apparatus is thermally insulated with several loose windings of domestic aluminium foil, the insulation being run up to the middle of the riser tube of the water separator. Then the apparatus is heated rapidly with a heated laboratory stirrer system to 250-255° C., measured with the Pt-100 temperature sensor which dips into the molten stirred reaction mixture. Over the next 1 h, the reaction mixture is kept at 250-255° C., in the course of which a small amount of condensate is distilled off and collects in the water separator. After 1 h, the mixture is allowed to cool down to 190° C., the heating mantle is removed and then 100 ml of ethylene glycol are added dropwise. After cooling to 100° C., 400 ml of methanol are slowly added dropwise. The beige suspension thus obtained is filtered through a double-ended frit, and the beige solid is washed three times with 50 ml of methanol and then dried under reduced pressure. Crude yield: quantitative. The solid thus obtained is dissolved in 200 ml of dichloromethane and filtered through about 1 kg of silica gel in the form of a dichloromethane slurry (column diameter about 18 cm) with exclusion of air in the dark, leaving dark-coloured components at the start. The core fraction is cut out and concentrated on a rotary evaporator, with simultaneous continuous dropwise addition of MeOH until crystallization. After removal with suction, washing with a little MeOH and drying under reduced pressure, the orange product is purified further by continuous hot extraction five times with dichloromethane/acetonitrile 1:1 (v/v) (amount initially charged in each case about 200 ml, extraction thimble: standard Soxhlet thimbles made from cellulose from Whatman) with careful exclusion of air and light. The loss into the mother liquor can be adjusted via the ratio of dichloromethane (low boilers and good dissolvers):acetonitrile (high boilers and poor dissolvers). It should typically be 3-6% by weight of the amount used. Hot extraction can also be accomplished using other solvents such as toluene, xylene, ethyl acetate, butyl acetate, etc. Finally, the product is sublimed at 390° C. under high vacuum. Yield: 5.95 g (6.1 mmol), 61%; purity: >99.9% by HPLC.

Variant B:

Procedure analogous to Ir(L1) Variant A, except that 300 ml of ethylene glycol [111-46-6] are used rather than 120 g of hydroquinone and the mixture is stirred at 190° C. for 16 h. After cooling to 70° C., the mixture is diluted with 300 ml of ethanol, and the solids are filtered off with suction (P3), washed three times with 100 ml each time of ethanol and then dried under reduced pressure. Further purification is effected as described in Variant A. Yield: 6.35 g (6.5 mmol), 65%; purity: >99.9% by HPLC.

Variant C:

Procedure analogous to Ir(L1) Variant B, except that 3.53 g (10 mmol) of iridium(III) chloride x n H$_2$O (n about 3) are used rather than 4.90 g (10 mmol) of trisacetylacetonatoiridium(III) [15635-87-7] and 300 ml of 2-ethoxyethanol/water (3:1, vv) rather than 120 g of hydroquinone, and the mixture is stirred under reflux for 30 h. After cooling, the solid is filtered off with suction (P3), washed three times with 30 ml each time of ethanol and then dried under reduced pressure. Further purification is effected as described in Variant B. Yield: 4.67 g (5.1 mmol), 51%; purity: >99.9% by HPLC.

The metal complexes are typically obtained as a 1:1 mixture of the Λ and Δ isomers/enantiomers. The images of complexes adduced hereinafter typically show only one isomer. If ligands having three different sub-ligands are used, or chiral ligands are used as a racemate, the metal complexes derived are obtained as a diastereomer mixture. These can be separated by fractional crystallization or by chromatography, for example with an automatic column system (CombiFlash from A. Semrau). If chiral ligands are used in enantiomerically pure form, the metal complexes derived are obtained as a diastereomer mixture, the separation of which by fractional crystallization or chromatography leads to pure enantiomers. The separated diastereomers or enantiomers can be purified further as described above, for example by hot extraction.

Diastereomer1 refers hereinafter to that diastereomer which shows the greater Rf on thin-film chromatography plates (TLC silica gel 60 F254 from Merck) with ethyl acetate as eluent; Diastereomer2 refers to that diastereomer which shows the smaller Rf.

In an analogous manner, it is possible to prepare the following compounds:

| Ex. | Ligand | Product Variant/extractant* | Yield |
|---|---|---|---|
| Ir(L-Ref.1) | L-Ref.1 | Ir(L-Ref.1) B | 30% |
| Ir(L2) | L2 | Ir(L2) B | 63% |
| Ir(L3) | L3 | Ir(L3) A/Toluene | 65% |

-continued

| Ex. | Ligand | Product Variant/extractant* | Yield |
|---|---|---|---|
| Ir(100) | L100 | 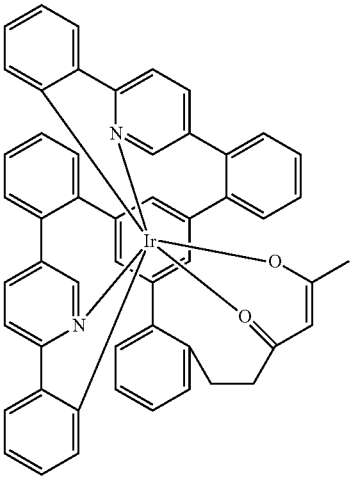 | 60% |
| Ir(L-Ref.2) | L-Ref.2 | Ir(L-Ref.2) B | 24% |
| Ir(L101) | L101 | Ir(L101) A | 57% |
| Ir(L102) | L102 | Ir(L102) B/toluene | 60% |
| Ir(L103) | L103 | Ir(L103) C/toluene | 66% |
| Ir(L104) | L104 | Ir(L104) A | 62% |
| Ir(L105) | L105 | Ir(L105) A | 58% |
| Ir1(L200) | L200 | 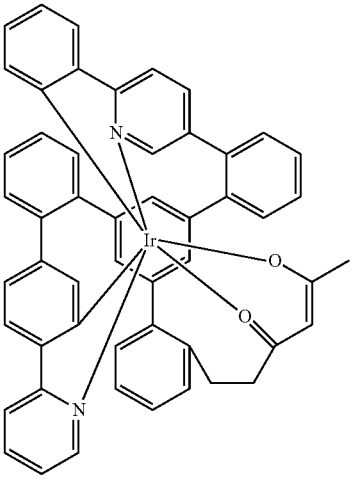 Ir1 (L200) A Diastereomer1 | 24% |
| Ir2(L200) | L200 | Ir2(L200) A Diastereomer2 | 27% |
| Ir1(L-Ref.3) | L-Ref.3 | Ir1(L-Ref.3) B Diastereomer1 | 10% |
| Ir2(L-Ref.3) | L-Ref.3 | Ir2(L-Ref.3) B Diastereomer2 | 13% |
| Ir(L201) | L201 | Ir(L201) A | 68% |

-continued

| Ex. | Ligand | Product Variant/extractant* | Yield |
|---|---|---|---|
| Ir1(L202) | L202 | Isomer mixture Ir1(L202) B Diasteromer1 | 30% |
| Ir2(L202) | L202 | Ir2(L202) B Diastereomer2 | 28% |
| Ir1(L203) | L203 | Ir1(L203) C Diastereomer1 | 25% |
| Ir2(L203) | L203 | Ir2(L203) C Diastereomer2 | 29% |
| Ir1(L204) | L204 | Ir1(L204) C Diastereomer1 | 35% |
| Ir2L204) | L204 | Ir2L204) C Diastereomer2 | 23% |
| Ir1(L205) | L205 | Ir1(L205) A Diastereomer1 | 31% |
| Ir2L205) | L205 | Ir2L205) A Diastereomer2 | 33% |
| Ir1(L206) | L206 | Ir1(L206) A Diastereomer1 | 27% |
| Ir2(L206) | L206 | Ir2L206) A Diastereomer2 | 34% |
| Ir1(L207) | L207 | Ir1(L207) B Diastereomer1 | 30% |
| Ir2L207) | L207 | Ir2L207) B Diastereomer2 | 35% |
| Ir1(L208) | L208 | Ir1(L208) B Diastereomer1 | 28% |
| Ir2L208) | L208 | Ir2L208) B Diastereomer2 | 31% |
| Ir1(L209) | L209 | Ir1(L209) B Diastereomer1 | 30% |
| Ir2L209) | L209 | Ir2L209) B Diastereomer2 | 30% |
| Ir1(L210) | L210 | Ir1(L210) A Diastereomer1 | 32% |
| Ir2L210) | L210 | Ir2L210) A Diastereomer2 | 27% |
| Ir1(L211) | L211 | Ir1(L211) A Diastereomer1 | 33% |
| Ir2L211) | L211 | Ir2L211) A Diastereomer2 | 30% |
| Ir1(L212) | L212 | Ir1(L212) C Diastereomer1 | 33% |
| Ir2L212) | L212 | Ir2L212) C Diastereomer2 | 29% |
| Ir1(L213) | L213 | Ir1(L213) A Diastereomer1 | 35% |
| Ir2L213) | L213 | Ir2L213) A Diastereomer2 | 31% |
| Ir1(L214) | L214 | Ir1(L214) B Diastereomer1 | 27% |

-continued

| Ex. | Ligand | Product Variant/extractant* | Yield |
|---|---|---|---|
| Ir2L214) | L214 | Ir2L214) B Diastereomer2 | 23% |

*if different

Sublimation Temperatures and Rates:

By comparison with the tripodal complexes having three phenylpyridine-like sub-ligands, the compounds of the invention sublime at lower temperatures and with higher sublimation rates (g/h) at a given sublimation temperature, as detailed in the table below. The exact temperatures and sublimation rates always depend on the exact pressure and the particular geometry of the sublimation apparatus used. The temperatures and sublimation rates are determined at a base pressure of about $10^{-5}$ mbar in the same apparatus in each case.

| Complex | Sublimation temperature [° C.] | Sublimation rate at the given sublimation temperature [g/h] |
|---|---|---|
| Ir-Ref. 1 | ~440 | 0.6 |
| Ir-Ref. 2 | ~440 | 0.5 |
| Ir-Ref. 3 | ~420 | 1.0 |
| Ir(L1) | ~390 | 1.4 |
| Ir(L100) | ~390 | 1.3 |
| Ir(L200) | ~380 | 1.8 |

Example: Production of the OLEDs

1) Vacuum-Processed Devices:

OLEDs of the invention and OLEDs according to the prior art are produced by a general method according to WO 2004/058911, which is adapted to the circumstances described here (variation in layer thickness, materials used).

In the examples which follow, the results for various OLEDs are presented. Cleaned glass plaques (cleaning in Miele laboratory glass washer, Merck Extran detergent) coated with structured ITO (indium tin oxide) of thickness 50 nm are pretreated with UV ozone for 25 minutes (PR-100 UV ozone generator from UVP) and, within 30 min, for improved processing, coated with 20 nm of PEDOT:PSS (poly(3,4-ethylenedioxythiophene) poly(styrenesulfonate), purchased as CLEVIOS™ P VP Al 4083 from Heraeus Precious Metals GmbH Deutschland, spun on from aqueous solution) and then baked at 180° C. for 10 min. These coated glass plaques form the substrates to which the OLEDs are applied. The OLEDs basically have the following layer structure: substrate/hole transport layer 1 (HTL1) consisting of HTM doped with 5% NDP-9 (commercially available from Novaled), 20 nm/hole transport layer 2 (HTL2)/optional electron blocker layer (EBL)/emission layer (EML)/optional hole blocker layer (HBL)/electron transport layer (ETL)/optional electron injection layer (EIL) and finally a cathode. The cathode is formed by an aluminium layer of thickness 100 nm.

First of all, vacuum-processed OLEDs are described. For this purpose, all the materials are applied by thermal vapour deposition in a vacuum chamber. In this case, the emission layer always consists of at least one matrix material (host material) and an emitting dopant (emitter) which is added to the matrix material(s) in a particular proportion by volume by co-evaporation. Details given in such a form as M1:M2:Ir(L2) (55%:35%:10%) mean here that the material M1 is present in the layer in a proportion by volume of 55%, M2 in a proportion by volume of 35% and Ir(L1) in a proportion by volume of 10%. Analogously, the electron transport layer may also consist of a mixture of two materials. The exact structure of the OLEDs can be found in Table 2. The materials used for production of the OLEDs are shown in Table 4.

The OLEDs are characterized in a standard manner. For this purpose, the electroluminescence spectra, the current efficiency (measured in cd/A), the power efficiency (measured in lm/W) and the external quantum efficiency (EQE, measured in percent) as a function of luminance, calculated from current-voltage-luminance characteristics (IUL characteristics) assuming Lambertian emission characteristics, and also the lifetime are determined. The electroluminescence spectra are determined at a luminance of 1000 cd/m$^2$, and the CIE 1931 x and y colour coordinates are calculated therefrom. The lifetime LT80 is defined as the time after which the luminance drops to 80% of the starting luminance in the course of operation with a constant current of 40 mA/cm$^2$.

Use of Compounds of the Invention as Emitter Materials in Phosphorescent OLEDs

One use of the compounds of the invention is as phosphorescent emitter materials in the emission layer in OLEDs. The iridium compounds according to Table 4 are used as a comparison according to the prior art. The results for the OLEDs are collated in Table 2.

TABLE 1

Structure of the OLEDs

| Ex. | HTL2 thickness | EBL thickness | EML thickness | HBL thickness | ETL thickness |
|---|---|---|---|---|---|
| Ref.-D1 | HTM 40 nm | — | M1:Ir-Ref. 1 (90%:10%) 30 nm | ETM1 10 nm | ETM1:ETM2 (50%:50%) 30 nm |
| Ref.-D2 | HTM 40 nm | — | M1:Ir-Ref. 2 (90%:10%) 30 nm | ETM1 10 nm | ETM1:ETM2 (50%:50%) 30 nm |
| Ref.-D3 | HTM 40 nm | — | M1:I Ir-Ref. 3 (90%:10%) 30 nm | ETM1 10 nm | ETM1:ETM2 (50%:50%) 30 nm |
| Ref.-D4 | HTM 40 nm | — | M1:M2:Ir-Ref. 1 (60%:30%:10%) 30 nm | ETM1 10 nm | ETM1:ETM2 (50%:50%) 30 nm |

TABLE 1-continued

Structure of the OLEDs

| Ex. | HTL2 thickness | EBL thickness | EML thickness | HBL thickness | ETL thickness |
|---|---|---|---|---|---|
| Ref.-D5 | HTM 40 nm | — | M1:M2:Ir-Ref. 2 (60%:30%:10%) 30 nm | ETM1 10 nm | ETM1:ETM2 (50%:50%) 30 nm |
| Ref.-D6 | HTM 40 nm | — | M1:Ir(L-Ref. 1) (90%:10%) 30 nm | ETM1 10 nm | ETM1:ETM2 (50%:50%) 30 nm |
| Ref.-D7 | HTM 40 nm | — | M1:Ir(L-Ref. 2) (90%:10%) 30 nm | ETM1 10 nm | ETM1:ETM2 (50%:50%) 30 nm |
| Ref.-D8 | HTM 40 nm | — | M1:I Ir1 (L-Ref. 3) (90%:10%) 30 nm | ETM1 10 nm | ETM1:ETM2 (50%:50%) 30 nm |
| D1 | HTM 40 nm | — | M1:Ir(L1) (90%:10%) 30 nm | ETM1 10 nm | ETM1:ETM2 (50%:50%) 30 nm |
| D2 | HTM 40 nm | — | M1:Ir(L100) (90%:10%) 30 nm | ETM1 10 nm | ETM1:ETM2 (50%:50%) 30 nm |
| D3 | HTM 40 nm | — | M1:Ir(L200) (90%:10%) 30 nm | ETM1 10 nm | ETM1:ETM2 (50%:50%) 30 nm |
| D4 | HTM 40 nm | — | M1:M2:Ir(I1) (60%:30%:10%) 30 nm | ETM1 10 nm | ETM1:ETM2 (50%:50%) 30 nm |
| D5 | HTM 40 nm | — | M1:M2:Ir(L100) (60%:30%:10%) 30 nm | ETM1 10 nm | ETM1:ETM2 (50%:50%) 30 nm |
| D6 | HTM 40 nm | — | M1:M2:Ir(L200) (60%:30%:10%) 30 nm | ETM1 10 nm | ETM1:ETM2 (50%:50%) 30 nm |
| D7 | HTM 30 nm | EBM 10 nm | M1:M2:Ir(L200) (60%:30%:10%) 30 nm | ETM1 10 nm | ETM1:ETM2 (50%:50%) 30 nm |

TABLE 2

Results for the vacuum-processed OLEDs

| Ex. | EQE (%) @ 1000 cd/m² | Voltage (V) @ 1000 cd/m² | CIE x/y @ 1000 cd/m² | LD80 (h) @ 40 mA/cm² |
|---|---|---|---|---|
| Ref.-D1 | 20.3 | 3.1 | 0.34/0.62 | 220 |
| Ref.-D2 | 20.7 | 3.0 | 0.40/0.58 | 240 |
| Ref.-D3 | 16.0 | 3.1 | 0.38/0.57 | 250 |
| Ref.-D4 | 20.6 | 3.1 | 0.34/0.62 | 250 |
| Ref.-D5 | 21.0 | 3.1 | 0.39/0.59 | 270 |
| Ref.-D6 | 19.9 | 3.2 | 0.37/0.60 | 150 |
| Ref.-D7 | 20.1 | 3.3 | 0.45/0.52 | 130 |
| Ref.-D8 | 20.4 | 3.2 | 0.43/0.53 | 160 |
| D1 | 22.6 | 2.9 | 0.39/0.59 | 220 |
| D2 | 22.9 | 3.0 | 0.43/0.55 | 250 |
| D3 | 23.4 | 3.0 | 0.44/0.54 | 280 |
| D4 | 22.2 | 2.9 | 0.39/0.59 | 280 |
| D5 | 22.5 | 3.0 | 0.43/0.55 | 310 |
| D6 | 23.0 | 3.0 | 0.44/0.54 | 300 |
| D7 | 22.9 | 3.0 | 0.44/0.54 | 320 |

Solution-Processed Devices:
From Soluble Functional Materials of Low Molecular Weight The compounds of the invention may also be processed from solution and in that case lead to OLEDs which are much simpler in terms of process technology compared to vacuum-processed OLEDs, but nevertheless have good properties. The production of such components is based on the production of polymeric light-emitting diodes (PLEDs), which has already been described many times in the literature (for example in WO 2004/037887). The structure is composed of substrate/ITO/hole injection layer (60 nm)/interlayer (20 nm)/emission layer (60 nm)/hole blocker layer (10 nm)/electron transport layer (40 nm)/cathode. For this purpose, substrates from Technoprint (soda-lime glass) are used, to which the ITO structure (indium tin oxide, a transparent conductive anode) is applied. The substrates are cleaned in a cleanroom with DI water and a detergent (Deconex 15 PF) and then activated by a UV/ozone plasma treatment. Thereafter, likewise in a cleanroom, a 20 nm hole injection layer is applied by spin-coating. The required spin rate depends on the degree of dilution and the specific spin-coater geometry. In order to remove residual water from the layer, the substrates are baked on a hotplate at 200° C. for 30 minutes. The interlayer used serves for hole transport; in this case, HL-X092 from Merck is used. The interlayer may alternatively also be replaced by one or more layers which merely have to fulfil the condition of not being leached off again by the subsequent processing step of EML deposition from solution. For production of the emission layer, the triplet emitters of the invention are dissolved together with the matrix materials in toluene or chlorobenzene. The typical solids content of such solutions is between 16 and 25 g/l when, as here, the layer thickness of 60 nm which is typical of a device is to be achieved by means of spin-coating. The solution-processed devices of type 1 contain an emission layer composed of M3:M4:IrL (20%:60%:20%), and those of type 2 contain an emission layer composed of M3:M4:IrLa:IrLb (30%:34%:30%:6%); in other words, they contain two different iridium complexes. The emission layer is spun on in an inert gas atmosphere, argon in the present case, and baked at 160° C. for 10 min. Vapour-deposited above the latter are the hole blocker layer (10 nm ETM1) and the electron transport layer (40 nm ETM1 (50%)/ETM2 (50%)) (vapour deposition systems from Lesker or the like, typical vapour deposition pressure 5×10$^{-6}$ mbar). Finally, a cathode of aluminium (100 nm) (high-purity metal from Aldrich) is applied by vapour deposition. In order to protect the device from air and air humidity, the device is finally encapsulated and then characterized. The OLED examples cited are yet to be optimized; Table 3 summarizes the data obtained.

TABLE 3

Results with materials processed from solution

| Ex. | Emitter Device | EQE (%) 1000 cd/m$^2$ | Voltage (V) 1000 cd/m$^2$ | CIE x/y | LD50 (h) 1000 cd/m$^2$ |
|---|---|---|---|---|---|
| Sol-Ref. 1 | Ir-Ref. 4 Type 1 | 20.6 | 5.2 | 0.36/0.61 | 220000 |
| Sol-Ref. 2 | Ir-Ref. 5 Type 1 | 21.4 | 5.0 | 0.31/0.62 | 11000 |
| Sol-D1 | Ir(L2) Type 1 | 22.3 | 5.1 | 0.38/0.59 | 230000 |
| Sol-D2 | Ir(L202) Ir(L213) Type 2 | 21.4 | 4.7 | 0.68/0.32 | 320000 |

TABLE 4

Structural formulae of the materials used

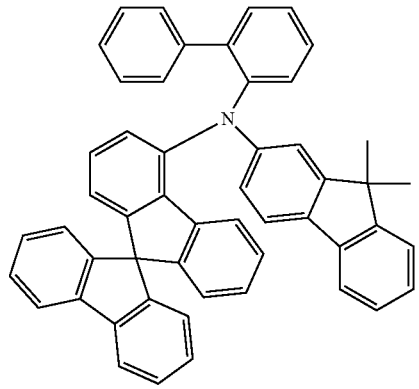

HTM
[1450933-44-4]

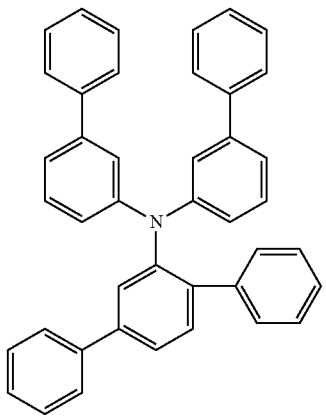

EBM
[1443540-48-4]

TABLE 4-continued
Structural formulae of the materials used
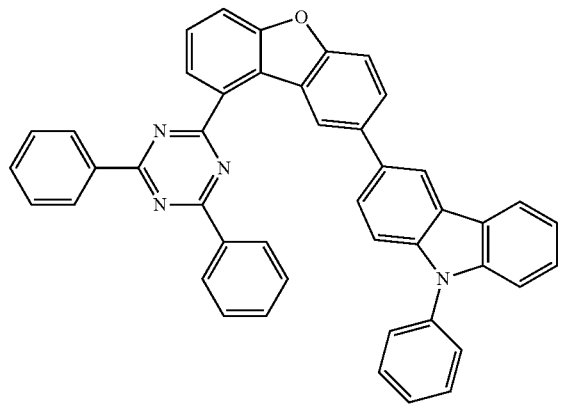
M1
[1822310-78-0]
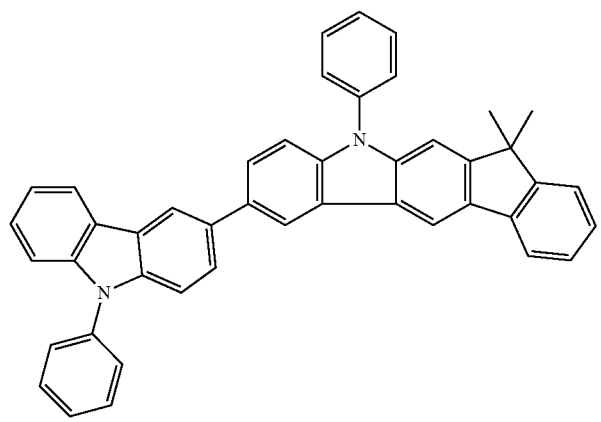
M2
[1357150-54-9]

TABLE 4-continued
Structural formulae of the materials used
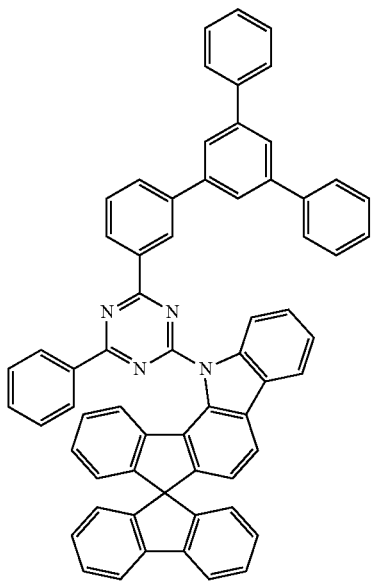
M3
[1616231-60-7]
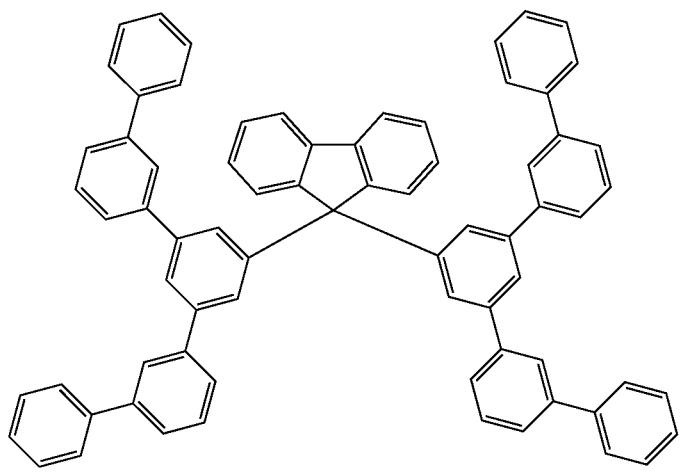
M4
[1246496-85-4]

TABLE 4-continued
Structural formulae of the materials used
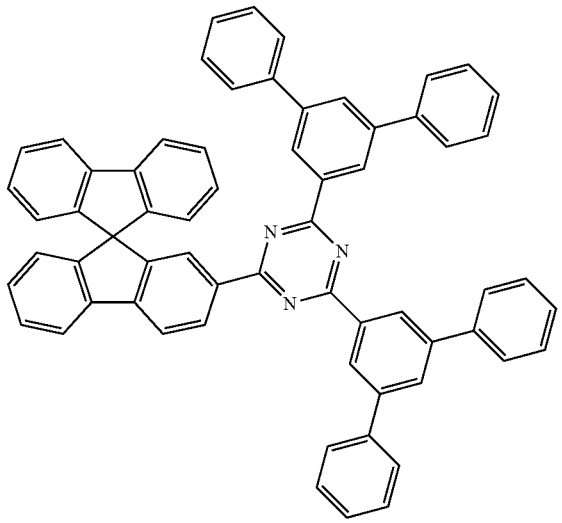
ETM1 = M10
[1233200-52-6]
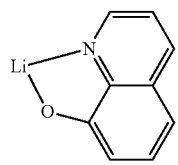
ETM2
[25387-93-3]
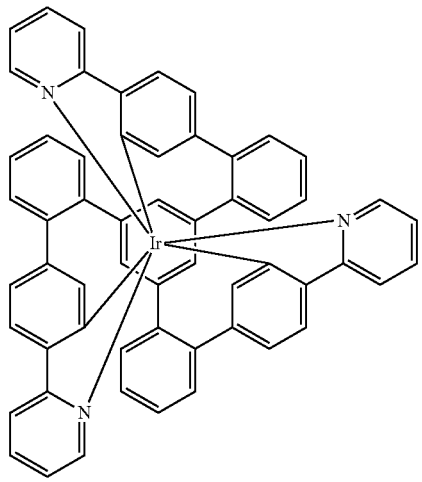
[1989600-78-3]
Ir-Ref.1

TABLE 4-continued
Structural formulae of the materials used
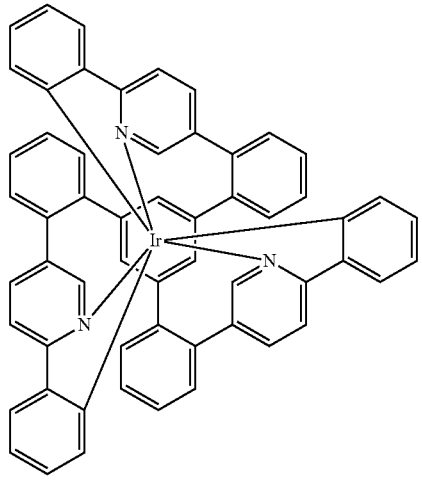
[1989600-75-0]
Ir-Ref.2
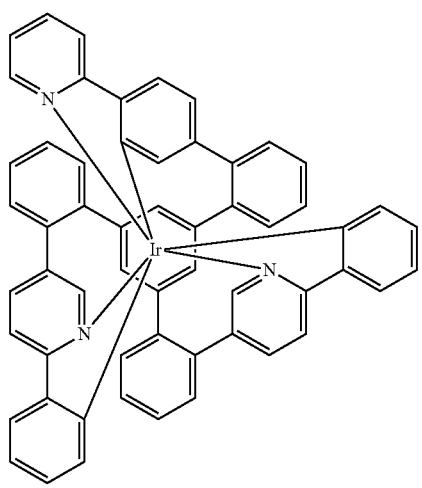
[1989600-79-4]
Ir-Ref.3

421
422
TABLE 4-continued
Structural formulae of the materials used
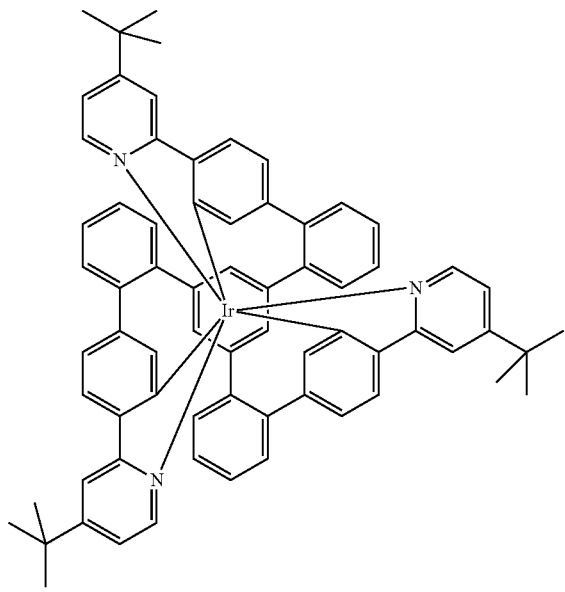
[1989606-01-0]
Ir-Ref.4
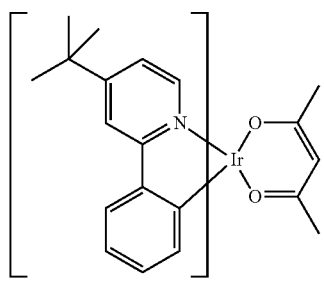
Ir-Ref.5
[1375601-05-0]
The invention claimed is:
1. A compound of formula (1):
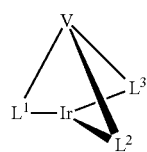
wherein
$L^1$ is a sub-ligand of formula (2):
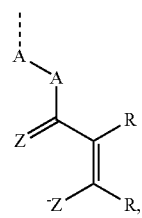

which coordinates to the iridium via the two Z groups and which is bonded to V via the dotted bond;

A is the same or different in each instance and is $CR_2$, O, S, or NR, wherein at least one A group is $CR_2$;

Z is the same or different in each instance and is O, S, or NR;

$L^2$ is a bidentate, monoanionic sub-ligand which coordinates to the iridium via one carbon atom and one nitrogen atom or via two carbon atoms;

$L^3$ is a bidentate, monoanionic sub-ligand which coordinates to the iridium via one carbon atom and one nitrogen atom or via two carbon atoms, or is a sub-ligand of the formula (2) which is optionally the same as or different from $L^1$;

V is a group of formula (3), wherein the dotted bonds each denote the linkage of sub-ligands $L^1$, $L^2$ and $L^3$,

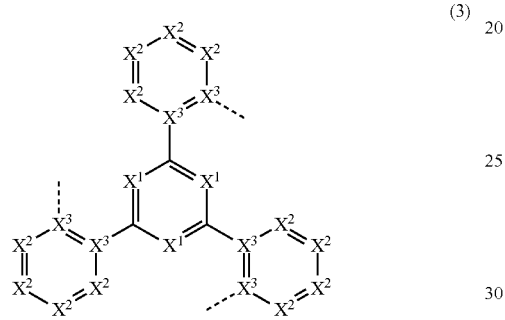

(3)

$X^1$ is the same or different in each instance and is CR or N;

$X^2$ is the same or different in each instance and is CR or N, or two adjacent $X^2$ groups together are NR, O, or S, so as to define a five-membered ring; or two adjacent $X^2$ groups together are CR or N when one of the $X^3$ groups in the cycle is N, so as to form a five-membered ring; with the proviso that not more than two adjacent $X^2$ groups in each ring are N;

$X^3$ is C in each instance in one cycle or one $X^3$ group is N and the other $X^3$ group in the same cycle is C, wherein the $X^3$ groups in the three cycles are optionally selected independently, with the proviso that two adjacent $X^2$ groups together are CR or N when one of the $X^3$ groups in the cycle is N;

R is the same or different in each instance and is H, D, F, Cl, Br, I, $N(R^1)_2$, $OR^1$, $SR^1$, CN, $NO_2$, COOH, $C(=O)N(R^1)_2$, $Si(R^1)_3$, $B(OR^1)_2$, $C(=O)R^1$, $P(=O)(R^1)_2$, $S(=O)R^1$, $S(=O)_2R^1$, $OSO_2R^1$, a straight-chain alkyl group having 1 to 20 carbon atoms or an alkenyl or alkynyl group having 2 to 20 carbon atoms or a branched or cyclic alkyl group having 3 to 20 carbon atoms, wherein the alkyl, alkenyl, or alkynyl group in each case is optionally substituted by one or more $R^1$ radicals and wherein one or more nonadjacent $CH_2$ groups are optionally replaced by $Si(R^1)_2$, $C=O$, $NR^1$, O, S, or $CONR^1$, or an aromatic or heteroaromatic ring system which has 5 to 40 aromatic ring atoms and is optionally substituted in each case by one or more $R^1$ radicals; and wherein two R radicals together optionally define a ring system;

$R^1$ is the same or different in each instance and is H, D, F, Cl, Br, I, $N(R^2)_2$, $OR^2$, $SR^2$, CN, $NO_2$, $Si(R^2)_3$, $B(OR^2)_2$, $C(=O)R^2$, $P(=O)(R^2)_2$, $S(=O)R^2$, $S(=O)_2R^2$, $OSO_2R^2$, a straight-chain alkyl group having 1 to 20 carbon atoms or an alkenyl or alkynyl group having 2 to 20 carbon atoms or a branched or cyclic alkyl group having 3 to 20 carbon atoms, wherein the alkyl, alkenyl, or alkynyl group in each case are optionally substituted by one or more $R^2$ radicals, wherein one or more nonadjacent $CH_2$ groups are optionally replaced by $Si(R^2)_2$, $C=O$, $NR^2$, O, S, or $CONR^2$, or an aromatic or heteroaromatic ring system which has 5 to 40 aromatic ring atoms and is optionally substituted in each case by one or more $R^2$ radicals; and wherein two or more $R^1$ radicals together optionally define a ring system;

$R^2$ is the same or different in each instance and is H, D, F, or an aliphatic, aromatic, and/or heteroaromatic organic radical having 1 to 20 carbon atoms, wherein one or more hydrogen atoms is optionally replaced by F; and wherein the three bidentate ligands $L^1$, $L^2$, and $L^3$, in addition to bridge V, are also optionally connected via a further bridge so as to form a cryptate.

2. The compound of claim 1, wherein V is selected from the group consisting of formulae (4a) through (7a):

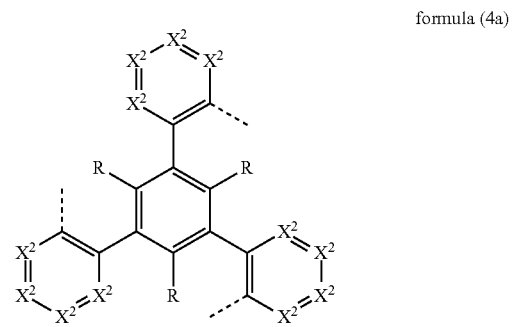

formula (4a)

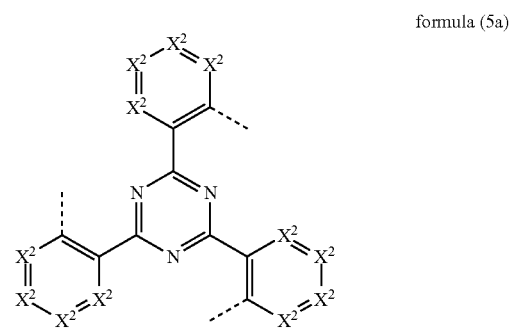

formula (5a)

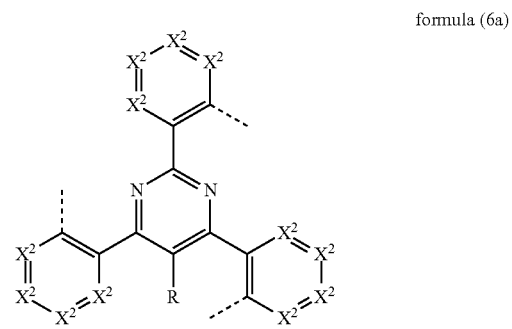

formula (6a)

formula (7a)

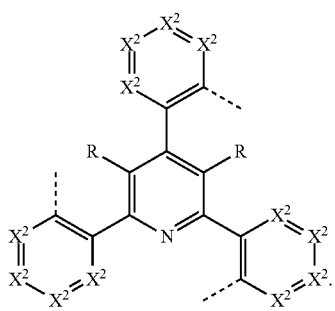

3. The compound of claim 1, wherein V has a structure of formula (4b'), (4c), or (5c):

(4b')

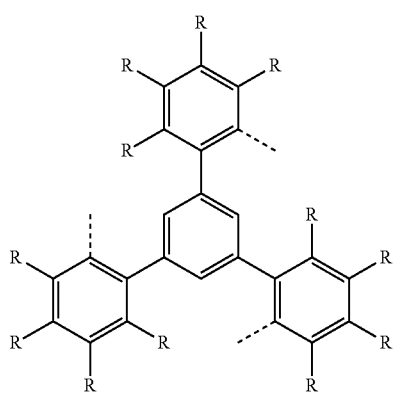

(4c)

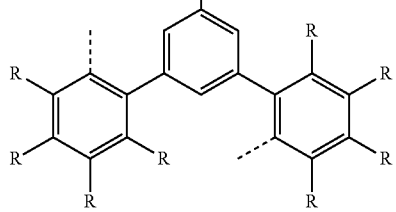

(5c)

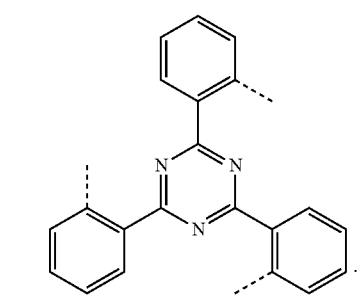

4. The compound of claim 1, wherein both A groups in sub-ligand $L^1$ are $CR_2$.

5. The compound of claim 1, wherein both Z groups in sub-ligand $L^1$ are O.

6. The compound of claim 1, wherein $L^1$ has a structure of formula (2c):

(2c)

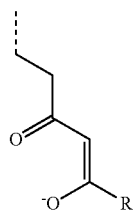

wherein the dotted bond denotes the bond to V, and R is the same or different in each instance and is selected from the group consisting of H, D, $OR^1$, a straight-chain alkyl group having 1 to 10 carbon atoms, optionally substituted in each case by one or more $R^1$ radicals, a branched or cyclic alkyl group having 3 to 10 carbon atoms, optionally substituted in each case by one or more $R^1$ radicals, and an aromatic or heteroaromatic ring system having 5 to 24 aromatic ring atoms optionally substituted in each case by one or more $R^1$ radicals.

7. The compound of claim 1, wherein the two sub-ligands $L^2$ and $L^3$ each have one carbon atom and one nitrogen atom as coordinating atoms.

8. The compound of claim 1, wherein the sub-ligands $L^2$ and $L^3$ are the same or different at each instance and are a structure of the formula (L-1) or (L-2):

(L-1)

(L-2)

wherein
the dotted bond represents the bond of the sub-ligand to V;
CyC is the same or different in each instance and is a substituted or unsubstituted aryl or heteroaryl group which has 5 to 14 aromatic ring atoms and coordinates in each case to the metal via a carbon atom and which is bonded to CyD via a covalent bond;
CyD is the same or different in each instance and is a substituted or unsubstituted heteroaryl group which has 5 to 14 aromatic ring atoms and coordinates to the metal via a nitrogen atom or via a carbene carbon atom and which is bonded to CyC via a covalent bond; and
wherein two or more of the optional substituents together optionally define a ring system.

9. The compound of claim 8, wherein one of the sub-ligands $L^2$ and $L^3$ has a structure of formula (L-1) and the other of the sub-ligands $L^2$ and $L^3$ has a structure of formula (L-2).

10. The compound of claim 8, wherein CyC is selected from the group consisting of structures of formulae (CyC-1) through (CyC-19), wherein the CyC group binds to CyD in each case at the position identified by # and to the iridium at the position identified by *, and wherein the CyD group is selected from the group consisting of structures of formulae (CyD-1) through (CyD-12), and wherein the CyD group binds to CyC in each case at the position identified by # and to the iridium at the position identified by *:
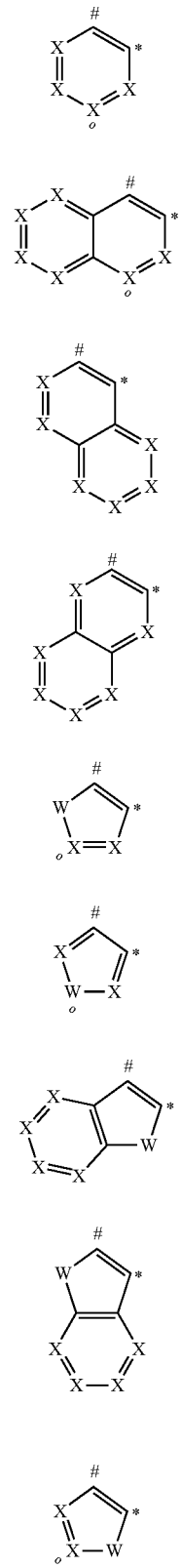
(CyC-1)
(CyC-2)
(CyC-3)
(CyC-4)
(CyC-5)
(CyC-6)
(CyC-7)
(CyC-8)
(CyC-9)
-continued
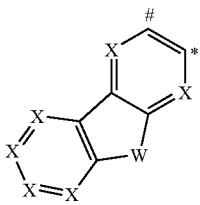
(CyC-10)
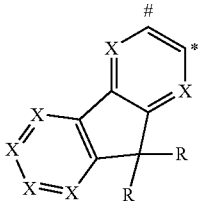
(CyC-11)
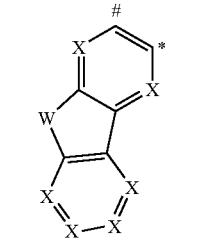
(CyC-12)
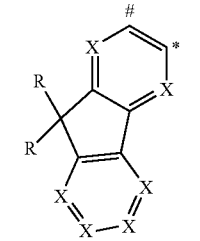
(CyC-13)
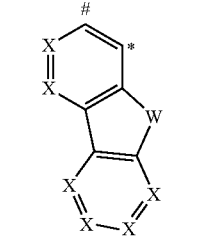
(CyC-14)
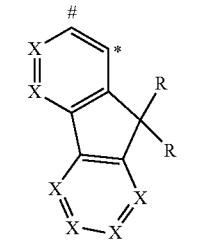
(CyC-15)
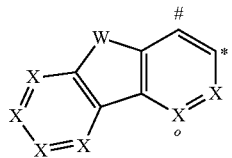
(CyC-16)

-continued (CyC-17)
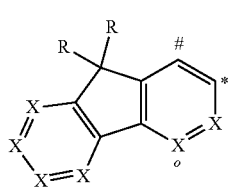

(CyC-18)
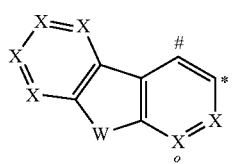

(CyC-19)
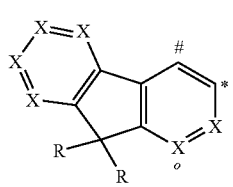

(CyC-20)
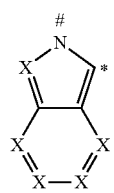

(CyD-1)
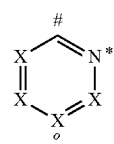

(CyD-2)
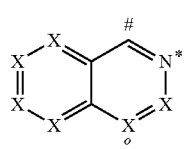

(CyD-3)
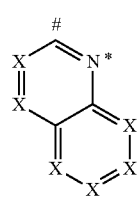

(CyD-4)
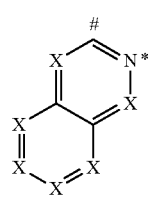

(CyD-5)
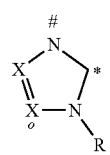

-continued (CyD-6)
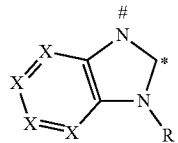

(CyD-7)
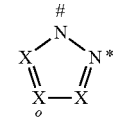

(CyD-8)
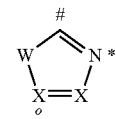

(CyD-9)
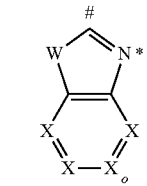

(CyD-10)
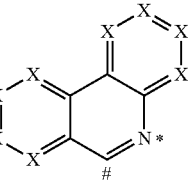

(CyD-11)
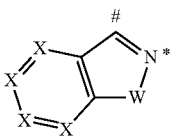

(CyD-12)
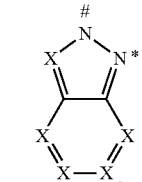

wherein

X is the same or different in each instance and is CR or N, with the proviso that not more than two symbols X per cycle are N;

W is the same or different in each instance and is NR, O, or S;

with the proviso that when the bridge V is bonded to CyC, one symbol X in the corresponding CyC group is C, to which the bridge V is bonded, and, when the bridge V is bonded to CyD, one symbol X in the corresponding CyD group is C, to which the bridge V is bonded; wherein the bond to the bridge V is via the position denoted by "o".

11. A process for preparing the compound of claim 1 comprising reacting a free ligand with an iridium alkoxide of formula (52), an iridium ketoketonate of formula (53), an iridium halide of formula (54), or an iridium carboxylate of formula (55):

Ir(OR)₃ (52)

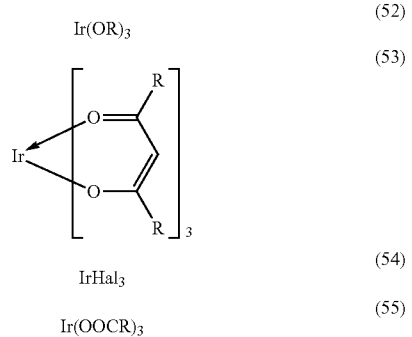
(53)

IrHal₃ (54)

Ir(OOCR)₃ (55)

wherein
Hal is F, Cl, Br, or I; and
wherein the iridium reactants of formulae (52) through (55) are optionally in the form of a hydrate.

12. A formulation comprising at least one compound of claim 1 and at least one further compound.

13. The formulation of claim 12, wherein the at least one further compound is a matrix material and/or a solvent.

14. An electronic device comprising at least one compound of claim 1.

15. The electronic device of claim 14, wherein the electronic device is selected from the group consisting of organic electroluminescent devices, organic integrated circuits, organic field-effect transistors, organic thin-film transistors, organic light-emitting transistors, organic solar cells, organic optical detectors, organic photoreceptors, organic field-quench devices, light-emitting electrochemical cells, infrared sensors, oxygen sensors, and organic laser diodes.

16. The electronic device of claim 15, wherein the electronic device is an organic electroluminescent device, wherein the organic electroluminescent device comprises one or more emitting layers, and wherein the one or more emitting layers comprises a compound of formula (1).

17. The compound of claim 1, wherein $R^2$ is a hydrocarbyl radical having 1 to 20 carbon atoms, wherein one or more hydrogen atoms is optionally replaced by F.

* * * * *